(12) United States Patent
Mujeeb-U-Rahman et al.

(10) Patent No.: US 11,806,136 B2
(45) Date of Patent: *Nov. 7, 2023

(54) WIRED IMPLANTABLE MONOLITHIC INTEGRATED SENSOR CIRCUIT

(71) Applicant: Integrated Medical Sensors, Inc., Irvine, CA (US)

(72) Inventors: Muhammad Mujeeb-U-Rahman, Irvine, CA (US); Meisam Honarvar Nazari, Irvine, CA (US); Mehmet Sencan, Tustin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/093,532

(22) Filed: Jan. 5, 2023

(65) Prior Publication Data

US 2023/0277095 A1    Sep. 7, 2023

Related U.S. Application Data

(63) Continuation of application No. 17/993,516, filed as application No. PCT/US2022/042401 on Sep. 1, 2022.

(Continued)

(51) Int. Cl.
*A61B 5/145*    (2006.01)
*A61B 5/00*    (2006.01)
*A61B 5/1486*    (2006.01)

(52) U.S. Cl.
CPC ........ *A61B 5/14532* (2013.01); *A61B 5/0004* (2013.01); *A61B 5/14865* (2013.01); *A61B 5/6849* (2013.01)

(58) Field of Classification Search
CPC .............. A61B 5/14865; A61B 5/0004; A61B 5/14532; A61B 5/6849; A61B 5/6848
See application file for complete search history.

(56) References Cited

U.S. PATENT DOCUMENTS 11,571,148 B1 *   2/2023  Puttananjegowda .. C12Q 1/002
2018/0075267 A1 * 3/2018  O'Driscoll ......... G06K 7/10316
(Continued)

FOREIGN PATENT DOCUMENTS

WO    WO2016133778 A1    8/2016

OTHER PUBLICATIONS

PCT/US2022/042401—International Search Report, dated Dec. 13, 2022.

(Continued)

*Primary Examiner* — Eric J Messersmith

(57) ABSTRACT

There is provided a glucose sensor system comprising: a transmitter (2) for containing a battery (212), the transmitter being for placement on top of patient skin; a transcutaneous connector (3) comprising at least one conductive path; and an implantable monolithic integrated circuit (I) for placement beneath the patient skin, wherein the implantable monolithic integrated circuit comprises a potentiostat and an electrochemical sensing element; wherein the potentiostat is electrically coupled to the transmitter (2) via the transcutaneous connector (3), and the electrochemical sensing element is configured to sense glucose concentration and generate an electrical signal representative of the glucose concentration, and wherein the potentiostat is electrically connected to the electrochemical sensing element.

3 Claims, 63 Drawing Sheets

Related U.S. Application Data

(60) Provisional application No. 63/336,299, filed on Apr. 28, 2022, provisional application No. 63/333,443, filed on Apr. 21, 2022, provisional application No. 63/318,790, filed on Mar. 11, 2022, provisional application No. 63/298,632, filed on Jan. 12, 2022, provisional application No. 63/239,484, filed on Sep. 1, 2021.

(56) References Cited

U.S. PATENT DOCUMENTS

| | | | |
|---|---|---|---|
| 2018/0321302 A1* | 11/2018 | Qu | G01R 31/2829 |
| 2019/0029577 A1* | 1/2019 | Koelker | A61B 5/14546 |
| 2019/0320903 A1 | 10/2019 | Mujeeb-U-Rahman | |
| 2020/0015720 A1 | 1/2020 | Peterson | |
| 2020/0182825 A1* | 6/2020 | Seitz | G01N 27/416 |
| 2021/0239648 A1* | 8/2021 | Huang | A61B 5/1473 |

OTHER PUBLICATIONS

PCT/US2022/042401—Written Opinion of the International Searching Authority, dated Dec. 13, 2022.

\* cited by examiner $I_{PTAT} = (k/q) \times T \times \ln(n)/R_1$ $I_{CTAT} = V_{BG} - (k/q) \times T \times \ln(n)/R_2$ Step 1
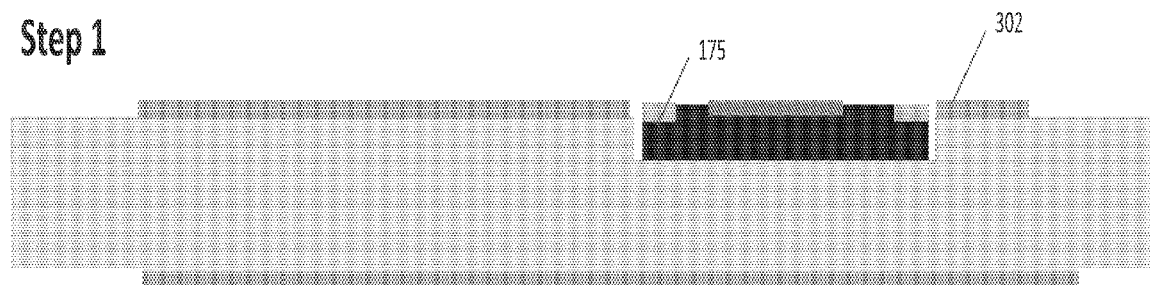
Step 2
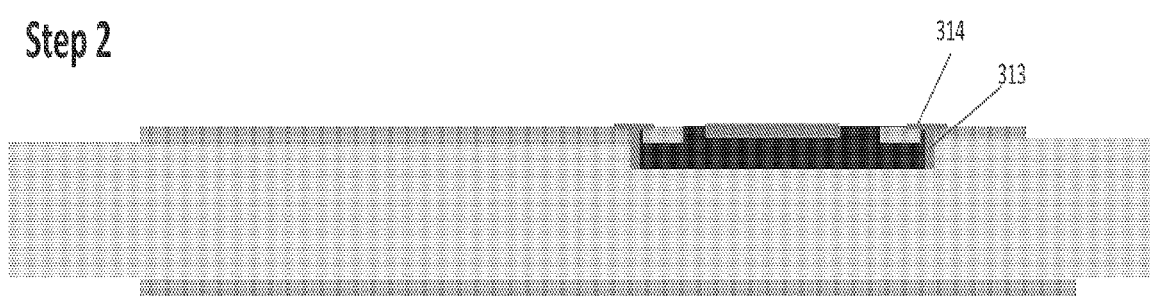
Step 3
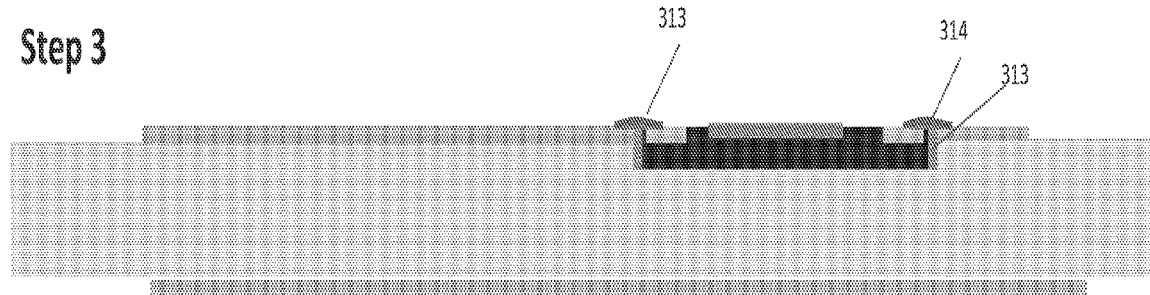
Fig. 32

View of Top
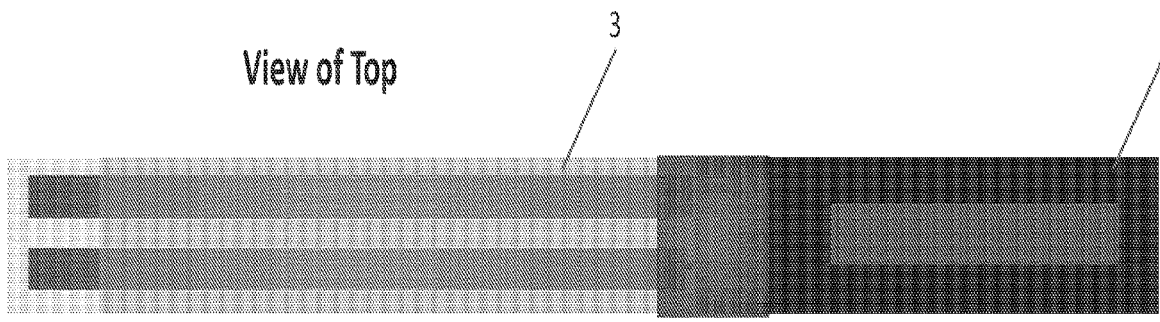
View of Bottom
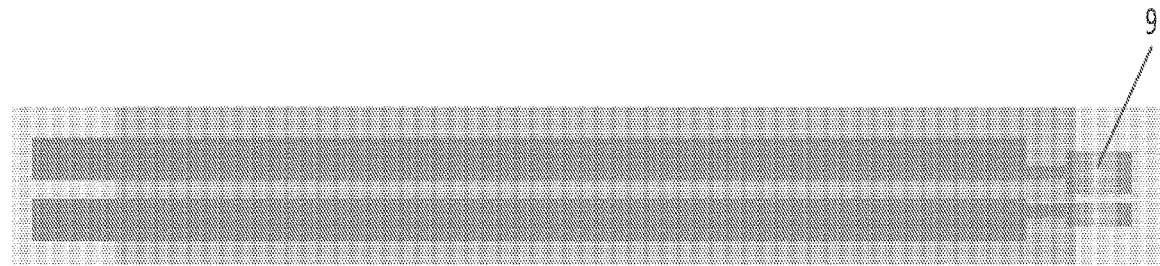
Fig. 33

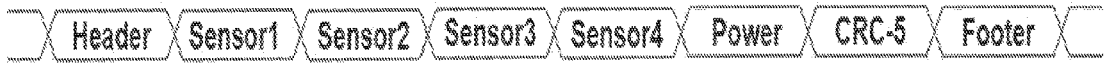

1. Keep unit in low power mode until powered on (e.g., by NFC, by photodiode)
2. After initialization (e.g., via NFC), BLE scan for a suitable reader periodically and connect,
3. Test if a valid sensor is attached to the transmitter (e.g., by current draw),
4. Send a tag signal in TX mode,
5. Wait for the silent period,
6. Turn on RX mode to read incoming data packet,
7. Pre-process the incoming data signal,
8. Read the received data via digital input of the microcontroller,
9. Decode the data packet according to the modulation (encoding) scheme,
10. Confirm proper Header, Footer to identify the data packet, discard if not correct,
11. Check CRC to confirm data integrity, discard if not correct,
12. Check power level to confirm if chip operation is proper,
13. De-multiplex sensor data,
14. Send all the sensor's data to the microprocessor for further processing.

Fig. 39

Step 1
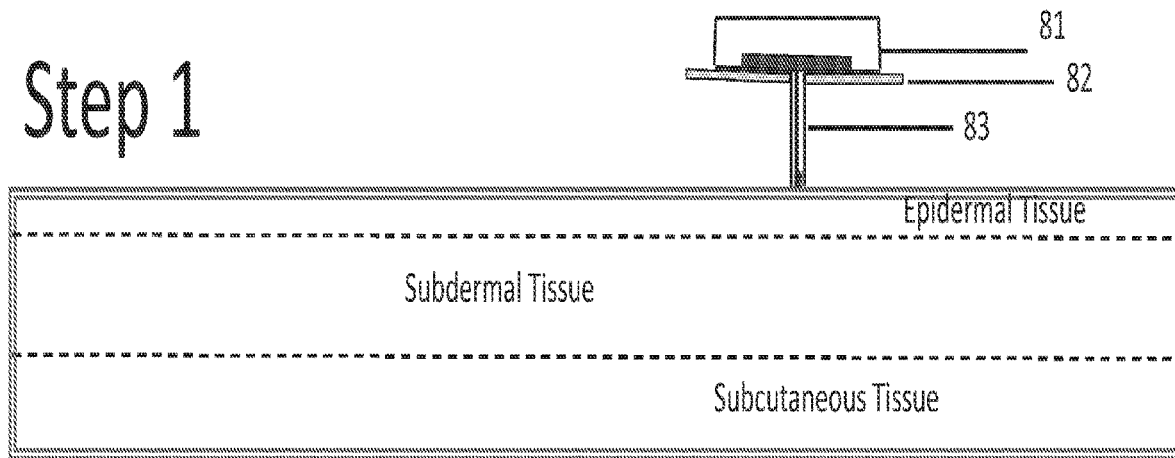
Step 2
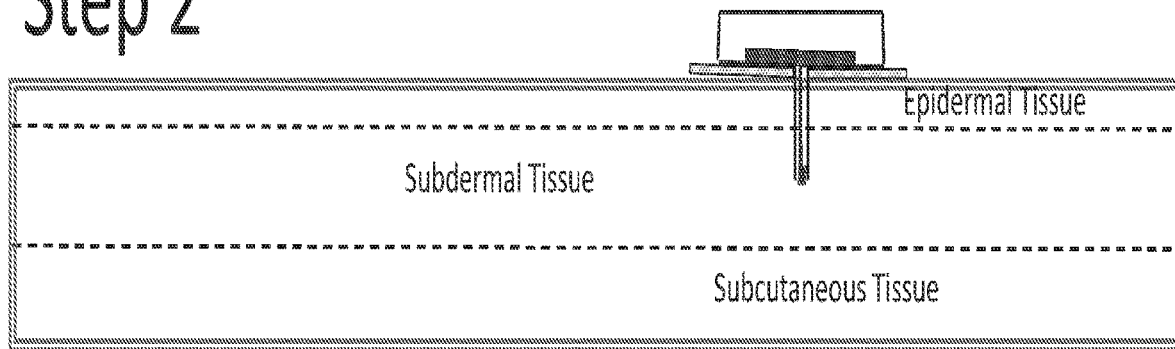
Fig. 41

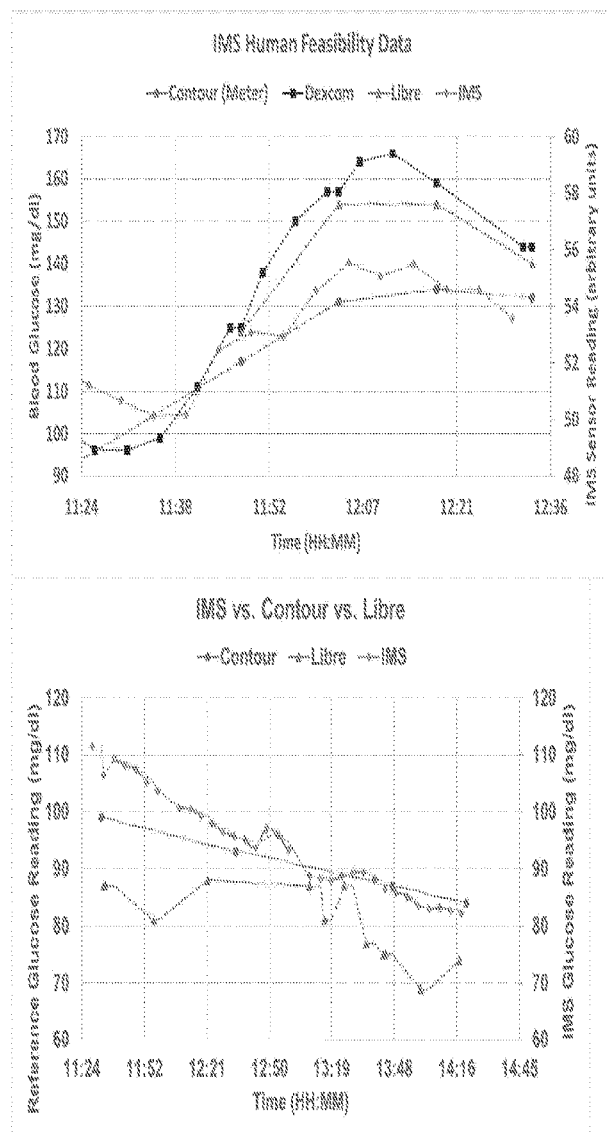
Fig. 60A
Fig. 60B
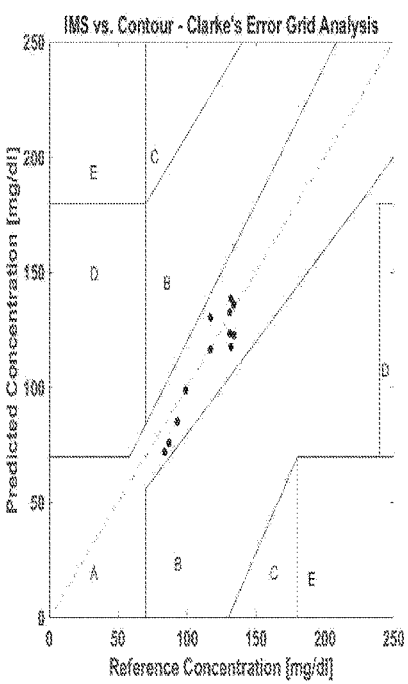
Fig. 60C

Response before FIH testing

Response after sensor removal from FIH subject

WIRED IMPLANTABLE MONOLITHIC INTEGRATED SENSOR CIRCUIT

CROSS-REFERENCE TO RELATED APPLICATIONS

This application claims any and all benefits as provided by law including benefits under 35 U.S.C. 119(e) of U.S. Provisional Application No. 63/239,484, filed Sep. 1, 2021, U.S. Provisional Application No. 63/298,632, filed on Jan. 12, 2022, U.S. Provisional Application No. 63/336,299, filed on Apr. 28, 2022, U.S. Provisional Application No. 63/318,790, filed on Mar. 11, 2022, and U.S. Provisional Application No. 63/333,443, filed on Apr. 21, 2022, the contents of each of the above are incorporated herein by reference in their entirety.

STATEMENT REGARDING FEDERALLY SPONSORED RESEARCH

This invention was made with government support under contract no. R44DK111001, and no. R43DK121621 awarded by the National Institutes of Health. The government has certain rights in the invention.

BACKGROUND

Field of the Invention

The present disclosure provides a scalable, flexible, electrochemical sensing platform including a transmitter, a wire, and a monolithic integrated sensor circuit containing one or more integrated sensors.

Description of the Related Art

Continuous monitoring of personal health has the potential to revolutionize healthcare by enabling preventative health management compared to traditional treatment strategies which rely upon a few measurements at discrete points. Continuous monitoring should enable the detection of diseases and conditions before users would be drawn to a doctor's office for a discrete blood test.

Realization of the potential of continuous monitoring of health requires new tools to measure analytes in the body effectively and continuously. There are currently some health monitoring devices being used to continuously measure in-vivo analyte levels. However, the technologies which have been thus far deployed have suffered from shortcomings preventing widespread adoption.

An excellent example of a continuous monitoring system that has come to market can be seen with Continuous Glucose Monitoring (CGM) systems. CGM systems from MEDTRONIC® and DEXCOM® are available for continuous glucose monitoring for diabetics using transdermal systems. Less than 10% of diabetics currently use Continuous Glucose Monitoring (CGM) systems of any kind, although it has been shown to be the best method for diabetes management.

The disadvantages of transdermal CGM technologies from, for example, MEDTRONIC® and DEXCOM®, include their high complexity, large size and high cost. These devices are prone to rejection by the body due to the immune system response, use bulky external transmitters for sensor control and data processing, and have high manufacturing costs associated with utilizing and integrating discrete components. The bulky external transmitters require strong skin adhesives which cause irritation and skin allergies. These devices are also short-lived and require frequent removal and insertions. Their response speed and accuracy can become limiting factors in some situations, e.g., during sleep, at mealtimes.

In view of these shortcomings, efforts have been made to make better, more affordable, and user-friendly CGM devices.

Implantable CGM systems avoid the transdermal wire set-up of classical CGM systems and thus reduce infection and skin irritation issues. Implantable glucose monitoring systems commercially available include those by, for example, SENSEONICS®, including the EVERSENSE® system. However, these implantable systems have suffered from miniscule uptake by consumers because they are beset by their own limitations. Implantation of the device requires the scheduling of a medical procedure to ensure that the device is properly positioned within the user at great cost. Additionally, removal of the device can be challenging. First the device must be exactly located. Then a skilled medical professional must remove the device. Additionally, the risks posed by device movement within the human body have forced implantable devices to have a large surface area. The exposed area of the implantable devices has increased the rate of foreign body response and rejection by users.

SUMMARY

Accordingly, a clear need exists for an improved platform in the continuous health monitoring industry. The present disclosure addresses several of these shortcomings of the prior art to finally make continuous health monitoring more mainstream.

In various instances, the present disclosure provides for a monolithic integrated sensor circuit for placement inside the body which senses the concentration of an analyte by an electrode and transmits digital data to a transmitter outside the body. The monolithic integrated sensor circuit and the transmitter are connected by a transdermal wire. By combining in a single monolithic integrated circuit, the sensor chemistry driving analyte detection as well as the circuitry needed to translate the concentration of the analyte into digital information, embodiments of the present disclosure reduce complexity, size, and cost of traditional transdermal CGM systems. Additionally, by placing the electronics adjacent to the electrodes which measure analyte, the present disclosure permits the determination of a superior signal for a longer period as compared to traditional systems because of the permissive use of multiple discrete electrodes with minimal electronic signal travel. Moreover, this also reduces the complexity of the transmitter and hence enables a smaller, and lighter transmitter. This increases sensor wear time and decreases the need of strong adhesives, hence minimizing skin irritation and allergies.

Unlike implantable wireless CGM systems, such as the EVERSENSE® system, the embodiments of the present disclosure present a wired connection for the transdermal delivery of power and, optionally, the exchange of digital information. The wired connection permits easier insertion of the device as well as a more stable supply of power. The transdermal wired connection also fixes the device allowing a smaller size for the device. Lastly, the wire connection allows the device to be much more easily removed by the user.

According to a first aspect of the present disclosure, there is provided a transdermal analyte concentration measurement system comprising: 1) an implantable monolithic integrated circuit containing: an integrated sensing element which senses one or more analytes and generates a signal representative of an analyte concentration; an integrated sensor signal acquisition unit which receives and processes the signal from the integrated sensing element; an integrated communication unit connected to the integrated sensor signal acquisition unit which transmits data representative of said analyte concentration; and an integrated power management unit connected to and providing power to the sensing element, the sensor signal acquisition unit, and the communications unit; and 2) a transmitter, configured for operation outside of the body of a user, connected by a wire to the integrated communication unit and integrated power management unit of the implantable monolithic integrated circuit, said transmitter providing power to the integrated power management unit of the implantable monolithic integrated circuit via the wire and receiving data from the integrated communication unit of the implantable monolithic integrated circuit via the wire, and said wire configured to cross from the skin surface into the user.

The integrated sensing element of the implantable monolithic integrated circuit may include one or more integrated electrodes.

At least one of the one or more integrated electrode(s) may comprise a conductive surface of one or more conductive materials.

The integrated electrode(s) may be made using lithography.

The integrated electrode(s) may be coated with a hydrogel formed from a cross linking agent, an enzyme, and a proteinaceous material. The hydrogel may further comprise one or more co-protein. The co-protein(s) may be configured to improve longevity, decrease foreign body response, and/or increase signal of the integrated sensing element.

The cross linking agent may comprise glutaraldehyde. Further or alternatively, the enzyme may comprise glucose oxidase. Further or alternatively, the proteinaceous material may comprise human serum albumin.

The hydrogel may further comprise a co-protein of catalase or horseradish peroxidase.

The wire may be comprised within a flexible printed circuit board.

The transdermal analyte concentration measurement system may comprise the flexible printed circuit board. The wire may comprise more than one conductive path. In particular, the wire may comprise at least two conductive paths.

According to a second aspect of the present disclosure, there is provided a glucose sensor system comprising: a transmitter for containing a battery, the transmitter being for placement on top of patient skin; a transcutaneous connector comprising at least one conductive path; and an implantable monolithic integrated circuit for placement beneath the patient skin, wherein the implantable monolithic integrated circuit comprises a potentiostat and an electrochemical sensing element; wherein the potentiostat is electrically coupled to the transmitter via the transcutaneous connector, and the electrochemical sensing element is configured to sense glucose concentration and generate an electrical signal representative of the glucose concentration, and wherein the potentiostat is electrically connected to the electrochemical sensing element.

It would be understood that a monolithic integrated circuit (also referred to as an IC, a chip, or a microchip) is a set of electronic circuits integrated on one small piece (or chip) of semiconductor material (for example but not limited to silicon).

By combining the electrochemical sensing element and the potentiostat in a single monolithic integrated circuit, the glucose sensor system has an improved performance and reduced complexity, size and costs. In particular, the short distance (e.g., in microns) between the electrochemical sensing element and the potentiostat allows for minimal electronic signal travel. Thus, the glucose sensor system can determine a more superior signal for a longer period, as compared to traditional systems where the potentiostat is placed within the transmitter on top of patient skin. This arrangement also enables a smaller and lighter transmitter, and accordingly provides a more pleasant user wear experience.

It would further be understood that the potentiostat is an electronic hardware used for controlling and measuring the electrochemical sensing element. The potentiostat may comprise an electric circuit which controls (or maintains) the voltage potential of an electrode (e.g., a working electrode) of the electrochemical sensing element and senses changes in the resistance of the electrode, by outputting a current which is inversely proportional to the varying resistance of the electrode. Therefore, the electrochemical sensing element and the potentiostat collectively generate an electrical signal (e.g., an electric current) representative of the glucose concentration.

The transcutaneous connector wire may be configured to cross from the skin surface into the user. The glucose sensor system may further comprise a reader wirelessly linked to the transmitter. The wireless technology used is one that is suitable for such link. For example, Bluetooth technology is suitable for short distance (e.g., 20 meters) communication. Zigbee is a different technology that can be used for a slightly longer-range (e.g., 100 meters) communication.

The glucose sensor system may further comprise a smart insulin pen or pump wirelessly linked to the transmitter. Such a system can be used for an open-loop or closed-loop glucose control as an artificial pancreas or a part of an artificial pancreas system.

The glucose sensor system may further comprise a secure database wirelessly linked to the transmitter. The database can be used to communicate the long-term data trends and important events (e.g., hypoglycemia events) to the care team.

The potentiostat may be continuously powered by the battery.

The transmitter and the sensor many have other features (e.g., a temperature sensor, photodetectors) to detect any changes in the environment.

By "continuously powered", it is meant that when the battery contains sufficient electric power (e.g., before it is drained up), the battery continuously supplies power to the potentiostat via the transcutaneous connector. By continuously powering the potentiostat, the potentiostat is able to maintain the potential of the working electrode(s) of the electrochemical sensing element continuously without any break. In this way, there is no need to frequently calibrate the glucose sensor system during the lifetime of the battery.

The glucose sensor system maybe a continuous glucose sensor system.

The continuous glucose sensor system may also be referred to as a Continuous Glucose Monitoring (CGM) system. A CGM system essentially measures glucose levels 24/7, from once every tens of seconds to once every few minutes. The measurement frequency may be adjusted at the transmitter side. Generally speaking, the CGM system requires the potential of the working electrode(s) of the electrochemical sensing element to be continuously maintained.

The transcutaneous connector may be a flexible connector.

The transcutaneous connector may comprise a printed circuit board. The printed circuit board may be a flexible printed circuit board (e.g., the flexible printed circuit board according to the ninth aspect described below).

The potentiostat may be placed at a depth of 1 to 10 mm beneath the patient skin.

The potentiostat may be at a depth of 1 to 5 mm beneath the patient skin. More specifically, the potentiostat may be at a depth of 2 to 3 mm beneath the patient skin. The 2-3 mm depth allows the potentiostat to generate a superior signal indicative of glucose concentration, and also significantly shortens the communication distance between the potentiostat and the transmitter.

The electrochemical sensing element may comprise at least one working electrode coated with a chemistry which converts glucose concentration into current.

The electrochemical sensing element may be configured to transduce changes in glucose concentration into changes of an electrical current.

The electrical signal representative of the glucose concentration may comprise the current.

The potentiostat may be configured to control a potential of the at least one working electrode based upon a reference voltage (e.g., $V_{WE}$). The potential of the at least one working electrode is controlled to be substantially the same as the reference voltage.

The reference voltage may be programmable by the transmitter.

The implantable monolithic integrated circuit may further comprise a digital to analog converter configured to generate the reference voltage based upon a user input transmitted from the transmitter via the transcutaneous connector.

The potentiostat may be further configured to buffer the current to an analog to digital converter connected to the potentiostat.

The analog to digital converter may be configured to convert the current into a digital signal.

The electrochemical sensing element may further comprise a reference electrode and a counter electrode. The counter electrode may be used to balance the current generated by the at least one working electrode. The reference electrode may be used to provide a stable voltage reference signal beneath the patient skin.

The at least one working electrode may share a common reference electrode.

The at least one working electrode may share a common counter electrode. Alternatively, the at least one working electrode may each be associated with a respective counter electrode.

The potentiostat may be configured to maintain a predetermined voltage between the at least one working electrode and the reference electrode while providing current through the counter electrode.

The potentiostat may comprise a first operational amplifier controlling a voltage of the reference electrode (e.g., through negative feedback) while providing current through the counter electrode and a second operational amplifier controlling a voltage of the at least one working electrode (e.g., through negative feedback) and buffering the current of the at least one working electrode to an analog to digital converter connected to the potentiostat. Advantageously, this arrangement of the potentiostat allows for independently controlling the potential difference between working and reference electrodes in a multi-analyte sensor where there are multiple working electrodes for sensing different analyte.

The at least one working electrode may comprise a conductive surface of one or more conductive materials. The conductive material can be a noble metal. The conductive metal can be platinum. The at least one working electrode may be made using lithography.

The chemistry may comprise a hydrogel including a cross linking agent, an enzyme, and a proteinaceous material. The hydrogel may further comprise a co-protein. The co-protein may be configured to improve longevity, decrease foreign body response, and/or increase signal of the integrated sensing element.

The cross-linking agent may comprise glutaraldehyde. The enzyme may comprise glucose oxidase. The proteinaceous material may comprise human serum albumin.

The hydrogel may further comprise a co-protein of catalase or horseradish peroxidase.

The potentiostat may be connected within 2 millimeters to the at least one working electrode. More preferably, the potentiostat may be connected within half a millimeter to the entirety of the at least one working electrode. By the expression "the entirety of the at least one working electrode", it is meant that the potentiostat may have different connection distances to different ones of the working electrodes, but the distance between the potentiostat and the furthest working electrode is within half a millimeter.

The at least one working electrode may be patterned to increase surface area. Utilizing patterned or non-planar working electrodes (instead of conventional planar electrodes) increases the effective signal strength, because the strength of the sensing element signal can be proportional to surface area of the electrode.

The at least one working electrode may be patterned by forming pillars. The pillars may have a spacing of 0.25 μm-25 μm and a height of 0.1 μm-10 μm.

The at least one working electrode may be integrated with the potentiostat into the same CMOS die.

The implantable monolithic integrated circuit may be CMOS based. The implantable monolithic integrated circuit and the CMOS die may be used interchangeably.

The implantable monolithic integrated circuit may be from 30 microns to 600 microns in thickness. In particular, the implantable monolithic integrated circuit may be from 50 microns to 150 microns in thickness.

The implantable monolithic integrated circuit may be from 30 microns to 600 microns in thickness, 500 microns to 10,000 microns in length and in a range from 100 microns to 4,000 microns in width. More preferably, the implantable monolithic integrated circuit may be from 50 microns to 150 microns in thickness, 1,500 microns to 3,000 microns in length and in a range from 100 microns to 4,000 microns in width.

The implantable monolithic integrated circuit may comprise holes extending therethrough.

The implantable monolithic integrated circuit may be coated with a biocompatible soft material.

The implantable monolithic integrated circuit may comprise rounded edges.

The implantable monolithic integrated circuit may comprise a sensor signal acquisition unit which receives and processes the electrical signal from the electrochemical sensing element. The sensor signal acquisition unit may comprise the potentiostat.

The implantable monolithic integrated circuit may further comprise a communication unit electrically connected to the sensor signal acquisition unit and transmitting data representative of the glucose concentration.

The data representative of the glucose concentration may be based upon the processed electrical signal by the sensor signal acquisition unit.

The implantable monolithic integrated circuit may further comprise a power management unit electrically connected to and providing power to the electrochemical sensing element, the sensor signal acquisition unit, and the communication unit.

The transmitter may be electrically connected by the transcutaneous connector to the communication unit. The transmitter may be configured to receive data from the communication unit via the transcutaneous connector.

The data received by the transmitter may comprise the data representative of the glucose concentration, and optionally temperature data. The temperature data may be generated by a temperature sensor of the implantable monolithic integrated circuit.

The transmitter may be configured to transmit data to the communication unit via the transcutaneous connector.

The transmitter may be configured to communicate with the communication unit in a bidirectional and time multiplexed fashion.

The communication unit may comprise a receiver subsystem and a transmission subsystem.

The transmitter may be electrically connected by the transcutaneous connector to the power management unit, and the transmitter may be configured to provide power to the power management unit via the transcutaneous connector.

The power management unit may comprise a voltage regulator which is configured to regulate the power from the transmitter into a DC voltage.

The power management unit may further comprise a reference generator which is configured to generate reference voltage and/or currents used by the sensor signal acquisition unit (e.g., the potentiostat, the analog to digital converter).

The communication unit may further comprise a MUX/DEMUX (i.e., couple-decouple) network which is configured to decouple the data from the power.

The electrochemical sensing element may comprise at least three working electrodes with each connected to a respective potentiostat. The use of at least three working electrodes is beneficial for reducing noise in the electrical signal representative of the glucose concentration and for improving the accuracy of the glucose sensor system. In particular, the output of the at least three working electrodes may be compared with one another and further processed (e.g., by averaging and/or removing one output which significantly deviates from the other output) to reduce the impact of noise or fault occurring in some of the electrodes. The glucose sensor system may further comprise an analog to digital converter for placement beneath the patient skin, wherein the analog to digital converter is electrically connected to the potentiostat.

The implantable monolithic integrated circuit (in particular, the sensor signal acquisition unit thereof) may comprise the analog to digital converter.

The glucose sensor system may further comprise a multiplexer electrically connected between the potentiostats associated with the at least three working electrodes and the analog to digital converter. The multiplexer allows the analog to digital converter to be shared by the at least three working electrodes through time division multiplexing.

The implantable monolithic integrated circuit (in particular, the sensor signal acquisition unit thereof) may comprise the multiplexer.

The at least three working electrodes may be functionalized towards glucose.

The glucose sensor system may further comprise a control logic configured to denoise the information from one or more of the at least three working electrodes.

The control logic may compare and/or further process the information obtained from the at least three working electrodes, by for example averaging the information and/or discarding information obtained from one electrode which significantly deviates from information obtained from other electrodes. In this way, the noise level contained in the information can be reduced.

The glucose sensor system may further comprise a temperature sensor for placement beneath the patient skin.

The implantable monolithic integrated circuit may comprise the temperature sensor.

The temperature sensor may comprise a bandgap circuitry to generate current proportional to absolute temperature (PTAT) and current complementary to absolute temperature (CTAT). The glucose sensor system may further comprise a control logic programmed to process information from the at least one working electrode by taking into account information from the temperature sensor.

Advantageously, taking into account information from the temperature sensor is useful for improving reliability of glucose level determination. The control logic may calibrate the information from the at least one working electrode using the information from the temperature sensor.

The control logic described above may also be referred to as a processor, a processing unit, a controller, or a microcontroller. The implantable monolithic integrated circuit may comprise the control logic. Alternatively, the transmitter may comprise the control logic. Further alternatively, the reader wirelessly linked to the transmitter may comprise the control logic.

The transcutaneous connector may comprise at least two conductive paths, and one of the conductive paths may be a ground connected to the potentiostat and another one of the conductive paths may function as data over power. In other words, the another one of the conductive paths is used to carry both a power signal and a data signal, with the data signal superimposed over the power signal.

Alternatively, the transcutaneous connector may comprise three conductive paths, with two paths used to carry power and ground signals and a third path used for data communication to and from the electrochemical sensing element.

The implantable monolithic integrated circuit (or the CMOS die) may be bonded to the flexible connector and the at least one conductive path by wire bonding. Alternatively, the implantable monolithic integrated circuit (or the CMOS die) may be bonded to the flexible connector and the at least one conductive path by flip chip packaging.

The at least one working electrode may be coated with a glucose oxidase hydrogel.

According to a third aspect of the present disclosure, there is provided a transdermal analyte concentration measurement system comprising: a sensing element for placement beneath patient skin and for sensing one or more analytes, and wherein the sensing element comprises at least three working electrodes each of which is configured to generate a signal indicative of a concentration of an analyte; and a control logic configured to generate a fused signal representative of the analyte concentration within the patient based upon at least some of the signals generated by the at least three working electrodes.

The control logic and the sensing element may be an integrated device. The control logic and the sensing element may be integrated within an implantable monolithic integrated circuit.

The transdermal analyte concentration measurement system may further comprise a transmitter configured for operation outside of a body of the patient. The transmitter may be coupled to the sensing element via a transcutaneous connector. The transmitter may comprise the control logic.

The transdermal analyte concentration measurement system may further comprise a device wirelessly coupled to the transmitter. The device may comprise the control logic.

The control logic may be configured to generate a weighted average of the signals generated by the at least three working electrodes. The fused signal may be the weighted average.

The control logic may be configured to discard one or more of the signals generated by the at least three working electrodes, and to generate the fused signal based upon the remaining signals. This means that the weight(s) of the discarded signal(s) is zero.

The discarded signal(s) may significantly deviate from the remaining signals. The fused signal may be generated as a weighted average of the remaining signals.

The discarded signal(s) may significantly deviate from a median value or an average value of the signals generated by the at least three working electrodes.

The discarded signal(s), within the signals generated by the at least three working electrodes, may have the greatest distance to the median value or the average value. Alternatively, the discarded signal(s) may have a distance that is greater than a predetermined distance to the median value or the averaged value.

The control logic may be configured to filter the signal(s) generated by one or more of the at least three working electrodes so as to remove noise from the signal(s).

The control logic may be configured to generate a series of the fused signals at different time points, and to determine a rate of change of the analyte concentration within the patient.

The control logic may be configured to alert the patient based upon the rate of change.

The control logic may be configured to estimate the future analyte concentration within the patient based upon the series of the fused signals and the rate of change.

According to a fourth aspect of the present disclosure, a continuous glucose monitoring system for a subject is provided comprising: a transmitter for containing a battery, said transmitter for placement on top of subject skin; a transcutaneous connector comprising at least one conductive path; an electrochemical sensing element comprising a conductor configured to sense glucose concentration and generate an electrical signal representative of the glucose concentration; and a temperature sensor located within 10 microns of the electrochemical sensing element.

Each of the electrochemical sensing element and the temperature sensor may be for placement beneath the subject skin.

By locating the temperature sensor within 10 microns of the electrochemical sensing element, the temperature sensor is able to measure the local temperature at a same location where the glucose concentration is sensed. In this way, the temperature sensor can be used to efficiently calibrate the sensor reading of the electrochemical sensing element, thereby improving the accuracy of the continuous glucose monitoring system. Further, the temperature reading from the temperature sensor can be used to accurately indicate the position (e.g., depth) of the electrochemical sensing element (e.g., beneath the subject skin)

The temperature sensor may not share a conductor with the electrochemical sensing element.

The temperature sensor may be formed on a monolithic semiconductor substrate shared with the electrochemical sensing element. The semiconductor substrate may comprise silicon.

The temperature sensor may be a silicon-based bandgap temperature sensor.

The temperature sensor may contain a pair of semiconductor junctions, and a difference between the voltage across the pair of semiconductor junctions may indicate a temperature beneath the skin. The semiconductor junctions may be PN junctions.

The temperature sensor may comprise a pair of bipolar junction transistors.

The temperature sensor may be implemented by a circuit that generates a current proportional to absolute temperature (PTAT) and a current complementary to absolute temperature (CTAT).

The continuous glucose monitoring system may further comprise a control logic in communication with the temperature sensor and/or the electrochemical sensing element. The control logic described above may also be referred to as a processor, a processing unit, a controller, or a microcontroller. The control logic may also be formed on the monolithic semiconductor substrate. Alternatively, the transmitter may comprise the control logic. Further alternatively, a reader wirelessly linked to the transmitter may comprise the control logic.

The control logic may be configured to process (e.g., calibrate) the electrical signal representative of the glucose concentration based upon a temperature measurement from the temperature sensor, so as to generate processed data representative of the glucose concentration.

The control logic may be configured to determine whether the electrochemical sensing element is inserted beneath the subject skin, based upon a temperature reading from the temperature sensor.

The continuous glucose monitoring system may comprise a second and/or third temperature sensor. The second and/or third temperature sensor may share the same semiconductor substrate as the first temperature sensor and/or the electrochemical sensing element. The control logic may be configured to generated a fused temperature data based upon temperature readings from two or more of the temperature sensors. The fused temperature data may be generated in a way similar to the generation of the fused signal according to the third aspect.

The transmitter may comprise a further temperature sensor. The control logic may be in communication with the further temperature sensor.

The control logic may be configured to determine whether the electrochemical sensing element is inserted beneath the subject skin, based upon a difference between the temperature readings of the temperature sensor and the further temperature sensor.

The control logic may be configured to determine a depth of the electrochemical sensing element beneath the subject skin, based upon a difference between the temperature readings of the temperature sensor and the further temperature sensor.

The control logic may be configured to detect hypoglycemia within the subject based upon a change of temperature readings from the temperature sensor and a change of temperature readings from the further temperature sensor during a same time period. More specifically, if the readings from the temperature sensor indicates a drop of temperature but the readings from the further temperature sensor during the same time period does not indicate a drop of the same level, it is considered that the subject is suffering from hypoglycemia. According to a fifth aspect of the present disclosure a method for determining the temperature of the epidermis, dermis, and/or subcutaneous tissue of a subject is provided, said method comprising changing the environment of a temperature sensor to a predefined fixed temperature sweep, wherein the temperature sensor is formed on a semiconductor substrate comprising silicon; devising a calibration scheme using raw readings of the temperature sensor generated during the predefined fixed temperature sweep, so as to enable the temperature sensor to accurately determine temperature; attaching the temperature sensor to a flexible transcutaneous connector comprising at least one conductive path and a transmitter containing a battery, the transmitter being for placement on top of the subjects skin; inserting the temperature sensor into the dermis of the subject while attached to the transcutaneous connector and transmitter on top of the subjects skin; and measuring the temperature of the dermis, epidermis and/or subcutaneous tissue using the devised calibration scheme.

The temperature sweep may comprise varying the temperature between 35 to 41 degrees Celsius.

The calibration scheme may be stored in the transmitter.

Devising a calibration scheme may comprise determining calibration coefficients, wherein the calibration coefficients are configured to map the raw readings of the temperature sensor generated during the predefined fixed temperature sweep to actual temperatures used by predefined fixed temperature sweep.

Changing the environment of the temperature sensor comprises placing the temperature sensor in a saline solution and changing the temperature of the salient solution according to the predefined fixed temperature sweep. According to a sixth aspect of the present disclosure, there is provided a method for changing the redox potential of an implanted potentiostat and paired working, control, and reference electrodes comprising: receiving a command for setting the redox potential to a predetermined value, programming (or reconfiguring) a programmable voltage generator based upon the command, so as to generate a voltage corresponding to the predetermined value; and feeding the generated voltage from the programmable voltage generator to the potentiostat.

It would be understood that the predetermined value is a voltage.

The programmable voltage generator may comprise a digital to analog converter.

The command may be sent from a transmitter configured for placement on the skin of a subject and comprising a battery across a flexible transcutaneous connector including at least one conductive path to the implanted potentiostat and its paired working, control, and reference electrodes.

The digital to analog converter may comprise a resistor ladder connected between a voltage regulator output and a ground to form an m-bit digital to analog converter capable of generating m different voltages.

The potentiostat and paired working, control, and reference electrodes may be monolithically integrated on a single semiconductor substrate comprising silicon.

The potentiostat may be configured to control a potential of the working electrode based upon the redox potential. The potential of the working electrode is controlled to be substantially the same as the redox potential.

According to a seventh aspect of the present disclosure, there is provided a transdermal analyte concentration measurement system comprising: a transmitter for placement on top of subject skin; an implantable monolithic integrated circuit for placement beneath the subject skin, wherein the implantable monolithic integrated circuit comprises a potentiostat and an electrochemical sensing element for sensing an analyte within the subject, wherein the electrochemical sensing element comprises at least one working electrode configured to generate a signal indicative of a concentration of the analyte, and the potentiostat is electrically connected to the electrochemical sensing element and configured to control a potential of the at least one working electrode based upon a reference voltage; wherein the reference voltage is programmable by the transmitter.

The transmitter may be configured to send a command to the implantable monolithic integrated circuit, with the command indicating a desired value of the reference voltage (also referred to as redox potential).

The implantable monolithic integrated circuit may comprises a digital to analog converter configured to generate the reference voltage based upon the command.

The electrochemical sensing element may comprise more than one working electrode, and the reference voltage of each working electrode may be independently programmable by the transmitter. Advantageously, this arrangement allows different working electrodes to have different reference voltages, thus enabling a wide variety of analytes to be detected by the transdermal analyte concentration measurement system. According to an eighth aspect of the present disclosure, there is provided an implantable monolithic CMOS-based integrated circuit for placement beneath subject skin, comprising a potentiostat and an electrochemical sensing element for sensing the analyte within the subject, wherein the electrochemical sensing element comprises at least one working electrode configured to generate a signal indicative of a concentration of the analyte, and the potentiostat is electrically connected to the electrochemical sensing element, and wherein the at least one working electrode comprises a surface with a plurality of holes formed therein.

A bottom surface of the holes may have a combined area which is less than an area of the surface of the at least one working electrode. In other words, the at least one working electrode has a patterned surface comprising a hole structure (or a reverse-pillar structure). Utilizing the patterned or non-planar working electrode (instead of conventional planar working electrode) increases the surface area of the working electrode, thereby improving the sensitivity of the electrochemical sensing element. This is because the strength of the sensing element signal is generally proportional to a surface area of the electrode. The holes may be formed (e.g., etched) during a CMOS fabrication process. Further, the reverse-pillar structure is more robust than a complementary pillar structure.

The surface may be a surface of a metal layer (e.g., a top metal layer of the CMOS fabrication process).

The holes may be formed by etching top metal pillars embedded within top insulator such that each pillar is microscale in size and has top insulator removed during CMOS fabrication process such that the hole is exposed for post processing.

The surface may be coated with another metal layer comprising platinum. The at least one working electrode may include interlayer conductive vias. The conductive vias may be formed at a bottom surface of the holes to enable a connection with bottom metals and/or the potentiostat.

The non-planar structure may be coated with a subsequent metal layer comprising platinum.

The holes may be formed by etching top metal pillars embedded within top insulator such that each pillar is microscale in size and has top insulator removed during CMOS fabrication process such that the hole is exposed for post processing. The at least one working electrode may be coated with a chemistry which converts the analyte concentration into current. At least a part of the chemistry may fill the holes. Therefore, the patterned surface of the working electrode is also useful for improving the adhesion between the surface and the chemistry.

The electrochemical sensing element may further comprise a reference electrode and a counter electrode. The counter electrode may be used to balance the current generated by the at least one working electrode. The reference electrode may be used to provide a stable voltage reference signal beneath the patient skin. One or more of the counter electrode and the reference electrode may also comprise a surface with a plurality of holes etched therein.

According to a ninth aspect of the present disclosure, a flexible printed circuit board is provided. The flexible printed circuit board comprises a first metal layer configured to route electrical signals, a second metal layer configured to provide mechanical strength for the flexible printed circuit board without routing any electrical signals, and a dielectric substrate arranged between the first metal layer and the second metal layer and made of a flexible material.

It would be understood that the first and second metal layers and the dielectric substrate are stacked along a thickness direction of the flexible printed circuit board.

The second metal layer therefore controls the stiffness of the flexible printed circuit board. The second metal layer advantageously allows the flexible printed circuit board to have mechanical strength to a certain extent while the entire printed circuit board remains flexible. In this way, the flexible printed circuit board is suitable for use as a transcutaneous connector in a continuous glucose monitoring system. This is because the mechanical strength provided by the second metal layer allows the flexible printed circuit board to be easily inserted under a subject's skin (e.g., by using a needle) and the overall flexibility of the printed circuit board is useful for reducing tissue damage within the subject in use.

The second metal layer may be made of copper. In same thickness, copper provides more stiffness than the stiffeners (e.g., FR4, Polyimide, Glass) commonly used in PCBs. Therefore, using copper to control the stiffness of the flexible printed circuit board enables the flexible printed circuit board to have a thinner profile as compared to the use of common stiffeners, and hence enable the use of smaller needle sizes which reduces insertion pain and foreign body response.

The first metal layer may be a patterned metal layer. The first metal layer may have at least two and at most four conductive traces. The traces may range in width and spacing from 1 mil to 5 mils. It would be understood that the second metal layer is not one of the conductive traces.

The flexible printed circuit board may comprise a first insulating layer covering the first metal layer. The first insulating layer and the dielectric substrate may be placed at opposite sides of the first metal layer. The first insulating layer may cover the entirety of the first metal layer except at interfacial areas of the first metal layer which are used to make electrical connections with external components (e.g., of the continuous glucose monitoring system).

The flexible printed circuit board may comprise a second insulating layer covering the second metal layer. The second insulating layer and the dielectric substrate may be placed at opposite sides of the second metal layer. The second metal layer may be completely covered by the second insulating layer.

The first and/or second insulating layer may be made from a biocompatible material such as parylene-C or polyimide. The first and/or second insulating layer are useful for preventing interaction between the first and/or second metal layers with the body fluids of the subject.

The first and/or second insulating layer may be made of the same material(s) as the dielectric substrate.

The flexible printed circuit board may have a total thickness between 2 mils to 20 mils.

The flexible printed circuit board may have a length from 2 mm to 20 mm.

The substrate may be made from polyimide, liquid crystal polymer, polyethylene ethylene, or polyether ether ketone.

The first metal layer may be made of copper. A thickness of the first metal layer may be between 0.25 and 0.5 Oz.

A thickness of the second metal layer may be between 0.25 and 2 Oz.

The flexible printed circuit board may be of a dimension which can fit in a 16 gauge to 32 gauge needle.

According to a tenth aspect of the present disclosure, an electrochemical sensor for measuring interstitial glucose is provided. The electrochemical sensor is configured to detect a rate of change of >10 mg/dl/minute. The features of "(electrochemical) sensing element" and "integrated sensing element" as set out above also apply to the "electrochemical sensor" of the tenth aspect.

The electrochemical sensor may be configured to detect a rate of change of >20 mg/dl/minute. The electrochemical sensor may include an enzyme layer and a polymer membrane.

The polymer membrane may be configured to act as a diffusion barrier that allows oxygen to go through unhindered but hinders glucose diffusion. The polymer membrane may comprise polyurethane, a mixture of polyurethane and silicone, or a mixture of polyurethane and PEG.

The enzyme layer may be under 3500 nm in thickness. Alternatively, the enzyme layer may be less than 1000 nm in thickness. Further alternatively, the enzyme layer may be between 200 nm and 800 nm in thickness. Further alternatively, the enzyme layer may be between 600 nm and 800 nm in thickness.

The polymer membrane may be between 200 nm and 10500 nm thick. Alternatively, the polymer membrane may be between 200 nm and 1500 nm thick.

Optionally, the electrochemical sensor may further include a biocompatibility layer. The biocompatibility layer thickness may be between 1000 nm and 20000 nm. A biocompatibility layer with a thickness of less than 1000 nm may be used alternatively.

One or more of the enzyme layer, the polymer membrane and the biocompatibility layer may be made by spin coating or spray coating.

According to an eleventh aspect of the present disclosure, there is provided an applicator device for use with the glucose sensor system of the first aspect to insert the implantable monolithic integrated circuit under subject skin, the applicator device comprising: a needle for accommodating the implantable monolithic integrated circuit and at least a part of the transcutaneous connector attached to the implantable monolithic integrated circuit; an actuation mechanism configured to push the needle towards the subject skin so as to pierce the subject skin and to insert the implantable monolithic integrated circuit under the subject skin; wherein the needle comprises a sidewall and a slot in the sidewall, wherein the slot is configured to allow the transcutaneous connector and the implantable monolithic integrated circuit to escape from the needle.

It would be understood that the cross sectional size of the needle is sufficient for the needle to receive (surround) the implantable monolithic integrated circuit and the at least a part of the transcutaneous connector, and that a width of the slot is sufficient to allow the implantable monolithic integrated circuit and the at least a part of the transcutaneous connector to leave the internal space surrounded by the sidewall of the needle.

Advantageously, the applicator device allows the transcutaneous connector to remain attached to each of the implantable monolithic integrated circuit and the transmitter during the insertion process. As such, a user (e.g., the subject or his/her physician) would not be required to attach the transcutaneous connector to the transmitter after inserting the implantable monolithic integrated circuit under the subject skin. The applicator device may further comprise a retraction mechanism configured to retract the needle from the subject skin.

The applicator device may further comprise a transmitter holder configured to support the transmitter of the glucose sensor system (e.g., by friction). The actuation mechanism may be configured to push the transmitter holder (hence the transmitter) towards the subject skin.

The applicator device may be operable in a loaded state in which the transmitter, the implantable monolithic integrated circuit and the transcutaneous connector are loaded inside the applicator device for insertion under the subject skin. The transcutaneous connector remains attached between the implantable monolithic integrated circuit and the transmitter during the loaded state.

The actuation mechanism may comprise an external cover and a chassis slidably received by the external cover, wherein the needle is mechanically coupled to the external cover such that movement of the external cover towards the chassis pushes the needle out of the chassis.

The retraction mechanism may comprise a spring which is configured to push the needle back into the chassis.

The needle may be a hypodermic needle.

The transmitter may comprise a needle guide (e.g., a through hole) which allows the needle to pass through the transmitter.

According to a twelfth aspect of the present disclosure, there is provided a method of operating the applicator device of the eleventh aspect, the method comprising: loading the transmitter, the implantable monolithic integrated circuit and the transcutaneous connector of the glucose sensor system of the first aspect inside the applicator device, wherein the transcutaneous connector remains attached to each of the implantable monolithic integrated circuit and the transmitter during the loaded state; pressing the applicator device against subject skin to push the needle towards the subject skin so as to pierce the subject skin and to insert the implantable monolithic integrated circuit under the subject skin; and retracting the needle by a spring force of a retraction spring of the applicator device.

It would be understood that the transcutaneous connector and the implantable monolithic integrated circuit escape from the needle via the slot extending through the sidewall of the needle during the retracting step.

In the present disclosure, the term "implantable" may be used interchangeably with "minimally invasive" or "insertable", and is intended to mean that the respective monolithic integrated circuit (or sensing circuit) is suitable for measuring analytes (such as but not limited to glucose) in the tissue under subject skin. The subject may be a human being or an animal.

In the present disclosure, the terms "wire", "transcutaneous connector", "flexible connector" or "flexible PCB" refer to a structure comprising conducive traces and insulations to enable taking power and signal to/from the implantable sensing circuit to the transmitter.

In the present disclosure, the terms "applicator", "inserter" or "applicator device" refer to a device comprising mechanical parts to enable inserting the implantable sensing circuit under the subject skin via a small needle.

It will be appreciated that features described in the context of one aspect of the disclosure may be used with another aspect of the disclosure.

It would further be appreciated that the various numerical ranges described above allow for a degree of variability, for example, ±10%, in the stated values of the end points of the ranges. For instance, a stated limit of 0.5 mm may be any number between 0.5 mm*(1-10%), and 0.5 mm*(1+10%). Further, values expressed in a range format should be interpreted in a flexible manner to include not only the numerical values explicitly recited as the end points of the range, but also to include all the individual numerical values or sub-ranges encompassed within that range as if each numerical value and sub-range is explicitly recited.

BRIEF DESCRIPTION OF THE FIGURES

Embodiments of the present invention will now be described, by way of example, with reference to the accompanying drawings, in which:

FIG. 2A shows a top view. The monolithic integrated sensor circuit 1 includes a communication unit 140, a power management unit 120, an integrated sensing element 160, a sensor signal acquisition unit 130, and on-chip connectors 175 located on an interface unit, silicon substrate 110. The sensing element 160 comprises working (i.e., WE1, WE2, and WE3), reference (RE), and counter (CE) electrodes. Exemplary dimensions are provided for the monolithic integrated sensor circuit 1. FIG. 2B shows a side view. The monolithic integrated sensor circuit 1 includes a silicon substrate 110 with integrated contact pad 175 attached to flexible connector 3, the integrated working electrodes, WE1, WE2, and WE3, representing the integrated sensing element, said working electrodes separated by insulation walls 118, with the working electrodes coated with the functional matrix example Gox-loaded hydrogel 158 and the polymer coating example PU membrane 168.

Figure 1:
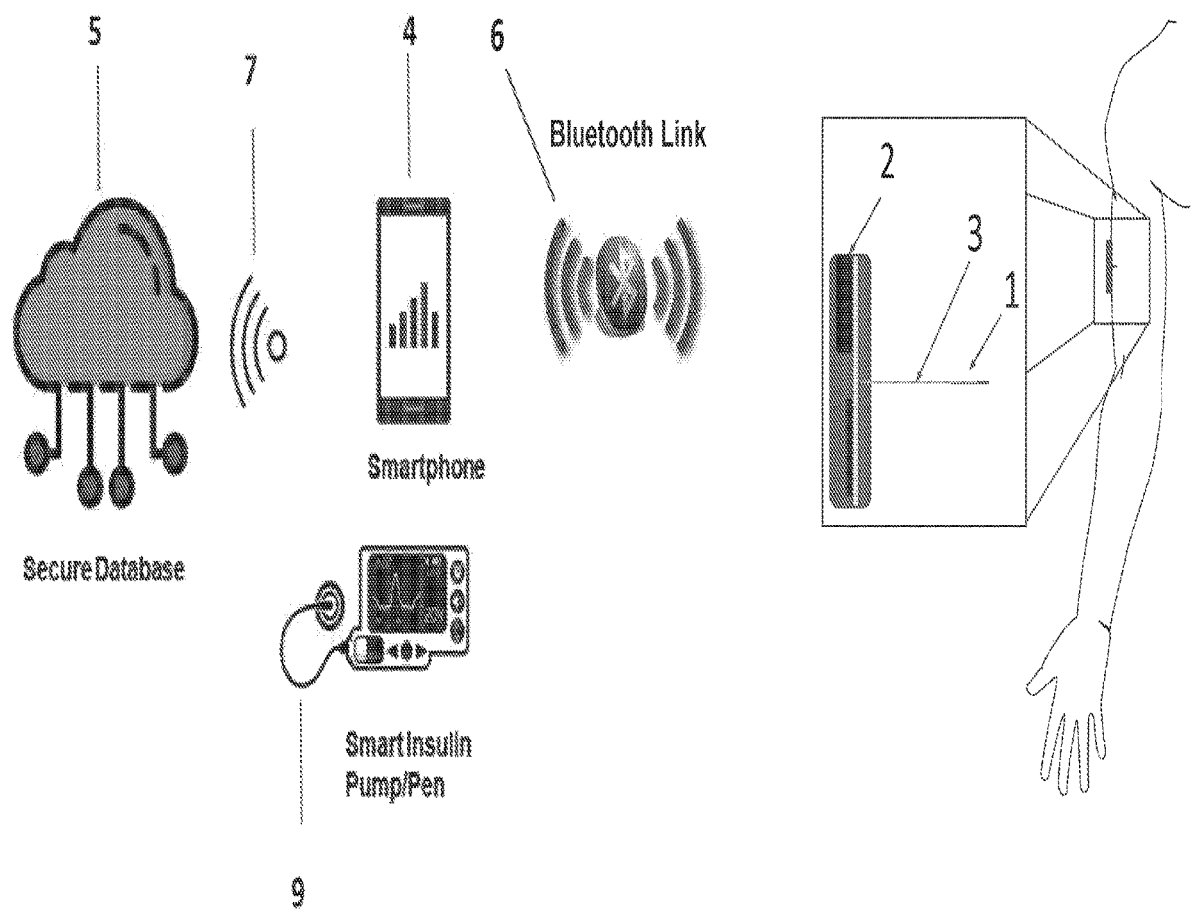
FIG. 1 shows a diagrammatic view of a system according to an embodiment of the disclosure, including an implantable monolithic integrated sensor circuit 1 connected to a transmitter 2 by wire 3, the transmitter 2 connected by wireless connection 6 with a smart reader (e.g., smartphone, tablet) 4 and an insulin infusion mechanism 9 (e.g., infusion pump). The same wireless connection or a different wireless connection 7 can be used to upload encrypted sensor data in a secure cloud 5.

Underneath the top metal is the further Metal-Insulator-Metal (MIM) structure 129 found in CMOS devices. A silicon substrate under the CMOS structure is 110. Note that several electrodes can be isolated from each other by top insulation 118 (Top insulation in CMOS process is often a stack of Silicon Nitride layer on top of Silicon oxide layer). Top insulation can be further augmented by an additional layer (e.g., Polyimide layer). The third step is a precursor etched to remove the top metal 128 leaving the area which was protected by photoresist 148 and further exposing a second further layer of the Metal-Insulator-Metal (MIM) structure 129. The silicon substrate remains at 110. Electrodes remain isolated from each other by top insulation 118. The fourth step is a precursor coated with a thin layer of desired material (e.g., Platinum) 138 using a thin-film coating method, for example thermal evaporation, electron beam deposition, or sputtering. The coating method is significantly important as it enables fine control on metal surface morphology. For example, a sputtering process done at low power (e.g., 200 Watts) and high pressure (e.g., >10 millitorr) can provide a high surface area Platinum (also known as Platinum Black) like one that is achieved using electroplating in conventional fabrication methods. Moreover, use of different types of plasma conditions (e.g., a mixture of Argon and Oxygen) plasma in the sputtering chamber enables fine control of the surface morphology and coating type. This results in a scalable method to generate black Platinum which has high electrochemical activity as compared to uniform Platinum deposited using low-pressure sputtering or electron beam evaporation. Moreover, controlling plasma conditions (e.g., incorporating Oxygen in the plasma) in the sputtering system can enable formation of desired compounds like Platinum Oxide (PtOx) which can be a more suitable material for reference electrode. In a different embodiment, a chlorine plasma can be used to convert silver (Ag) into Silver Chloride (AgCl) near the surface which makes a more suitable reference electrode than Ag by itself. This Plasma exposure can also be done after the sputtering plasma so surface reactions are desired instead of reactions during deposition. A substrate 110, a metal-insulator-metal stack 129 and a top insulator with an optional additional insulator/protection polymer layer 118 remains. The top insulation electrode isolation region remains protected by photoresist 148. The fifth step is a precursor cleaned to remove the photoresist 148 and excess deposited material and leave deposited material only in desired places (e.g., on integrated sensing element electrodes). A substrate 110, a metal-insulator-metal stack 129, a thin layer of desired material 138 and a top insulator with an optional additional insulator/protection polymer layer 118 remains. The sixth step uses a solenoid and/or piezoelectric controlled actuation-based spray heads 188 to deposit, in nanoliters, precise amounts of Glucose Oxidase solutions and crosslinking agents (e.g., Glutaraldehyde) solution droplets to make a glucose oxidase-based hydrogel on the sensing electrode. The substrate can be spun after the droplet deposition to control the thickness of the hydrogel layer more precisely. A substrate 110, a metal-insulator-metal stack 129, a thin layer of desired material 138, and a top insulator with an optional additional insulator/protection polymer layer 118 remains. Optionally, the solenoid and/or piezoelectric controlled actuation-based spray heads 188 can be used simultaneously with spinning on table to improve the uniformity of the hydrogel. The seventh step shows an embodiment of a precursor after deposition of the functionalization layer 158 using solenoid and/or piezoelectric controlled actuation-based spray heads. A substrate 110, a metal-insulator-metal stack 129, a thin layer of desired material 138, and a top insulator with an optional additional insulator/protection polymer layer 118 remains. The eighth step uses a spray coating (e.g., using fine dispensing heads 186) to make a film (stack of one or more thin films) on a sensor surface to coat the functionalization layer, using an appropriate spray head 186 which showers microdroplets on an area of the sensing element. A substrate 110, a metal-insulator-metal stack 129, a thin layer of desired material 138, a functionalization layer 158 and a top insulator with an optional additional insulator/protection polymer layer 118 remains. Spin coating enables a fine control on the thickness of the surface functionalization layers. Such layers can be patterned using standard techniques like Photolithography (e.g., using a sacrificial layer). The ninth step shows an embodiment of a device after deposition of a film 168 on the sensing element. A substrate 110, a metal-insulator-metal stack 129, a thin layer of desired material 138, a functionalization layer 158 and a top insulator with an optional additional insulator/protection polymer layer 118 remains. The tenth step shows an instance of how dipping can be used to apply a small volute of material (e.g., polymer 178) on the sidewalls. A substrate 110, a metal-insulator-metal stack 129, a thin layer of desired material 138, a functionalization layer 158, a film 168 and a top insulator with an optional additional insulator/protection polymer layer 118 remains.

Figure 15:
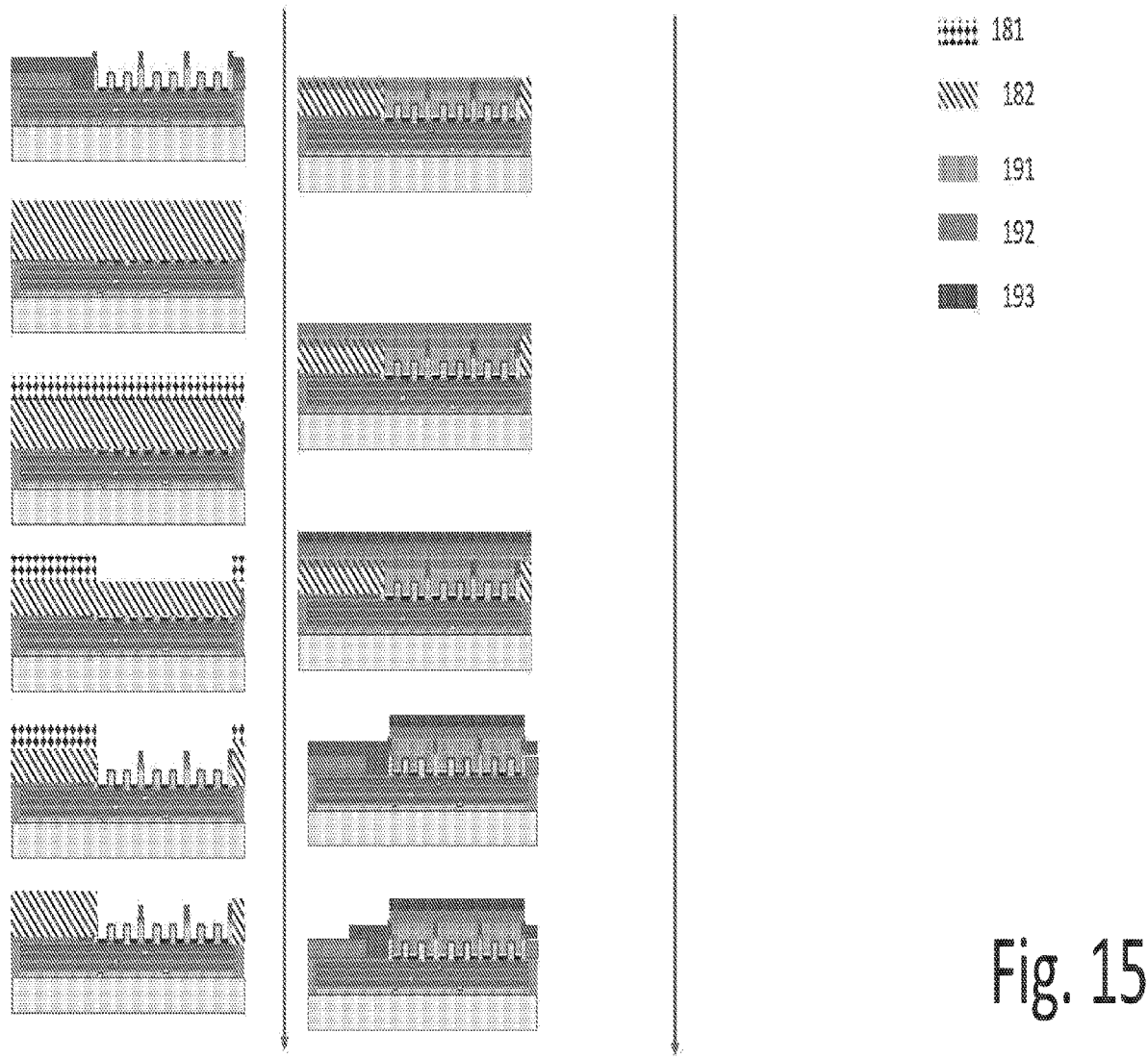

FIG. 15 shows a scheme to selectively coat parts of the integrated sensor circuit 1 with multiple layers of chemistry. It shows a photoresist 181, a sacrificial layer 182, a soft biomaterial (e.g., enzyme hydrogel) 191, a polymer membrane 192, and a biocompatible layer 193.

Figure 16A:
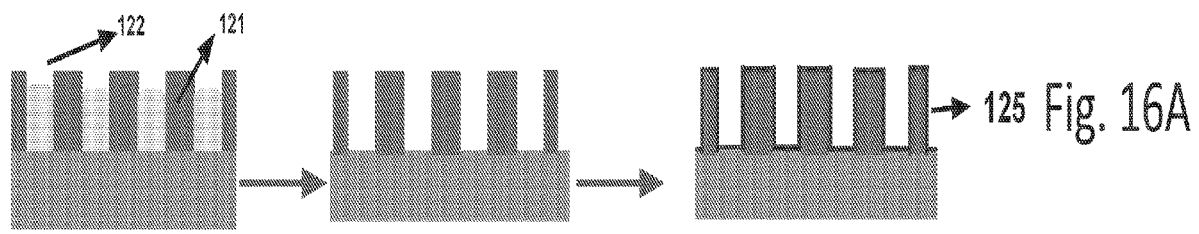
Figure 16B:
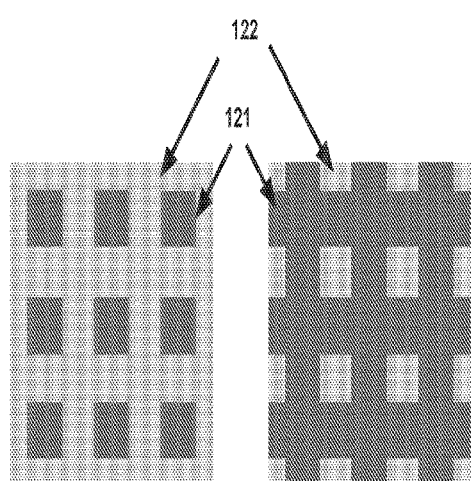
Figure 16C:
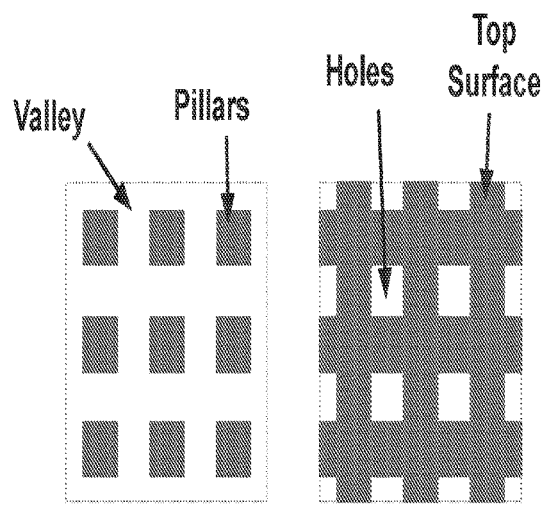

FIG. 16A, FIG. 16B, and FIG. 16C show schemes of patterning integrated sensor electrodes (of the integrated sensing element 160). FIG. 16A shows how a sequence of top metal 121 pillar structures can be made using semiconductor processes with top insulation 122 covering the spacing in between, by designing the top metal as multiple smaller electrodes instead of one large electrode. The metal pillar or the top insulator can then be etched to create open areas between the pillar-like structures. For example, FIG. 16A shows the etching of top metal to create this spacing. Afterwards, the pillar-like structure can be coated with suitable metal (e.g., Titanium/Platinum) using thin-film coating techniques (e.g., electron beam evaporation, thermal evaporation, sputtering, or atomic layer deposition). It also shows Platinum coating 125. FIG. 16B and FIG. 16C show two common patterns that can be used to create high surface area structures. FIG. 16B is before etching. FIG. 16C is after etching. After etching of either the top insulator or top metal, these structures reveal reverse patterns of 3D structures (e.g., pillars and valleys or holes and top surface) that can then be coated with suitable metal (e.g., Titanium and Platinum). In a pillar design, the metals are designed as separated electrodes with insulator filled in the gap areas. In a hole-based pillar design, the electrodes are designed as metal mesh and the hole is filled by the insulator.

Figure 17:
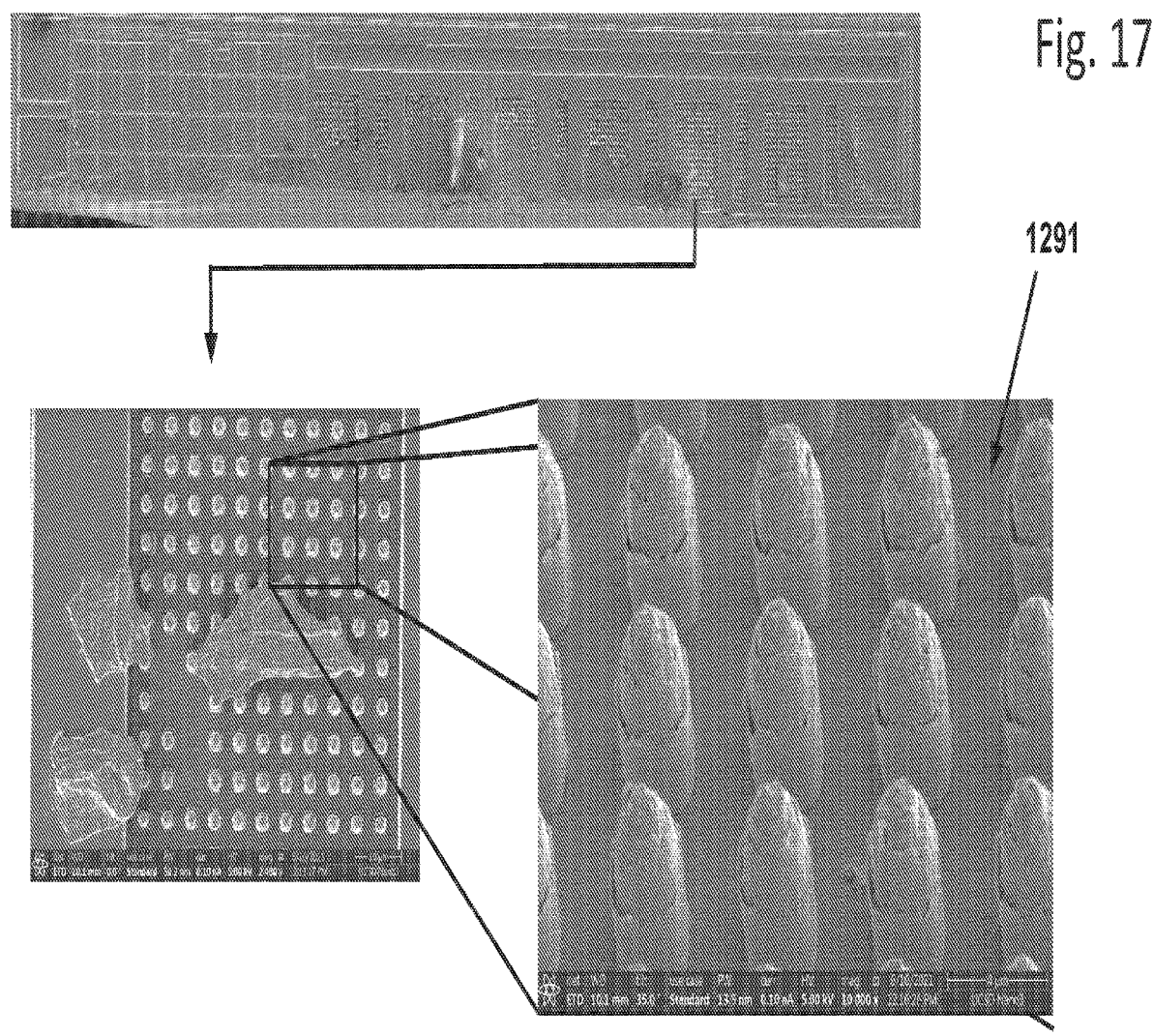

FIG. 17 shows an example of the integrated sensor circuit 1 with working and counter electrodes patterned to have pillars structure. It shows that the pillar structures can have defects which manifest either as breakage of a set of pillars or coverage of a set of pillars with some debris from other processes. It also shows the position of interlayer vias on the bottom surface (valley area) of the electrode. It also shows the vias 1291.

Figure 18:
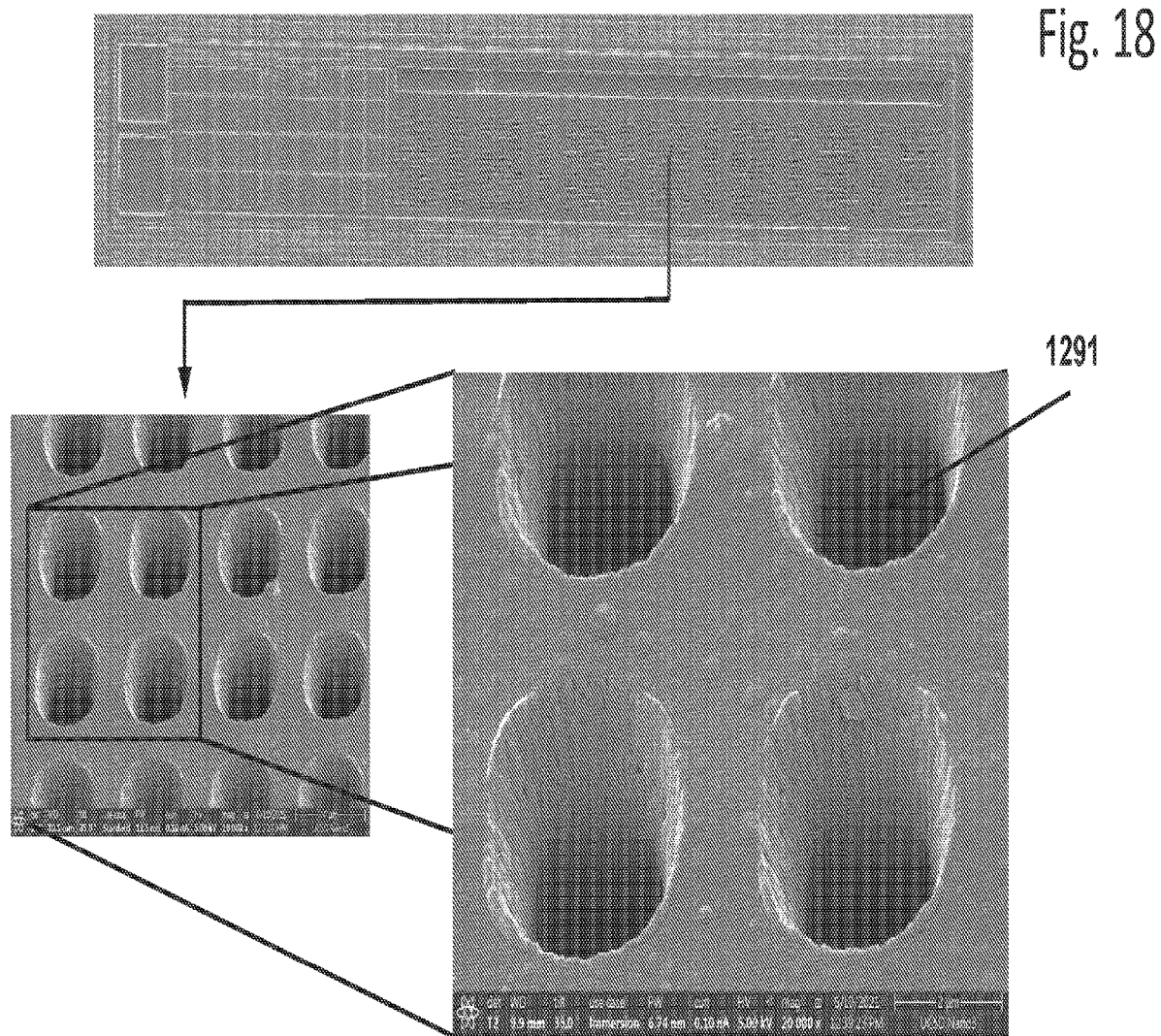

FIG. 18 shows an example of the integrated sensor circuit 1 with working and counter electrodes patterned to have inverted-pillars (holes) structure. It shows that such a structure has much lower defects than the pillar structure from FIG. 17. It also shows the position of interlayer vias on the bottom surface (valley area) of the electrode. It also shows the vias 1291.

Figure 19:
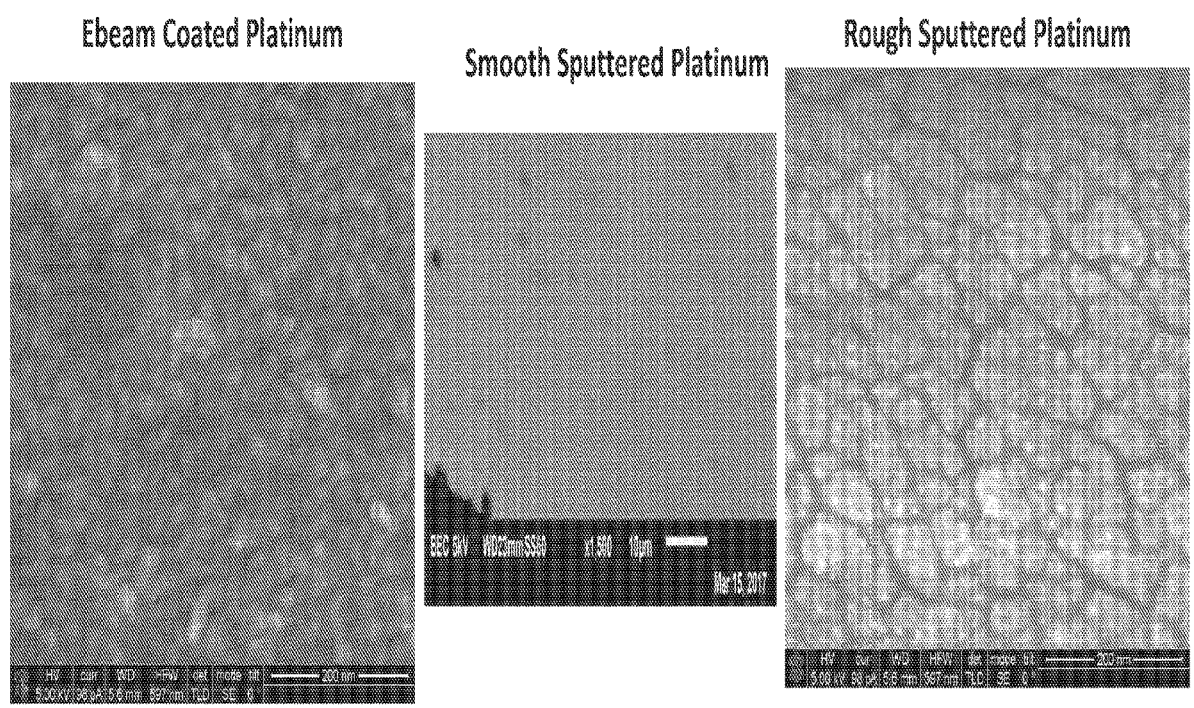

FIG. 19 show a comparison between smooth Platinum coated using electron beam deposition and low-pressure sputter deposition vs. rough platinum deposited using high-pressure sputter deposition. It shows the smooth platinum layers of range 30-150 nm (typical 100 nm) vs. rougher platinum layer of range 30-150 nm (typical 100 nm). A typical smooth layer of 100 nm thickness has rms roughness in <3 nm range for 100 nm thickness while the rough platinum has rms roughness >3 nm. Moreover, the rough Platinum appears to be porous under an SEM while the smooth Platinum appears more like a continuous film. The rough surface of the rough platinum gives it higher surface area on the same geometric area and also makes it more electrochemically active. This increases the electrochemical activity of the sensor as compared to the smooth Platinum.

Figure 20:
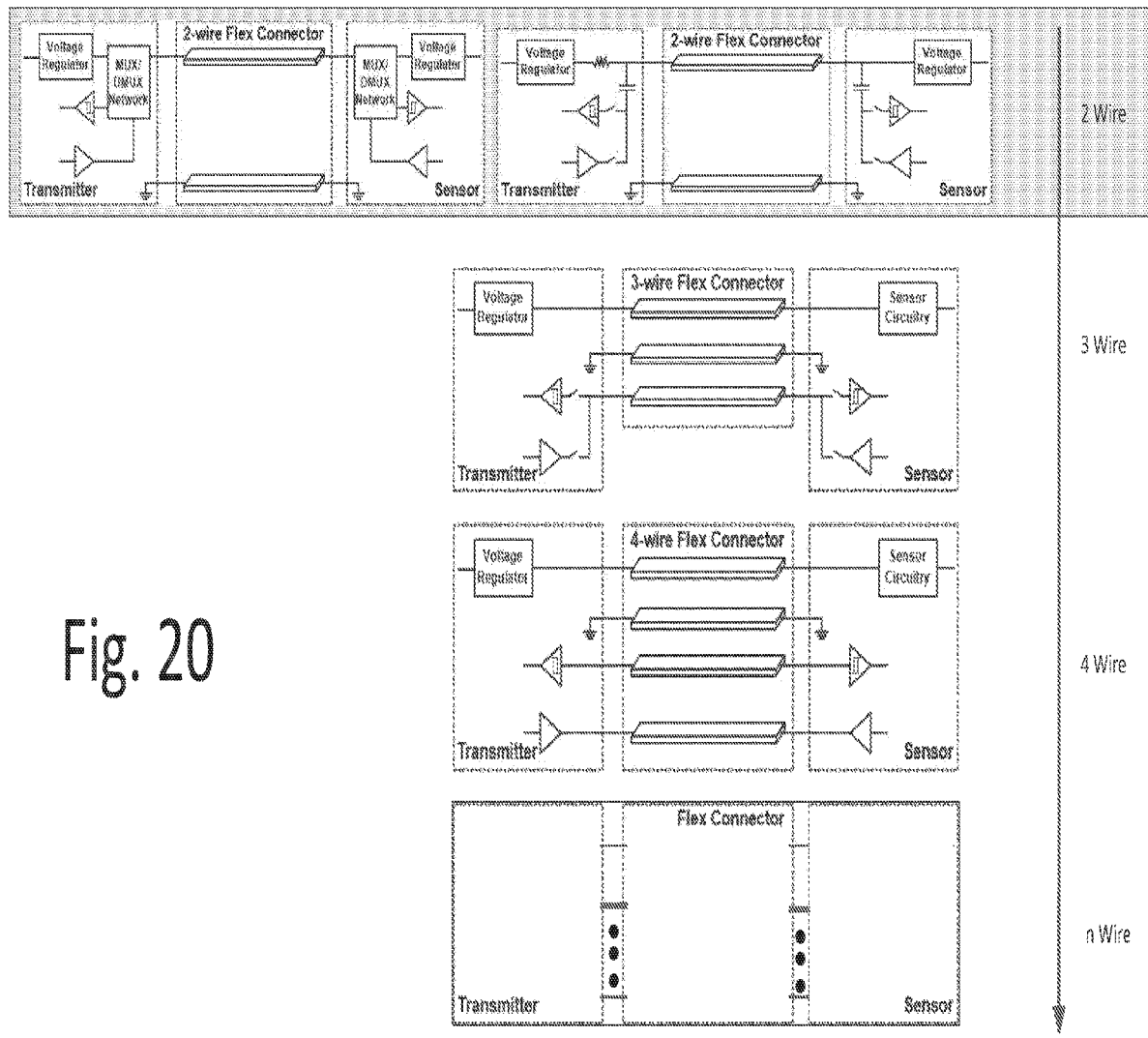

FIG. 20 shows a high-level description of an embodiment of a power/data connection two-wire scheme 3 between the implantable monolithic integrated sensor circuit 1 and the transmitter 2.

Figure 21A:
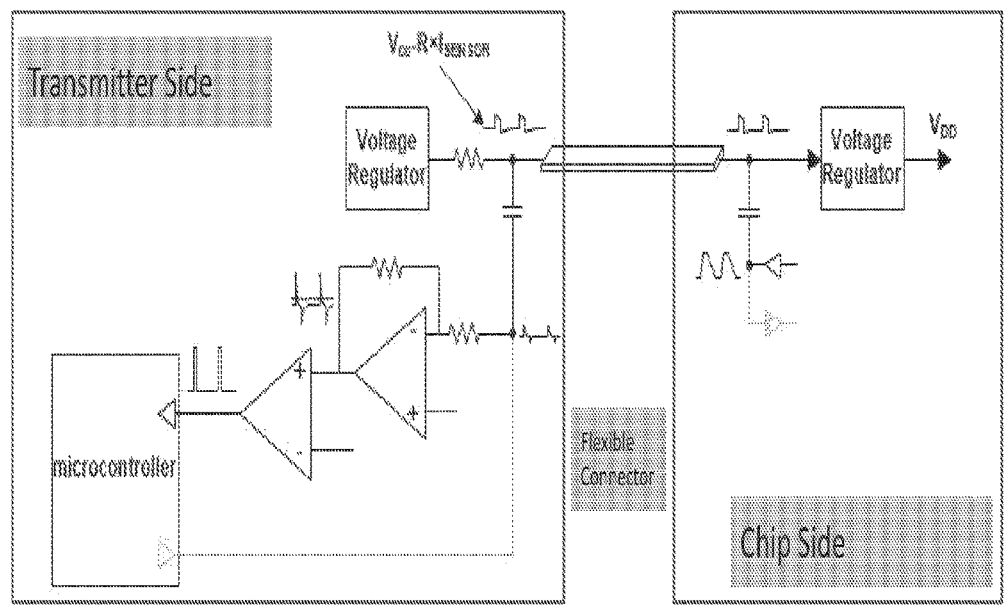
Figure 21B:
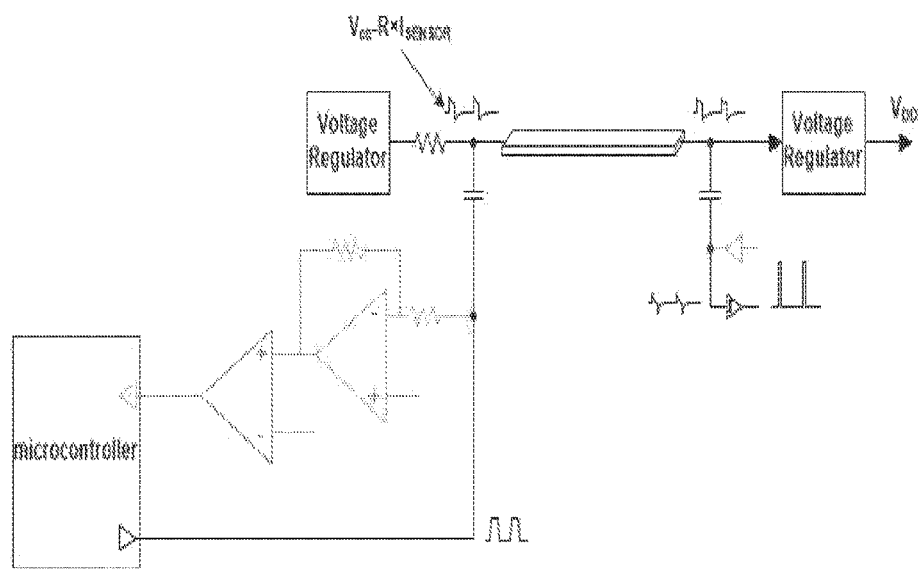

FIGS. 21A, 21B, 22A, 22B, 23A, 23B, and 24A, 24B, show different examples of the implementations of the communication over power. These figures highlight the path in use in each case and show the rest of the circuit in a lighter tone. For example, FIG. 21A shows signal transmission from the chip side to the RX circuit (e.g., the amplifiers on the transmitter side feeding to an input port of the microcontroller) on the transmitter side via the flexible connector. The TX side of the transmitter is not active in this state and hence is shown in a lighter tone color, and so are the receive circuits on the chip side. The signals on the different points of the transmission from the sensor circuit 1 to the input pin of the transmitter are shown in FIG. 21A. It shows that the signals starting from the TX side of the chip are perfect digital signals which decrease in their amplitude as those are coupled with the power line. Hence, on the RX side of the transmitter, those are amplified and restored back to the original shape (e.g., rail-to-rail digital signal) and are then fed to the digital circuit of the transmitter for detection and demodulation. FIG. 21B shows a scheme for moving data from the transmitter to the chip.

Figure 22A:
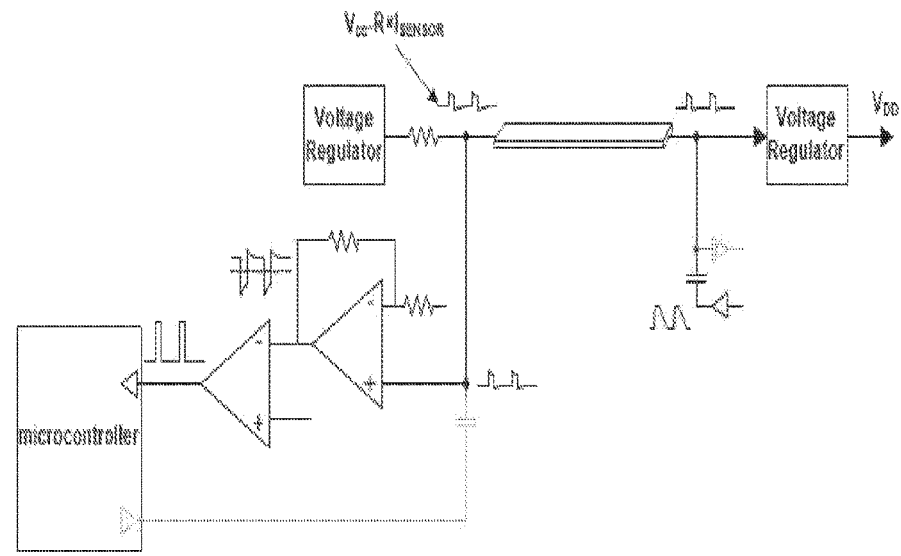
Figure 22B:
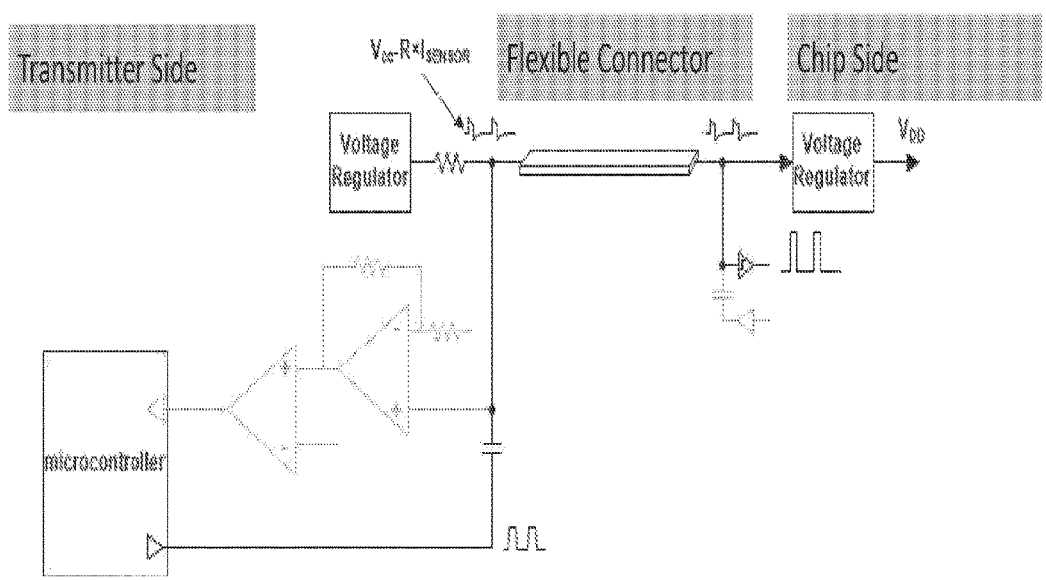

FIGS. 22A, and 22B show a different coupling-decoupling scheme (i.e., use different mux/demux circuits for combining and separating the data and the power signals) in which no capacitor is used on the RX side on the transmitter but only on the TX side. Also, on the chip side, the capacitor is used in the TX mode, but no capacitor is used in the RX mode.

Figure 23A:
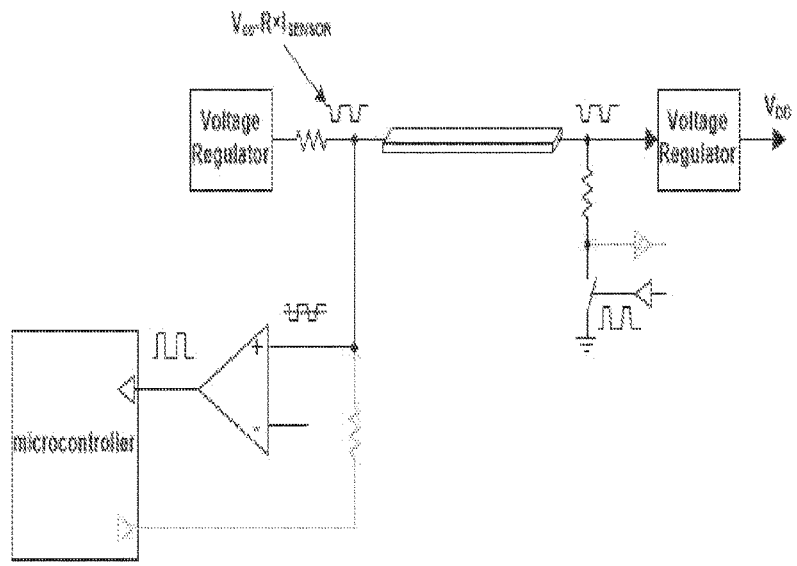
Figure 23B:
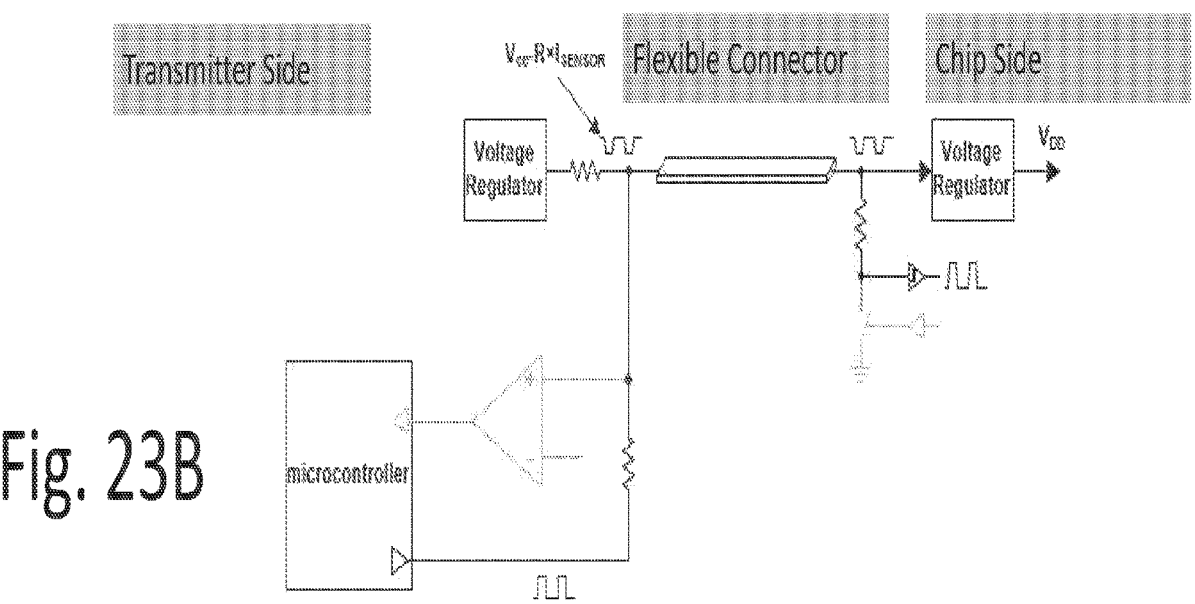

FIGS. 23A and 23B show another coupling-decoupling scheme in which no coupling capacitor is used i.e., neither the transmitter side nor the chip side.

Figure 24A:
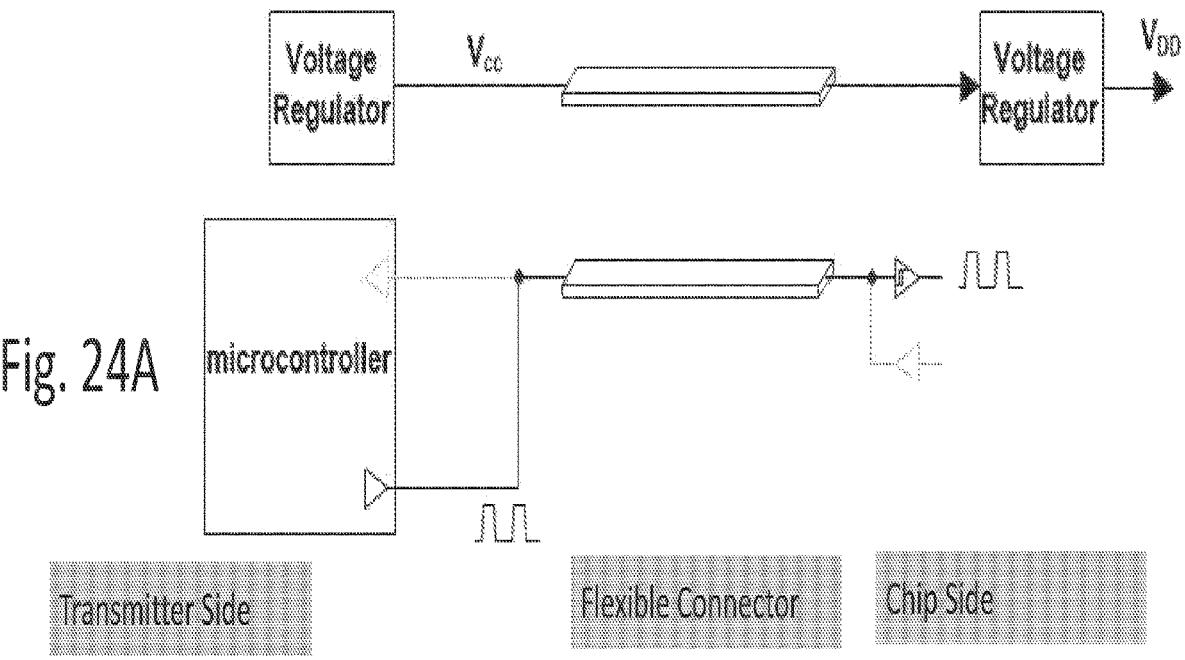
Figure 24B:
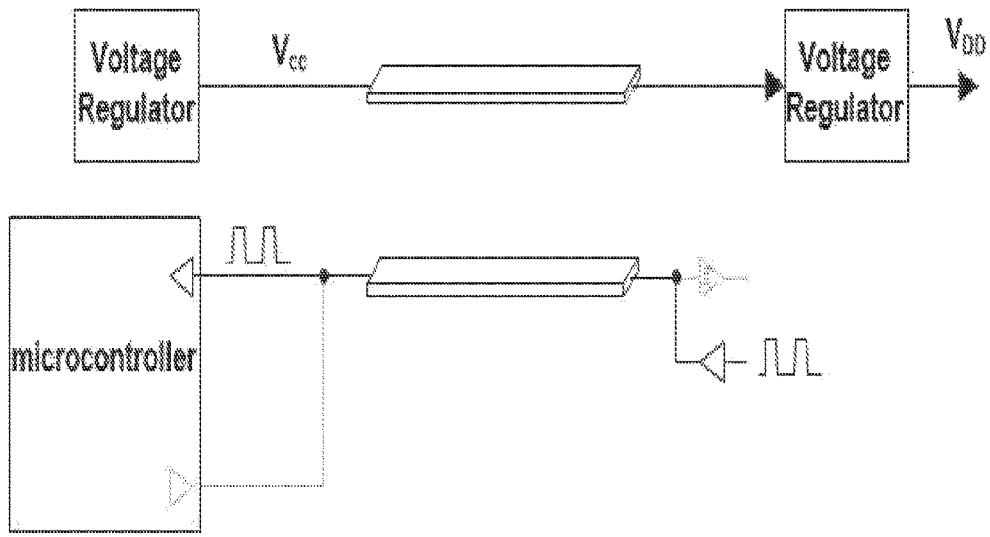

FIGS. 24A and 24B show a scheme in which the power and data lines are separate. Hence, the TX and RX data on both the transmitter and chip side need to be combined but the power signal flows on a separate dedicated wire.

Figure 25:
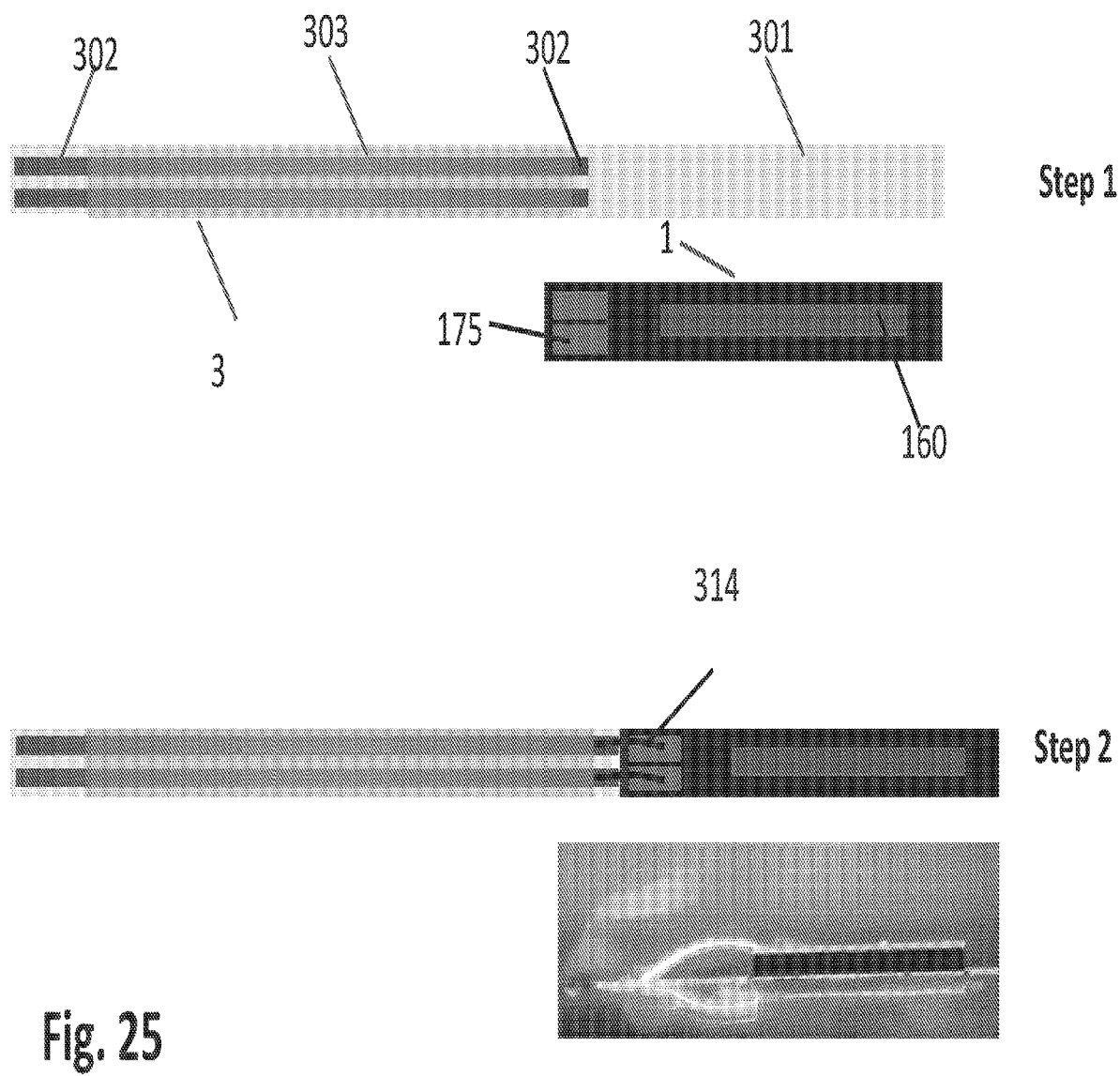

FIG. 25 provides a packaging process scheme of the monolithic integrated sensor circuit 1 onto the connector (or wire) 3 which may be flexible. Step 1 illustrates a sensor circuit 1 positioned adjacent to a flexible connector 3 (e.g., a flexible PCB panel). The flexible connector 3 may include conductive traces 302 in a middle layer of the flexible PCB panel, i.e., under a PCB top layer 303. The sensor circuit 1 can include multiple sensors (or sensing elements) 160 at some distance from CMOS pads 175. Step 2 shows the bonding of the sensor circuit 1 to the flexible connector 3 at the substrate 301 through die attach, followed by forming conductive traces between the sensor circuit 1 and flexible connector 3 via CMOS pads 175 and wire bonds 314. An image of a wire bonded sensor circuit 1 can be seen below.

Figure 26:
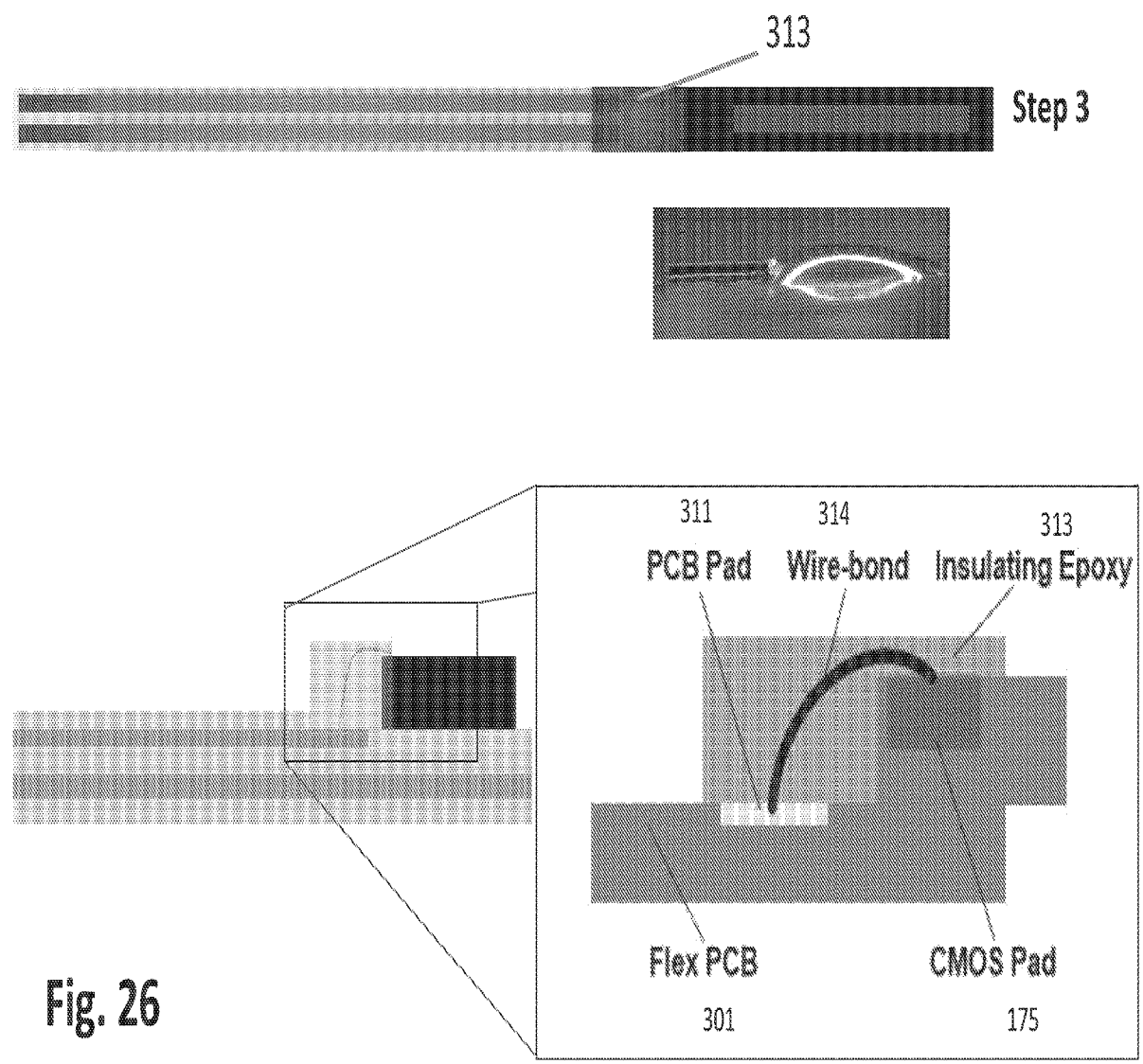

FIG. 26 shows a continuation of the packaging process scheme. Step 3 shows the conductive pads and the conducting interface on the sensor circuit 1 and the flexible connector array 301 protected for water ingress and mechanical abrasion by covering those with a biocompatible insulating material 313. An image of a wire bonded sensor circuit 1 can be seen coated below. At the bottom of the figure is shown a side view of the flex PCB shown above. Bonding the implantable monolithic integrated sensor circuit 1 to the two-wire flexible connector 3 is accomplished through wire-bonding and insulating the connection using biocompatible polymers such as epoxy, parylene-C. 311 shows the conductive pad on Flex PCB 301. 311 makes contact with wire-bond 314 which in turn contacts CMOS pad 175. The wire bond can be covered by an insulating epoxy 313.

Figure 27:
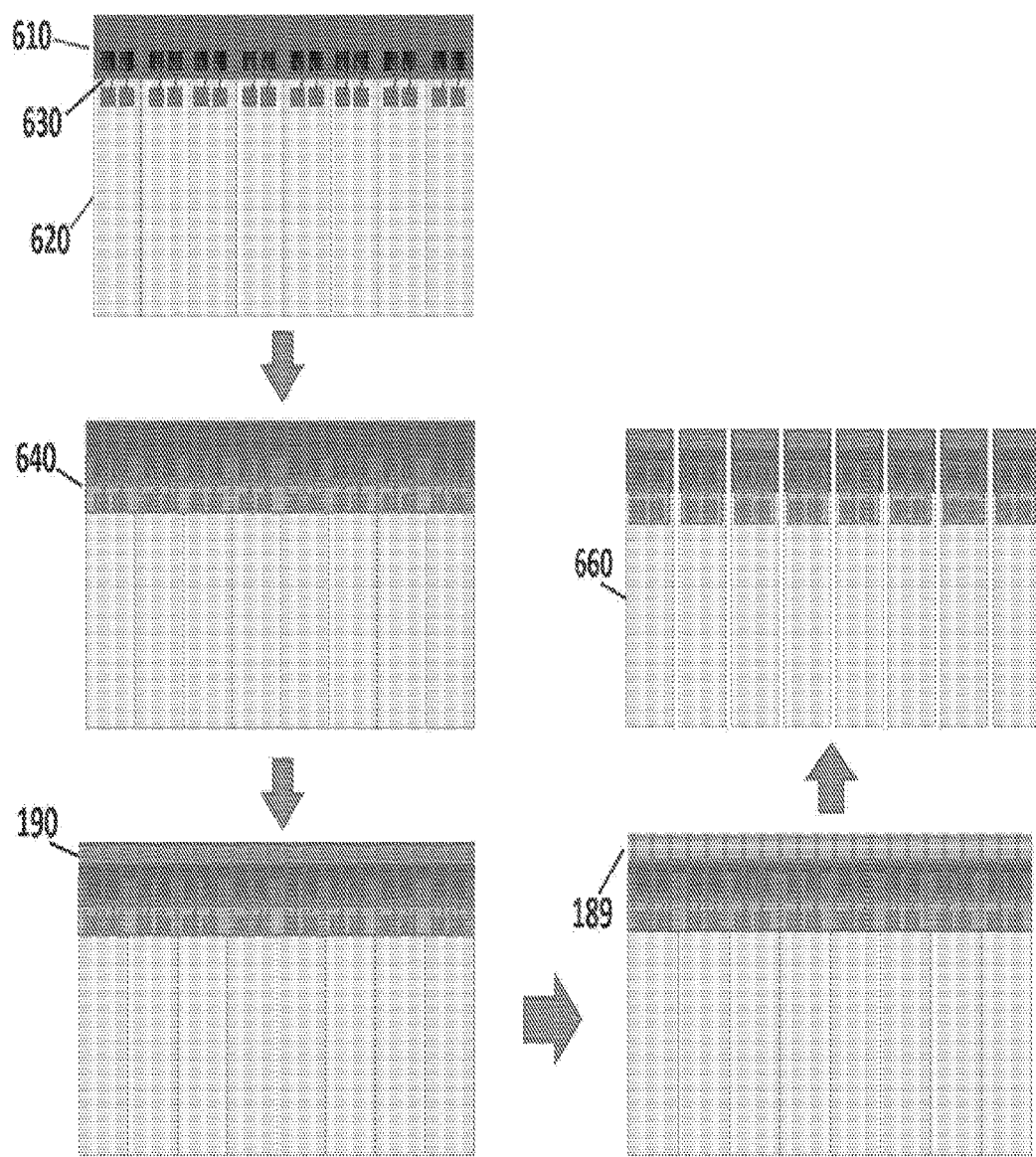

FIG. 27 shows a process of wire bond encapsulation followed by functionalization in a scalable manner. The first step shows an instance of how a strip of monolithic integrated circuits 610 (each of which is an example of the monolithic integrated circuit 1) can be attached to a flexible PCB panel 620 (which can be cut to produce multiple instances of wire or connector 3) using, for example, die attaching followed by wire bonding using wires 630. The second step shows how an insulating material 640 can be used to hermetically seal the sensor-PCB interface (the pads on the sensors, the wire bonds, and the pads on the PCB). The third step shows how one or more soft materials like enzyme hydrogel 190 can be coated on the sensors using a thin-film coating process (e.g., spin coating, spraying). This can be followed by multiple similar steps to coat a second soft material like polyurethane 189, followed by a third soft material lie Polyvinyl Alcohol (PVA). The fourth step shows an instance of how the individual monolithic integrated circuits 1 attached to wire 3 (combination of which is labeled 660) can be separated by dicing the sensor-PCB assembly together. This can be done using different dicing methods like mechanical (e.g., saw) dicing or laser dicing. This process enables scalability by allowing a strip (can be extended to have two sensor rows, one on each side of the strip instead of one) of sensors to be handled together with a larger Flex PCB panel in a manufacturing process, instead of handling individual monolithic sensor circuits 1. The materials used (e.g., epoxies, wire bonding wires, functional materials, membranes) are same as those used for a single sensor example.

Figure 28:
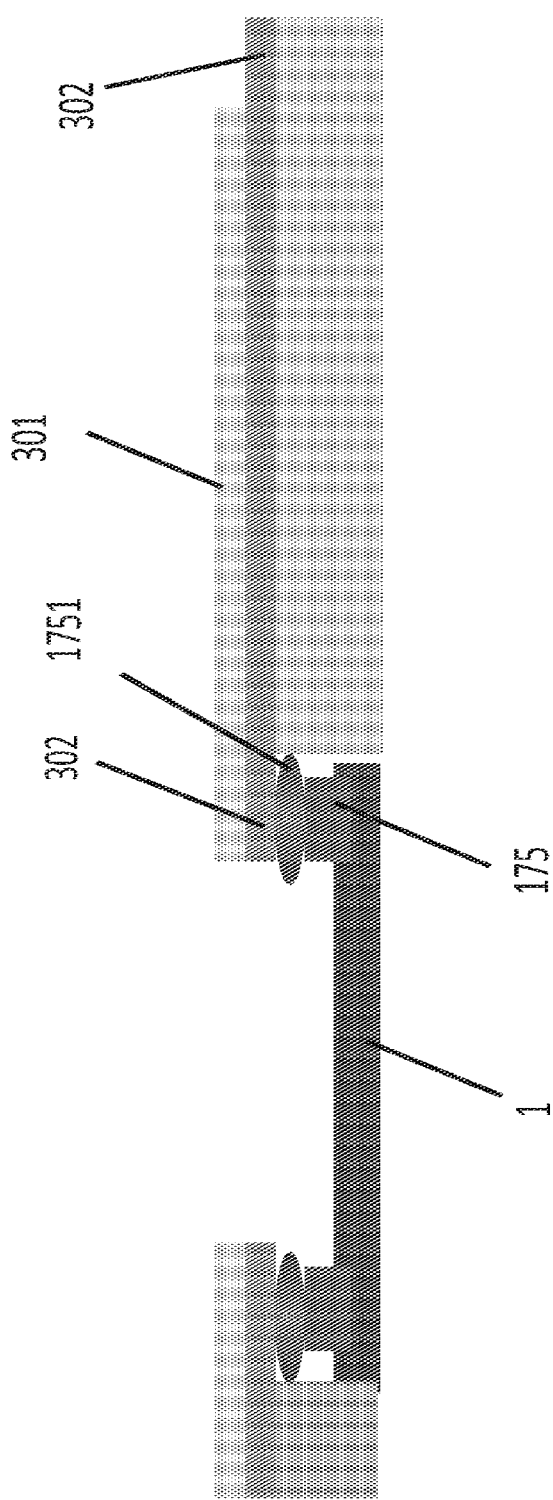

FIG. 28 shows another packaging scheme to attach one monolithic integrated sensor circuit 1 with the flexible PCB 301 through flip-chip bonding while making the packaged device more planar and more uniform. For this, conductive bumps 1751 are formed on the CMOS pads 175 or on the flexible PCB conductive traces 302 or both (corresponding pads provide for stronger and more symmetric bonding). Afterward, the CMOS and Flex connector pads are aligned and pressed together for a certain duration at controlled temperature and pressure, through a suitable dielectric or multilayer stack of the Flexible PCB 301 to minimize the height difference between the PCB connector and the monolithic integrated sensor. Typically, the pads on the CMOS sensor circuit 1 are covered with a metal bump made of soft metal (e.g., Gold or Indium-Tin) to enable reflow and strong conductive connection with the flex pads. It is possible to add these bumps on the flex PCB conductive traces 302 as well, although it is not typically required.

Figure 29:
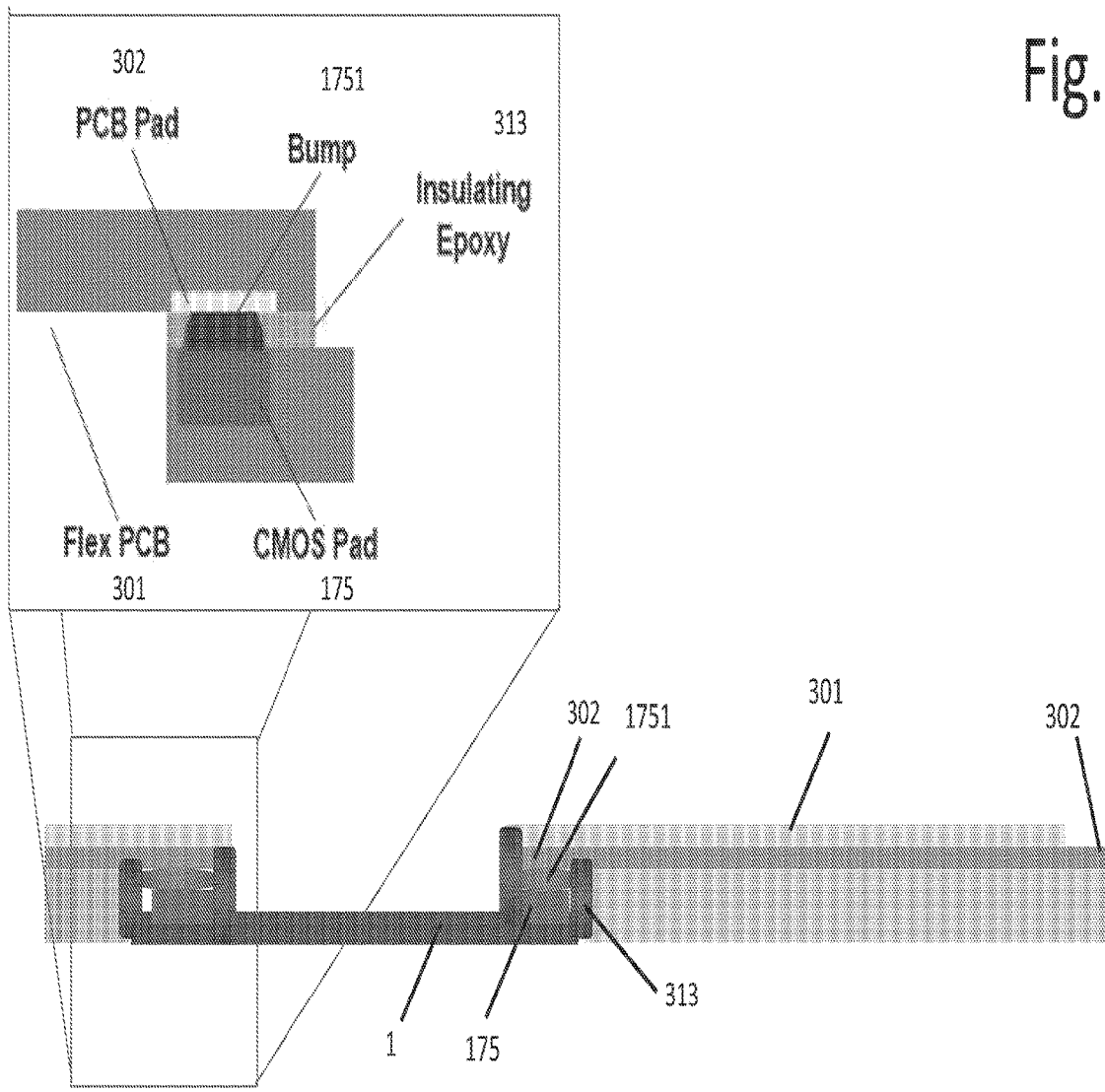

FIG. 29 shows a continuation of the packaging scheme. The interface between the flex PCB Pads 302 and the CMOS pads 175 can be covered in insulating material 313, e.g. using an underfill or a similar process. The zoomed portion of the figure provides a packaging of the implantable monolithic integrated sensor circuit 1 to PCB trace 302 (e.g., a two-wire flexible connector). This can be accomplished through bonding the monolithic integrated sensor circuit 1 to the two-wire flexible connector through flip-chip bonding. 302 shows the conductive pad (or conductive trace) on Flex PCB 301. 302 makes contact with a conductive bump 1751. Conductive bump 1751 sits on CMOS pad 175. The interface between the flex PCB 301 and the CMOS pad 175 can be covered in insulating epoxy 313.

Figure 30:
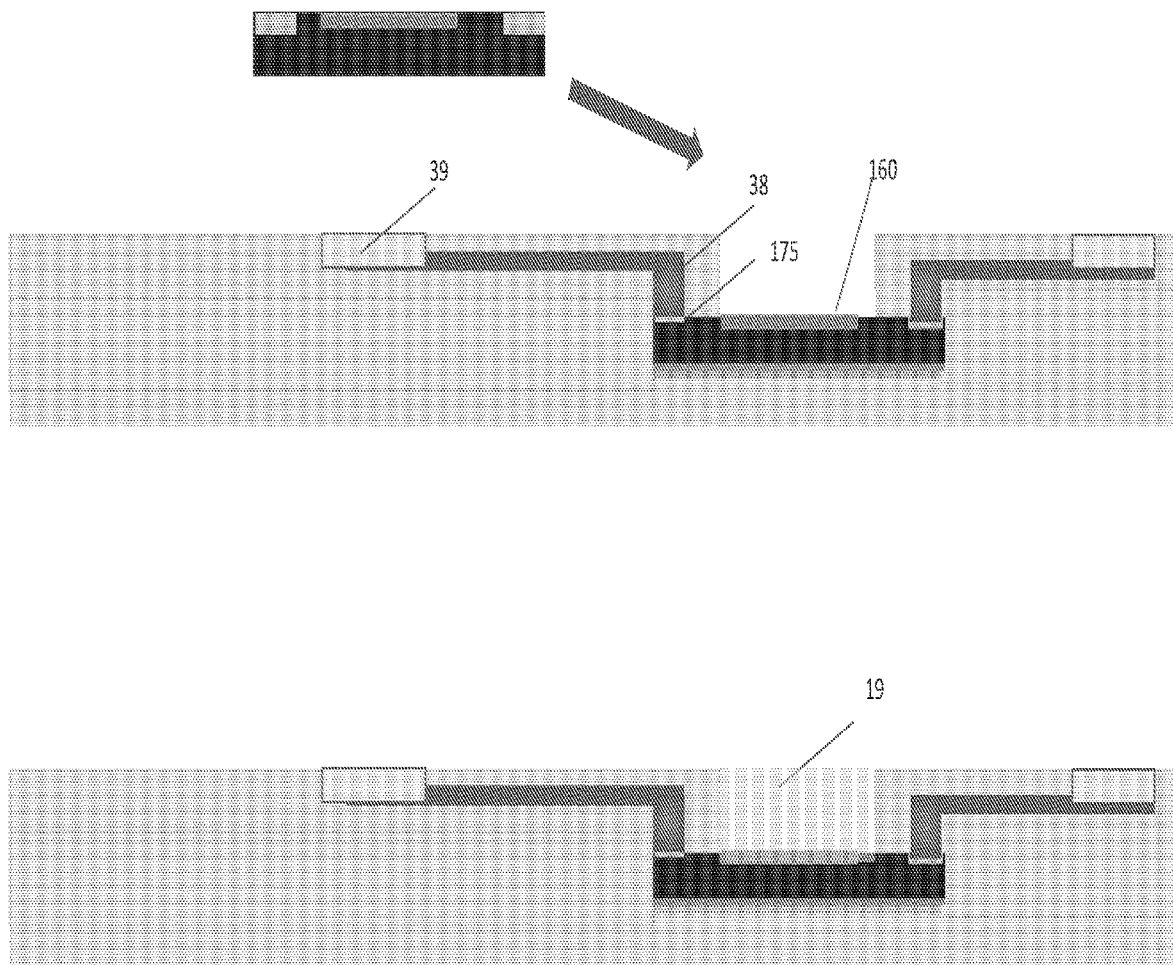

FIG. 30 shows another scheme of connecting the monolithic integrated sensor circuit 1 and the flexible connector 3. In this scheme, the sensor circuit 1 is embedded within the flexible connector (e.g., flexible PCB) and is electrically connected using small conducive connections (e.g., inter-layer vias) 38 which on one side connect to the chip pads 175 and on the other side connect to flexible PCB contact pads 39 via conductive traces. This method avoids having to use any extra insulating materials and use the flexible PCB material (e.g., Kapton, LCP, PEEK, etc.) as the insulating material. Another advantage of this technique is that the layer thicknesses can be controlled to result in a planar device by coating the sensing surface 160 with functional material 19. Moreover, embedding the sensor circuit 1 within the flexible PCB improves the mechanical robustness of the system. For this embedding, the sensor circuit 1 is typically thinned down and coated with a polymer (e.g., polyimide) layer followed by dicing and embedding within the flexible PCB layers (e.g., using thermal bonding between the backside Polyimide and the Flexible PCB polyimide). The contact pads at the sensor circuit 1 are connected with the conductive traces of the flexible connector 3 by via-like metal fills in small holes in the interlay insulator or by an anisotropic conductive adhesive (ACA).

Figure 31:
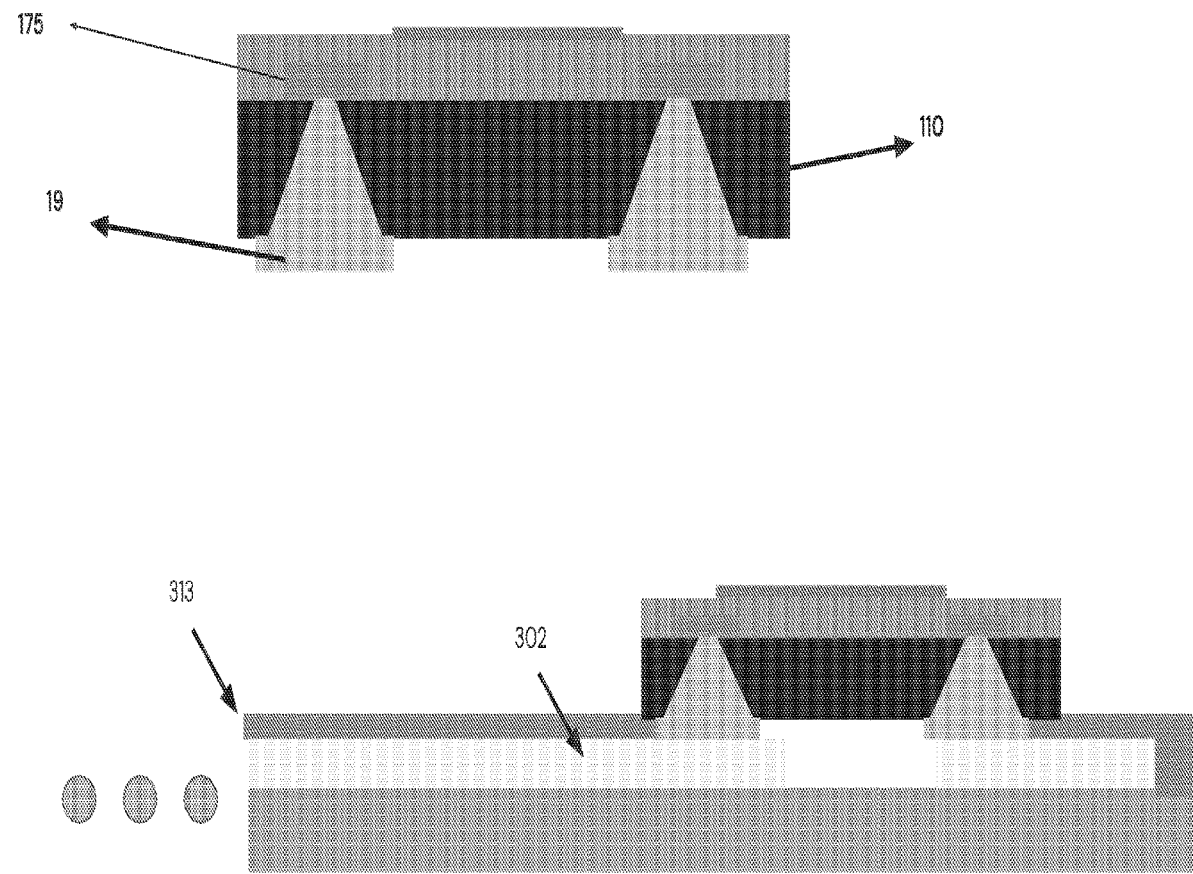

FIG. 31 shows another scheme of connecting the monolithic integrated sensor circuit 1 and the flexible connector 3 (e.g., flexible PCB). In this scheme, the sensor 1 uses through-silicon-via (TSV) technology to have contact pads 19 under it. In this scheme, a trench is etched from the backside (through the substrate 110) of the CMOS sensor circuit 1 to the conductive trace using a combination of wet and/or dry etching methods. Then the sidewall of the silicon is covered with and insulator and finally with a conductive material that runs from the backside of the CMOS sensor circuit to the front side e.g., to chip pad 175). These pads on the backside of the CMOS sensor circuit 1 can be attached to the flexible PCB using different methods (e.g., bump bonding, conducting adhesive like Anisotropic conductive adhesive or ACA) depending upon the size and the application. Next, the conducting interface is covered with an insulating material 313.

FIG. 32 shows another embodiment of the packaging scheme. In this case, the monolithic integrated sensor circuit 1 is placed inside a well in the flexible connector 3. The gap between the sensor circuit pads 175 and the flexible connector pads 302 is filled with an insulating material 313, followed by forming the connection between the two pads 314 (e.g., using wire bonding, or conducting epoxy, etc.) followed by covering it with a thin layer of insulating material 313.

FIG. 33 shows a scheme of using the IMS integrated sensor circuit 1 on one side of the flexible connector and using the other side of the flexible connector as a secondary sensor 9. The flexible connector 3 on the other far side uses a connector that can connect with its conducting traces on both sides, thus enabling connection with both the integrated sensor circuit 1 and the secondary sensor 9. The secondary sensor can be used for validation and control purposes.

Figure 34:
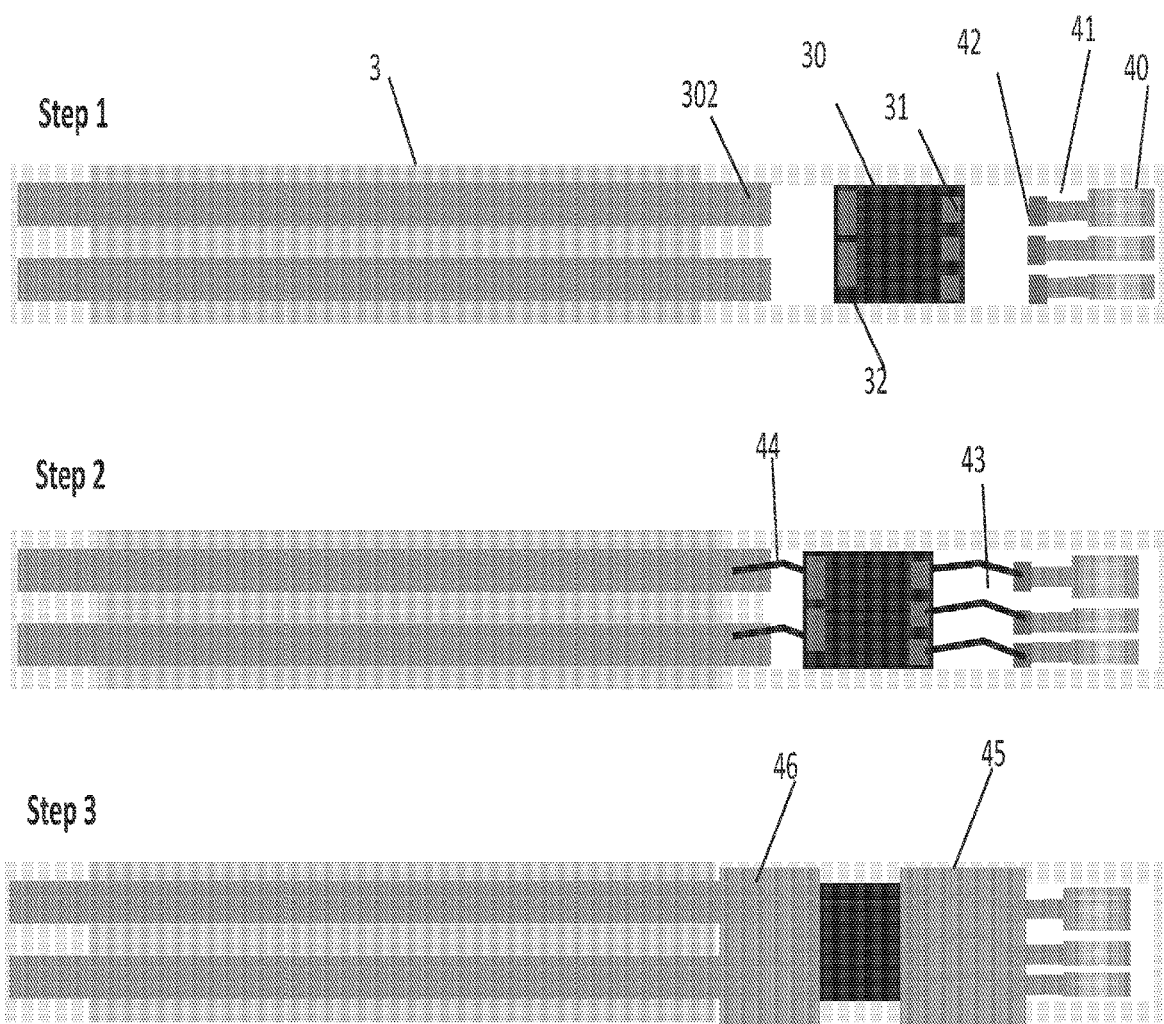

FIG. 34 shows a scheme of using an ASIC chip 30 without an on-chip sensor, connected with an off-chip (e.g., on the flex connector 3 with conductive traces 302 that lead to the transmitter 2) sensor to take advantage of a hybrid sensor design. The ASIC 30 has contact pads 31 on one side to be connected to a sensor (e.g., Potentiostat contact pads) and contact pads 32 on the other hand which are to be connected to the external transmitter. In one example, a 3-electrode sensor consisting of flexible PCB metal layer electrodes 40 terminate into contact pads 42 via conductive traces 41. The contact pads are attached to contact pads 31 on the CMOS sensor circuit 1 using different methods (e.g., wire bonding, flip-chip bonding) by forming a conductive path 43 between the two. The other end of the CMOS chip is also connected to the flex PCB pads 302 via similar methods (e.g., using wire bonding). The conductive interfaces are then covered into suitable insulating materials (e.g., insulating epoxy) 45 and 46.

Figure 35:
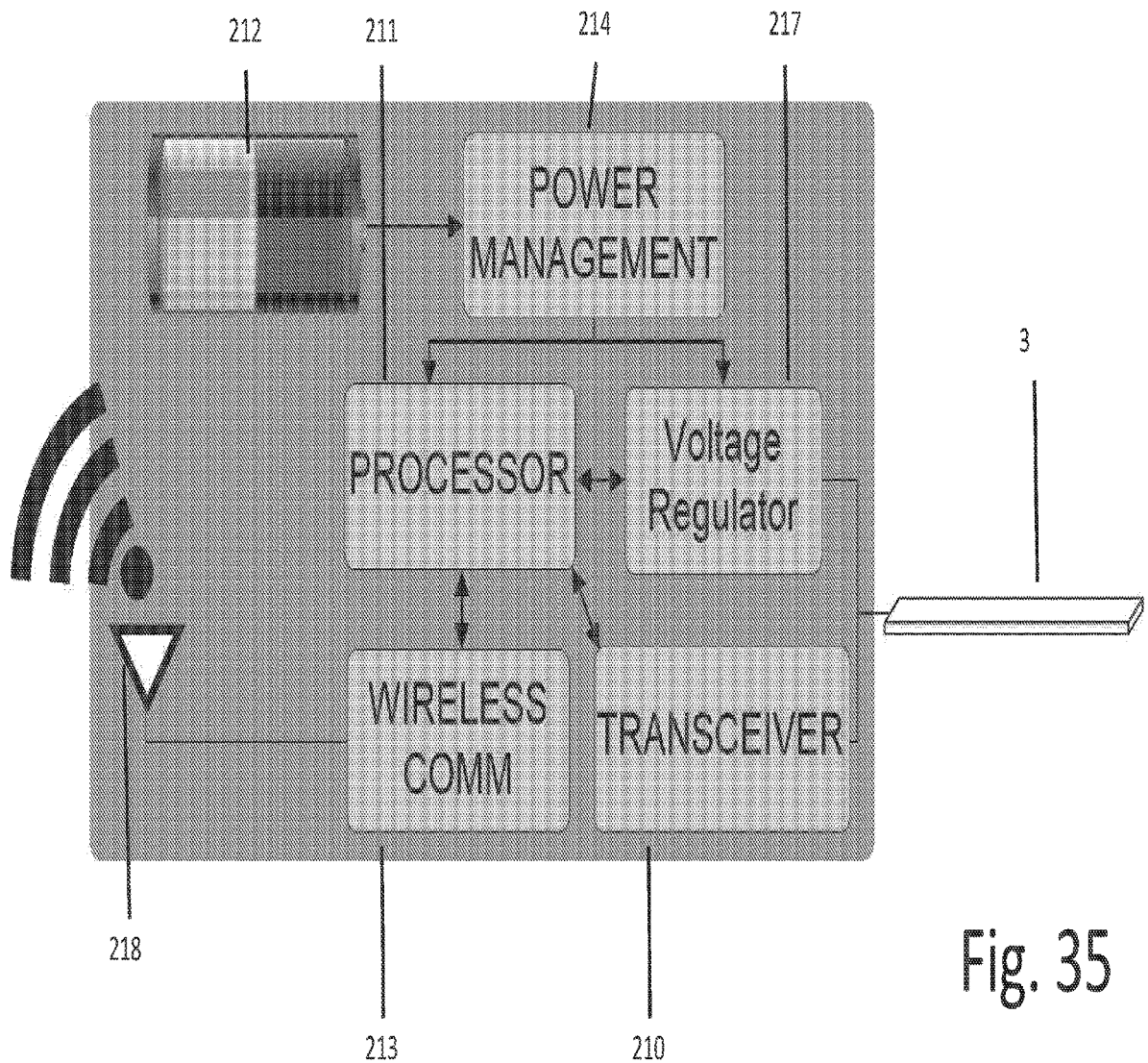

FIG. 35 shows a high-level schematic of the transmitter 2 according to some embodiments of the disclosure. The transmitter 2 can include a transceiver 210 that can generate and detect communication signals flowing over a combined power/data connection through wire 3, a high-performance digital microprocessor unit 211 for system control, a low-energy wireless communication chipset 213 (e.g., Bluetooth), an antenna 218 for wireless communication (e.g., Bluetooth antenna), a power management unit 214 connected to a battery 212, and a voltage regulator unit 217 to provide regulated power to the implantable monolithic integrated sensor circuit 1.

Figure 36:
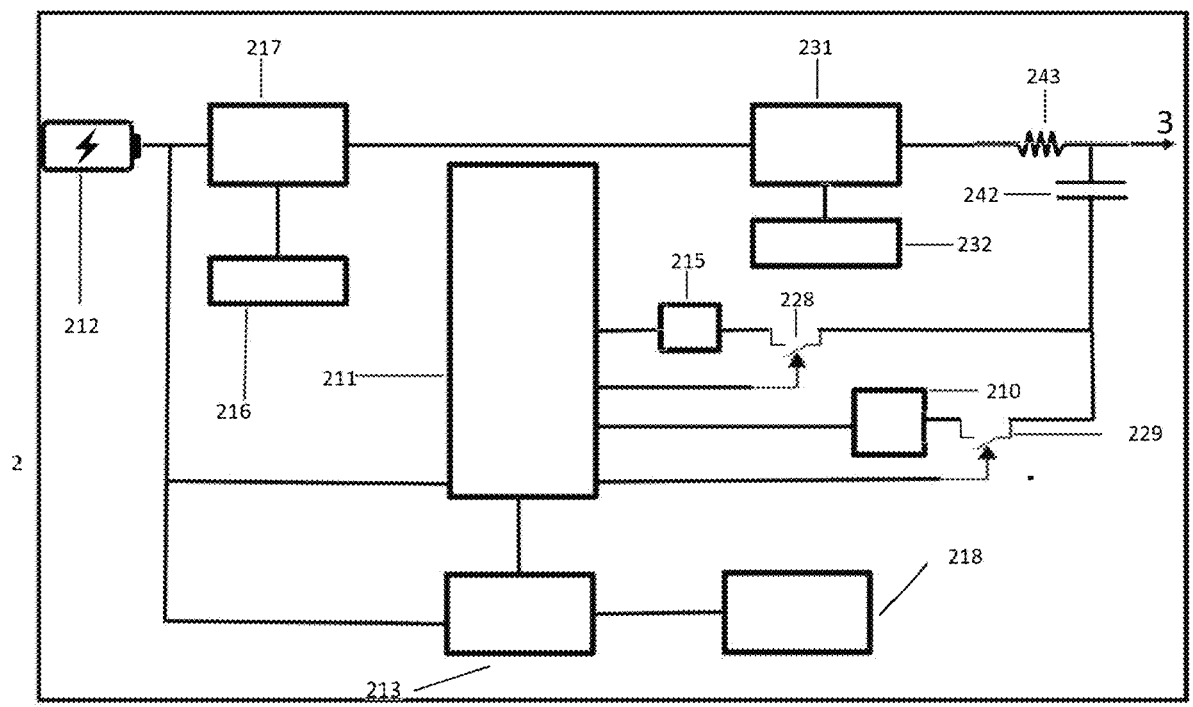

FIG. 36 shows a detailed schematic of an embodiment of transmitter 2 which includes a battery 212, a voltage regulator 217, a voltage reference 216, a microprocessor/microcontroller 211, a wireless communication transceiver 213, an antenna 218, wire 3, a DC decoupling capacitor 242, a switch 228, a switch 229, an Rx unit 210, a Tx unit 215, a secondary voltage regulator 231, a voltage reference circuit 232, and resistor 243.

Figure 37A:
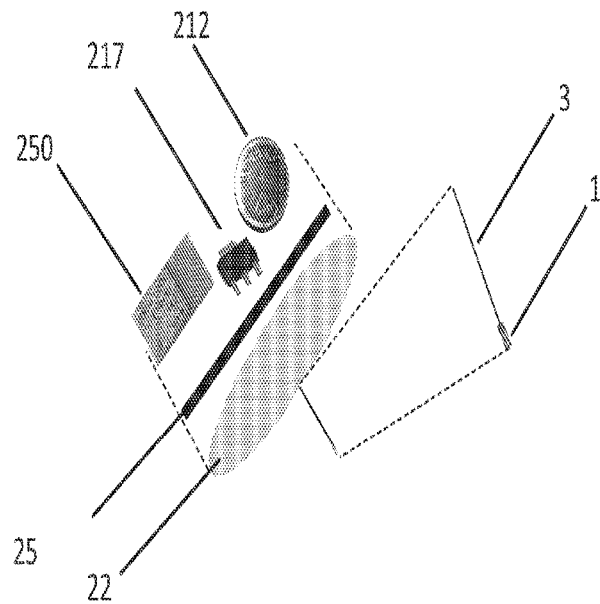
Figure 37B:
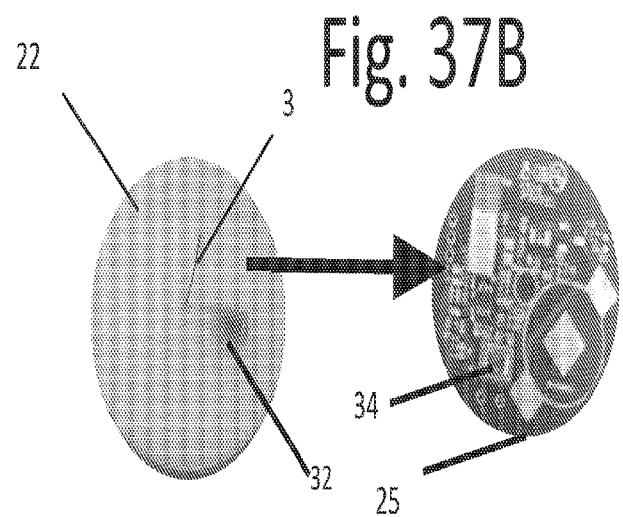

FIGS. 37A and 37B show an implementation of the transmitter circuit 2. FIG. 37A shows a diagram view including sensor 1 with connector 3 attached (e.g., by wire bonding, soldering, through a medical grade micro-connector, etc.) with the transmitter 2 which further comprises a printed circuit board 25 housing the battery 212, regulator 217, and integrated BLE transceiver and application controller/processor System-on-chip 221. The transmitter is housed in a sealed plastic/rubber housing 22 for environmental protection and easy handling during usage. FIG. 36B shows images further inclusive of connectors 32 and 34, which can mate to connect the printed circuit board and wire 3. The wire 3 may also be referred to as a "transcutaneous connector" or "flexible connector".

Figure 38:
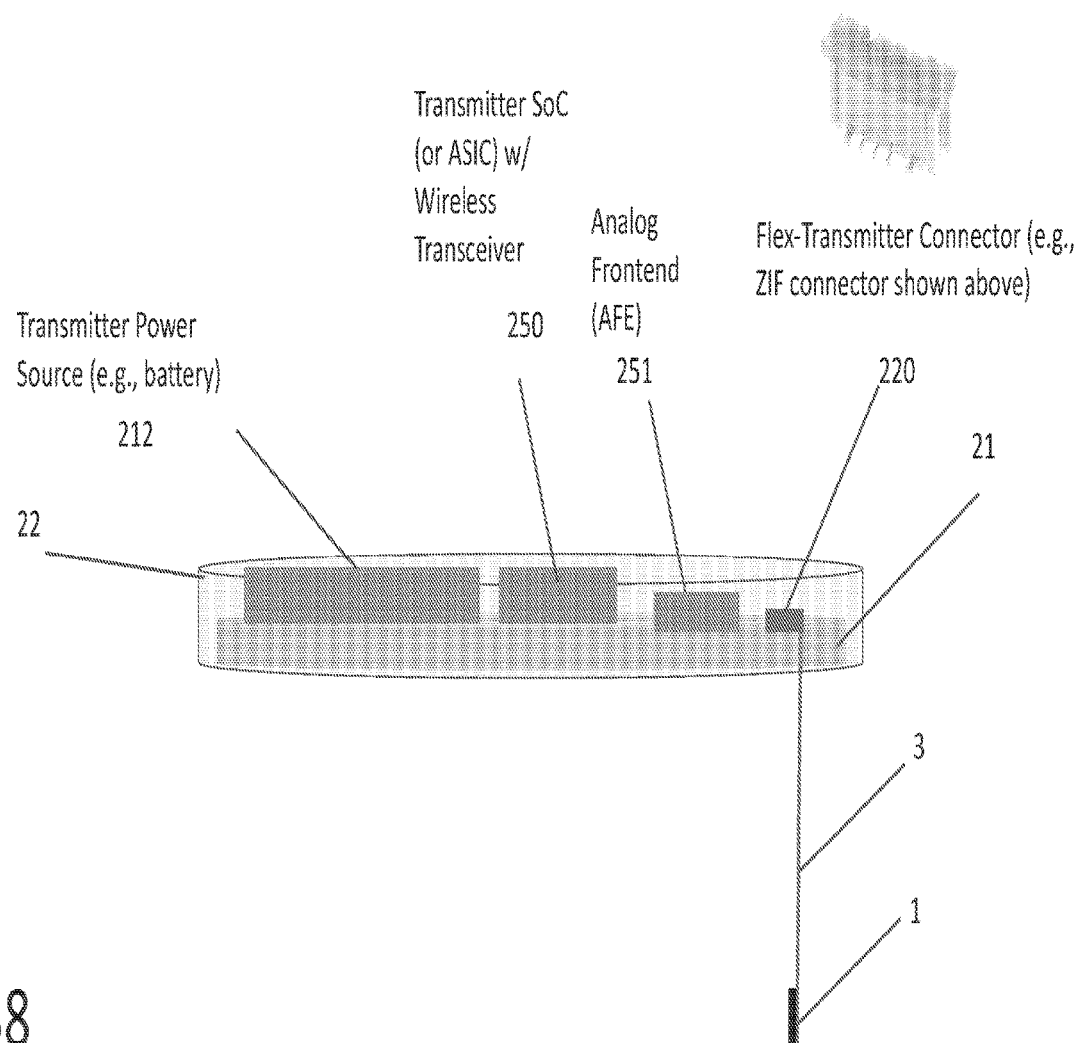

FIG. 38 provides a scheme to package the transmitter electronics inside a sealed casing 22 such that the wire 3 can be connected to the transmitter PCB 25 using a suitable connector or connector pair 220 (e.g., mated pair of connectors 32 and 34) used to connect the flexible (e.g., 3) and rigid (e.g., 25) PCBs. In case of connectors pair, 220 represents a mated pair. However, it can also be a single connector (e.g., a ZIF connector) that mates directly with contact pads designed on the flexible connector or flexible PCB 3. This is different than other transcutaneous CGMs that use soft conductors to mate their sensors with the transmitter PCB and not standard flexible electronics-based connectors used in the IMS design. The figure also shows the other main components of the transmitter electronics including the Analog frontend 251, the transmitter System-on-chip or ASIC 250 which contains the microcontroller along with some peripherals and the communication (e.g., BLE) chip as well as a power source 212.

FIG. 39 shows an algorithmic scheme to program the processor (e.g., a microcontroller) in the transmitter (which acts as the brain of the transmitter) with a firmware to control its operation. It shows that the transmitter (microcontroller) is programmed to stay in a low power (e.g., deep sleep) state. After the user opens the packaging and performs a turn-on operation (e.g., either by using an NFC device to pair with it) or the transmitter automatically detects the user's intent to use it (e.g., by detecting a change in background conditions like light via a photodiode), it performs an initialization sequence which includes a self-test as well as a scan for the reader via BLE. Once it finds a matching reader, it connects with it via BLE. Next, it tests if a good sensor is connected by performing electrical measurements (e.g., voltage drop, current draw) and by sending a command signal and testing the response. After that, it starts transmitting the tag signal and start reading the corresponding data from the sensor chip. The transmitter separates the power and data signals (via mux/demux) and sends it to the microcontroller which preprocesses the data (e.g., check for proper preamble, proper data coding scheme, packet length, packet duration), checks if it detects any error (via error detection/correction code), and separates the data from all 4 (3 electrochemical and 1 temperature) sensors. It then sends the data to the reader via BLE.

Figure 40:
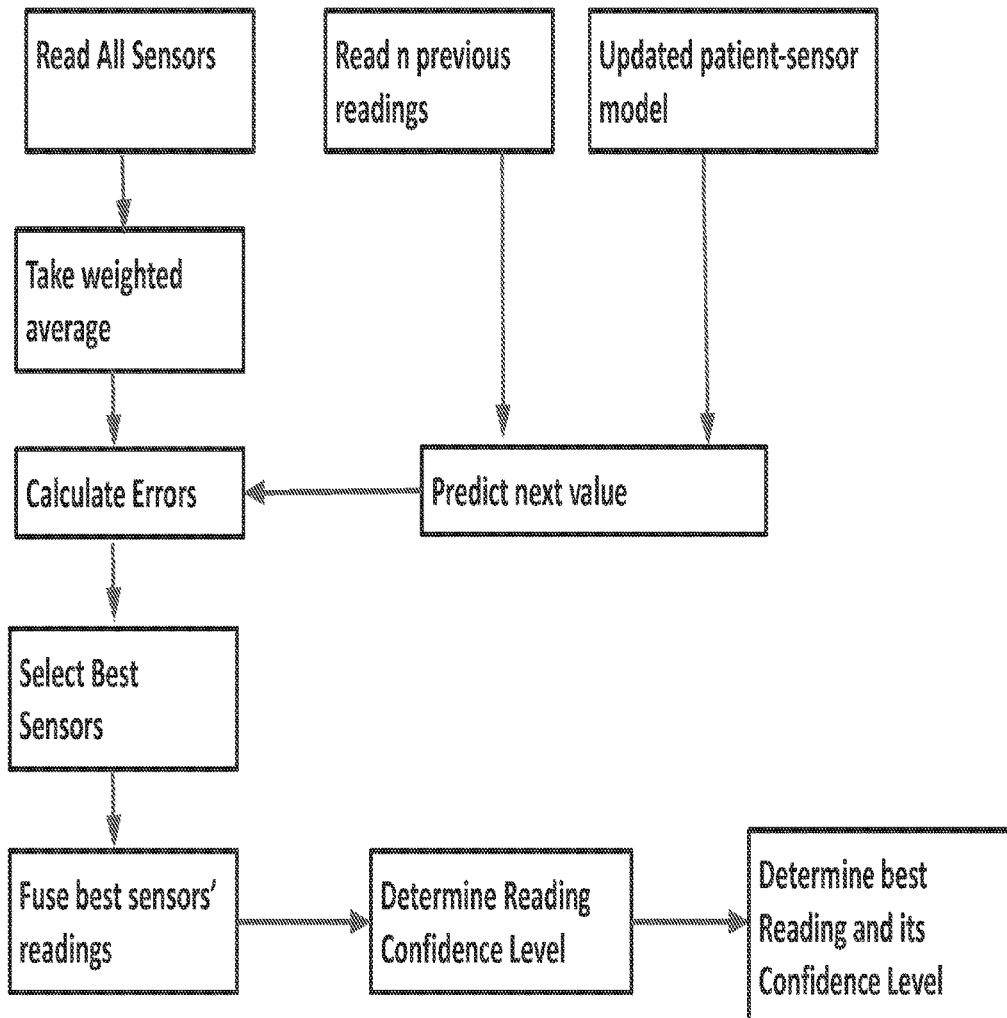

FIG. 40 shows a scheme for using the multiple on-chip sensors (working electrodes) data as well as previous readings and a personalized (for each patient) patient-sensor model to generate the best outcome (glucose value) at a given time. The scheme uses the current data from all sensors (3 electrochemical and 1 temperature). and uses that to calculate errors among the sensor values. It also compares the readings with the previous reading to decide if the new values are physiologically accurate. By comparing the sensor readings among themselves and the errors, the system decided if a sensor has unacceptable level of error. In that case, it discards that sensors and uses rest of the sensors data to generate a weighted average as the current value of the sensor.

FIG. 41 shows the process of insertion of an embodiment of the disclosure. In step one the monolithic integrated circuit, wire, and transmitter are placed inside an applicator consisting of an external plastic body 81, adhesive patch 82, and needle 83. In step two the sensor and injector assembly are pushed towards the skin. This allows body analyte to reach the sensor surface and the system to start monitoring the concentration of one or more analyte in the body.

Figure 42:
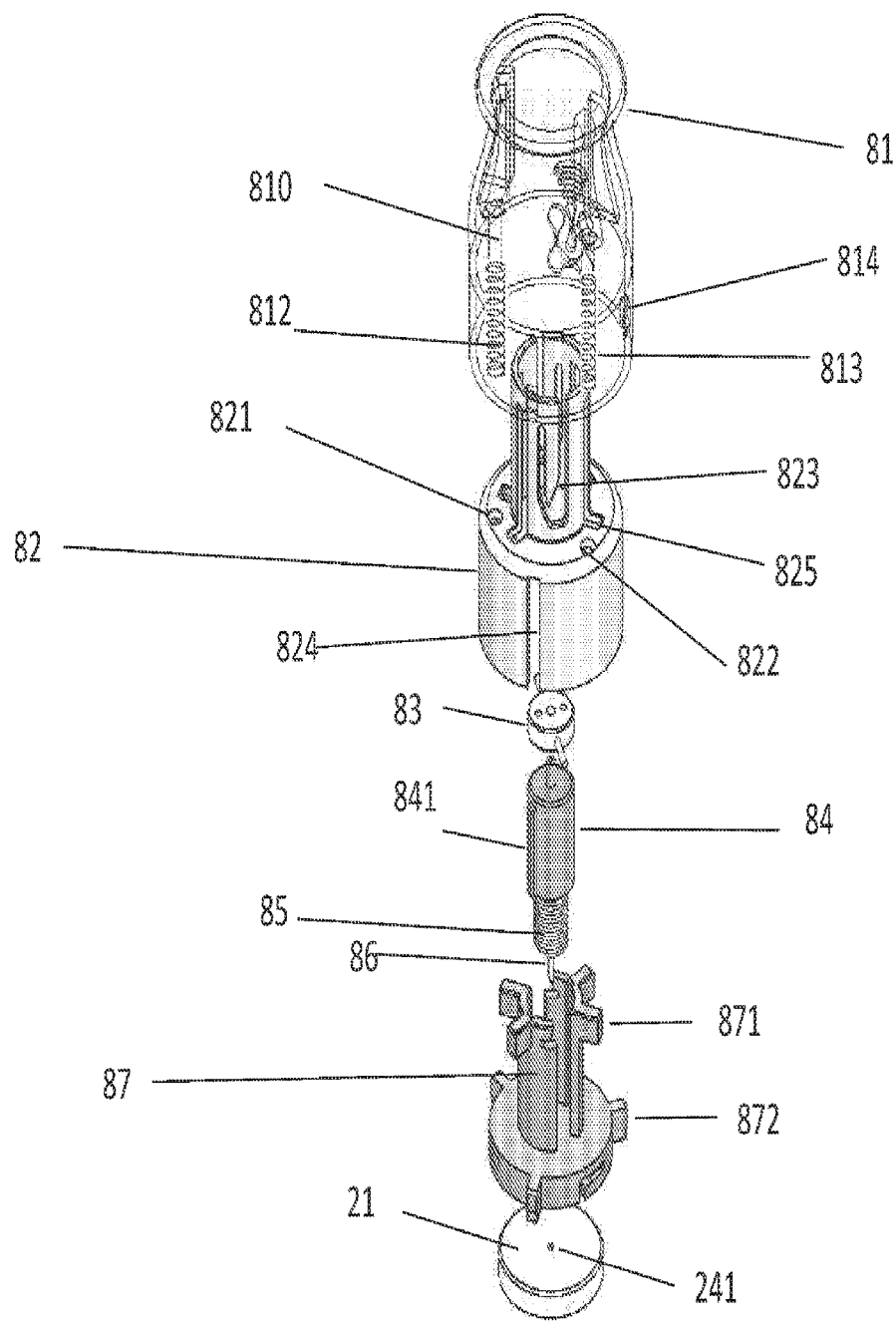

FIG. 42 shows a different scheme of sensor insertion using a disposable applicator. The figure shows an exemplary design of such an applicator 8 comprising an external cover 81, a triggering guide 82, a small triggering arm 83, a needle holder 84, a retracting spring 85, an insertion needle 86, a transmitter assembly holder 87, and the sensor-transmitter assembly 21 with a needle guide 241. The needle guide allows the needle to pass through the transmitter casing and in turn around the flexible connector which is attached to the transmitter on one end and to the integrated sensor on the other end. The external cover 81 also includes two rods 810 extending from the interior of the anterior top towards the bottom posterior open circular aperture. The rods 810 function as guide poles for springs 812 wherein the rods are configured to have an exterior diameter smaller than the mean diameter of the respective spring. The rods can extend from bases which can be similarly shaped to protrusions 88 and can operate as bases for the tip of the coil of springs 812 to sit thereon. The external cover 81 has three groves 814 to fit the assembly holder 87 via three features 874. It also has two springs 812 and 813 to provide smooth movement of the assembly. The triggering guide 82 has corresponding holes 821 and 822 to match with the springs 812 and 813 of the cover 81. Additionally, it has three cut-outs 824 to allow sliding movement of the assembly holder 87 via three holders 872 on the assembly holder 87. It also has 4 slots 825 to enable alignment of assembly holder 87 with it (triggering guide 82). The needle holder 84 has a holding structure 841 that enables it to slide with the assembly holder 87 within the groves 824 of the triggering guide 82. The applicator involves internal alignment markers 871 and 825, and then mating 3 mm external alignment markers 872 and 824.

Figure 43:
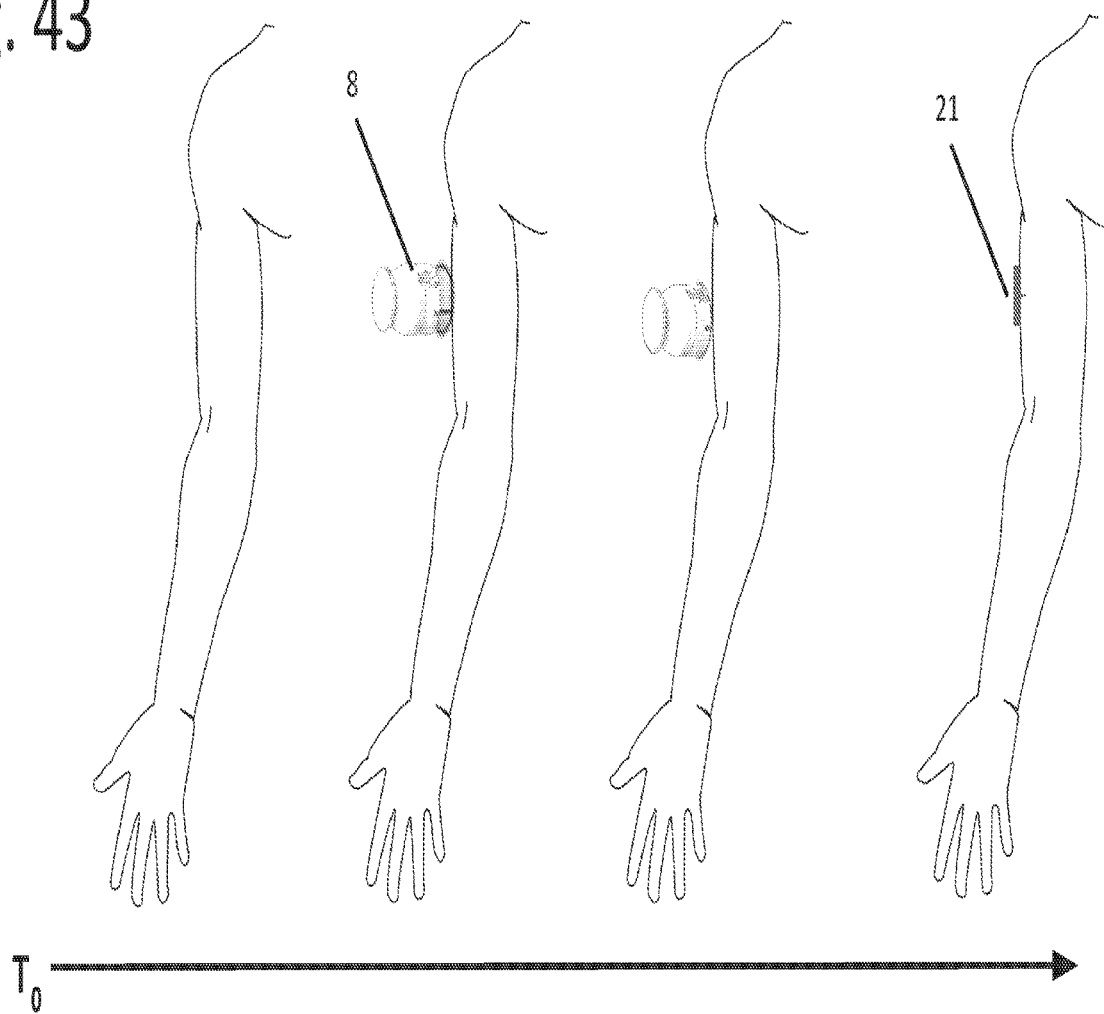

FIG. 43 shows a step-by-step process of how the applicator 8 is used to insert the sensor-transmitter assembly 21 on the user body having the sensor connected to the flexible connector under the skin while keeping the transmitter attached to the skin surface. It shows the first step in which the applicator is in a loaded state and is pushed against a body location (e.g., upper arm), after which it inserts the sensor under the skin and retracts the needle (release state). The last part of the figure shows the arm with the transmitter is on the skin and the sensor 1 is under the skin connected via the flexible connector.

Figure 44:
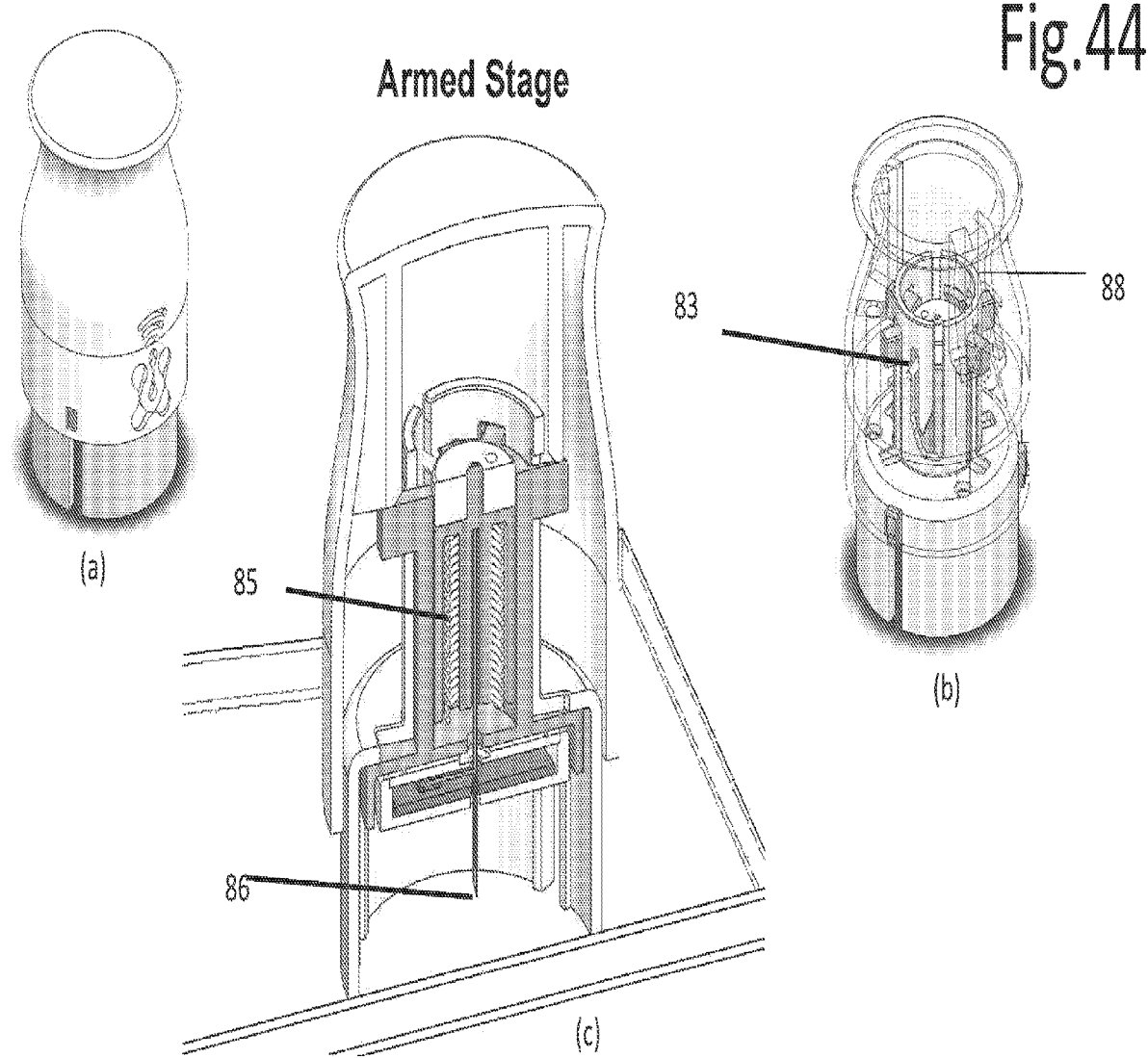

FIG. 44 shows the armed (loaded) state of the applicator i.e., the state in which the transmitter-sensor assembly is loaded inside the applicator for insertion in the patient. In the loaded stage, the needle 86 is in a position such that the needle 86 is away from the skin surface and the spring 85 is in the compressed stage. FIG. 44(a) shows a perspective view of the applicator 8 during the armed state. FIG. 44(b) shows a perspective view of the applicator 8 during the armed state but with the external cover 81 being invisible. FIG. 44(c) shows a cross-sectional view of the applicator 8 during the armed state.

Figure 45:
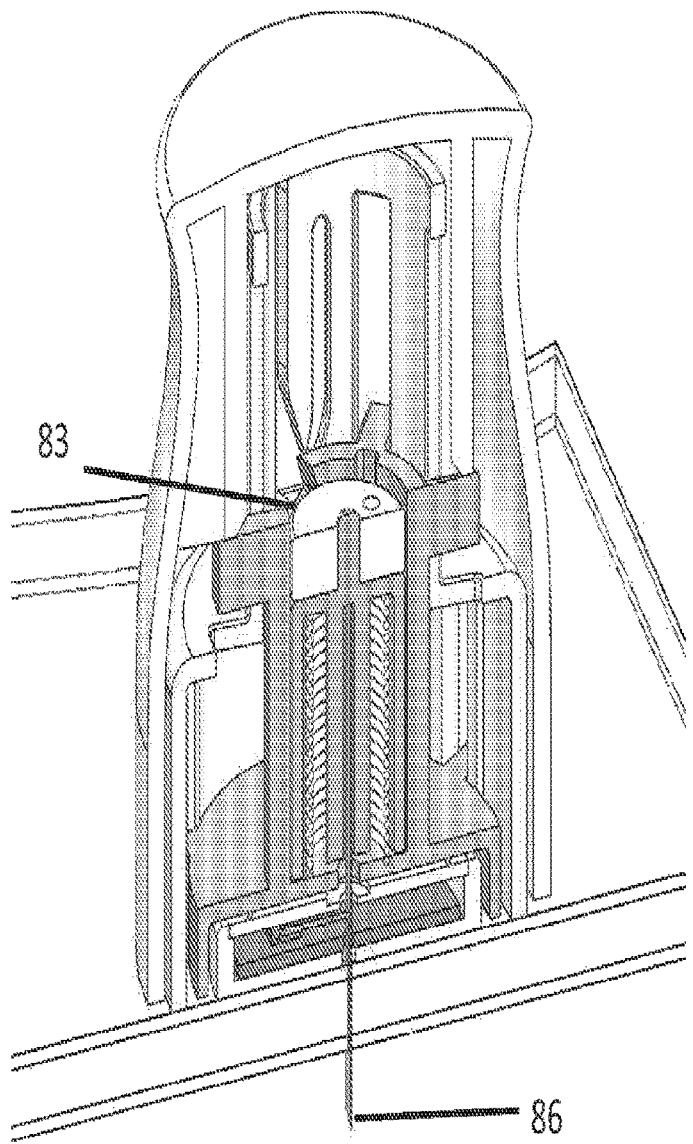

FIG. 45 shows the next stage of sensor insertion (trigger) in which the applicator is put on the skin in a desired region (e.g., upper arm) and is pressed against the skin. This pushes the needle holder 84 and the transmitter holder 872 towards each other. This pushes the needle 86 down to pierce the skin. Once and the triggering arm 83 reaches the maximum depth, this defines the maximum depth of the needle under skin.

Figure 46:
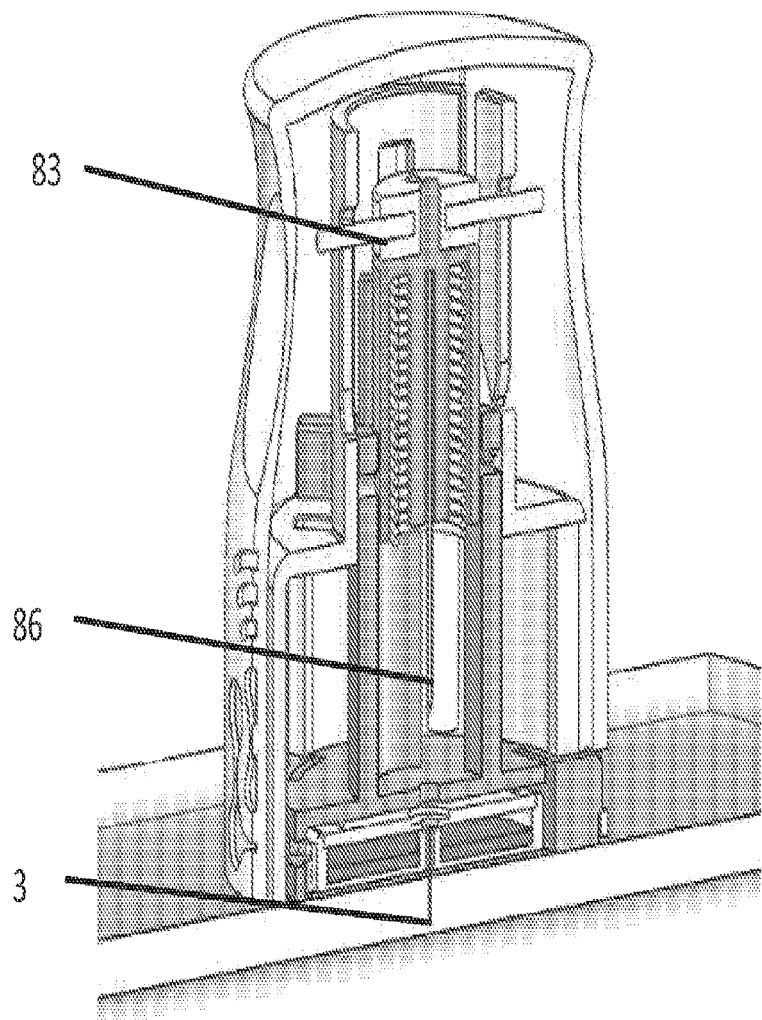

FIG. 46 shows the next stage of sensor insertion (release) in which the needle is retracted back to the applicator assembly by the spring force of retraction spring (85 in FIG. 42) after the triggering arm 83 reaches the maximum depth in the triggering guide in the transmitter assembly holder. This needle retraction mechanism ensures the needle doesn't cause any accidental injury afterwards. At this step, the biocompatible adhesive attached to the transmitter-sensor assembly 21 keep the transmitter attached to the skin which ensures that the sensor remains under the skin at the desired depth and is connected to the transmitter via the flexible connector 3. The needle 86 is retracted inside the applicator at this stage.

Figure 47:
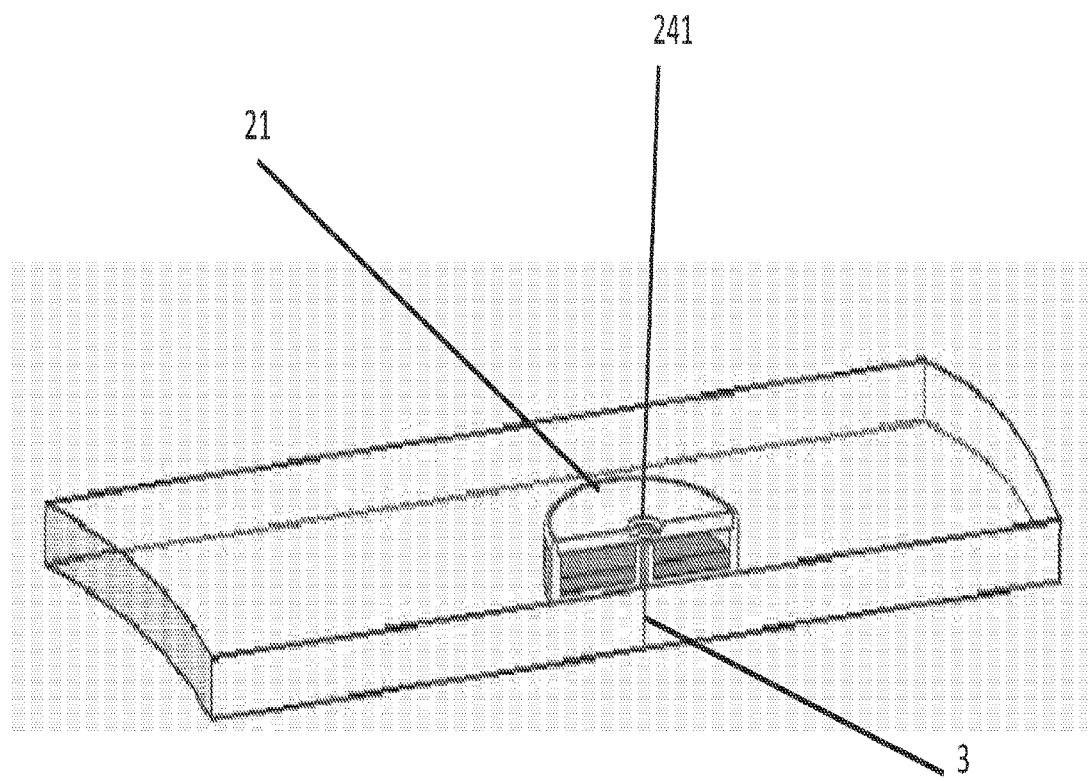

FIG. 47 shows an example of the sensor-transmitter assembly 21 on the skin with the flexible connector 3 passing through the skin (transcutaneous) after the applicator performs its operation and is removed from the skin. It also shows the cut-out of the needle guide 241 which ensures the needle passes around the sensor such that the sensor sits within the needle body through the slot in the needle.

Figure 48:
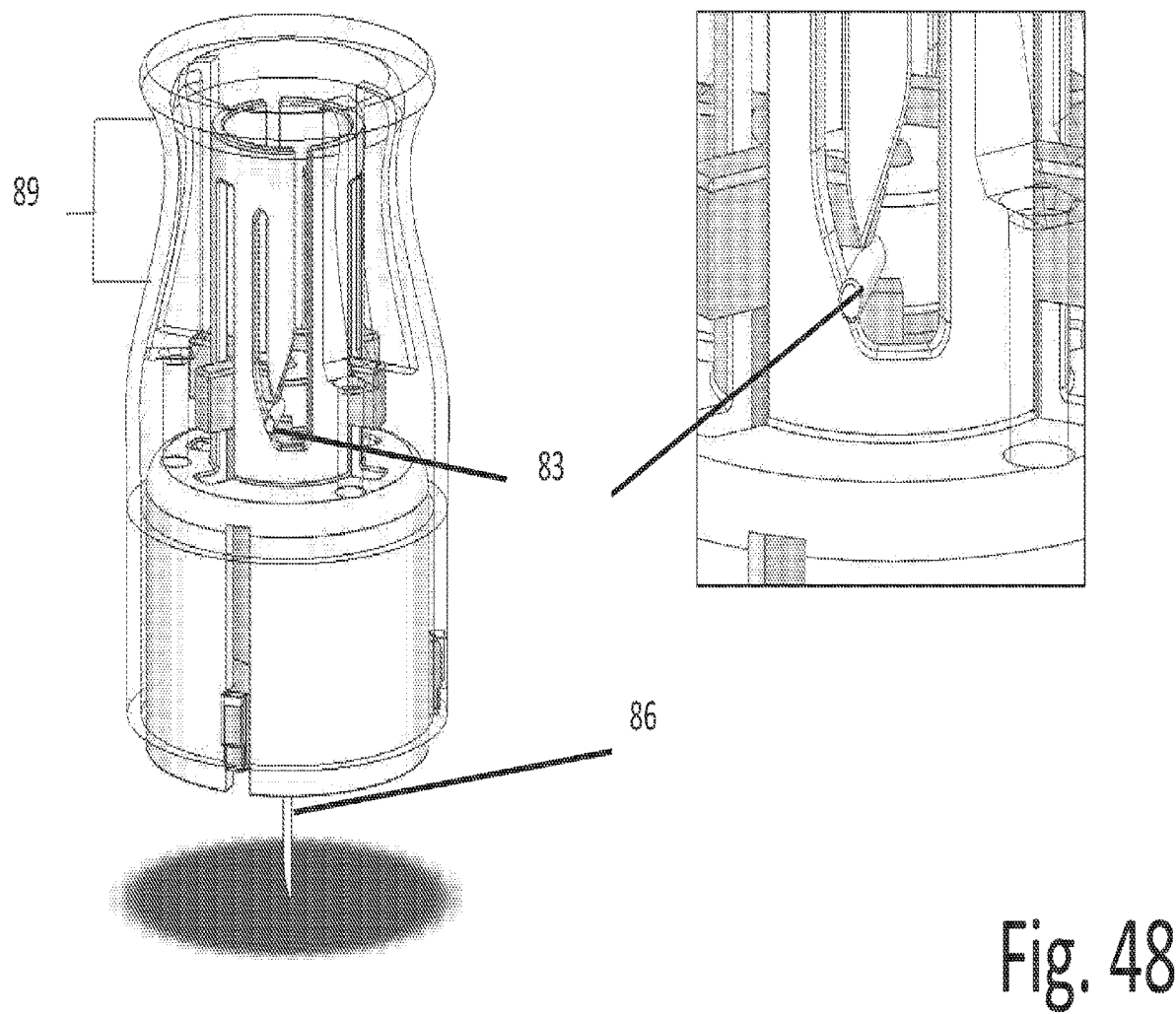

FIG. 48 shows a side view of the trigger state of the applicator and how the triggering arm 83 moves past the lowest point (maximum depth) in the triggering guide when the user pushes the applicator down on the skin so that the needle 86 can pierce the skin. It also shows the optional curves 89 on the top cover that are designed to make it easier to hold the applicator. As the triggering arm moves just past the maximum depth in the triggering guide, it is pulled up by the spring force in the next stage (release stage).

Figure 49:
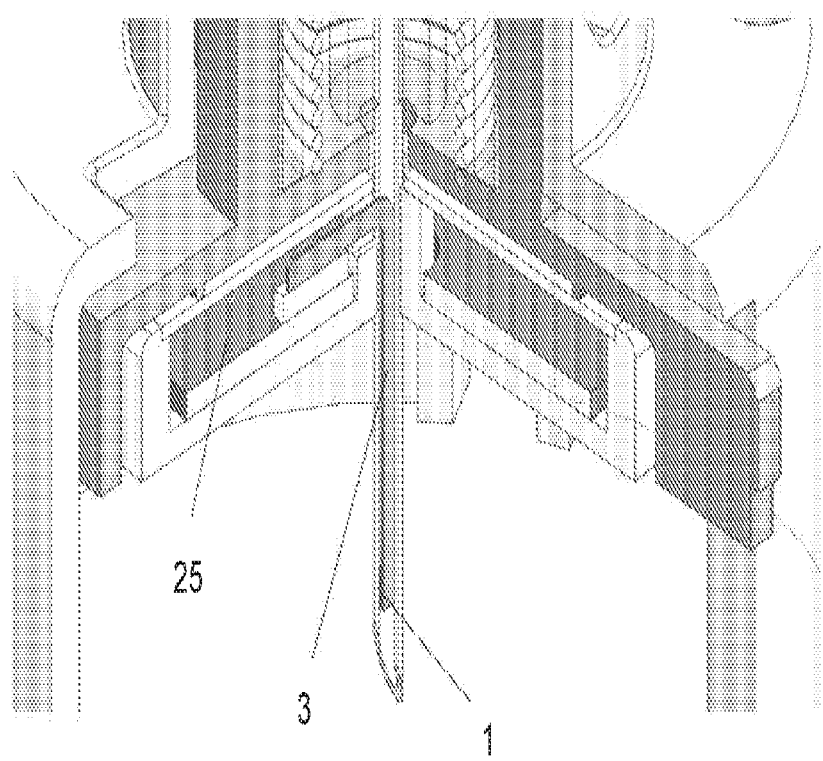

FIG. 49 shows a close-up view of how the sensor 1, the connector 3, and the transmitter (with a PCB 25 inside it) are assembled such that the sensor-connector assembly passes through the cut needle during applicator operation.

Figure 50A:
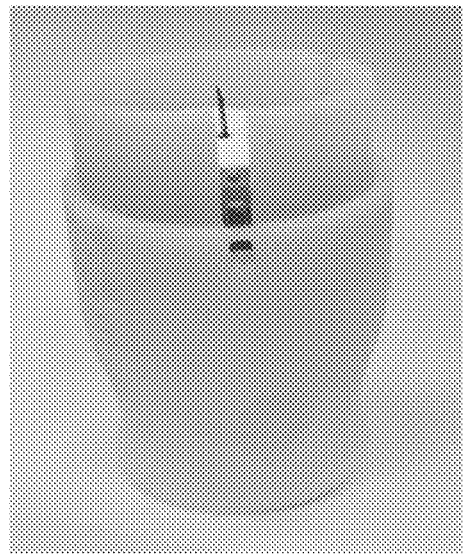
Figure 50B:
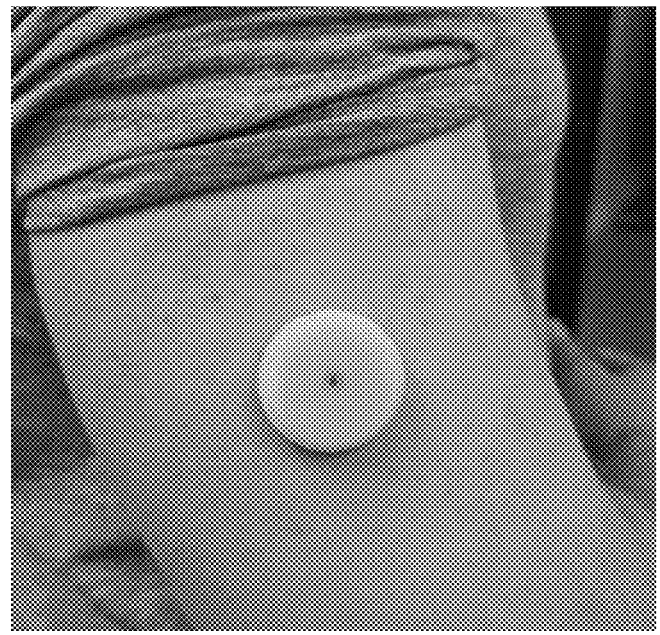

FIG. 50A shows a view of an actual applicator built using the design presented here and loaded with a sensor-transmitter assembly with the sensor-connector part of the assembly passing through the applicator needle. FIG. 50B shows an image of an actual applied sensor assembly.

Figure 51A:
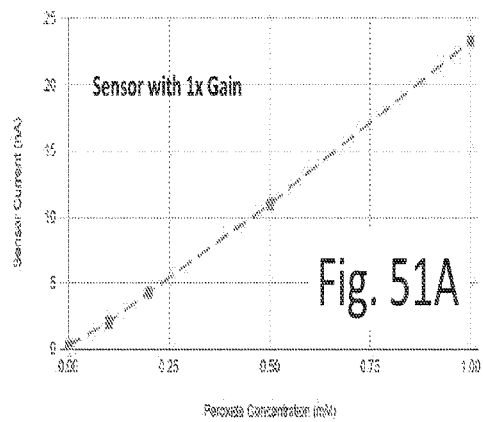
Figure 51C:
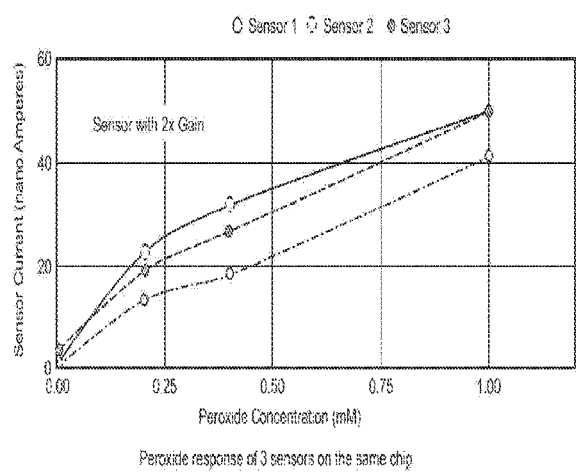
Figure 51B:
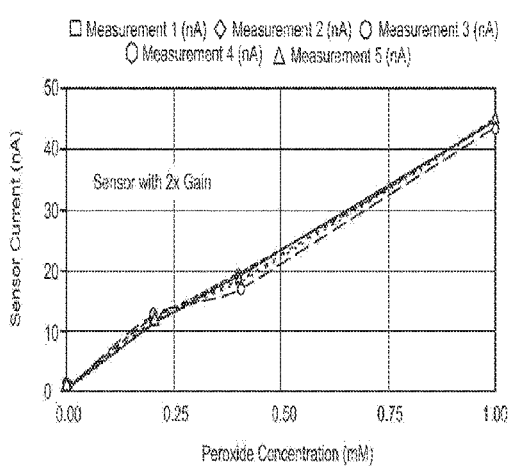

FIG. 51A, FIG. 51B, and FIG. 51C show peroxide response of a sensor during repeated testing. FIG. 51A shows peroxide concentration versus sensor current for a sensor with a lower current range (designed in the potentiostat) while FIG. 51B shows peroxide concentration versus sensor current for a sensor with higher range. FIG. 51C shows example peroxide responses of three different sensors on the same chip. The small variations can be decreased using more repeated processing and cleaning of the sensor surface.

Figure 52A:
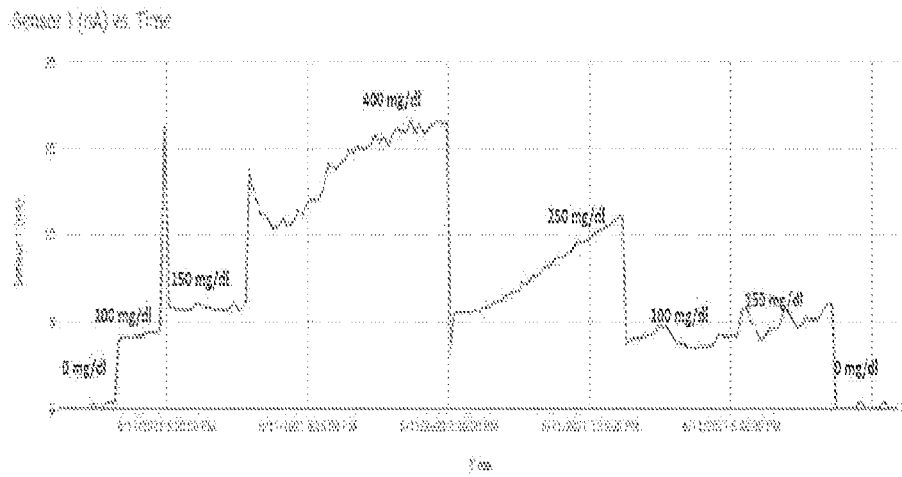
Figure 52B:
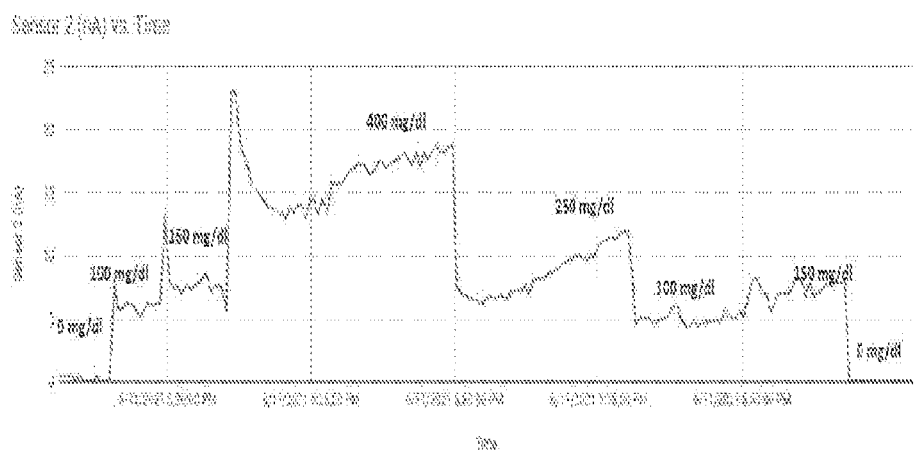
Figure 52C:
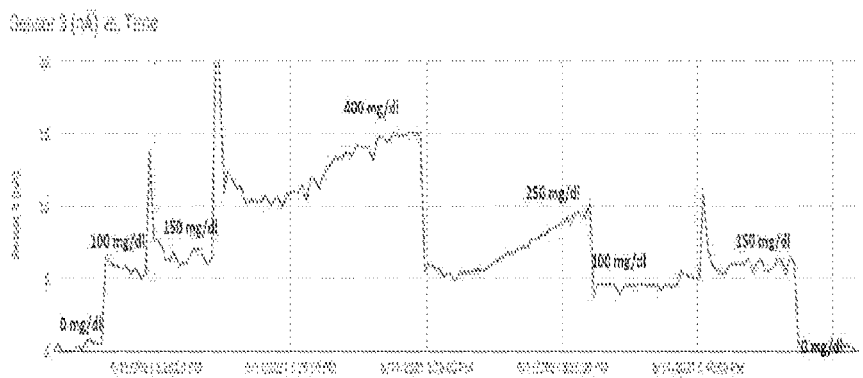

FIGS. 52A, 52B, and 52C show glucose concentration versus sensor current. FIG. 52A shows a chart for sensor one chip. FIG. 52B shows a chart for sensor two. FIG. 52C shows a chart for sensor three.

Figure 53A:
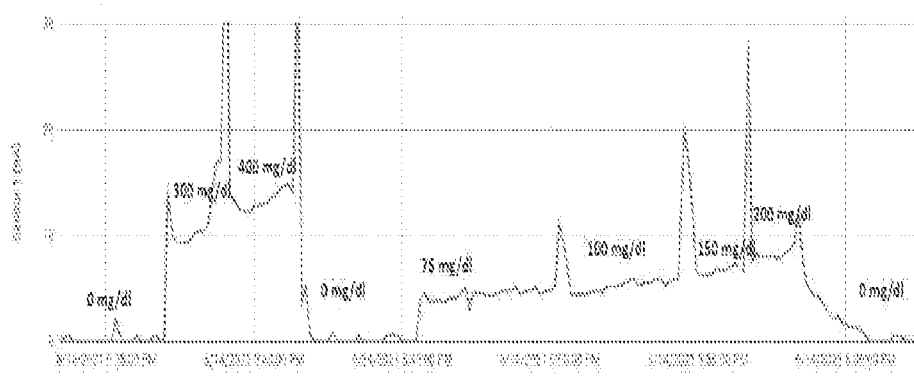
Figure 53B:
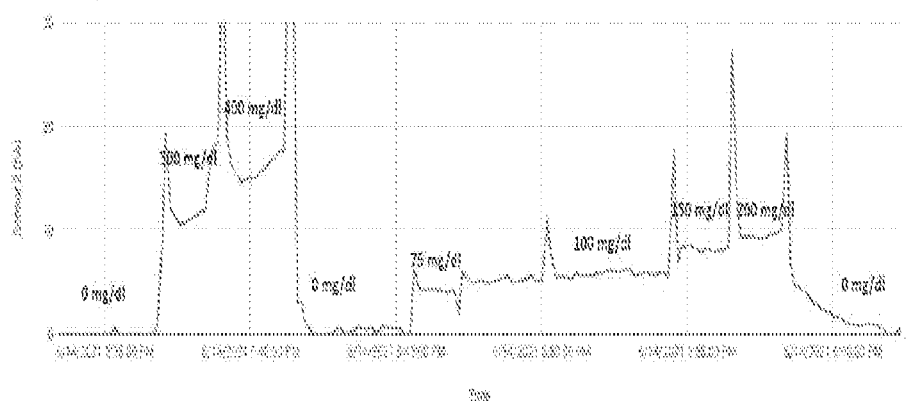
Figure 53C:
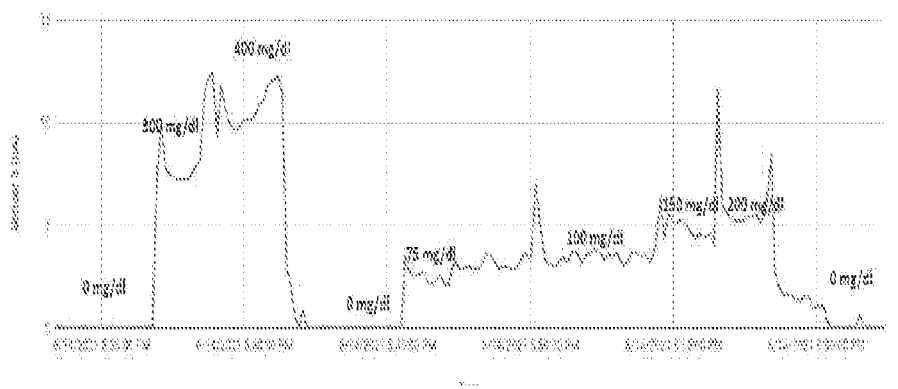

FIG. 53A, FIG. 53B, and FIG. 53C show an in vitro glucose titration for each of three sensors on another sensor chip. FIG. 53A shows the response curve of sensor one. FIG. 53B shows the response curve of sensor two. FIG. 53C shows the response curve of sensor three.

Figure 54A:
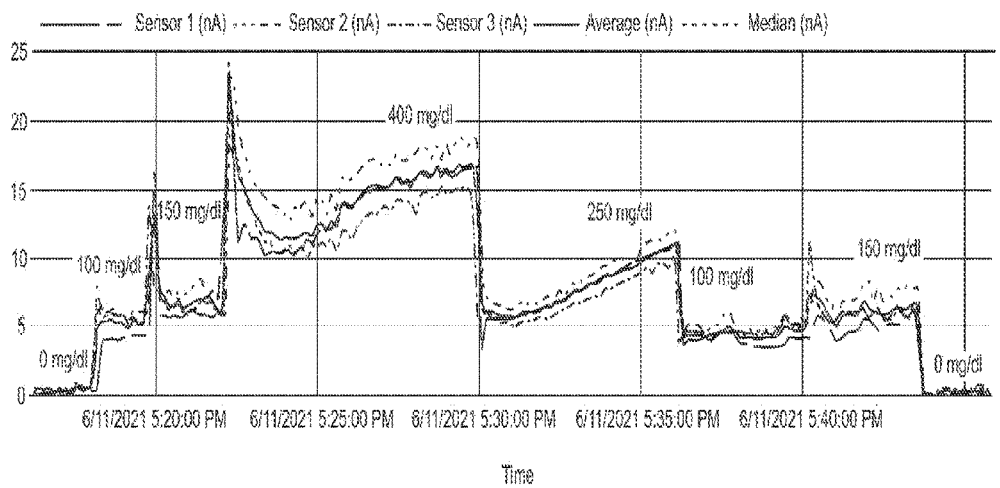
Figure 54B:
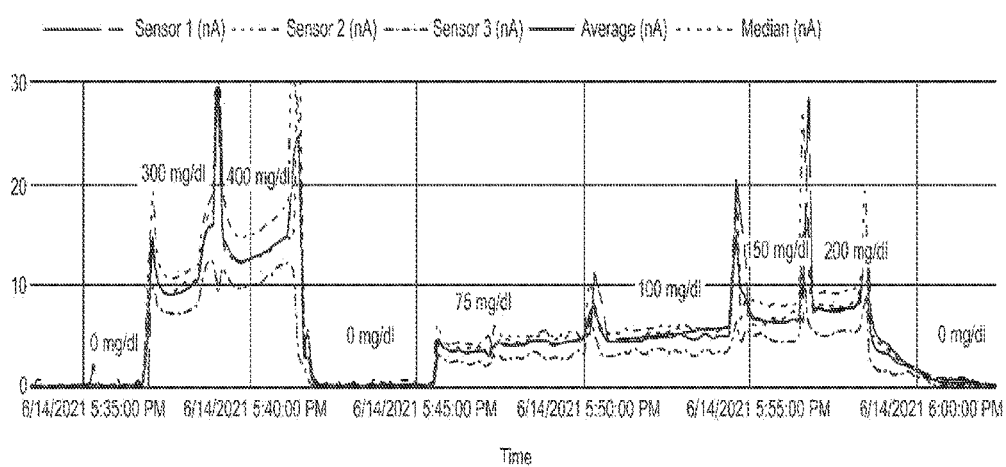

FIG. 54A and FIG. 54B show in vitro glucose response for each of three sensors on two separate dies, along with their median and average readings. FIG. 54A shows data from all 3 sensors on one integrated sensor chip while 54B shows the data from all 3 sensors on a second integrated sensor: together with average and median of all 3 sensors from respective dies in both cases.

Figure 55:
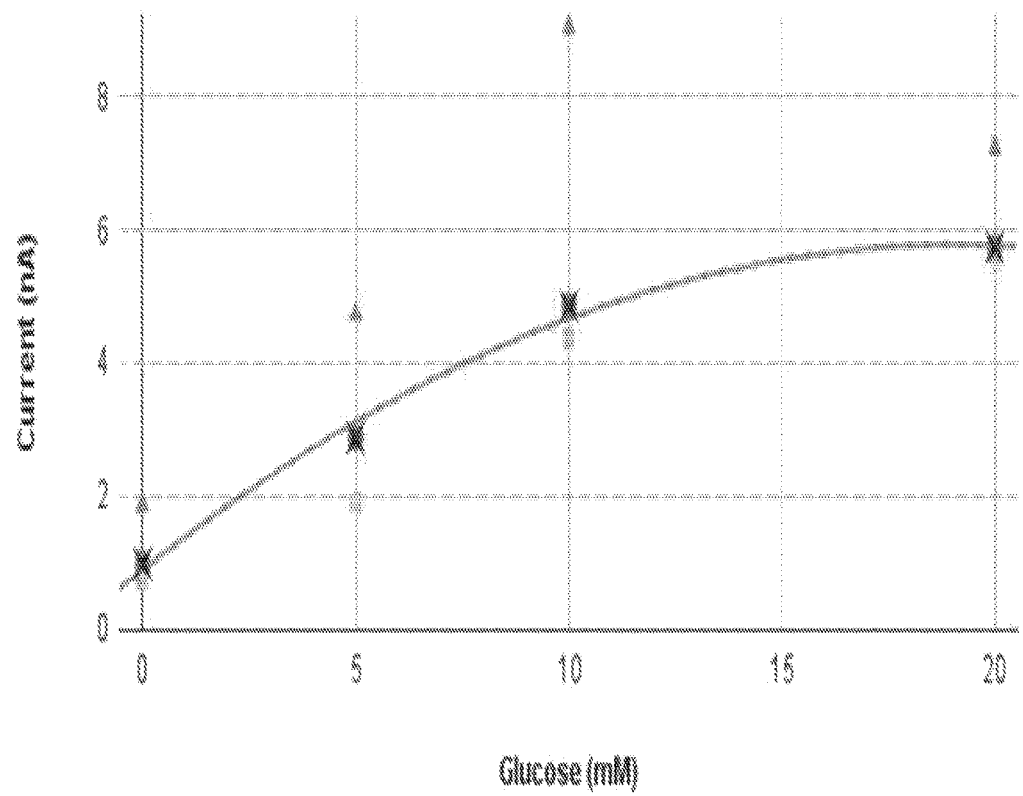

FIG. 55 shows how the reading from all 3 sensors can be used together to generate a more accurate overall result than any single sensor individually using a statistical combination of the sensors" data (e.g., median in this figure).

Figure 56:
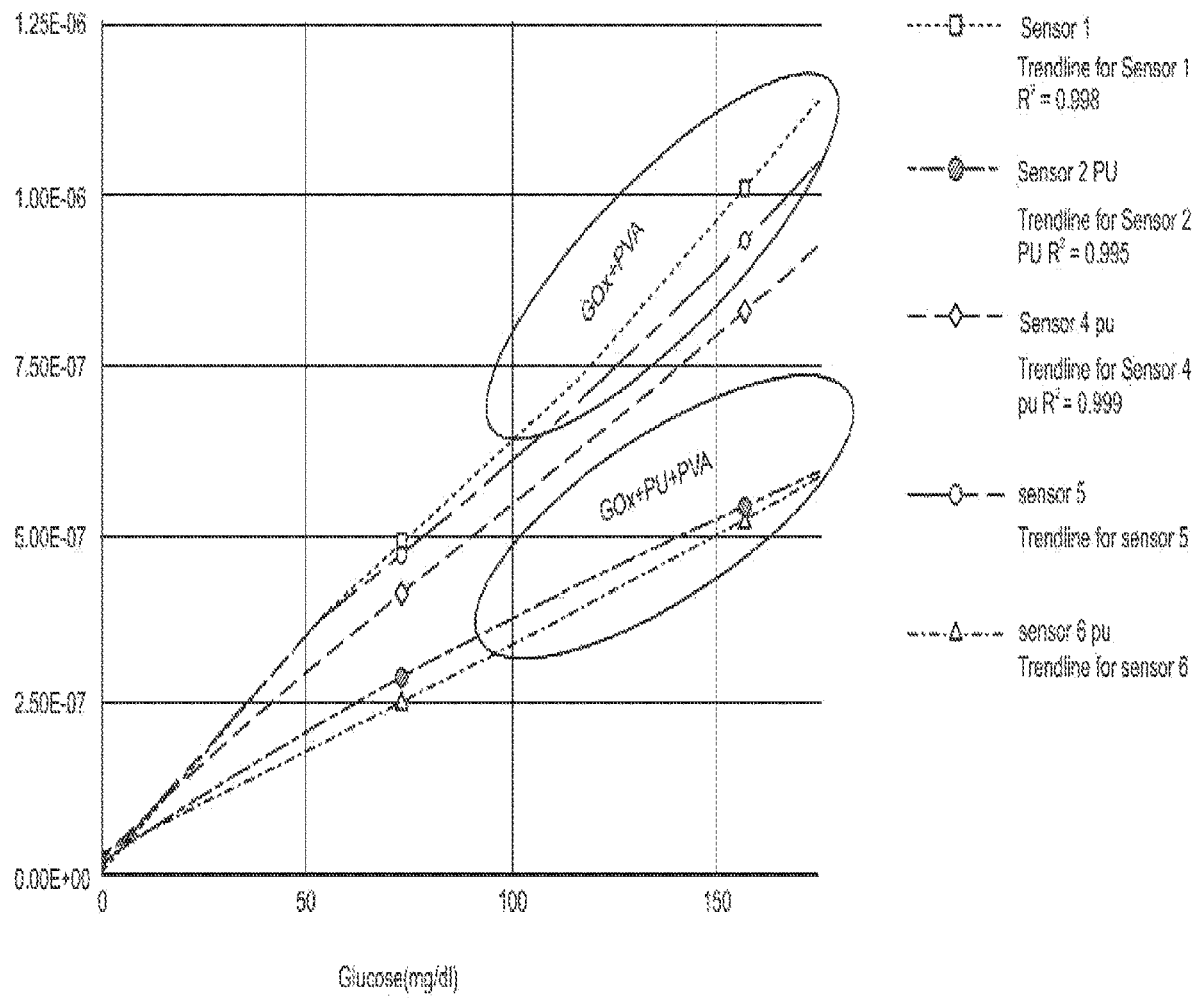

FIG. 56 shows the effect of hydrophilic coating (PVA) on sensor response. It shows that the PVA coating can be done both with and without the polymer membrane (e.g., PU) and it doesn't impact the glucose sensing properties of the sensor negatively.

Figure 57A:
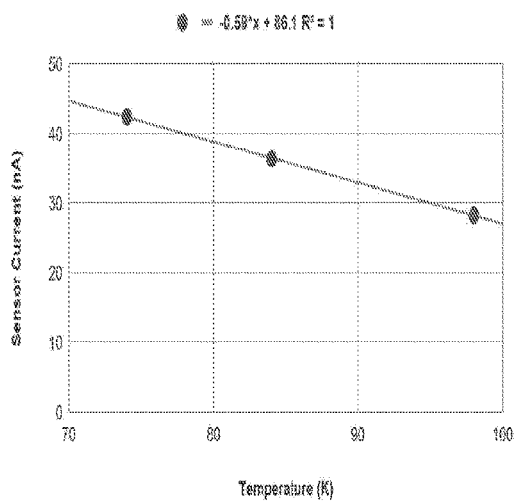
Figure 57B:
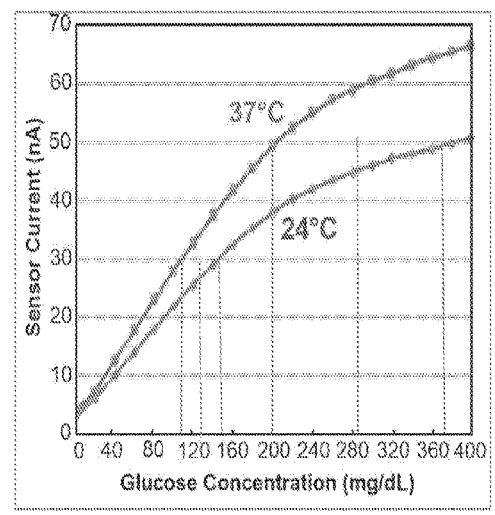

FIG. 57A and FIG. 57B show data from the integrated temperature sensor. FIG. 57A shows the simulation results for the sensor response. FIG. 57B shows one reason why the temperature sensor data is required as the enzyme activity is proportional to temperature, leading to change in current if temperature changes.

Figure 58A:
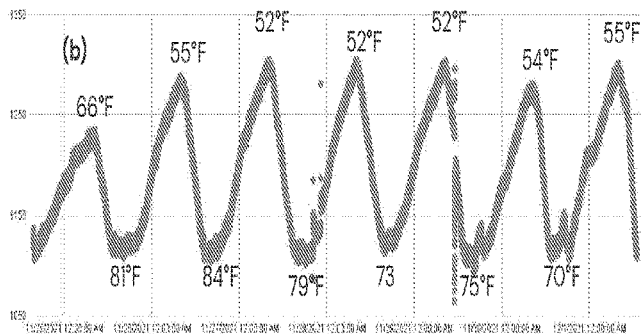
Figure 58B:
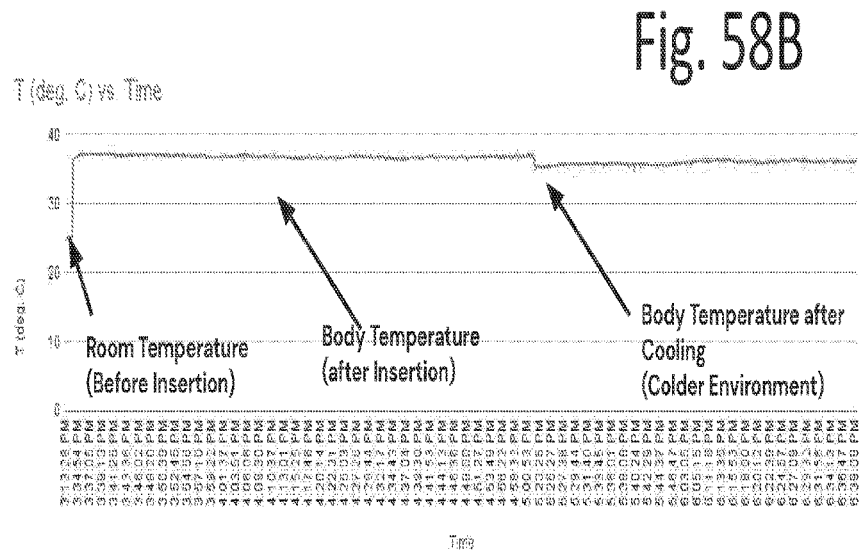

FIG. 58A and FIG. 58B show the testing results for the integrated temperature sensor. FIG. 58A shows a 7-day test of the sensor in a saline solution to track changes in the environment temperature (daily temperature cycle). FIG. 58B shows how the sensor can track the change in environment temperature after insertion in a person vs. the room temperature before insertion, as well as how it can detect a change in the tissue temperature created by blowing cold air on the skin.

Figure 59A:
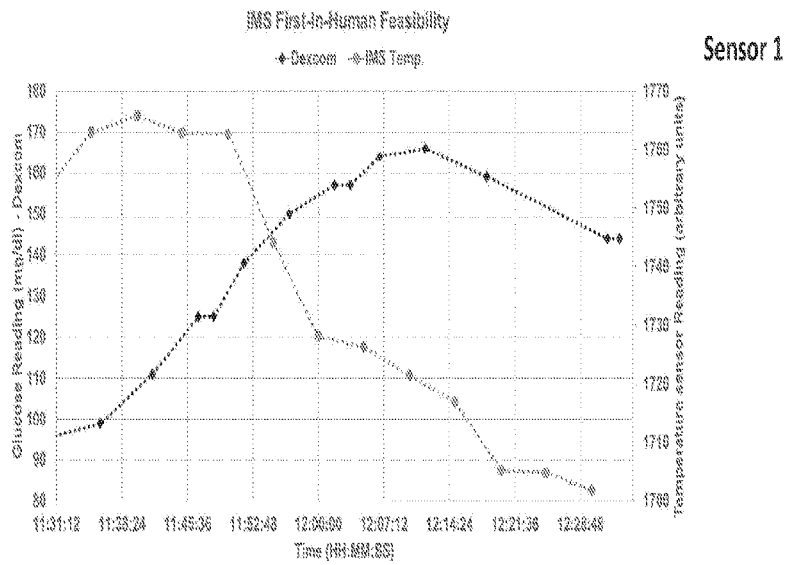
Figure 59B:
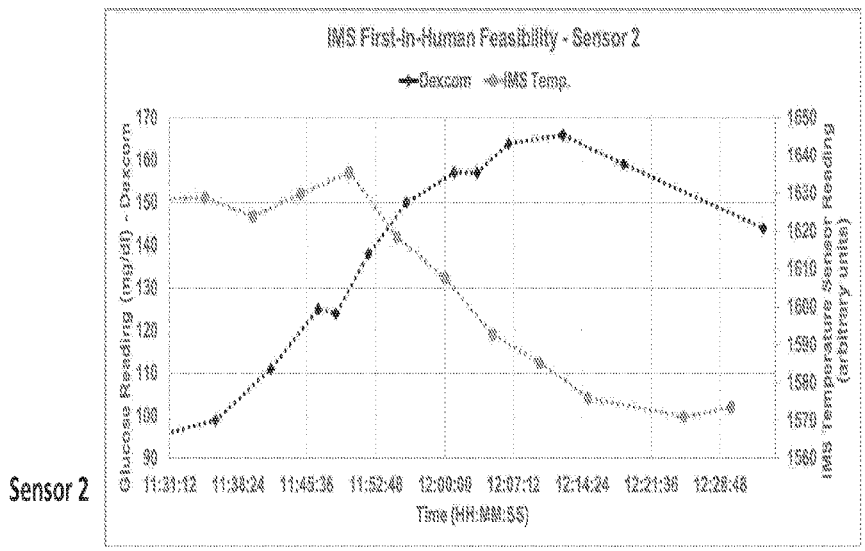

FIG. 59A and FIG. 59B show human data of the temperature sensor. FIG. 59A and FIG. 59B show the temperature sensor can detect fall in subcutaneous tissue temperature due to decrease in glucose and can detect increase in subcutaneous temperature as glucose excursion drives this temperature up. This is consistent among two different sensors worn by the same person.

FIG. 60A, FIG. 60B, and FIG. 60C show the IMS glucose sensor response in a First-in-Human (FIH) study. FIG. 60A and FIG. 60B show that two different IMS sensors can trace glucose excursions vs. a contour meter (primary references) as well as commercial CGM references (Dexcom G6, Abbott Libre 2). The Clarke-error grid of FIG. 60C shows the IMS sensor following the contour reference quite accurately.

Figure 61A:
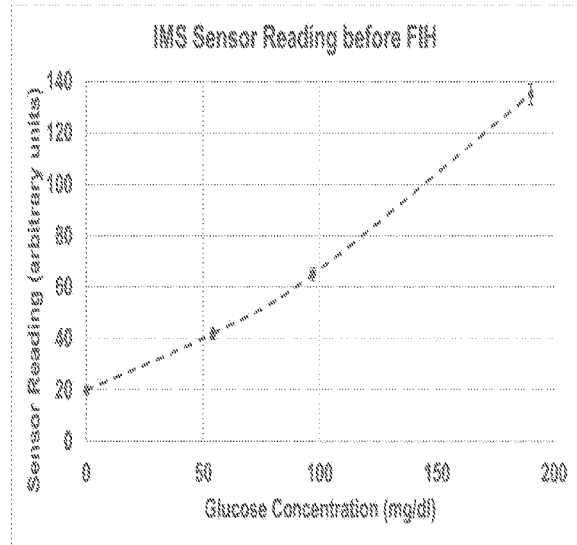
Figure 61B:
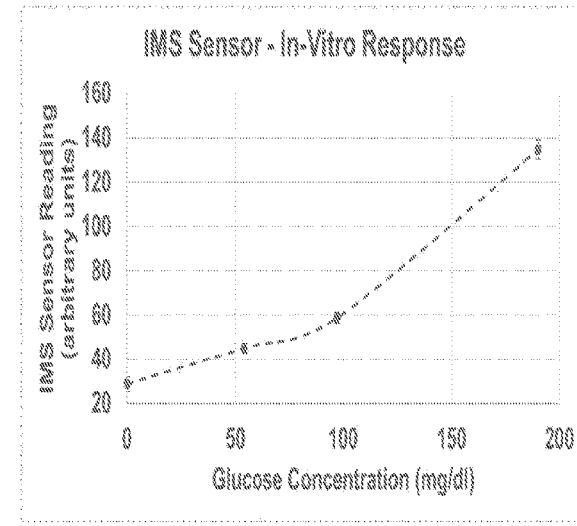

FIG. 61A and FIG. 61B show the response of the FIH sensor before and after the FIH study. FIG. 61A shows the sensor was responsive to glucose in the target range for a prediabetic individual (50-200 mg/dl). FIG. 61B shows that the sensor was still responsive without a significant loss of its performance after the FIH study (for a 3-day wear period).

Figure 62A:
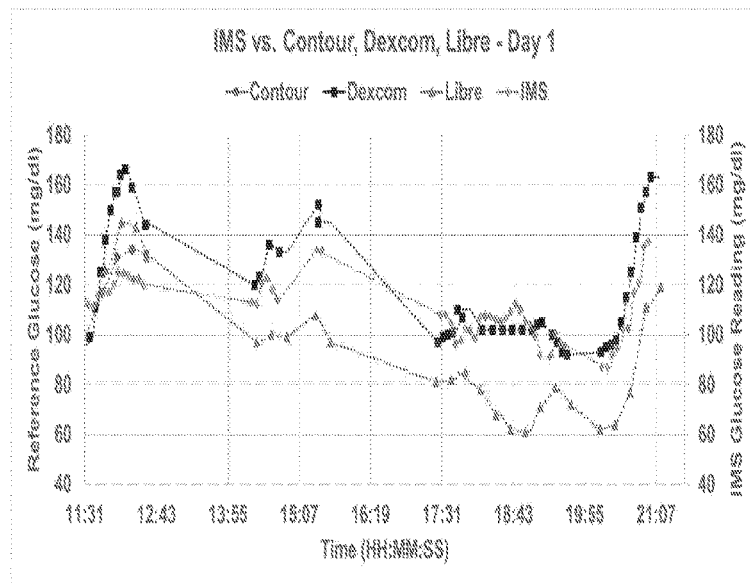
Figure 62B:
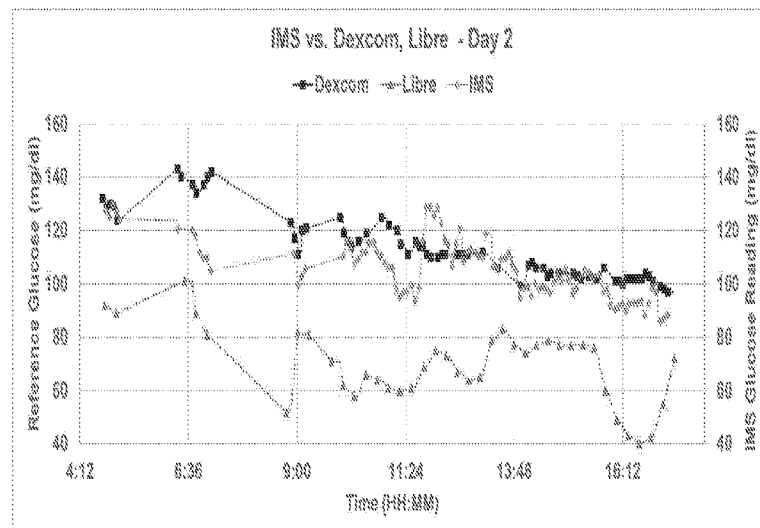
Figure 62C:
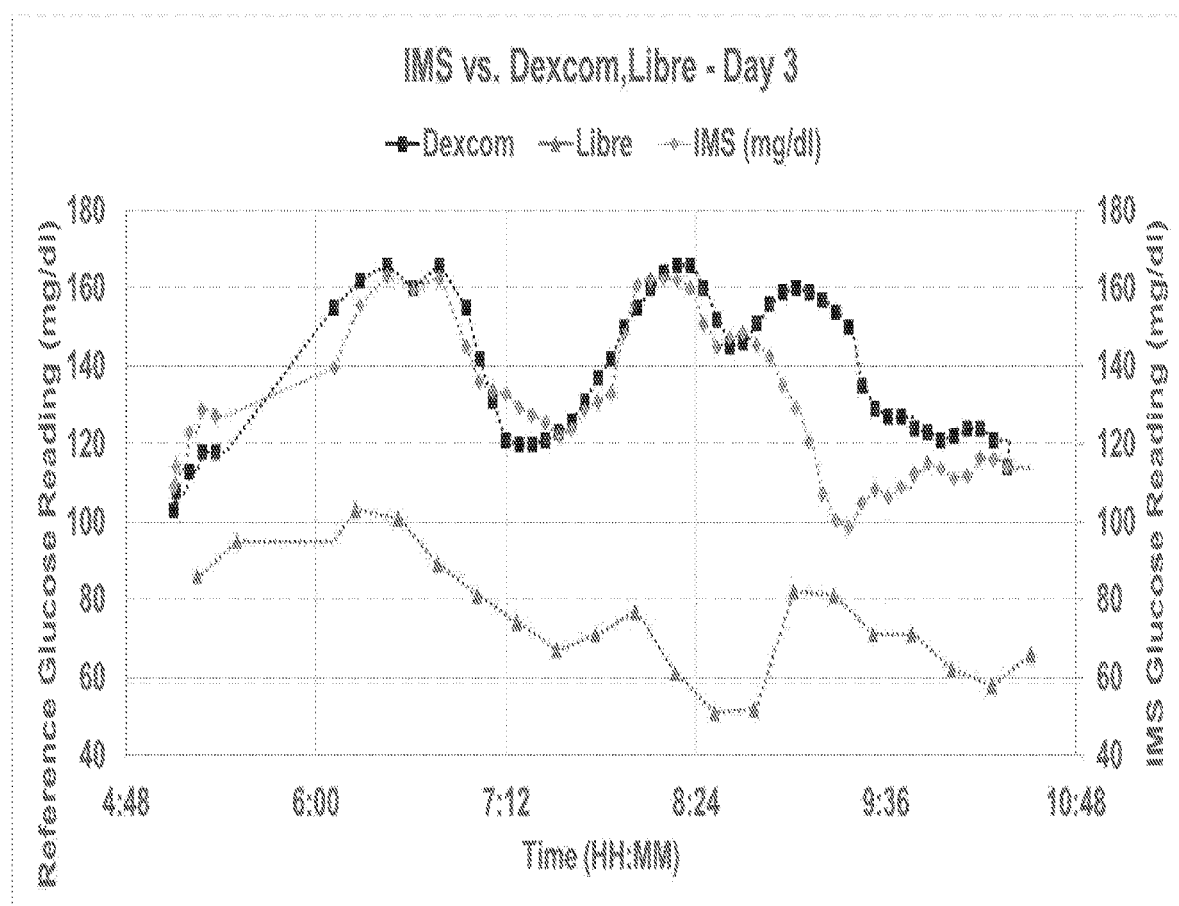

FIG. 62A, FIG. 62B, and FIG. 62C show the human testing data from a 3-day wear period. FIG. 62A shows day 1, FIG. 62B shows day 2, and FIG. 62C shows day 3.

Figure 63:
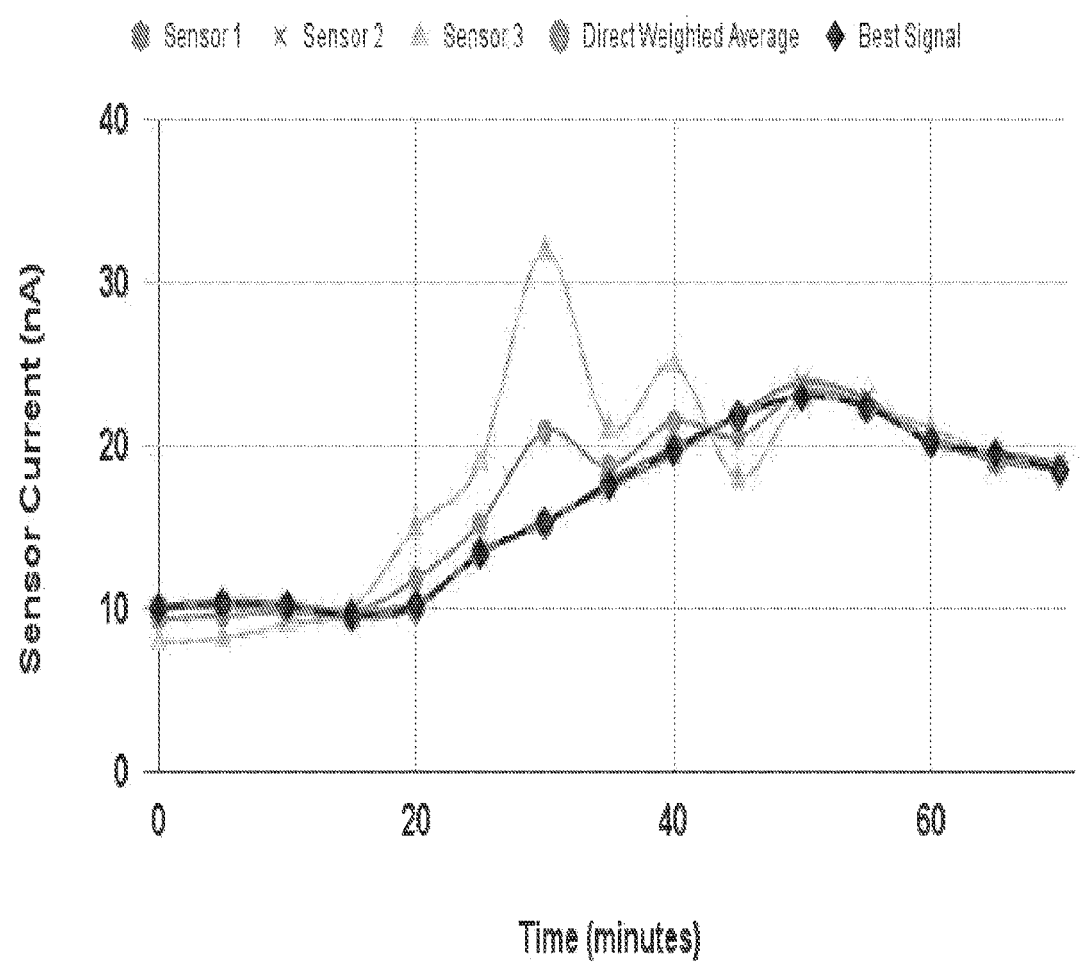

FIG. 63 shows the effect of a simple multi-sensor data fusion scheme in improving the overall outcome of the sensor. It shows that the data fusion scheme results in a more accurate output, even in cases where some of the on-chip sensors have some error.

Figure 64:
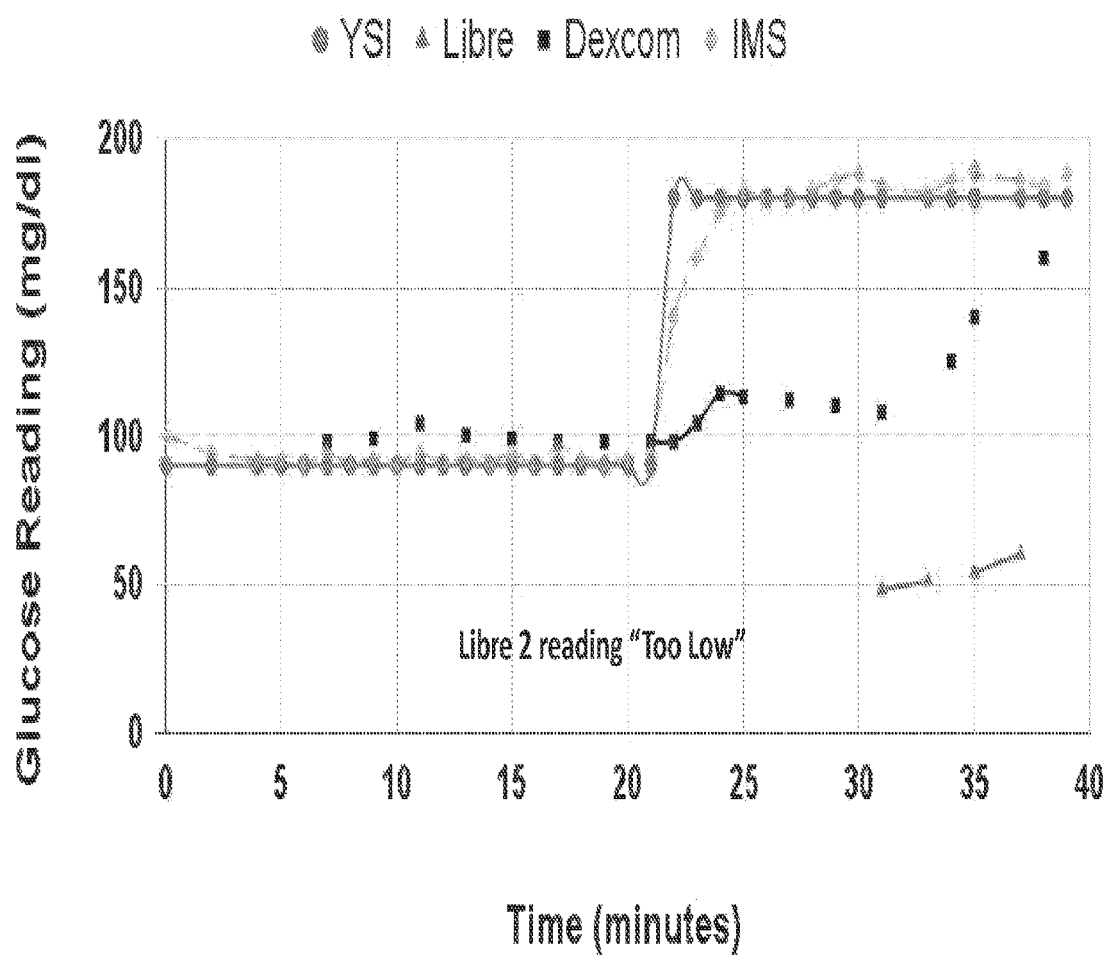

FIG. 64 shows the improvements in rate responsiveness for the IMS device as compared to the commercial references, due to the thin sensor coatings and higher accuracy (requiring lesser averaging)

DETAILED DESCRIPTION

The present disclosure is directed to an implantable monolithic integrated sensor circuit and system that can be used in a variety of in-vivo applications providing continuous measurement of one or more types of health or biological markers (e.g., metabolites). Glucose is an example analyte discussed herein. As a person having ordinary skill in the art will appreciate, the described devices, systems and methods can be more generally applied to other analytes and analyte combinations. Additionally, some ex-vivo uses are easily envisioned.

System Design

An overview of an embodiment of the system of the present disclosure can be seen in FIG. 1. The system can include a monolithic integrated sensor circuit 1 that is connected to an external transmitter 2 through a connector 3 made of conductive material which may be coated with a biocompatible polymer. The connector 3 may be a flexible connector. The transmitter 2 provides electrical power to the monolithic integrated circuit 1 via the flexible connector 3. It also communicates to the monolithic integrated circuit 1 via the flexible connector 3. The communication can be bi-directional or unidirectional. Transmitter 2 can be wirelessly linked to a smart reader (e.g., smartphone) 4, smart insulin pump/pen 9, and/or a secure database 5 using a wireless communication technology such as Bluetooth, Zigbee, or WiFi 6, 7. Alternatively, the smart reader 4 can act as a bridge between the transmitter and the secure database 5. The details of the important parts of the system are provided next.

Monolithic Integrated Sensor Circuit

In accordance with some embodiments of the disclosure, the monolithic integrated sensing circuit is, for example, an integrated circuit chip fabricated using CMOS fabrication technologies known to the person skilled in the art.

An important element of the monolithic integrated circuit is the small size of the chip. The monolithic integrated sensor circuit can include many interconnected functional modules or subsystems and can be in a range from 30 microns to 600 microns in thickness (e.g., 50 microns to 150 microns), 500 microns to 10,000 microns in length (e.g., 1500 microns to 3000 microns) and in a range from 100 microns to 4,000 microns in width (e.g., 400 microns to 1000 microns).

The small size of the monolithic integrated sensor circuit along with shaping can minimize scar tissue formation in the body to a point where it only helps in keeping the system position stable but does not significantly isolate the implantable monolithic integrated sensor circuit from accessing body fluids. This allows real-time measurement of important analytes (e.g., metabolic glucose level) for critical applications requiring instant changes to be reported as soon as possible (e.g., for hypoglycemic diabetic patients).

Designing the monolithic integrated circuit in accordance with the specific implantation/insertion site (tissue orientation etc.) can help in reducing post-implantation complexities. For example, for implantation/insertion in biological tissues, the sensing platform can be shaped to minimize sharp edges to minimize tissue damage and hence immune system response. The monolithic sensor circuit can be shaped to be longer in one dimension and much smaller in other dimensions to inject or insert the monolithic circuit using very small needles. This also allows the monolithic circuit to fit within the subcutaneous or subdermal space more easily. Minimizing the device thickness and coating it with a biocompatible soft material can also make it more flexible and reduce tissue damage.

A precisely controlled minimization of solid-state sensor size also reduces detection noise levels and can increase the Signal-to-Noise ratio (SNR), thus improving the sensitivity of the sensor. This miniaturization and accompanying SNR improvement is not possible without the added on-chip circuitry which can read the low current without much added noise of a longer-distance transmission. Furthermore, a compact integrated design minimizes contact resistance and capacitance between the sensor and the electronics, further enhancing sensitivity by improving the SNR of the sensor. Moreover, the decrease in electrode size reduces its capacitance which further reduces non-faradaic (charging) currents, thus improving SNR and decreasing the time it takes for the sensor to stabilize. The minimum SNR for a reliable detection is typically considered to be 3 (Signal to Noise Ratio: unitless). In glucose oxidase functionalized embodiments, when in patient, the integrated sensor circuit of the present disclosure is capable of SNR ranges of 5-30, or more preferably 10-20. In post-processed form, when in peroxide, the integrated sensor circuit of the present disclosure is capable of SNR ranges of 5-100, or preferably 60-100, or more preferably 70-80. (Please see, Donald M. Morgan and Stephen G. Weber, Noise and Signal-to-Noise Ratio in Electrochemical Detectors, Anal. Chem. 1984, 56, 13, 2560-2567, herein incorporated by reference in its entirety).

Sensor fabrication can start with submitting the chip design files to a semiconductor manufacturer (e.g., TSMC (Taiwan), ON Semiconductor (Phoenix, AZ)). The standard semiconductor fabrication processes can generate standard wafers of certain sizes (e.g., 12-inch diameter wafers). To reduce the dimension of the device, the original thickness (e.g., 750 µm) of the semiconductor wafer can be thinned down (e.g., to 50-250 µm) through mechanical grinding, chemical and/or mechanical polishing or chemical etching (e.g., Xenon Difluoride ($XeF_2$) etching from backside). This step can be done before or after surface functionalization and membrane chemistry deposition. Once thinned, the silicon becomes more flexible and can improve the integration of the sensor device within the surrounding tissue and reduce foreign body response. Thinning and/or grinding can be performed by a thinning and grinding facility (e.g., Advanced International Technologies, Quick-Pak). Some common exemplary CMOS process nodes which can be used for fabrication of the monolithic integrated sensor are TSMC 180 nm, 65 nm, 55 nm, 250 nm, 90 nm.

Different types of dicing methods (saw, laser, stealth, etc.) along with some polishing methods can be used to realize any desirable shape (e.g., circular, rectangular, oval). Laser cutting can be used to form rounded edges on the final diced device and help reduce potential implantation injury and subsequent foreign body response. Laser dicing can be accompanied by appropriate environmental condition (e.g., oxygen flow) to create a thin layer of thermal oxide on sidewalls during dicing. Steam can also be used to generate a wet oxide on sensor sidewalls. Sidewall polishing after dicing can also be used to reduce and remove sharp edges. Further, coating with biocompatible membranes can also be used to minimize any sharp edges.

Figure 3:
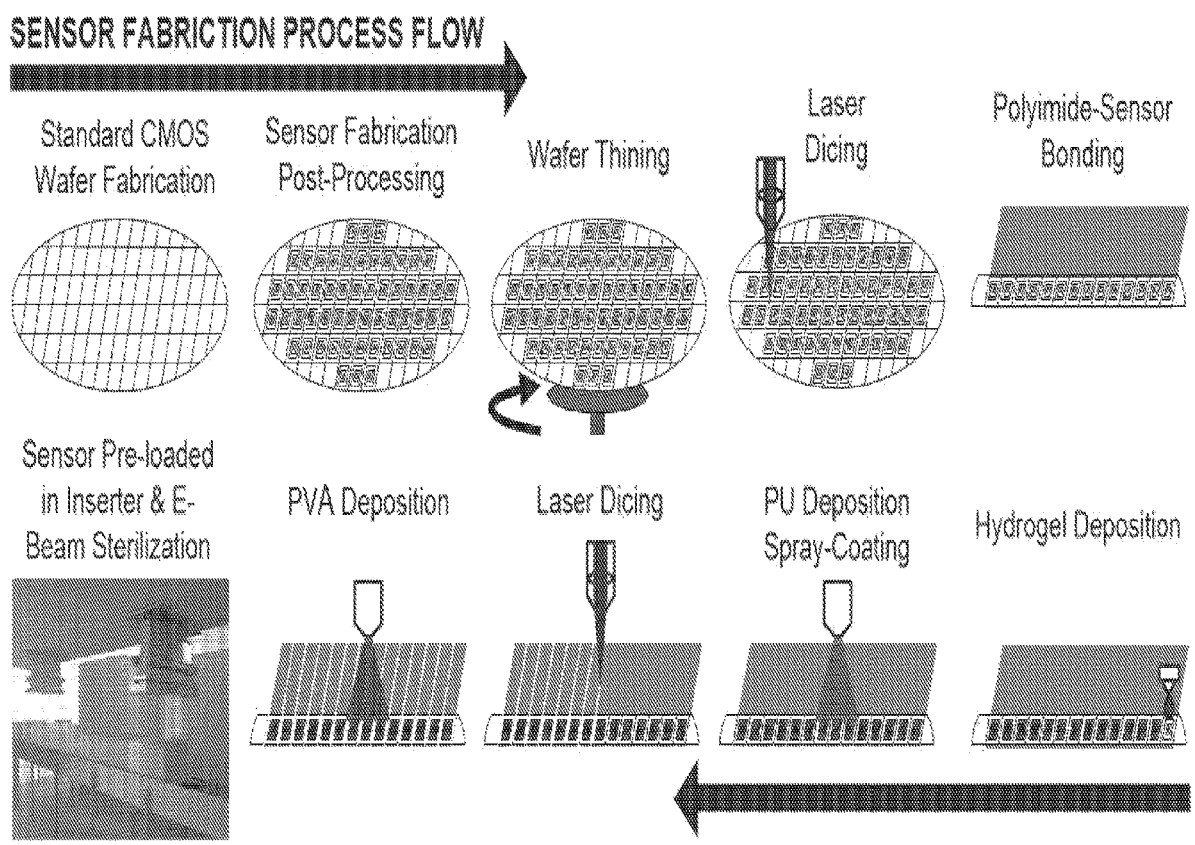
FIG. 3 shows a scheme of fabricating the integrated sensor 1, the flexible connector 3, the transmitter 2, and the applicator (inserter) 8 and assembling them together in a scalable manner. This fabrication uses a series of process steps commonly used in the semiconductor industry including CMOS fabrication, Postprocessing, Wafer thinning, Spin coating, dicing, bonding, enzyme chemistry deposition and spin coating, Polymer (e.g., PU) membrane deposition and spin coating or spray coating (both possible), dicing pf the bonded substrates to separate the bonded sensors, coating of the separated devices with biocompatible material (e.g., PVA) to cover the sidewalls, and assembly of the sensor with the transmitter and the applicator following sterilization.

FIG. 3 shows an embodiment of a complete wafer with multiple rows of the monolithic integrated sensor circuits fabricated using a CMOS process. FIG. 3 and FIG. 27 show an instance of how a row of monolithic integrated circuits 610 can be separated from the wafer using dicing. Note that, individual or rows of monolithic integrated sensor circuit can be diced before post processing or as a final step after processing. FIG. 3 and FIG. 27 show an instance of how finished individual monolithic integrated circuits 660 can be separated by dicing the sensor-PCB assembly together.

Figure 2A:
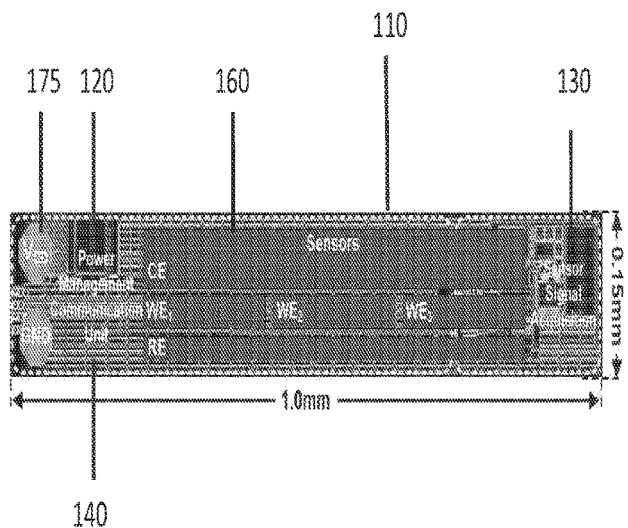
FIG. 2A and FIG. 2B show an embodiment of an implantable monolithic integrated sensor circuit 1 with multiple on-chip electrodes.
Figure 2B:
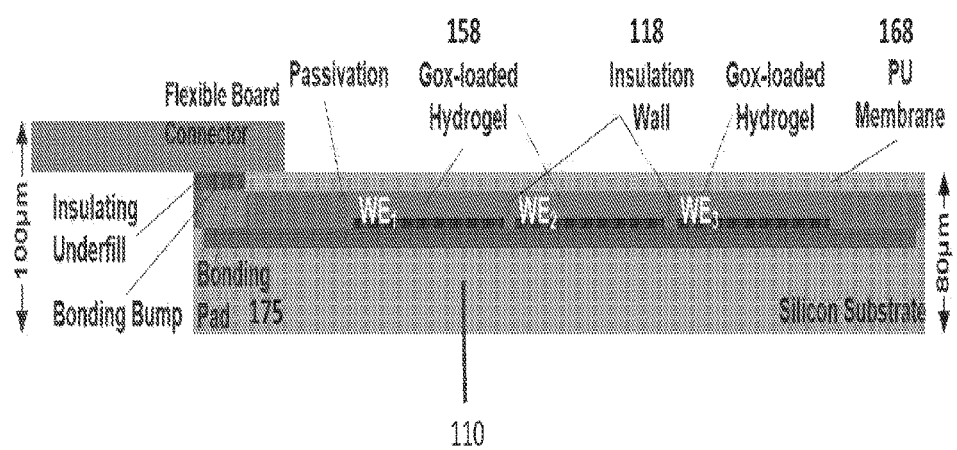

An overview of an embodiment of the monolithic integrated sensor circuit 1 of the present disclosure can be seen in FIG. 2A and FIG. 2B. In some embodiments of the disclosure, the monolithic integrated sensor circuit 1 can include an integrated sensing element 160. The integrated sensing element 160 may also be referred to as an "electrochemical sensing element". The monolithic integrated circuit can further contain a power management unit 120, a sensor signal acquisition unit 130, a communication unit 140, and an optional interface unit 175. The interface unit may provide further circuitry to better communicate with other components of the system, e.g., the transmitter. The interface unit is most often wired in the present instance. In its simplest embodiment, the interface unit may consist of a couple of contact pads that provide a convenient interface for the wired connector which links the transmitter. The monolithic integrated sensor circuit includes on-chip connectors 175 in the interface unit. Exemplary dimensions are also included at 35 µm and 0.15 mm.

Figure 4:
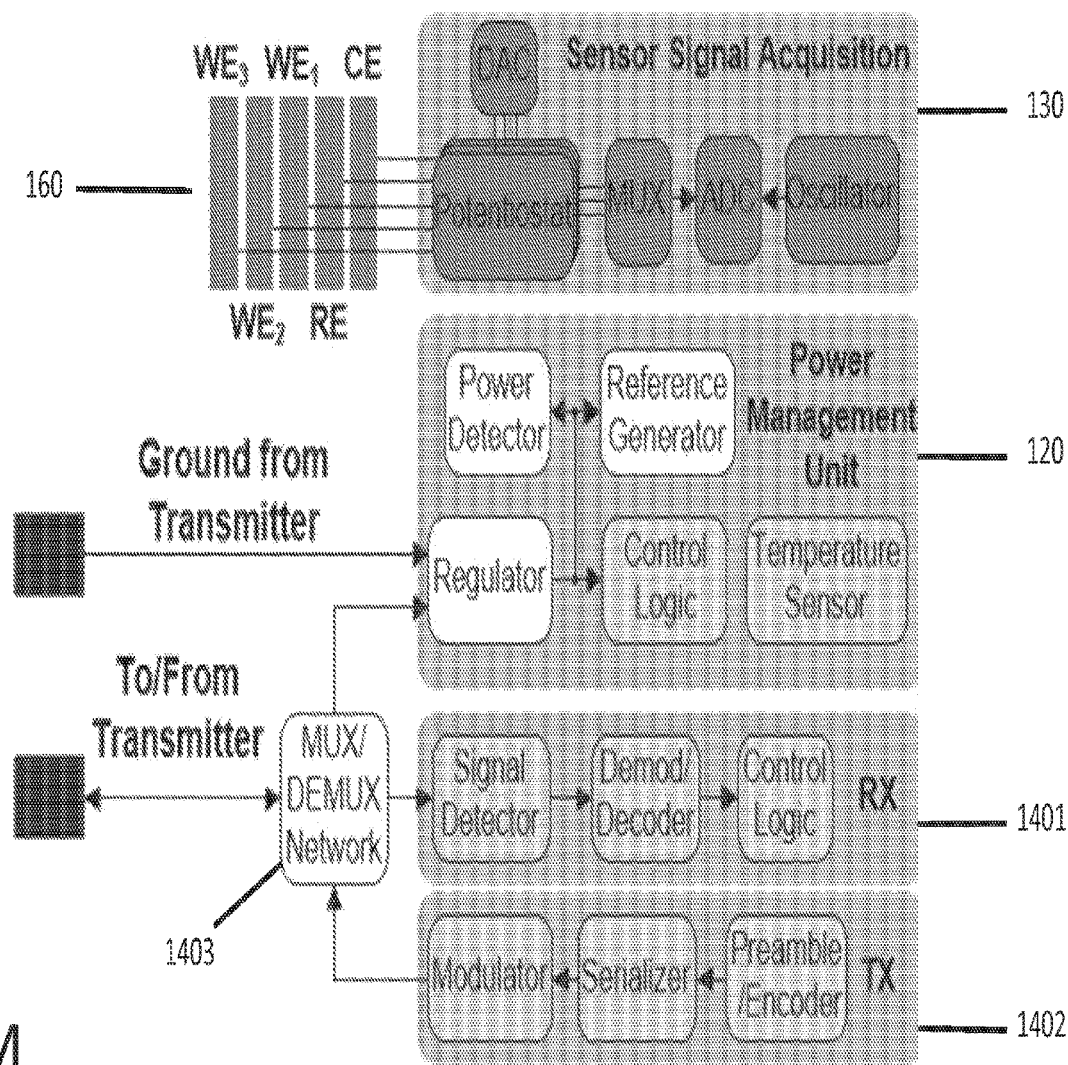
FIG. 4 shows a schematic of the components of an implantable monolithic integrated sensor circuit 1 according to some embodiments of the disclosure. The implantable monolithic integrated sensor circuit 1 can include an integrated sensing element 160, a power management unit 120, a sensor signal acquisition unit 130, and a communication unit which comprises a signal receiver unit 1401, a signal transmitter unit 1402, and a MUX/DEMUX unit 1403.

A more specific design view of an embodiment can be seen in FIG. 4. The monolithic integrated circuit again includes an integrated sensing element 160, sensor signal acquisition unit 130, power management unit 120, and a communication unit 140. The communication unit 140 further comprises a receiver subsystem (RX) 1401, a transmitter subsystem (TX) 1402, and a MUX/DEMUX network 1403 to separate the communication signal for the power signal. FIG. 4 shows an interface unit comprising two electrical pads. One pad functions as ground from the transmitter. The other pad functions as data over power connected to the MUX/DEMUX network 1403.

Figure 5:
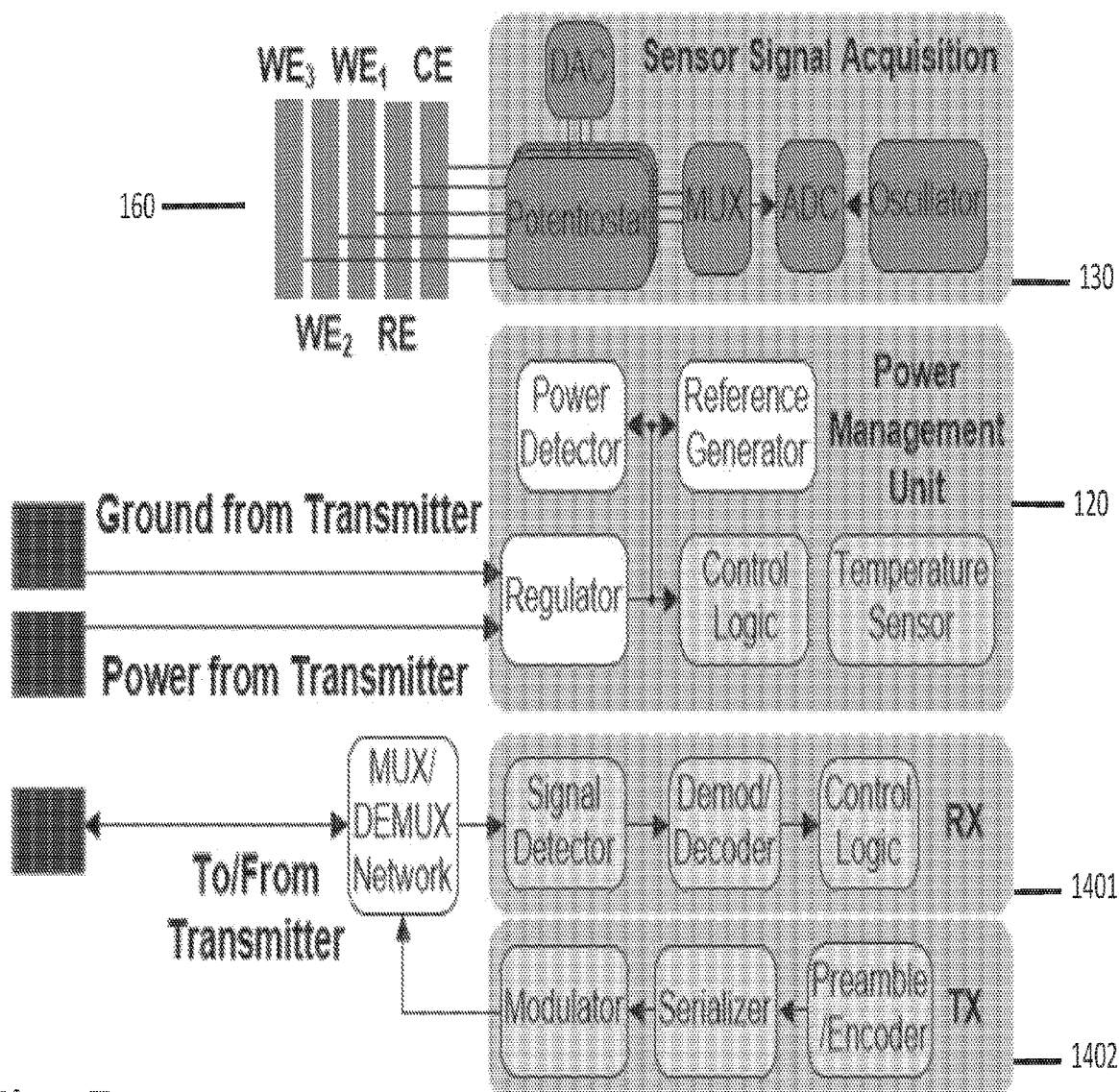
FIG. 5 shows a schematic of the components of an implantable monolithic integrated sensor circuit 1 according to some embodiments of the disclosure. The implantable monolithic integrated sensor circuit 1 can include an integrated sensing element 160, a power management unit 120, a sensor signal acquisition unit 130, and a communication unit which comprises a signal receiver unit 1401, a signal transmitter unit 1402, and a specific example form of MUX/DEMUX in the form of a capacitor.

FIG. 5 contains a specific example wherein data is separated from power. The interface unit comprises three pads. A pad is connected to ground into the power management unit 120. A pad is connected to power into the power management unit 120. A pad functions as data connected to the MUX/DEMUX network.

As shown in FIG. 4 and FIG. 5, the receiver subsystem 1401 can compose of a signal detector, a demodulator/detector, and control logic. In the receiver subsystem 1401, the signal detector (e.g., envelope detector) can be used to extract the data transmitted from the external transmitter through, for example, a two-wire flexible connector.

A data encoding scheme (such as pulse width modulation or coding, pulse interval modulation or coding, pulse code modulation or coding, pulse count modulation or coding, Manchester Coding etc.) is used to send data from the transmitter to the sensor. Pulse code modulation being a preferred embodiment. Therefore, a data demodulator/decoder is utilized in the sensor receiver to decode the received signal which can include an activation tag for the implant as well as the sensor current measurement range. The control logic can perform signal conditioning and interpretation of the received data from the external transmitter 2.

As shown in FIG. 4 or FIG. 5, the transmission subsystem 1402 can include a preamble/encoder, serializer, and modulator. The TX unit can take sensor data from the sensor signal acquisition unit (e.g., ADC), encode it using a specific data encoding scheme for minimizing communication error (e.g., Pulse count coding), add predefined sequences (e.g., preambles, pilot sequences) and transmit the encoded data to the external transmitter using data communication-over-power scheme.

In the transmission subsystem 1402, the preamble/encoder can combine the sensor data into one or more packets that can be sent to the external transmitter. The packetized data can include the sensors (e.g., electrochemical, temperature) measured data and power level indicator. For example, the preamble/encoder can, in embodiments, combine all the data elements into a single data packet and add a preamble sequence at the beginning of the data packet for ease of detection by the external transmitter 2. The serializer can serialize data packets received from the preamble/encoder. An error detecting and/or correcting sequence (e.g., cyclic redundancy check or CRC, hamming code) can be added to the packets for immunity to communication and detection noise. The modulator can take the data in digital form and change into waveform for sending to the transmitter 2 over the wire 3 of the implantable sensor circuit.

As shown in FIG. 4 or FIG. 5, the power management unit 120 can include a regulator (e.g., low V-LDO regulator), reference generator, power detector, temperature sensor, and control logic. In some embodiments the power management may also include a voltage limiter. The regulator can be a low-dropout regulator that regulates the incoming supply signal from the transmitter through a two-wire connector (which is an example of the wire 3) into a clean DC voltage (without ripples).

The reference generator can generate the reference voltages and currents used by the ADC, potentiostats, and the oscillator of the sensor signal acquisition unit 130. The reference generator can provide high power supply rejection to eliminate sensitivity to supply ripple. Although below the sensor signal acquisition unit 130 is described as optionally containing the digital to analog converter of FIG. 8 to allow the generated reference voltages to be programmable, in alternative embodiments, the reference generator of the power management unit 120 can comprise the digital to analog converted which allows the generated reference voltages to be programmable.

Figure 11:
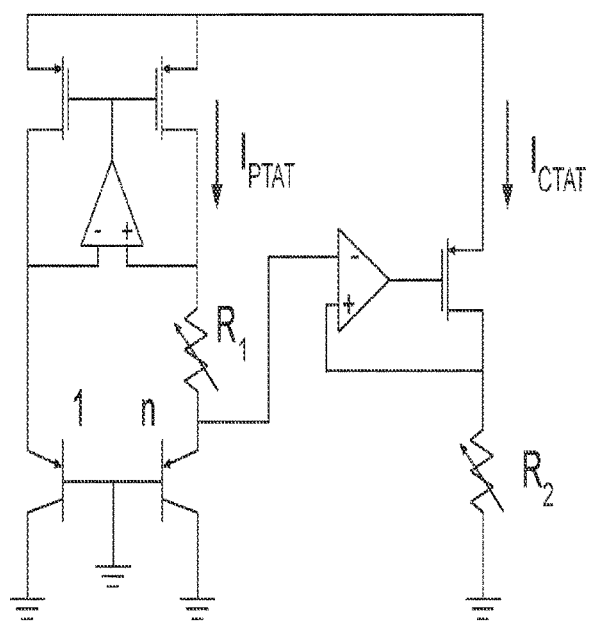
FIG. 11 shows a temperature sensor circuit. A bandgap circuitry generates currents proportional to absolute temperature (PTAT) and current complementary to absolute temperature (CTAT).
Figure 12:
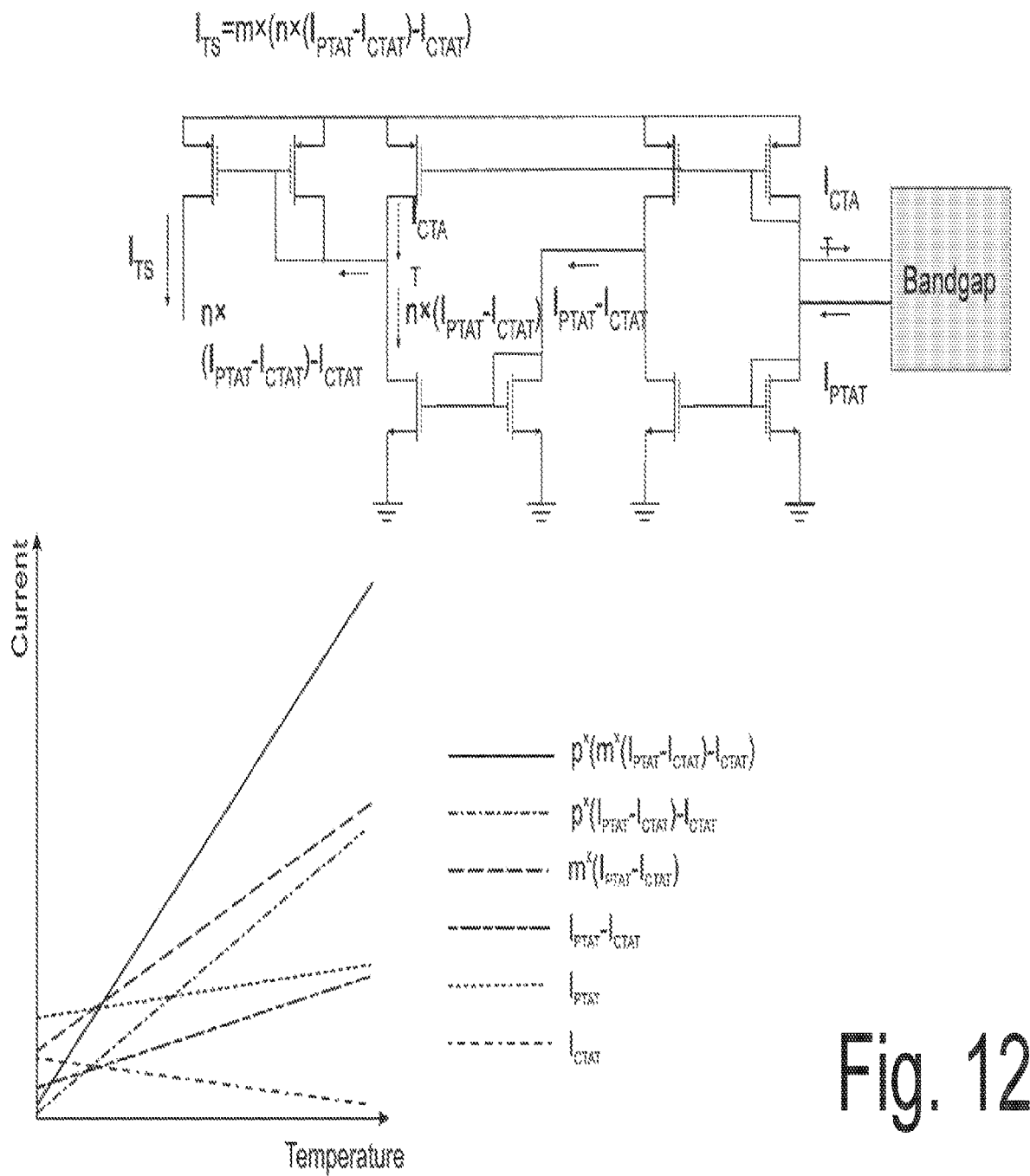
FIG. 12 shows an amplification scheme for the temperature sensor circuit current to increase sensitivity.

A temperature sensor may be included in embodiments of the power management unit of FIG. 4 or FIG. 5. An implementation of a temperature sensor can be seen in FIG. 11 and FIG. 12. FIG. 11 shows a temperature sensor circuit. A bandgap circuitry generates currents proportional to absolute temperature (PTAT) and current complementary to absolute temperature (CTAT). As shown in FIG. 11: k—Boltzmann, q—charge e, T—temperature, ln—natural log, n—ratio of the 2d area between the two bipolar transistors. FIG. 12 shows an amplification scheme for the temperature sensor circuit current to increase sensitivity. To increase the dynamic range of the temperature sensor, the offset of the temperature dependent current is removed so that at the temperature range of interest the current varies between a value close to zero and the full range of the ADC. Multiple current amplification stages bring the range of the current variation close to the ADC dynamic range. The bottom corner of FIG. 12 shows a mathematical representation of the amplification method implemented.

Another method to implement the temperature sensor is via a resistance temperature detector (RTD). In this case, a thin filament like electrode can be made on to of the CMOS device (e.g., on the top layer) using a material with good temperature sensitive resistance. The circuit underneath can read the resistance and hence any change in temperature. An example of the RTD is a Platinum based RTD. Since the IMS system enables fabrication of multiple electrodes on the CMOS substrate, fabrication of such a temperature probe is simple and can be done together with the fabrication of the electrochemical sensors. The RTD probe can be coated with a thin insulator layer afterwards (e.g., thin Silicon Nitride layer).

Various implementations of the reference generator of FIG. 4 or FIG. 5 may include a diode to provide a reference current. At different temperatures the performance of the diode may vary. Thus, a temperature sensor provides a means to measure the temperature and correct for the performance of the diode within the power management unit. These temperature measurements can be used outside of the power management unit. For instance, the temperature measurements can be provided to the user via the transmitter to calibrate the signal obtained from the sensing element 160. The temperature measurements themselves are also useful indications of the glucose concentration within a patient's body. This is because a higher glucose concentration tends to trap heat within the patient's body, causing the patient's temperature to rise.

The power detector of FIG. 4 or FIG. 5 can be used to measure the incoming power signal level and determine whether the implant is underpowered, properly powered, or overpowered, and report the power data to the external transmitter as part of packet data.

A control logic can be implemented within the power management to execute the tasks of the regulator, reference generator, power detector, temperature sensor, and voltage limiter, for instance a processor. The control logic can, in various embodiments, execute tasks for the sensor signal acquisition unit or communication unit.

In embodiments, the power management unit may include a voltage limiter. A voltage limiter can massage power to be more usable by the monolithic integrated circuit. For instance, the voltage limiter can protect the system from over-voltage by using different methods including by sinking more current and hence reducing the supply voltage from the transmitter. In accordance with some embodiments of the invention, an implantable monolithic integrated sensor circuit 1 can be powered through a power management using the two-wire flexible connector and the data transmission can use a low-power wireless communication scheme (e.g., Bluetooth Low Energy, ANT, Zigbee) as implemented through the optional interface unit.

FIGS. 21, 22, and 23 illustrate examples of different implementations of the MUX/DEMUX (Couple-Decouple) network as well as power and ground both at the sensor side as well as the transmitter side.

In FIG. 21 a capacitive decoupling network is utilized at the transmitter and the sensor to decouple the data from the power signal. At the transmitter side an amplifier and a comparator are following the network to amplify and resolve the data sent from the sensor. Communication is performed in a time multiplexed fashion, meaning when signal is being sent from the transmitter, the sensor is in the receive mode, once the transmitter sends out its data, it turns into receive mode to collect sensor data. This is shown in FIG. 21 in color code showing one direction of communication in black and the other in gray. FIG. 21A shows the scheme for sensing data from the chip (i.e., the sensor circuit 1) to the transmitter (i.e., the transmitter 2) and FIG. 21B shows the reverse scheme, i.e., from the transmitter to the chip.

FIG. 22 illustrates another variant of capacitive decoupling of the data and power at the transmitter and the sensor side. In this case, the capacitor is positioned differently with respect to the transmit and receive circuitry and the input is fed to the transmitter circuit differently as compared to the scheme in FIG. 21. FIG. 22A shows the scheme for sensing data from the chip to the transmitter and FIG. 22B shows the reverse scheme, i.e., from the transmitter to the chip. The analysis and modeling results show that this scheme can also be sued for communication.

FIG. 23 illustrates a resistive decoupling network instead of the capacitive schemes shown in FIG. 21 and FIG. 22. In this case, a resistor along with a switch is used to transmit data commands from the transmitter to the chip and vice versa. FIG. 23A shows the scheme for sensing data from the chip to the transmitter and FIG. 23B shows the reverse scheme, i.e., from the transmitter to the chip. The modeling and simulation results show that the data can be reliably coupled and decoupled with this scheme.

FIG. 24 illustrates a three-wire system in which two wires are utilized to carry power and ground signals and the third wire is used for data communication to and from the sensor. Data communication is bidirectional in a time multiplexed fashion. When transmitter is sensing data, the sensor operates in receive mode. Once data transmission is done by the transmitter, it turns to receive mode to collect data from the sensor. FIG. 24B shows the scheme for sensing data from the chip to the transmitter and FIG. 24A shows the reverse, i.e., from the transmitter to the chip.

As shown in FIG. 4 or FIG. 5, the sensor signal acquisition unit 130 can include an oscillator, potentiostat(s), an analog to digital converter (ADC), and a multiplexer (MUX) (as well as an optional digital to analog converter DAC to externally control electrode redox potential). The oscillator can be used to provide an accurate and clean reference clock for the implant that is used by the communication unit, power management unit, and the sensor signal acquisition unit.

The potentiostat is connected to on-chip electrodes. The potentiostat maintains a fixed defined voltage between working electrode(s) and a reference electrode while providing current through a counter electrode. Each working electrode can have a dedicated potentiostat to maintain the appropriate voltage between the working and reference electrode and minimize crosstalk. However, a shared potentiostat is also workable. In a preferable embodiment, regarding the potentiostat, multiple working electrodes share common reference and counter electrodes. In such instance, an op-amp (e.g., 512 in FIG. 7) can control the reference electrode voltage while providing source/sink capability at the counter electrode and another op-amp (e.g., 513 in FIG. 7) can be utilized to control the potential for each working electrode where the amplifier sets the working electrode voltage through establishing negative resistive feedback and converting the sensor redox current into a voltage for subsequent processing.

Figures 6, 7:
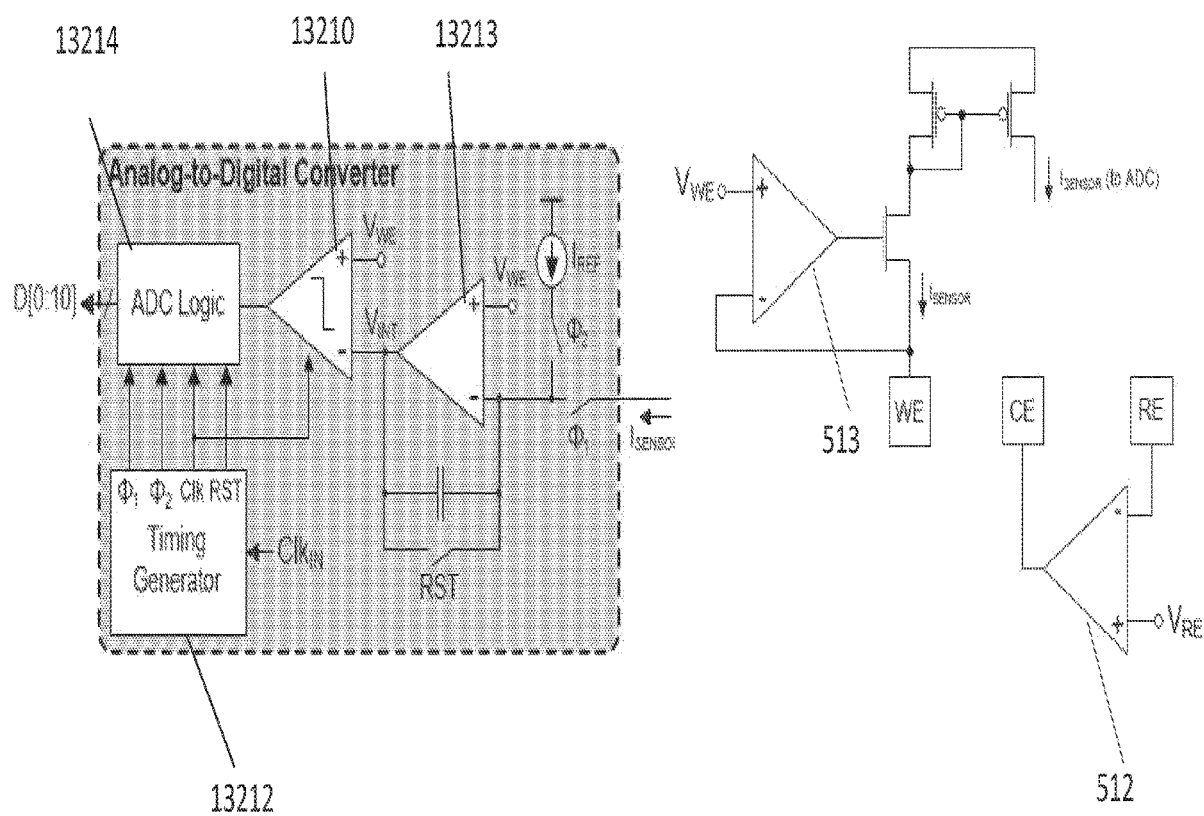
FIG. 6 describes an embodiment of an element of a sensor signal acquisition unit 130. An ADC is depicted which can convert a sensor signal (e.g., sensor current) into a digital signal (e.g., bit stream) using a mixed-mode circuit consisting of an amplifier 13213, a comparator 13210, a timing circuit 13212, and a control and logic unit 13214. A reset switch RST is used to reset the system before conversion of a new signal from the sensor. A capacitor is used to accumulate the sensor current over a given time period, after which it is converted to a digital signal using the rest of the circuit. The reset switch discharges this capacitor to restart the process.
FIG. 7 describes an embodiment of working, counter, and reference electrodes with corresponding wiring schemes. At the top, an analog front end (AFE) of a model working electrode includes an amplifier 513 which can be used in negative feedback to maintain the potential at the working electrode, $V_{WE}$, while buffering the sensor current to the ADC. The bottom shows an amplifier 512 which can be utilized to form negative feedback between reference and counter electrodes. The reference electrode's potential is maintained at $V_{RE}$ through the negative feedback, while the amplifier provides counter electrode current.

An embodiment of wiring schemes of the sensor signal acquisition unit (in particular the potentiostat) connected to working, counter, and reference electrodes can be seen in FIG. 7. At the top, an analog front end (AFE) of a model working electrode includes an amplifier 513 which can be used in negative feedback to maintain the potential at the working electrode, $V_{WE}$, while buffering the sensor current $I_{SENSOR}$ to the ADC. The sensor current $I_{SENSOR}$ is inversely proportional to the resistance of the working electrode which varies with the glucose concentration in the blood. The bottom shows an amplifier 512 which can be utilized to form negative feedback between reference and counter electrodes. The reference electrode's potential is maintained at $V_{RE}$ through the negative feedback, while the amplifier provides counter electrode current. The AFE and the amplifier 512 may be collectively referred to as the potentiostat. There-fore, the potentiostat senses the changes in the resistance of the working electrode, by outputting a current which is inversely proportional to the varying resistance of the electrode. This method allows for independently controlling the potential difference between working and reference electrodes in a multi-analyte sensor where there are several working electrodes for sensing different analyte.

The potentiostat is continuously powered by the battery 212 of the transmitter 2 (shown in FIG. 35) via the connector 3. By continuously powering the potentiostat, the potentiostat is able to maintain the potential of the working electrode continuously. After installation of the battery 212 into the transmitter 2, it may be required to calibrate the system of FIG. 1 once. However, after the initial calibration, there is no need to further calibrate the system before the battery 212 is drained up. Therefore, the system of FIG. 1 is able to continuously measure the glucose level of a patient during the lifetime of the battery 212. The measurement frequency may be from once every tens of seconds to once every few minutes, and may be adjusted at the transmitter side (e.g., by a user using the smartphone 4 wirelessly connected to the transmitter 2). Note that it is still possible to supplement the initial calibration with second, third, or further calibration points to enhance accuracy or in the event the user believes deviation has occurred.

The potentiostat is placed at a depth of 2-3 mm beneath the patient skin. The 2-3 mm depth has been found to allow the potentiostat to generate a superior signal indicative of glucose concentration. The 2-3 mm depth also significantly shortens the communication distance between the potentiostat and the transmitter 2. It would be understood that the potentiostat may be placed at a depth of 1 to 5 mm beneath the patient skin or a depth of 1 to 10 mm beneath the patient skin.

With further reference to FIGS. 4 and 5, the potentiostat can be connected within 9, 5, or 2 millimeters of the entirety of at least three working electrodes WE1, WE2, and WE3. This means that, for example, when WE1 is arranged closest to the potentiostat within the working electrodes WE1 to WE3 and WE3 is arranged furthest from the potentiostat, the distance between the potentiostat and all the area of the furthest electrode WE3 is within 9, 5, or 2 millimeters. Alternatively, the potentiostat is connected within 0.5 millimeter or 400 microns to the entirety of working electrodes WE1, WE2, and WE3. The short connection distance between the working electrodes and the potentiostat allows for minimal electronic signal travel, which in turn improves the signal quality and reduces the power consumption of the system of FIG. 1. It should be pointed out that other continuous glucose monitoring systems have substantially larger distances between the potentiostat and the working electrodes. For example, the Dexcom G6 contains a wire that is at least 15 mm long, and thus, the distance between the entirety of the working electrode and the potentiostat of this device is far greater than those proposed in the instant disclosure.

A dual slope ADC can be used to directly convert the sensing element current coming from the potentiostat into the digital domain. The ADC can, for example, include an 8-12 bit ADC that converts the potentiostat current into digital data values. Since in-vivo glucose readings don't change rapidly, each electrode pairing can be sampled every millisecond to once every 100 milliseconds, but preferably once every 10 milliseconds (100 samples/second). An ADC with high sampling rate (1K samples/s) can be utilized to sequentially digitize the signal from multiple electrodes as well as the temperature sensor.

An embodiment of an ADC of a sensor signal acquisition unit can be seen in FIG. 6. An ADC is depicted which can convert a sensor signal (e.g., sensor current) into a digital signal (e.g., bit stream) using a mixed-mode circuit consisting of an amplifier 13213, a comparator 13210, a timing circuit 13212, and a control and logic unit 13214. A reset switch RST is used to reset the system before conversion of a new signal from the sensor. A capacitor is used to accumulate the sensor current over a given time, after which it is converted to a digital signal using the rest of the circuit. The reset switch discharges this capacitor to restart the process.

A multiplexer (MUX) in the sensor signal acquisition unit can compare and compile data from multiple working electrodes on the monolithic integrated circuit. In accordance with some embodiments, to support multi-analyte sensing without an excessive increase in power consumption, resource sharing can be enabled across the sensor signal acquisition unit by the multiplexer. In some embodiments of the disclosure, each individual working electrode can be controlled by a dedicated potentiostat while an analog-to-digital converter can be shared among all potentiostats through time division multiplexing in which the digitization period is divided among some or all the working electrode-potentiostat pairs. During each time slot, the output of one working electrode-potentiostat pair is digitized. In accordance with some embodiments of the disclosure, the sampling rate can be set to a rate that is well above the rate at which relevant physiological body changes occur to avoid sensed signal loss. Normally, the ADC can operate at a much faster rate than that of the physiological signals, hence such multiplexing doesn't create any loss of needed data.

Figure 9:
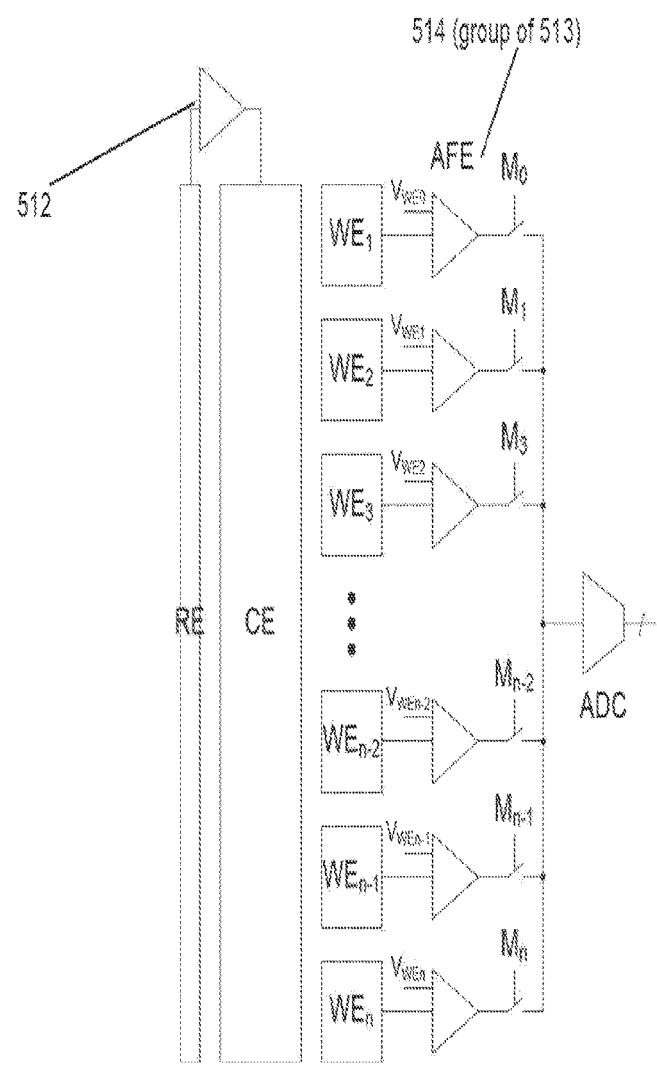
FIG. 9 describes an embodiment of sensing circuitry (e.g., the integrated sensing element 160 and the sensor signal acquisition unit 130) using minimal chip area through time multiplexing and sharing of counter (CE) and reference electrodes (RE). Multiple separate working electrodes ($WE_1 \ldots WE_n$) with respective analog front-ends (AFEs) can be used for this. Multiple AFEs (e.g., 513 of FIG. 7) can be used as each AFE with the grouping denoted as 514. The multiple working electrodes can be managed each by multiplexer connections $M_1$-$M_n$. The redox potential at each WE is controlled by the corresponding $V_{WE}$ voltage. This enables the design to have different working potentials for different working electrodes, thus enabling a wide variety of analytes to be detected.

An embodiment of multiplexing sensing circuitry can be seen in FIG. 9. Multiplexing and sharing of counter (CE) and reference electrodes (RE) is shown. Multiple separate working electrodes ($WE_1 \ldots WE_n$) with respective analog front-ends (AFE) can be used for this. Multiple AFEs 513 (e.g., based upon op-amps 513) of FIG. 7 can be used as each AFE with the grouping denoted as 514. The multiple working electrodes can be managed each by multiplexer connections $M_1$-$M_n$ to feed their corresponding signals (data) to the ADC in a time-multiplexed manner.

The redox potential at each WE can be controlled by the corresponding $V_{WE}$ voltage (which may also be referred to as a reference voltage). This enables the design to have different working potentials for different working electrodes, thus enabling a wide variety of analytes to be detected. In particular, each of these op-amps 513 is connected to the desired redox potential (e.g., $V_{WE1}$, $V_{WE2}$, $V_{WE3}$, and so on) for that WE. These voltages can be either internally generated as a fixed value for each application (e.g., using on-chip reference voltage generators), or can be generated using a Digital to Analog Converter (DAC) so that they can be programmed (FIG. 8) by the user from a given set of values to allow for programmability in choosing what analyte to measure. The user input of given set of values (also referred to as "command") may be transmitted from the transmitter 2 to the implantable monolithic integrated sensor circuit 1 via the connector 3.

Figure 8:
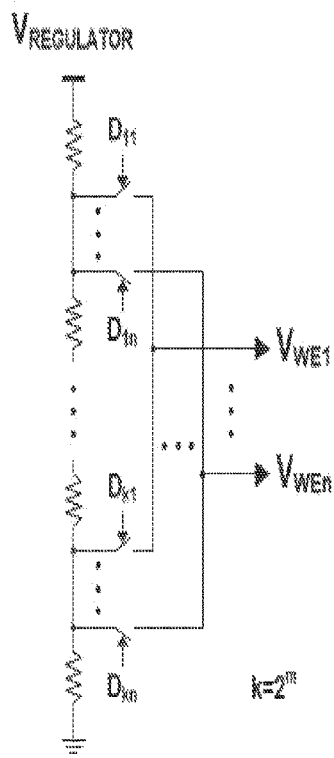
FIG. 8 shows one embodiment of the circuit to generate different WE potentials for the different on-chip redox reactions. In one embodiment, the $V_{WEn}$'s are generated using a Digital-to-Analog Converter (DAC). An example of a DAC is shown implemented using a resistor divider network. Utilization of the DAC also allows for programmability of the redox potentials.

An example of the DAC circuitry can be seen in FIG. 8 including a resistor ladder comprising $2^m$ resistors connected between the voltage regulator output and the ground to form an m-bit DAC capable of generating $2^m$ different voltages. These voltages are connected to each working electrode through a set of switches controlled by $D_{ij}$, where i represents $WE_i$ and j is between 1 and $2^m$ for selecting the desired voltage level. For each working electrode there are $2^m$ dedicated switches.

As shown in FIG. 4 and FIG. 5, in some embodiments of the disclosure, the implantable monolithic circuit can include an electrochemical integrated sensing element that comprises multiple working electrodes (e.g., a detection reaction can occur at this electrode), a single counter electrode (e.g., can be used to balance the current generated by working electrode) and a single reference electrode (e.g., to provide a stable voltage reference signal inside the body). The electrochemical integrated sensing element transduces changes in analyte concentration into changes of electrical current. In an embodiment the integrated sensing element includes three working electrodes, one counter electrode, and one reference electrode. The sharing of a single counter and a single reference electrode does not create crosstalk as the current in each potentiostat can be determined by the corresponding working electrode. However, in a separate optional embodiment one counter and one reference electrode can be used corresponding to each single working electrode. In an example, the desired redox potential may be between −1.5V to 1.5V. In the event that the resistor ladder of FIG. 8 is connected between a positive voltage and a negative voltage, the desired redox potential may be between −1.5V to 1.5V.

Figure 13:
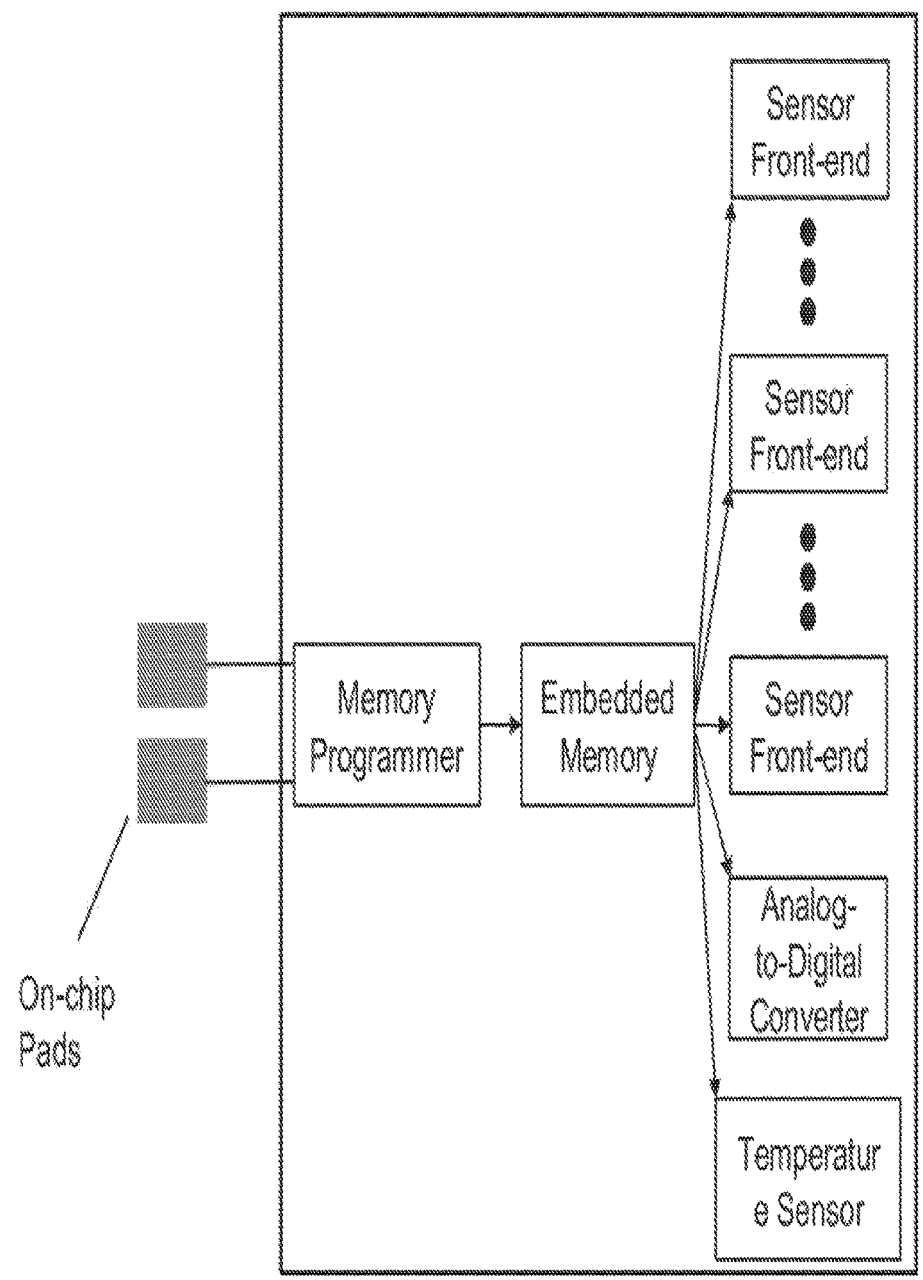
FIG. 13 shows a diagram of an embodiment of on-chip pads and programming circuitry of the monolithic integrated sensor circuit 1 which can be used to store some critical information on the chip itself.

The monolithic integrated sensor circuit 1 can be programmable. An exemplary programming circuitry of the monolithic integrated sensor circuit 1 is shown in FIG. 13. In FIG. 13, the sensor front-end refers to the potentiostats connected to the integrated sensing element 160 as described above. The process of narrowing down the parameters associated with some chip functions (e.g., temperature sensor, electrochemical readout circuitry, and the ADC) is also called trimming. As shown in FIG. 13, an embedded memory is electrically connected to the sensor front-ends, the ADC and the temperature sensor so as to provide the trimming parameters to those blocks. The embedded memory is an on-chip memory and can be programmed via an on-chip memory programmer which is connected to an external memory controller (not shown in FIG. 13) by on-chip pads (e.g., 175). During the electrical testing and trimming, the on-chip pads interface with the external memory controller. The information from the external memory controller can be written into the embedded memory using the memory programmer, which generates high voltage signals required to program the embedded memory. In some other cases, the memory programmer may be omitted and direct electrical connections may be established for the external memory controller to provide correct signals to program the embedded memory. For example, the reference voltages $V_{Wei}$ (i=0, 1, 2 . . . n) of the working electrodes (described with reference to FIG. 7, FIG. 8, and FIG. 9) may be programmed during the above trimming process.

The embedded memory mostly only requires to be programmed once. Hence, simpler one-time programmable (OTP) memories can be used (e.g, optical ROM, EPROM) as the embedded memory. However, in some cases if more flexibility is desired, a reprogrammable memory (e.g., EEPROM, eFlash) can also be implemented as the embedded memory. The exact type of memory used depends upon both the application and the CMOS process. The CMOS foundries (e.g., TSMC) offer a range of memory options for different CMOS processes that can be chosen appropriately.

Alternatively, optical beams (e.g., lasers) can be used to program the embedded memory without requiring the use of the on-chip pads.

Individual electrodes can be defined by openings in a top passivation layer (e.g., 118 in FIG. 14) of the CMOS fabrication process. An integrated design wherein electrodes are defined by the top most Aluminum metal layer in the CMOS process can be used. However, since Aluminum may not be suitable for stable electrochemical sensing due to corrosion, lithographic post-processing can be performed to replace or coat it with a noble metal (e.g., platinum, gold, silver) for working electrodes and counter electrodes and Pt/PtOx (more stable reference than Pt, easier to fabricate than Ag/AgCl) for reference electrodes. These post-processing steps are more specifically discussed below. Note that the reference electrode can also be coated with a noble metal instead of Pt/PtOx.

To directly detect glucose, working electrode(s) can be functionalized with GOx hydrogel (the chemistry and deposition of GOx hydrogel is discussed more below). In an embodiment, indirect glucose sensing through differential Oxygen sensing can be implemented by using one working electrode to measure background $O_2$ using a non-enzyme loaded hydrogel, while another working electrode is functionalized by GOx hydrogel to measure left-over Oxygen from the Glucose-Oxygen reaction (Oxygen consumed by the enzyme). The difference between these two Oxygen concentrations can indicate the glucose concentration. The GOx functionalized electrodes can be intentionally placed apart (by having WE, in between) to minimize crosstalk. On the electronics side, multiple potentiostats (n) can be included to control the sensors. For example, GOx sensor working electrode can be held at +0.3V-0.6V with respect to the reference electrode while an $O_2$ sensing working electrode can be held at −0.3V−−0.5V with respect to the reference electrode (oxygen detection potential). The current from the potentiostats and the temperature sensor can be digitized by the shared on-chip ADC in a time multiplexed manner.

The strength of the sensing element signal can be proportional to surface area of the electrode and the effective signal strength can be increased by utilizing patterned or non-planar electrodes instead of conventional planar electrodes. The working electrodes (and optionally counter and reference electrodes) can be designed to have pillar structures by patterning the top metal and passivation layers to enhance sensitivity as well as improving adhesion between the solid-state sensor and the hydrogel. Such structures can be formed using a semiconductor fabrication process, by post-processing or by a combination of both. Pillars created during a CMOS manufacturing process can have a size and spacing (determined by the CMOS process) of about 0.25 µm-25 µm and preferably 2 µm-5 µm and height of about 0.1 µm-10 µm and preferably 2 µm-5 µm (theoretically resulting in about 2-3× increase in sensor signal). Post-processed pillar structures are discussed below. Both foundry and post-processed pillars share similar dimensions and can be rounded or square. In accordance with some embodiments of the disclosure, the pillars can be partially or completely etched to form a more planar structure. When completely etched, the pillars are totally removed. However, the resulting insulation structure on the surface results in surface texturing after deposition of metal. When partially etched, pillars are thinned down and are shorter in height and possibly width.

An example of surface patterning which can be accomplished via foundry semiconductor processes and a degree of post processing can be seen in FIG. 16A, FIG. 16B, and FIG. 16C. FIG. 16A, FIG. 16B, and FIG. 16C show how pillar or hole structures can be made using semiconductor processes with top insulation 122 generating spacing in top metal 121. The top insulator can then be etched in post processing to create open areas between the pillar-like structures or the holes in the top surface.

In a hole-based pillar design, the electrodes are designed as metal mesh and the hole is filled by the insulator. This method uses the small features size available in the CMOS process to form structures that enable the formation of such high surface area structures with simple postprocessing steps like wet etching.

In a pillar design, the metals are designed as separated electrodes with insulator filled in the gap areas.

FIG. 16A shows the etching of top metal to create spacing. Afterwards, the pillar-like or hole containing structure can be coated with suitable metal 125 (e.g., Platinum) using thin-film coating techniques (e.g., electron beam evaporation, thermal evaporation, sputtering, or atomic layer deposition).

FIG. 16B and FIG. 16C show two of the most common patterns that can be used to create the high surface area structures. FIG. 16B is before etching. FIG. 16C is after etching. After etching of either the top insulator or top metal, these structures reveal reverse patterns of 3D structures (e.g., pillars and valleys or holes and top surface) that can then be coated with suitable metal (e.g., Titanium and Platinum). In FIG. 16C, the structure on the left is called the pillar structure and the structure on the right is called holes structure. It would be understood that in the holes structure, the bottom surface of the holes as a whole is typically less than a top surface of the structure.

The reverse-pillar or hole structure described above (and shown in FIG. 18) is more robust than the pillar structure since it is made by holes instead of free-standing pillars (shown in FIG. 17, prone to defects as shown). In particular, FIG. 17 shows that the pillar structures can have defects which manifest either as breakage of a set of pillars or coverage of a set of pillars with some debris from other processes. It also shows the position of interlayer vias 1291 on the bottom surface (valley area) of the electrode. FIG. 18 shows that the reverse-pillar or hole structure has much lower defects than the pillar structure. It also shows the position of interlayer vias 1291 on the bottom surface (bottom of each hole, bottom of some holes) of the electrode. Therefore, the reverse-pillar or holes structure provides better electrode integrity while still providing high surface area. It also provides good hydrogel adhesion as the hydrogel fills the holes and forms a 3D structure within the electrode.

These patterned electrodes are different than those reported elsewhere. These electrodes are formed by using the design rules and materials available in the CMOS process itself (e.g., insulator), instead of having to form all the patterning on a silicon substrate afterwards. This simplifies the design and enables scalable and more controlled structures. This also enables use of smaller features in advanced CMOS processes (e.g., 3 nm process) as those are achieved by advanced photolithography methods not available in cleanrooms outside of the advanced CMOS foundries. Moreover, this simplifies the post processing steps which are otherwise difficult to match with the features and control available in the CMOS fabrication process.

The size and shape of the electrode structure can be selected based upon the sensing application and the desired integrated sensor circuit 1 geometry. In accordance with some embodiments of the disclosure, the sensing element can include an arrangement of electrodes, e.g., a centrally located reference electrode (e.g., a rectangle of 50 µm by 1500 µm), an outer counter electrode (e.g., a rectangle of 600 um by 1500 µm), and a working electrode (e.g., a 150 µm by 1500 µm) located between the reference electrode and the counter electrode.

In another embodiment, the sensing element can include 2 working electrodes of 20 µm by 80 µm, 7 counter electrodes of 60 µm by 80 µm, and one reference electrode of 20 µm by 780 µm. In general, it would be acceptable to vary the area of the working electrode from half to double that listed directly previously. In various instances, it would be acceptable to make the working electrode with as little as 15× times smaller area. The counter electrode should be always larger than the working electrode. In various embodiments, the counter can be as little as 3× the area of the working electrode; however, the maximum size of the counter electrode is only limited by the area of the implantable monolithic integrated circuit. With respect to the reference electrode, smaller is better. For all practical purposes there is no electrical lower bound on the size of the reference electrode. It needs to be close to each counter. If, however, the reference electrode, is made of a material that may be consumed, such as AgCl, it is advisable for the counter to be of similar size to the working electrode.

Figure 10:
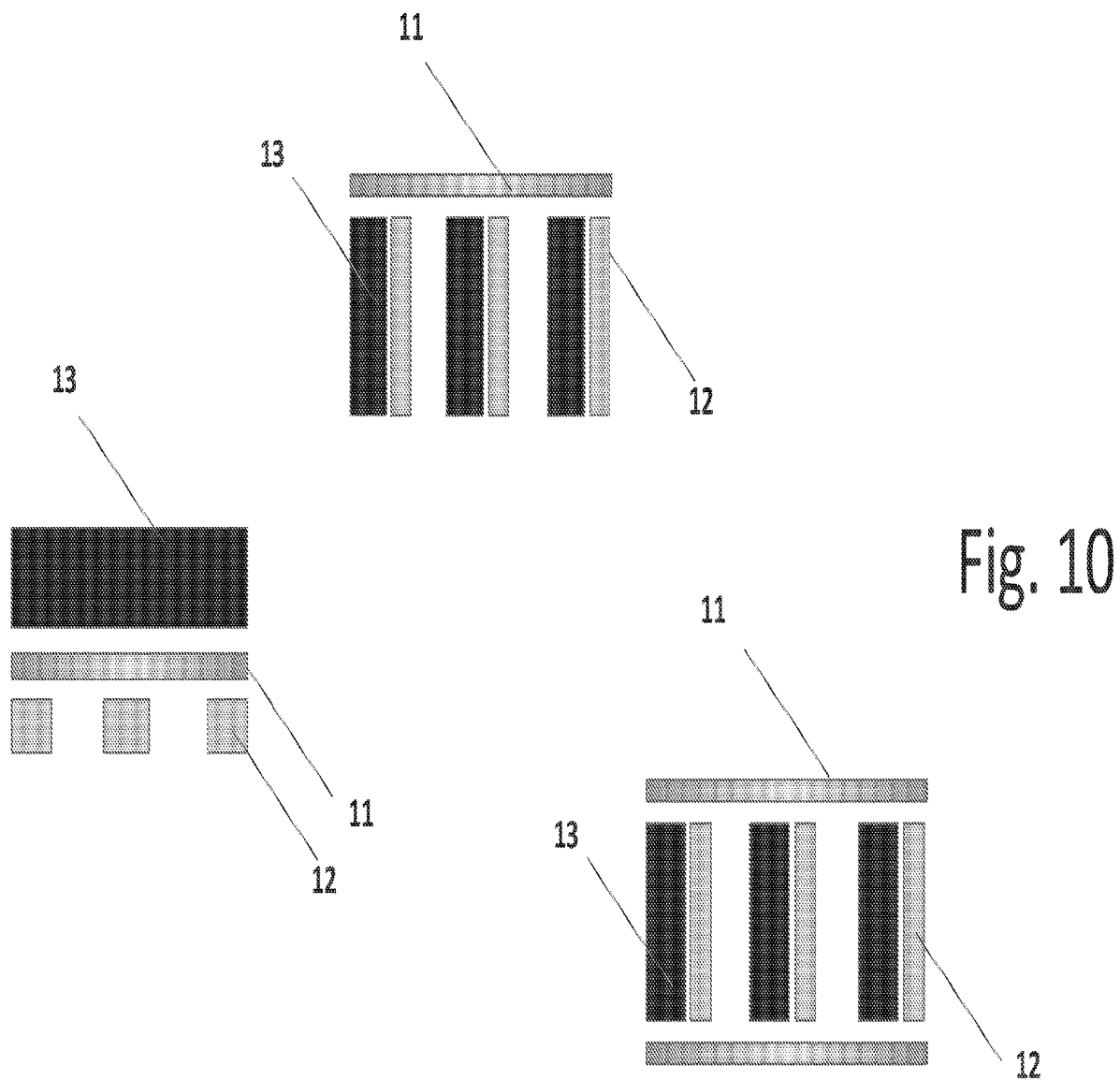
FIG. 10 shows embodiments of different electrode configurations of the working electrode 12, counter electrode 13, and reference electrode 11 that can be manufactured by various fabrication processes according to the present disclosure.

FIG. 10 shows embodiments of different electrode configurations of the working 12, counter 13, and reference electrode 11 that can be manufactured by various fabrication processes according to the present disclosure. This structure can be formed, for example, in the top metal layer by removing the top passivation layer of the chip to expose the metal sensor electrodes.

Monolithic Integrated Sensor Manufacturing

The process for forming the functionalized electrodes of the monolithic integrated sensor circuit after receipt of a wafer from a commercial foundry (e.g., TSMC) are now described in greater detail.

Figure 14:
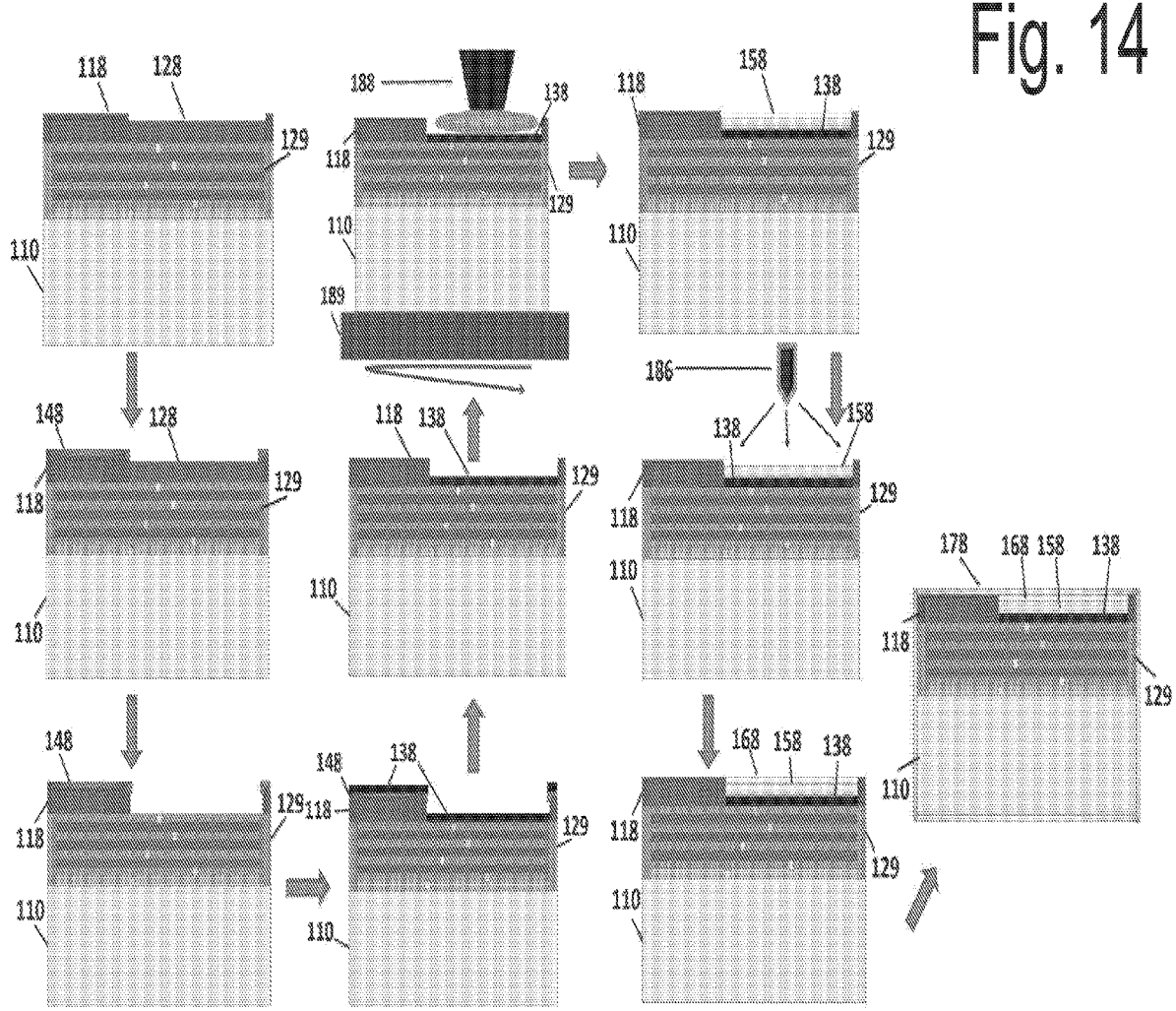
FIG. 14 shows the process of post processing and functionalization for the integrated sensor 1. The first step shows a side cross-section schematic view of a precursor of a monolithic integrated sensor circuit 1 as, for example, received from a commercial fab (e.g., TSMC, ON Semi). The schematic shows a substrate 110, a metal-insulator-metal stack 129, a top metal 128, and a top insulator with an optional additional insulator/protection polymer layer 118. The second step includes using a precursor patterned using lithography to create patterned photoresist 148. Top first layer metal 128 of a Metal-Insulator-Metal (MIM) structure is Aluminum in some cases.

The wafer (diced or un-diced) as being processed is hereafter referred to as a monolithic circuit precursor. An example of a wafer can be seen at FIG. 14 step 1. FIG. 14 at step 1 is a side cross-section schematic view of an integrated sensor circuit precursor, showing a substrate 110, a metal-insulator-metal stack 129, a top metal 128, and a top insulator with an optional additional insulator/protection polymer layer 118.

Note that the top metal can be thick in high frequency CMOS processes. In some cases, a more suitable material can be coated on the top metal without etching it. For some other cases, a first step of post-processing involves removal of this top metal layer for better control of the morphology of the more suitable material. This etching can be achieved by using wet etching (e.g., using a mixture of Nitric acid and Phosphoric acid) or dry etching (e.g., Chlorine based RIE Plasma).

After receipt of a precursor of an implantable monolithic sensor circuit from a commercial foundry or after post-processing for removing, for example, a thick top layer of top metal, lithographic (e.g., photolithography) patterning can be done to expose the sensing element electrode while covering the rest of the wafer with a suitable material (e.g., photoresist). Note that, for some applications, this patterning can be achieved using custom stencils, i.e., without lithography.

In FIG. 14 step 2 a precursor is patterned using lithography to create a patterned photoresist 148. Top first layer metal 128 of a Metal-Insulator-Metal (MIM) structure is Aluminum. Underneath the top metal is the further Metal-Insulator-Metal (MIM) structure 129 found in CMOS devices. A silicon substrate is at 110. Note that several electrodes can be isolated from each other by top insulation 118 (Top insulation in CMOS process is often a stack of Silicon Nitride layer on top of Silicon oxide layer). Top insulation can be further augmented by an additional layer (e.g., Polyimide layer).

In photolithography, after mask deposition, the mask is etched. In FIG. 14 step 3 a precursor is etched to remove the top metal 128 leaving the area which was protected by photoresist 148 and further exposing a second further layer of the Metal-Insulator-Metal (MIM) structure 129. The silicon substrate remains at 110. Electrodes remain isolated from each other by top insulation 118.

This patterning can be followed by deposition of a desired material (e.g., suitable metal stack); for example, a Ti (or Titanium-Tungsten) intermediate layer of small (e.g., 20 nm) thickness as the adhesion layer (and to avoid corrosion of an underlying Aluminum layer) can be deposited followed by deposition of relatively thicker (e.g., 100 nm) of Platinum (or any other noble metal or corrosion resistant conductive alloy). Physical vapor deposition (e.g., sputtering, e-beam deposition, and thermal evaporation), chemical vapor deposition, electroplating, and electroless plating are different methods that can be used for thin film deposition. Sputtering can form a relatively rough surface compared to e-beam or thermal deposition both of which result in smoother electrodes.

To achieve higher surface area and to enhance bonding between the sensing element and the subsequent chemistry layers, the metal surface can be designed to have rougher finish (as compared to smooth or mirror finish). This is achieved by controlling deposition method (e.g., electron beam deposition, thermal evaporation, chemical vapor deposition, sputtering), depositional environment (e.g., pressure), and deposition energy. In an embodiment, sputtering at 30 mTorr pressure and 100 W DC power generates a metal coating with a high surface area for a planar geometry.

FIG. 19 show a comparison between smooth Platinum coated using electron beam deposition and low-pressure sputter deposition vs. high-pressure sputter deposition. It shows the smooth platinum layers of range 30-150 nm (typical 100 nm) vs. rougher platinum layer of range 30-150 nm (typical 100 nm). A typical smooth layer of 100 nm thickness has rms roughness in <3 nm range for 100 nm thickness while the rough platinum has rms roughness >3 nm. Moreover, the rough Platinum appears to be porous under an SEM while the smooth Platinum appears more like a continuous film.

A precursor is coated with a desired material (e.g., suitable metal) in FIG. 14 step 4. A thin layer of desired material (e.g., Platinum) 138 is coated using a thin-film coating method. A substrate 110, a metal-insulator-metal stack 129 and a top insulator with an optional additional insulator/ protection polymer layer 118 remains. The top insulation electrode isolation region remains protected by photoresist 148.

The use of patterned electrodes with one or more pillars can be helpful as noted above because strength of the sensing element signal can be proportional to surface area of the electrode. As noted above patterned electrodes can be formed by post-processing in an embodiment. In post-processing, it is possible to lithographically form the pattern for electrodes in a lithographic material (e.g., photoresist) while covering the rest of the chip with the lithographic material. This is to be done before the deposition of a suitable metal stack. As an example, AZ 5214E resist can be spun at 3000 rpm, baked at 95 degrees Celsius for 5 minutes, and exposed using i-Line (e.g., 365 nm UV radiation) exposure in an MA6 mask aligner for 2 seconds. LOR resist can be used to help with liftoff. Image reversal can also be used for this purpose. In this case, a post-exposure bake at 110 degrees Celsius for 2 minutes is performed followed by a flood exposure in MA6 for 3 seconds. For both positive and negative patterns, the resist can be developed in a developer (e.g., AZ300). This can be followed by sputtering of Ti (e.g., 20 nm) and/or TiW (20 nm) followed by Pt (100 nm). Sputtering parameters are optimized to achieve the desired morphology of the coated material (e.g., Pt). After sputtering, a conformal coating is achieved. Solvent Lift-off can then be performed (e.g., dipping sensors in acetone for 30 minutes) to remove metal from unwanted areas and only keep those on sensing element electrodes. Alternatively, materials can first be deposited everywhere and then etched with appropriate wet and/or dry etching methods.

A next step of the post-processing can be lift-off to remove metal layers from the unwanted regions. This is achieved by soaking the coated devices in solvents. Alternatively, unwanted metals from coated devices can be etched in appropriate solutions (e.g., in aqua regia).

In FIG. 14 step 5 a precursor is cleaned to remove the photoresist 148 and excess deposited material and leave deposited material only in desired places (e.g., on integrated sensing element electrodes). A substrate 110, a metal-insulator-metal stack 129, a thin layer of desired material 138 and a top insulator with an optional additional insulator/protection polymer layer 118 remains.

It is possible to perform another lithography followed by silver deposition, liftoff and Chlorine exposure through wet solution (e.g., Ferric Chloride) or dry plasma (e.g., Chlorine Plasma) to create silver-based reference electrodes (e.g., Ag/AgCl). Ag/AgCl reference electrodes are more suitable for some applications (e.g., open circuit potential measurements).

It is also possible to create polymer structures around the sensing element electrode area to create isolation or to improve chemical functionalization. An example is the use of insulating material to cover the unexposed parts of the top metal. This layer may consist of Silicon Oxide and Silicon Nitride insulating layers found in standard CMOS process as well as additional insulating/polymer layers (e.g., polyimide) to protect the underlying circuitry. Polymer walls around the sensor can be used to act as 'well structures' as well as 'adhesion promoting structure' as some functionalization materials (e.g., Serum Albumin based Hydrogel) adhere better to an activated polymer surface than to a Silicon Nitride insulation structure. In some cases, such structures can be provided by the CMOS foundry or a similar foundry as part of the fabrication process. For example, polyimide structures can be provided to the end-user by the CMOS foundry and can work as adhesion promoters for some applications.

In accordance with some embodiments of the disclosure, the sensor electrode surfaces can be activated (e.g., with glutaraldehyde or air plasma, oxygen plasma, or argon plasma) prior to functionalization layer (e.g., hydrogel) deposition. This activation can help with adhesion of the sensor chemistry with the sensor or the previously deposited chemistry layers. Surface structures and/or modifications can also act as grafts for a functionalization layer (e.g., hydrogel) and result in a stronger adhesion and/or chemical interaction between the gel and the sensor electrodes.

Additionally, in optional embodiments of the disclosure, a layer that can limit sensor response to substances that interfere with sensor operation can be applied to the surface of one or more of the electrodes before coating a functionalization layer (e.g., a hydrogel). For example, a layer of thin polymers (e.g., polyaniline) can be formed on the sensor by spinning and UV/electron beam crosslinking. For example, a layer of poly-phenylenediamine polymer can be coated on electrodes surface using electrochemical deposition or UV crosslinking, before or after the enzyme coating. This allows the sensor to not react to ascorbic acid or acetaminophen which otherwise can create a false signal on platinum electrodes.

FIG. 14 step 6 demonstrates an embodiment of the use of fine droplet/spray deposition systems to precisely cover the integrated sensing element of a precursor with controlled amounts of a functionalization layer. Optionally, the use of a fine droplet/spray deposition system using solenoid and/or piezoelectric controlled actuation-based spray heads 188 simultaneously with spinning on table 189 can improve the uniformity of the functionalization layer (e.g., hydrogel). For example, solenoid and/or piezoelectric controlled actuation-based spray heads 188 can be used to deposit, in nanoliters, precise amounts of Glucose Oxidase solutions and crosslinking agents (e.g., Glutaraldehyde) solution droplets to make a glucose oxidase-based hydrogel on the sensing electrode. The substrate can be spun after the droplet deposition to control the thickness of the hydrogel layer more precisely. A substrate 110, a metal-insulator-metal stack 129, a thin layer of desired material 138, and a top insulator with an optional additional insulator/protection polymer layer 118 remains.

An enzyme hydrogel is an exemplary functionalization layer. As noted above, in one embodiment, an enzyme is immobilized on the sensing element in a hydrogel (e.g., a cross-linked protein hydrogel). This can be done at a thickness 0.01 µm to 50 µm. The enzyme hydrogel layer may be under 3500 nm in thickness. Alternatively, the enzyme hydrogel layer may be less than 1000 nm in thickness. Further alternatively, the enzyme hydrogel layer may be between 200 nm and 800 nm in thickness. Further alternatively, the enzyme hydrogel layer may be between 600 nm and 800 nm in thickness.

This can be done using different techniques. As an example, this can be done through immobilization of the enzyme such as GOx (Glucose Oxidase) in a hydrogel created by proteinaceous material with glutaraldehyde as the crosslinking agent. The proteinaceous material can be a blocking agent such Human Serum Albumin (HSA) or Bovine Serum Albumin (BSA) or some other Serum Albumin (SA). Herein a "blocking agent" is a material that blocks unwanted binding interactions of the sensor or sensor components with tissue materials and fluids and avoids or decreases fouling of the sensing element. Glutaraldehyde can be dispensed before application of the remaining elements of the hydrogel. Subsequently, a mixture of GOx, Serum Albumin, and in some embodiments, catalase, can be placed on the precursor. Glutaraldehyde can be used to aid hydrogel formation, and/or catalase can be used to increase sensor longevity by mitigating excess hydrogen peroxide production during glucose sensing. In accordance with some embodiments of the invention, it may be desirable to remove excess hydrogen peroxide from the hydrogel during glucose sensing, so a mixture of Catalase with GOx and Serum Albumin can be used. In accordance with some embodiments of the disclosure, it may be desirable to form the hydrogel after the solution is already dispensed on the electrode, by adding Glutaraldehyde to the mixture after it is dispensed on the electrode, for example, in a separate step. In accordance with some embodiments of the disclosure, Glucose Dehydrogenase can be used as the glucose sensing enzyme, in addition to or instead of Glucose Oxidase.

In accordance with some embodiments of the disclosure, to selectively functionalize the sensor electrodes, a precise deposition of nano- to pico-liter of the hydrogel can be utilized. In one embodiment, the substrate can be heated or cooled and kept at a controlled temperature (e.g., 25 degrees Celsius to 35 degrees Celsius, with 25 degrees Celsius being an embodiment) in a controlled environmental chamber (e.g., to control temperature, humidity, chemical composition of the environment). Then, an accurate dispensing instrument (such as a BioJet Elite on a AD6020 aspirate dispense system by Biodot, Irvine, CA) with precise x, y, and z position control can be utilized. In one embodiment, the sprayed solutions are a protein solution of GOx and/or Catalase and HSA (1200 mg, 12 mg, and 1000 mg respectively in 15 ml DPBS, Sigma Aldrich Product codes G2133, SRE0041, SRP6182, D8537) and a crosslinking agent solution of 1 w/w glutaraldehyde in DPBS (Sigma Aldrich, St. Louis, MO, product codes G5882, and D8537).

In accordance with some embodiments, deposition can be performed in three steps to achieve a hydrogel of repeatable and controlled hardness and composition: 1) dispensing glutaraldehyde, 2) dispensing the mixture of GOx and SA, 3) dispensing glutaraldehyde. The three deposition steps can be done almost simultaneously through the use of three dispensing nozzles as gel formation starts happening almost instantaneously once SA and glutaraldehyde come to contact. In a different method, glutaraldehyde is only dispensed once. With the three-step process, or with a process where only steps 1 and 2 are performed, controlled temperature (e.g., 25 degrees Celsius) of the sensing element electrode surface and controlled environment (e.g., 80% RH, low particle count in air) during and after dispensing helps with uniform gel formation.

In accordance with a different embodiment of the disclosure, spin coating and/or spray coating can be used to achieve functionalization by applying the sensing chemistry on the sensing elements, instead of precise deposition. In this method, enzyme hydrogel mixture is dispensed or sprayed on the precursor or even entire wafer using nano-droplet dispenser, spray head, or pipette. The hydrogel formulation can be the same as that used in precise deposition. The wafer is then spun to achieve a thin sensing layer at controlled speed (between 200 to 20000 rpm with 2000 rpm being an embodiment) for set time (10 seconds to 3 minutes, another embodiment being 1 minute) to achieve a thin (10-50000 nanometer thick, e.g., 2-6 micrometer thickness) layer sensing chemistry.

FIG. 15 shows one scheme of using spin-coating and/or spray coating to pattern a stack of 3 (as an example, chemistries 191, 192, 193) coatings uniformly across three electrodes on the sensing platform utilizing a sacrificial layer (note the use of a sacrificial layer is not shown in FIG. 14). The chemistries can be deposited in fewer or more steps depending on what steps each chemistry can tolerate, and on the treatments needed for each chemistry (e.g., plasma treatment, silane treatment).

FIG. 15 Step 1 shows a post processed sensor chip, i.e., wafer with conductive material deposited upon sensing electrodes as seen in Step 5 of FIG. 14.

In FIG. 15 Step 2, a sacrificial layer (e.g., Polyacrylic acid) is deposited on the sensor (e.g., by spin coating, spray coating). In some embodiments a water-soluble sacrificial layer can be used. For example, a mixture of Polyacrylic acid can be used to make a sacrificial layer. Same can be done by using Polyvinyl alcohol or other water-soluble materials as well as material that can be dissolved in other solvents. In some embodiments (not pictured) water-soluble sacrificial layers can be used to protect the sensing chemistries to allow for patterning the sensing chemistries with a photoresist via a lift-off process, where the water-soluble layer would protect the enzyme layer from the photoresist and chemical and physical methods used to pattern and clean the photoresist, including but not limited to developer, acetone, or plasma etching.

In FIG. 15 Step 3, a patterning chemistry 181 (e.g., photoresist, e-beam resist) is deposited over the sacrificial layer 182 (e.g., by spin coating, spray coating).

In FIG. 15 Step 4 the patterning chemistry 181 (e.g., photoresist, e-beam resist) is patterned.

In FIG. 15 Step 5, after patterning of the patterning chemistry 181 in Step 4, the sacrificial layer 182 is dissolved in a manner as to correspond to the pattern created by the patterning chemistry.

In FIG. 15 Step 6, the patterning chemistry 181 is completely removed.

In FIG. 15 Step 7, chemistry 191 is deposited by spin coating.

In FIG. 15 Step 8, chemistry 192 is deposited by spin coating.

In FIG. 15 Step 9, chemistry 193 is deposited by spin coating.

In FIG. 15 Step 10, sacrificial layer 182 is dissolved leaving the target chemistries 191, 192, and 193 only on the target electrodes.

In accordance with a further alternative embodiment, instead of precise deposition or spin coating and/or spray coating, the functionalization layer (e.g., hydrogel: crosslinking agent and or the protein mixtures) can be deposited on the wafer via dipping. In some instances, the sensor chips or the entire wafer can be mounted on a substrate that can be dipped vertically or horizontally in a solution of enzyme or enzymes and serum albumin and optionally glutaraldehyde. The hydrogel formulation can be the same as that used in precise deposition. The substrate can be dipped and dried one or more times for a total processing time ranging from 2 minutes to 2 hours depending on desired gel thickness and consistency. In some embodiments, the sensors can be dipped for one minute and dried in a chamber with 80% relative humidity for 5 minutes for 10 cycles for a total processing time of 60 minutes. In accordance with some embodiments, the sensors can be dipped in protein solutions and glutaraldehyde solution, sequentially. For instance, if there are a variety of sensing chemistries dispensed on the sensor, and many of these produce hydrogen peroxide, then, after the coating(s) are dispensed, the whole wafer can be dip coated in catalase solution followed by dip coating in glutaraldehyde to immobilize the catalase on the sensors' surface. In some embodiments of the disclosure, a cleaning solution such as DPBS can be used between dipping steps in order to prevent beading of the solutions on the sensors and resulting loss of uniformity.

In some cases, the hydrogel can conform to the pattern of underlying pillars to result in patterned layers. Such patterning can allow for faster response time (lesser delay) but may have a shorter lifetime compared to sensors with thicker hydrogels and polymer layers. The hydrogel and polymer can be shaped either like blocks of materials covering the pillars or shaped liked pillars with empty space in between the pillars. The different shapes can be obtained by process control (e.g., if droplet functionalization of hydrogel is used a block of hydrogel formed; however, if spray, a thin layer mostly sticks to pillars and provides a conformal coating).

In accordance with some embodiments of the disclosure, each working electrode can be isolated from the rest of the working electrodes and allow for unique functionalization of individual electrodes, e.g., different electrode sensing chemistries. These methods for selective functionalization of individual working electrodes are in addition to the ability of precise deposition to achieve this result as noted above. Options to facilitate selective functionalization include stencils, lithographic patterning, nanoimprint lithography, and selective activation. In accordance with some embodiments of the disclosure, where isolation is required, all the sensing element components for any one analyte application can be dedicated (e.g., separate working, reference and counter electrodes) and isolated from others.

Stencils can be used to selectively functionalize sensing elements with different chemistries. In these embodiments, a stencil, e.g., a metal sheet with holes corresponding to sensing element surfaces, can be placed on the die or wafer. Then sensing chemistries can be dispensed, dropped, dipped, or sprayed, or otherwise deposited. In some embodiments spraying is used. Then the stencil can be lifted from the surface to leave defined sensing chemistries deposited on sensors. The stencil process can be repeated or combined with other processes to achieve a variety of chemistries.

Alternatively, wafer scale lithographic patterning can be used. In some of these embodiments, a light-active chemical (e.g., a photoresist) can be placed on the die or wafer and patterned using light and a developer as known to those skilled in the art. Then dispensing, spin or spray coating, dipping, or any method described in the above surface functionalization paragraphs herein can be employed to deposit sensor chemistries on the specific sensors.

Nanoimprint lithography is yet another technique that can be used for this purpose. In this case, a special printing head/stamp can be used to transfer small gels on to the sensing element surfaces (e.g., electrode surfaces). The gel is first formed on this stamp (which can be made using lithographic patterning or molding) using any of the methods discussed herein (e.g., nano-droplet dispensing, spin coating, spray coating, dipping). Then the stamp is placed on the desired wafer and a method is used to release the hydrogel to the specific sensors on the wafer. This is facilitated either by increasing gel adhesion with the sensors on the wafer (e.g., by surface activation of sensors and particularly surfaces of sensing elements in a manner such as with oxygen argon or air plasma) or by using heat/UV to create some change on the stamp which releases the gel.

Specific sensing elements can also be patterned by selectively activating the sensing element surfaces (e.g., with an oxygen, argon, or air plasma, or chemical modification) and sensing chemistries can be deposited using any of the methods discussed herein (e.g., nano-droplet dispensing, spin coating, spray coating, dipping). Then, the sensing chemistries can be removed (e.g., washed with deionized water, or a mixture of deionized water and detergent such as 10% (w/w) Extran (MilliporeSigma, Burlington, MA) in deionized water) such that only sensing chemistries bonded to the activated surfaces remain.

FIG. 14 step 7 shows an embodiment of a device after deposition of the functionalization layer 158 using solenoid and/or piezoelectric controlled actuation-based spray heads. A substrate 110, a metal-insulator-metal stack 129, a thin layer of desired material 138, and a top insulator with an optional additional insulator/protection polymer layer 118 remains.

FIG. 14 step 8 shows an embodiment of the use of spray coating (e.g., using fine dispensing heads 186) to make a film (stack of one or more thin films) on sensor surface to coat the functionalization layer, using an appropriate spray head 186 which showers microdroplets on an area of the sensing element. A substrate 110, a metal-insulator-metal stack 129, a thin layer of desired material 138, a functionalization layer 158 and a top insulator with an optional additional insulator/protection polymer layer 118 remains. FIG. 27 similarly shows how a soft material like hydrogel 190 is coated on the sensors using a thin-film coating process (e.g., spin coating, spraying).

In an optional embodiment, a drying step can be done in a chamber saturated with crosslinking agent vapor, e.g., glutaraldehyde vapor, to aid or obviate the need for crosslinking via crosslinking agent via further application. For example, for vapor crosslinking a crosslinking agent in the solution may not be required. In accordance with some embodiments of the disclosure, the protein solutions can be precisely deposited (using a precision instrument as described above) on the sensor electrodes and spread using spinning in the presence of crosslinking agent vapor.

Before and/or after functionalization, (but typically after functionalization as noted in FIG. 14) different films (e.g., membrane materials) can be used to protect and/or restrain the functionalization materials on the sensing element 160 and achieve a desirable signal response for a particular sensor configuration. In some embodiments of the disclosure, a diffusion limiting layer can be useful.

For example, in the body there is 30 to 300 times more Glucose than Oxygen. If the sensing mechanism has a 1:1 stoichiometry (e.g., Glucose detection using GOx uses 1 molecule of Oxygen for every molecule of Glucose), then the sensor placed without a limiting membrane will be limited by oxygen concentration and will not be able to sense glucose for the entire physiological concentration (e.g., 40-400 mg/dl). A polymer membrane can be deposited to act as a suitable diffusion barrier that allows oxygen to go through unhindered but hinders glucose diffusion.

Examples of workable polymer membrane materials include polyurethane, a mixture of polyurethane and silicone, as well as a mixture of polyurethane and PEG. In accordance with some embodiments, the thickness of the polymer membrane can be in the range from 0.1 micron to 15 microns. The polymer membrane may be between 200 nm and 10,500 nm thick. Alternatively, the polymer membrane may be between 200 nm and 1500 nm thick.

Adhesion between the membrane coating and the underlying hydrogel, or between layers of coating, can be facilitated by use of chemicals (e.g., silanes, aldehydes) and/or physical processes (e.g., corona treatment, oxygen plasma, gas plasma, mechanical roughening). Specific membrane materials and construction can be used to further improve sensor performance. In one embodiment of the disclosure, a combination composition of polyurethane and silicone can act as a filter to regulate diffusion of glucose and as an oxygen recycling membrane as well as providing a biocompatible material. Oxygen recycling can improve the efficacy of the sensor, while the biocompatibility can allow the sensor to work for longer. To cover the sensor uniformly and minimize sensor to sensor and batch to batch variation, membranes can be deposited on the sensor through spotting (droplet coating), spraying or through wafer-level spin coating. Membranes can also be deposited on the backside of the wafer to increase biocompatibility. Another method to uniformly deposit membranes is to employ spray coating with a special instrument utilizing overlap between multiple depositions to achieve a uniform overall thickness.

A specific workable polyurethane membrane coating process includes loading 1% PurSil from DSM in THF (DSM Biomedical, Exton, PA and Sigma Aldrich, St. Louis MO)

into an Air-jet spray coating unit (BioDot, Irvine, CA). A single coat of 1.25 microliter/cm is applied at 9 PSI pressure on sensor area, with dispensing height and aperture optimized for each coating unit installation. The wafer is dried in a vacuum oven at 35 degrees Celsius and 25.6 mm-Hg pressure for an hour and in ambient conditions for at least 12 hours (overnight). A second coat is applied, and sensors are dried with the same parameters. The sensors are allowed to stabilize in PBS (Sigma Aldrich, St. Louis MO) for 72 hours and characterized for analyte response.

Optionally, a membrane coating can also be patterned to reduce cell attachment. This patterning can be done using oxygen plasma or using nanoimprint lithography (biostamping). For oxygen plasma, after the membrane is coated on the surface, it is exposed to a high-power oxygen plasma (e.g., 300 Watt) in a plasma chamber without any mask or with a lithographic mask (e.g., AZ5214E for Photolithography, PMMA for electron beam lithography) or a stencil. The oxygen plasma will etch the exposed material and the material under the etch mask will be protected, hence shaping the surface. For stamping, the membrane is coated and patterned while being on a different substrate (e.g., Silicon substrate). Next, the membrane and the sensor surfaces are exposed to some process that prepares their surface for strong adhesion. One example is to expose both materials to a short, low-power oxygen plasma dose or to chemical linkers like Xylene. Next, the membrane is placed on the sensor surface and the bonding process is allowed to continue for some time. At the end, the substrate is gently removed, and the patterned membrane remains on the sensor surface.

FIG. 14 step 9 shows an embodiment of a device after deposition of a second film 168, such as a interference rejection layers, immune response suppressing layer, and/or biocompatibility layer, on the sensing element. A substrate 110, a metal-insulator-metal stack 129, a thin layer of desired material 138, a functionalization layer 158 and a top insulator with an optional additional insulator/protection polymer layer 118 remains.

Another example of polymer coating, other than a membrane, is use of interference rejection layers that can be coated on the electrodes before or after surface functionalization. These layers can similarly be coated using spraying, dip coating, electrochemical coating, spin and/or spray coating. In accordance with some embodiments of the invention, a coating including o-phenylenediamine can be used for rejecting Ascorbic acid and/or Acetaminophen in glucose sensing applications.

Another example of polymer coating which can be used includes immune response suppressing layers. Implanted sensors can be attacked by the foreign body or immune response of the body. This can be mitigated by incorporating coatings that inhibit response and/or mitigate the effects and decrease this foreign body response. Drugs such as dexamethasone or nitric oxide limit such response. Note that, in some embodiments of the disclosure, drugs that inhibit adverse response by the body (e.g., dexamethasone, nitric oxide) can be mixed, encapsulated, or chemically included in the functionalization layers and/or membrane layers, instead of a separate coating, in a way that allows slow release of the drugs throughout the functional lifetime of the sensor. Another example of polymer coating which can be used includes a biocompatibility layer.

To improve biocompatibility of the system, the sensor can be coated with a biocompatible material. Proteins attach to hydrophobic surfaces; thus, an option to improve biocompatibility is to cover the device with a hydrophilic or superhydrophilic polymer (Note that polyurethane, an option for membrane formation, is hydrophobic). For example, the biocompatible material can be poly-HEMA. A layer of pHEMA can be formed with a thickness of 5 microns to 100 microns and a preferable thickness of about microns. In some cases, a copolymer of a biocompatible material can be made with polyurethane to coat the device in a single step.

An additional/alternative biocompatibility layer can be the deposition of Titanium and/or Platinum or a catalase hydrogel to mitigate the effects of reactive oxygen species. For example, a layer of catalase can be coated over top a layer of GOx hydrogel. The layer of catalase can be, for example 0.05 μm to 25 μm, alternatively 0.1 μm to 3 μm. It has been shown that reactive oxygen species from glucose oxidase can damage surrounding tissue. Platinum is known to breakdown the reactive species into less corrosive byproducts and hence is ideal for this application. For instance, platinum microspheres can be dispersed within the pHEMA hydrogel or any other hydrogel and used to coat the surface. In short, a solution of platinum spheres in water can be used to make the hydrogel and ultrasonic mixing of the components can be used to ensure proper dispersion of the spheres throughout the hydrogel. In a further embodiment of the disclosure both a hydrophilic biocompatibility layer and a means to quench reactive oxygen species are used in combination with an immune response limiting element. For example, dexamethasone (0.01%-3% w/w) can be mixed into the polyurethane layer. PolyHEMA layer can be patterned with nanoimprinting to achieve a super-hydrophilic surface. 2 nm thick Ti/2 nm thick Pt can then be sputtered on the surface to quench reactive oxygen species while maintaining super hydrophilicity and porosity. As noted above, multiple layers of membrane and/or polymer materials can be applied to the implantable monolithic sensing circuit.

Another example of biocompatible layer (also known as sensor-tissue interface layer) is PVA. A specific workable PVA includes the following: Poly(vinyl alcohol) (MW 89,00-98,000 99%+ Hydrolyzed, Sigma 341584) was mixed with DI water 4% (w/v) (1-10% acceptable), by slowly adding PVA into DI water heated to 80 C and stirred at 400 rpm with a stir bar. The solution was capped and let stir for 12 hours prior to use.

To make the PVA layer, the solution is drop casted or spin coated on the sensor surface. In a typical recipe, the solution is dispensed to cover more than 90% of the surface to be coated (e.g., wafer, die, or flex PCB with the sensors attached). The surface is then spun, first at a lower speed (e.g., 500 rpm) for 10 seconds to spread the solution and then accelerated to a higher speed (e.g., 500-5000 rpm with 3000 rpm as a typical case) to get to a desired thickness. The sensors are then left to sit in a controlled environment (e.g., an oven set at 35° C.) for a known time (e.g., 24 hours) for the PVA gel to form.

FIG. 14 step 10 shows an instance of how dipping can be used to apply a small volute of material (e.g., polymer 178) on the sidewalls. A substrate 110, a metal-insulator-metal stack 129, a thin layer of desired material 138, a functionalization layer 158, a film 168 and a top insulator with an optional additional insulator/protection polymer layer 118 remains. FIG. 27 shows how another material can be coated on the pre-coated sensors using a thin-film coating process (e.g., dip coating, spraying).

After deposition of one or more membrane and/or polymer materials, in an embodiment, the implantable monolithic sensing circuit can be considered complete. FIG. 2B shows the components of an embodiment of a completely processed implantable monolithic integrated sensor circuit including the silicon substrate with integrated contact pad 175 attached to flexible connector, the integrated working electrodes, WE1, WE2, and WE3, representing the integrated sensing element, said working electrodes separated by insulation walls 118, with the working electrodes coated with the functional matrix example Gox-loaded hydrogel 158 and the polymer coating example PU membrane 168.

In accordance with some embodiments of the disclosure, a post-processed sensor wafer can be cleaned with deionized water and/or pressurized gas and dried in vacuum oven (20-400 degrees Celsius, e.g., 40-200 Celsius; 0 to 30 mm-Hg below atmosphere, e.g., 26 mm-Hg). In accordance with some embodiments of the disclosure, a cleaning and drying step can be followed by a plasma cleaning and surface activation step. In some embodiments, the sensor can be cleaned under 50-600 mTorr pressure of oxygen or air or argon plasma with a power of 75-400 W. In some embodiments, Oxygen plasma at 100-500 mTorr, with a power of 90-200 W can be used. In accordance with some embodiments of the disclosure, after post-processing and drying, wafers or sensors can be placed in a humidity controlled nanoliter dispenser equipped with an aluminum chilled plate calibrated to be able to operate at 80% RH and 25 degrees Celsius plate temperature.

Flexible Connector

In the present disclosure, a physical intermediate transdermal component 3 is used to connect the external transmitter 2 located on the skin to the monolithic integrated sensor circuit 1 in the analyte concentration measurement system.

One typical embodiment of the intermediate component is a bidirectional connector. The connector can be a single wire, two wire, three wire, four wire, or higher instance flexible connector 3. In some embodiments, the connector can be a flexible printed circuit board with the wires being conductive trace(s) therein.

Wires/conductive trace(s) can be made of copper, aluminum, gold, or other conductive material. The connector can comprise a biocompatible polymer such as parylene-C, liquid crystal polymers (LCP), or polyimide, which may almost completely cover any wire/conductive trace(s) except for points necessary to connect to the external transmitter 2 or integrated sensor circuit 1.

FIG. 20 shows several schemes to connect the integrated sensor circuit 1 with the transmitter 2 via a flexible connector 3 comprising varying the numbers of wires/conductive traces. The connector 3 can have 1 or multiple wires/conductive traces to flow power and data between the sensor 1 and the transmitter 2.

Data communication can be performed using a two-wire connector per "communication over power" through superimposition of the data signal over the power wire. The same conductors can be used for both data and power (e.g., to save space) as shown in the 2-wire configurations shown in the top of the FIG. 20. One of the wires can act as the power supply and signal and the other as the ground. If data and power share a conducting line, a coupling-decoupling (Co-De) network (also termed as Multiplexing-Demultiplexing or MUX/DEMUX network) on both sides of the same conductor is to be used. The Co-De network can be designed to separate data from power on either or both sides.

With regard to MUX/DEMUX network, at the transmitting side, this can be done through an AC coupling capacitor and a tri-state driver in one particular embodiment. At the receiving end, an AC decoupling capacitor can be utilized to extract data by decoupling it from the power signal followed by a hysteresis comparator which detects the signal while being resilient to the signal noise. Since both transmitter and the monolithic integrated circuit will be operating in both transmitting and receiving modes, the aforementioned circuitries can be incorporated in both the transmitter and the sensor. Since the data is modulated over the power signal, the power signal received at the sensor is not clean. Hence a voltage regulator is utilized at the sensor to create a clean and stable DC supply. This DC power can be sent to the potentiostat which powers up the integrated sensing element. If a read command is received from the transmitter, the monolithic sensor circuit can send digital readings via the two-wire flexible connector to the transmitter.

However, different conductors for data and power can also be used to simplify the system design as shown in the 3-wire configuration of FIG. 20. If full-duplex communication is desired, separate conductors can be extended to use n number of conductors, e.g., for sending redox voltage from the transmitter to the sensor, for sending data for multiple sensors from the sensor to the transmitter and so on.

The flexible connector can fit in a 16 gauge to 32 gauge needle with 23 to 28 gauge being an alternative range and 26 gauge being a further alternative. Rectangular needles can be used instead of standard hypodermic needles, in which case an equivalent needle gauge description can be used as the standard needle gauges are defined for cylindrical tubes and the needles made from those tubes. The equivalent needle gauge can be defined by comparing the hypotenuse of the rectangular needle (based upon the triangle formed by the base and the wall height) with the diameter of the cylindrical needle.

With regard to the mechanical properties of the connector, said properties of the connector 3 can be controlled by controlling its conductive materials, insulating layers, and shape. It is important to manage the mechanical properties of the connector to provide a connector of sufficient rigidity and strength to be successfully applied by an applicator yet flexible enough as to not induce a strong immune response by damaging surrounding tissue during user movement.

For example, stiffeners (e.g., polyimide, glass, steel, FR4) can be attached as a bottom layer of the flexible connector 3 to provide additional rigidity.

Alternatively, a layer of bottom Cu can be used to increase the stiffness of the panel, as shown in FIG. 26. This use of standard flexible PCB insulated copper traces to control the stiffness of the flexible connector is a unique feature of this design. Control on size and thickness (e.g., 0.25 Oz, 0.5 Oz, 1 Oz, 2 Oz etc. Cu) can provide a control on the mechanical properties of the panel. For example, a panel with a dummy bottom metal underneath the top metal designs can be stronger than a panel without the bottom Cu. The Cu is completely covered with sealed insulators to prevent any interaction with the body fluids. In some cases, Cu can be covered with more biocompatible materials (e.g., noble metals like Palladium and Gold) or can even be replaced by those. This stiffness control enables thinner devices as compared to the use of stiffeners, and hence enables the use of smaller needle sizes which reduces insertion pain and foreign body response. The top metal and the bottom metal layers may also be referred to as "first metal layer" and "second metal layer", respectively.

With regard to a connector (e.g., flex-PCB), the total thickness in some embodiments can be 100 to 250 μm, preferably 150 μm. A flex-PCB can be made of three layers, five layers, or more depending on the design of the conductive traces and stiffness requirements.

In a specific exemplary embodiment, the flexible connector 3 is a flexible PCB. The flexible PCB is of five total layers (generally known as 2-layer PCB based upon 2 conductive layers) with a top Cu layer of ½ oz (18 µm) and bottom Cu layer of 2 oz (70 µm). A top overlay can be used of 1.5 mils (37 µm)–1 mil adhesive+0.5 mils. The substrate of the PCB can be for example 1 mil (25 µm). Preferably, a flex-PCB will involve a stiffener in areas where mechanical strength is requires, e.g., its connection with other electronics (e.g., the transmitter board). The stiffener can be for example 75 µm (3 mils of FR4) or a similar thickness of stainless steel or Polyimide.

The bonding pads of the flexible connector 3 can be made with different finishes including Electroless Nickel, Immersion Gold (ENIG), Electroless Nickel, Electroless Palladium, Immersion Gold (ENEPIG), Immersion Gold on Cu directly as few examples. The pads are used on one end to connect with the integrated sensor circuit 1 and on the other end with the transmitter 2 using different methods detailed next.

A variety of processes can be used to join the connector to the monolithic sensor circuit. In accordance with some embodiments of the disclosure, a two-wire connector 3 is made up of a flexible polymer substrate, e.g., polyimide or parylene-C, with thin copper traces (e.g., 20-100 µm wide, alternatively 20-50 µm wide; and 20-100 µm apart, alternatively preferably 20-50 µm apart; with 1-30 µm thickness, alternatively 10-30 µm thickness). The copper traces are sandwiched by the polymer substrate to avoid exposure to bodily fluids. On the implantable monolithic integrated circuit 1 side two bonding pads are created by removing a passivation layer during a CMOS manufacturing process, removing any biocompatible membrane and/or polymer and plating gold on top of the copper wire connection on the circuit. At the connection site to the implantable monolithic integrated circuit 1, the copper traces can be exposed and covered with gold for good connection to the sensor using a flip-chip bonding technique or wire bonding.

FIG. 25 provides a packaging process scheme of the sensor circuit 1 onto the connector 3. FIG. 25 Step 1 illustrates a sensor circuit 1 positioned adjacent to a connector 3 (e.g., a flexible PCB panel). The connector 3 may include conductive traces 302 in a middle layer of the flexible PCB panel, i.e., under a PCB top layer 303. The sensor circuit 1 can include multiple sensors 160 at some distance from CMOS pads 175. FIG. 25 Step 2 shows the bonding of the sensor circuit 1 to the flexible connector at 301 through die attach, followed by forming conductive traces between the sensor circuit 301 and flexible connector 3 via CMOS pads 175 and wire bonds 314. The wire bonds can be made using many metals like Aluminum, Gold, Copper, Platinum etc. The methods to make wire bonds include thermosonic bonding which uses a combination of heat and ultrasonic power to attach thin (e.g., 25 µm diameter) wire on CMOS pads and flexible connector pads. In one example, 25 µm gold wire is used to make connections between the CMOS pads and the flexible connector pads. An image of a wire bonded sensor circuit 1 can be seen below.

FIG. 26 Step 3 shows the conductive pads and the conducting interface on the sensor circuit 1 and the flexible connector array 301 protected for water ingress and mechanical abrasion by covering those with a biocompatible insulating material 313. An example is a biocompatible insulating material (e.g., 31CL) that is deposited in small volumes (e.g., 1-20 microliters) on the wire bonds followed by thermal curing (e.g., at 100° C. for 1 hour). Sometimes, the encapsulation process is done in multiple steps to ensure complete coverage of the wire bonds. An image of a wire bonded sensor circuit 1 can be seen below.

FIG. 27 shows an instance of how an entire row of implantable monolithic integrated circuits 610 can be attached to a flexible PCB 620 using wire bonding 630. In either flip-chip or wire bonding, the connection between the connector 3 and the implantable monolithic can be hermetically sealed with a biocompatible polymer (e.g., parylene-C). Smart nano-dispensing robots (e.g., Nordson EFD) can be used to precisely dispense appropriate biocompatible polymers (e.g., for hermetic sealing) like 31CL (Henkel Loctite EA M-31CL Medical Device Epoxy) in small and controlled volumes (e.g., 1-20 microliters, typical 2 microliters). FIG. 27 shows an example of how an insulating material 640 can be used to hermetically seal the sensor-PCB interface. One or more soft materials like enzyme hydrogel 190 can be coated on the sensors using a thin-film coating process (e.g., spin coating, spraying). This can be followed by coating a second soft material like polyurethane 189. The integrated sensor 1 and flexible PCB can then be diced together.

Another technique to integrate the sensor 1 with the flexible connector 2 is the use of flip-chip bonding. FIG. 28 provides an example of flip-chip bonding. In this method, the sensor 1 pads 175 and the flexible connector pads 302 are aligned and pressed together. A soft material (e.g, Au, InSn) bump 1751 is optionally used to fuse the two pads together via a combination of heat, pressure, and optionally ultrasonic energy. Conductive bump 1751 sits on CMOS pad 175. After fusion, the contact pads are covered with insulting epoxy (e.g., using underfill). As seen in FIG. 29, the interface between the flex PCB and the CMOS pad 175 can be covered in insulating epoxy 313.

Another method can use flip-chip bonding using anisotropic conductive adhesive (ACA). This can be accomplished through bonding the monolithic integrated sensor circuit 1 to the flexible connector using ACA. If desired, conductive bumps are formed on the CMOS pads, followed by ACA coating on the CMOS pads and/or the Flexible connector pads. Afterwards, the CMOS and Flex connector pads are aligned and pressed together for a certain duration at controlled temperature and pressure. This forms an electrical connection in one direction (e.g., vertical) between desired pads on CMOS and the flexible PCB. The interface between the flex PCB and the CMOS pad can be covered in insulating material, e.g., using an underfill or a similar process. Additional pads can be used on the CMOS and corresponding pads on the flexible PCB for a stronger and more symmetric bonding. An optional cutout in the flexible PCB can ensure that the sensor area 160 is exposed to the environment for sensing.

Another technique to integrate the sensor 1 with the flexible connector 3 is to embed the sensor within the flexible connector, as shown in FIG. 30. In this case, the sensor chip 1 is placed between the flexible connector layers. Electrical connection between the sensor chip 1 and the flexible connector 3 is made by using interlay conductors (like vias) 38 in the flexible connector. Flexible PCB contact pads are at 39. The active sensor area 160 is kept open by patterning the dielectric layers of the flexible connector as shown in FIG. 30. Functional material 19 can be deposited over active sensor area 160. This method enables a completely solid-state device with minimal height and can be scaled rapidly.

FIG. 31 shows another scheme of connecting the monolithic integrated sensor circuit 1 and the flexible connector 3 (e.g., flexible PCB). In this scheme, the sensor 1 uses through-silicon-via (TSV) technology to have contact pads 19 under it. In this scheme, a trench is etched from the backside of the CMOS sensor circuit 1 silicon substrate 110 to the conductive trace using a combination of wet and/or dry etching methods. Then the sidewall of the silicon is covered with and insulator and finally with a conductive material that runs from the backside of the CMOS sensor circuit to the front side, e.g., to chip pad 175. These pads on the backside of the CMOS sensor circuit 1 can be attached to the flexible PCB conductive trace 302 using different methods (e.g., bump bonding, conducting adhesive like Anisotropic conductive adhesive or ACA) depending upon the size and the application. Next, the conducting interface is covered with an insulating material 313.

Yet another embodiment for packaging together the monolithic integrated circuit 1 and the flexible PCB is provided in FIG. 32. In this case, the monolithic integrated sensor circuit 1 is placed inside a well in the flexible connector 3. The gap between the sensor circuit pads 175 and the flexible connector pads 302 is filled with an insulating material 313, followed by forming the connection between the two pads 314 (e.g., using wire bonding, or conducting epoxy, etc.) followed by covering it with a thin layer of insulating material 313.

Moving to connecting the connector 3 to the transmitter 2, various options exist. The 2-wire flexible connector can be soldered to the transmitter circuit board. Alternatively, it can be soldered to a medical grade connector which can then be connected to a connector on the transmitter. In a separate embodiment, micro connectors can be used to connect the connector 3 to the transmitter 2. In addition to connecting the wires of the connector to the implantable monolithic sensor circuit, in various embodiments the implantable monolithic sensor circuit 1 can be further secured to the connector 3.

FIG. 33 shows a scheme of using the integrated sensor circuit 1 on one side of the flexible connector and using the other side of the flexible connector as a secondary sensor 9 (e.g., a 2 electrode or a 3 electrode sensor design). The flexible connector 3 on the other far side uses a connector that can connect with its conducting traces on both sides of the flexible connector, thus enabling connection with both the integrated sensor circuit 1 and the secondary sensor 9. The secondary sensor can be used for validation and control purposes. It is read by the transmitter circuit which in a simple embodiment would just read its voltage (e.g., to confirm if the sensor is inserted under the skin, to confirm if the sensor is being perfused). In a different embodiment, the transmitter would use a potentiostat circuit to read the electrochemical signal from secondary sensor 9. The secondary sensor 9 can be functionalized as is the integrated sensor circuit 1 above. This secondary sensor 9 can then be compared with the reading from the integrated sensor 1 for reliability check of the platform as well as for other similar checks (e.g., to see if sensor is being properly perfused).

FIG. 34 shows another embodiment of the system architecture in which the flexible connector 3 not only has conductors for the electrical connections but also has conductors working as a sensor/sensor electrodes, e.g., electrochemical sensor 40. The flexible connector 3 has contact pads 42 that are connected with the sensor 40 via traces 41. Moreover, an application-specific integrated circuit (ASIC) 30 is placed in close proximity to the sensor to help process its data. The ASIC comprises at least a potentiostat. The contact pads 42 can be connected with the contact pads 31 on the ASIC 30. The ASIC 30 contains another set of contact pads 32 for connection with the conductors 302 of the flexible connector 3. The connection interface is covered with an insulator.

FIG. 34 Step 1 shows the ASIC attached to the flexible assembly. FIG. 34 Step 2 shows the connection between the contact pads 42 on the flexible connector and the pads 31 of the ASIC and between conductor 302 and the contact pad 32 of the ASIC via bonding wires 43 and 44 respectively. FIG. 34 Step 3 shows both exposed connection interfaces can be covered with insulators 45 and 46.

This scheme enables the passive CGM designs to benefit from most features of the integrated sensor 1 design (e.g., close proximity of the sensor and the electronics) without having to change the way existing manufacturers, like Medtronic, manufacture their electrochemical sensors 40.

Transmitter

The analyte concentration measurement system requires an external transmitter 2 located on top of the skin of the user to secure the transdermal connector 3 and the monolithic sensing circuit 1. The transmitter 2 can provide electrical power to the monolithic integrated circuit 1 via the flexible connector 3. The external transmitter 2 can be used to power monolithic integrated circuit 1 and to communicate with implantable monolithic integrated circuit 1, i.e., to receive data from and send data (e.g., commands) to sensor before and after the monolithic integrated circuit 1 is inserted.

The transmitter is an electronic device with a power source (e.g., a battery). A printed circuit board (PCB) can be used to make a transmitter system with all components to function as the transmitter 2. One or both of thick (rigid) and thin (flexible) PCB technologies can be used, depending upon the application.

In various embodiments, the transmitter 2 can also communicate with the monolithic integrated circuit 1 via the flexible connector 3. The communication can be bi-directional or unidirectional, wherein optionally bi-directional communication is sequential, meaning that first the transmitter sends a command (e.g., a tag) to the monolithic integrated circuit 1 to trigger analyte measurement by the sensor. After the transmitter sends this tag, it can go into receiving mode (i.e., it waits for the sensor to send it the measured data). Error correction schemes can be employed to minimize the error in this communication. Parity-bit based designs and more advanced error correction codes can be used as well. Different types of modulation schemes can be employed for this communication.

A schematic diagram of an example of a transmitter according to some embodiments of the disclosure can be seen in FIG. 35. The transmitter 2 can include a transceiver 210 that can generate and detect communication signals flowing over a combined power/data connection through wire 3, a high-performance digital microprocessor unit 211 for system control, a low-energy wireless communication chipset 213 (e.g., Bluetooth), an antenna 218 for wireless communication (e.g., Bluetooth antenna), a power management unit 214 connected to a battery 212, and a voltage regulator unit 217 to provide regulated power to the implantable monolithic integrated sensor circuit 1.

In an exemplary commercial off the shelf transmitter design, a system-on-chip can be used to provide the functions of a microprocessor, a wireless communication link (e.g., BLE) with an integrated antenna, as well as on-system memory. Similarly, a battery unit can contain the battery along with a battery management circuit. Examples of a suitable system-on-chip for use in the transmitter include TAIYO YUDEN® EYSHSNZWZ BLUETOOTH® Low Energy Module and Lilypad coin cell battery module. Additional electronic circuit like a transceiver can be implemented to pre-process the incoming data from the sensor circuit 1 to make it easier to be read by the processor. In one example, the transceiver may include operational amplifiers (e.g., Texas Instrument TLV9061) to amplify the incoming signal and a comparator (e.g., Texas Instrument TLV7011) to create a rail-to-rail signal. In some examples, this transceiver circuit can be implemented within the SoC e.g., by using on-chip amplifiers and comparators.

Although a transmitter could be implemented via a commercial off the shelf technology, it is possible to use a custom solution using application specific integrated circuits (ASIC). FIG. 36 shows a detailed electrical schematic of a transmitter embodiment which can be fully integrated into a custom ASIC. It shows a battery 212 powers the system via a voltage regulator 217 that uses a voltage reference 216 to set the output voltage. Different types of batteries can be used to power the system, including Lithium-ion, Silver, Zinc, Lithium polymer, thin-film etc. For example, a lithium-ion battery voltage can range from 3.3V to 2.8V based upon remaining charge. The voltage regulator can provide a stable output voltage (e.g., 3V) independent of such battery status, thus helping with stable circuit operation for longer duration. The voltage regulatory powers the rest of the transmitter components including a microprocessor/microcontroller 211, a wireless communication transceiver (e.g., BLE transceiver) 213 feeding an antenna 218. The microcontroller generates a suitable tag signal to communicate with the receiver (implantable monolithic sensing circuit 1). The tag signal is fed to a TX unit 215 that shapes the tag and couples it to the wired connection 3 via a DC decoupling capacitor 242. A switch 228 is closed when this tag signal is being transmitter while another switch 229 is kept open to prevent leakage of this signal into the Rx unit 210 of the transmitter. After the tag is sent and a certain duration is passed, a signal is expected from the sensor 2. At this time, the switch 228 is opened while the switch 229 feeding the signal to the Rx unit 210 of transmitter 2 is closed. The Rx unit 210 can shape the received signal, e.g., by using a monostable circuit to increase the width of received signal. The received signal passes through the DC decoupling capacitor 242 before being fed to the Rx unit 210. The main voltage regulator 217 feeds power to a secondary voltage regulator 231 that is used to generate a more suitable voltage (e.g., 2V) for the receiver (e.g., implantable monolithic sensing circuit 1) using voltage reference circuit 232. The resistor 243 is used to isolate the voltage regulator from the transmission line 3. The resistor 243 and the capacitor 242 are example embodiments and can be replaced with other types of electrical networks to perform this same function of combining the data with the power on one end (from transmitter to the sensor) and separating the data and power on the other end (from sensor to the transmitter).

The housing options for the PCB of the transmitter varies. FIG. 37 shows an implementation of the transmitter. It includes the connector 3 attached (e.g., by wire bonding, soldering, through a medical grade micro-connector, etc.) to the transmitter which further consists of a printed circuit board 21 housing the battery 212, regulator 217, and integrated BLE transceiver and application controller/processor System-on-chip 250. This part represents integration of several components (e.g., microprocessor, transceiver, antenna). The transmitter is housed in a sealed plastic/rubber housing 22 for environmental protection and easy handling during usage. FIG. 37B shows images further inclusive of connectors 32 and 34, which can mate to connect the printed circuit board and connector 3.

FIG. 38 shows another embodiment of the implementation of the transmitter 2 using a printed circuit board with electronic components and a power source, housed within a suitable casing. The connector 3 on one hand attaches to the transmitter circuit and on the other hand to the integrated sensor circuit 1. In embodiments, the connection between the transmitter circuit and connector 3 is off to a side of the transmitter assembly to enable more compact assembly.

The transmitter can wirelessly communicate the data to a hub or smart device (e.g., a phone, a tablet, or a special separate device 4). In accordance with some embodiments, the hub or smart device can be connected (either by wire or wirelessly) to a cloud server via a network (e.g., the Internet, a private network such as virtual private network (VPN), or a public network). The transmitter uses a low-power wireless communication technology (e.g., Bluetooth, Zigbee) to communicate with the smart device. The transmitter may use a standard BLE profile (e.g., the CGM profile) to enable a simple interface with other devices (e.g., to form artificial pancreas). A secure BLE connection can be stablished between the transmitter and the host device using techniques like dedicated digital keys.

The transmitter is programmed using a firmware to enable operations desired in a typical implementation. The firmware is designed to perform the operations necessary to control the operation of the transmitter hardware to match with system needs. The firmware is stored on a permanent memory block on the transmitter. The memory typically resides within the Bluetooth module of the transmitter. Many BLE modules have the option to wake-up the system using an NFC link. The transmitter firmware is designed to keep it in low power mode until any such wake-up calls are received. This can enable the transmitter to remain in low power mode till the user is ready to operate the unit (e.g., after sensor insertion). Then the transmitter can be taken out of the sleep mode to start a secure dedicated connection with a desired reader and start communicating the data.

After such wake-up, the transmitter firmware (designed as a BLE client) looks for a BLE master to connect to. If such a connection (device) is available, the transmitter establishes a connection to the device (e.g., smart reader). After this, the transmitter tests the available power level and upon validation of a stable power supply, it looks to see if a suitable sensor is attached (via the amount of current draw). It also checks sensor readings to be within normal range with a normal rate of change (as programmed in its memory during manufacturing) to confirm if the sensor is operating properly (e.g., in warm-up period). After the warm-up period is complete (prep-programmed during manufacturing), the transmitter checks the reading values and the rates of change to determine if the sensor is operating properly.

Since the sensor is a smart CMOS device, the data coming from it is different than the data coming from the passive CGMs in other applications (just the sensor current). In this case, the header (preamble), the footer contains the sensor batch and type and are compared against the IDs stored on the transmitter to confirm that the sensor and the transmitter are indeed matching. Moreover, the error detection schemes (e.g., CRC) can quickly tell if the received data is properly encoded. The data from the sensors, including the temperature sensor can then be compared against each other and the factory stored values (e.g., in a look-up table) to confirm if the sensor is completely operational and is properly inserted in the tissue. After this, the transmitter sends a tag to the sensor telling it to start sending the sensor data at a desired interval (e.g., once every 2 seconds). This data is then read by the transmitter, tested, and combined (e.g., averaged over 3 sensors) before sending it to the reader at a certain frequency (e.g., once/minute).

The transmitter can also include usability features like a temperature sensor to detect environment temperature reading which can then be compared with the temperature sensor on the integrated sensor 1 to detect change in temperature from the environment to the tissue around the sensor. Another optional embodiment is for the transmitter to have a light sensor (e.g., a Photodiode) that acts as a way for the system to detect its state (i.e., still in the packaging, vs outside of the packaging).

System Packaging and Operation

The sensing platform can be loaded inside an applicator device and the entire assembly can be sterilized (e.g., by Synergy Health (San Diego, CA)). To sterilize the device before embedding it inside the body, conventional methods of sterilization (e.g., steam, Ethylene Oxide) can be utilized. In one particular embodiment, Electron-beam (e-beam) sterilization can be used to sterilize the sensor as well as the applicator once the sensor is pre-loaded in the applicator. The underlying electronics can be designed to be resilient to e-beam radiation. The enzyme chemistry can be characterized to calibrate for any changes in the enzyme chemistry response due to sterilization. In one embodiment, 25 kGray of e-beam irradiation can be sufficient to sterilize the sensor without impeding its function. Sensors can be placed inside the applicator and then the whole assembly can be sterilized. In a different embodiment, the integrated sensor 1 and the connector 3 assembly, the transmitter 2, and the applicator can be sterilized separately using different methods (e.g., sensor 1 and connector 3 assembly using e-beam, transmitter 2 and applicator using ethylene oxide) followed by sterile assembly.

One or more sensors 1 can be placed in desired tissue locations using an applicator as noted above. As noted throughout the present disclosure, in embodiments, the implantable monolithic integrated sensor circuit 1 can be used to measure glucose levels in the user. The readout procedure for collecting glucose data from the implantable monolithic integrated circuit 1 can start with energizing the implantable monolithic integrated circuit 1 through transmission of power signal (through wired connection) from the external transmitter 2. The external transmitter 2 can be configured to select the appropriate powering mode (continuous/intermittent) based on user or clinician input.

The external transmitter 2 can receive sensor data, display sensor data, store the data, relay it to a smart device 4, or send it a remote server. External transmitter 2, smart device/communication device, or remote server can relay and process the sensor data in a manner commensurate with its processing, storage, or battery capability. The data processed in external transmitter 2, smart device/communication device, or remote server can be relayed to external transmitter 2, smart device/communication device, or remote server to provide, display, or store, information (e.g., blood glucose levels, daily trends) or predictions thereof or suggestions (e.g., behavioral changes, treatment changes) based on sensor data or predictions.

After the sensor assembly is removed from the packaging, the transmitter 2 needs to be turned on to power the sensor 1 and to communicate with the reader 4. Different schemes can be used for this purpose. For example, a photosensitive detector (e.g., a photodiode) can be used to detect opening of the package. This signal can then be used to turn on the transmitter power supply and start the initialization and connection procedure.

In a different embodiment, a wake-up-in-the-field method using an NFC pairing capability embedded in the transmitter can be used to turn on the transmitter operation after the user opens the sensor packaging. The transmitter is paired with an NFC enabled device to send it the turn-on signal. The transmitter then starts the initialization process.

FIG. 39 shows an algorithmic scheme to program the processor (e.g., a microcontroller) in the transmitter (which acts as the brain of the transmitter) with a firmware to control its operation. It shows that the transmitter (microcontroller) is programmed to stay in a low power (e.g., deep sleep) state. After the user opens the packaging and performs a turn-on operation (e.g., either by using an NFC device to pair with it) or the transmitter automatically detects the user's intent to use it (e.g., by detecting a change in background conditions like light via a photodiode), it performs an initialization sequence which includes a self-test as well as a scan for the reader via BLE. Once it finds a matching reader, it connects with it via BLE. Next, it tests if a good sensor is connected by performing electrical measurements (e.g., voltage drop, current draw) and by sending a command signal and testing the response. After that, it starts transmitting the tag signal and start reading the corresponding data from the sensor chip. The transmitter separates the power and data signals (via mux/demux) and sends it to the microcontroller which preprocesses the data (e.g., check for proper preamble, proper data coding scheme, packet length, packet duration), checks if it detects any error (via error detection/correction code), and separates the data from all 4 (3 electrochemical and 1 temperature) sensors. It then sends the data to the reader via BLE.

Multi-Sensor Signal Processing Schemes

As described above in relation to FIGS. 4 and 5, the integrated sensing element 160 includes three (or more) working electrodes, each of which generates a respective sensing data signal. The quantities and qualities of various parameters of interest can be determined as a function of these data signals. In some embodiments of the disclosure, the data signals can be combined with other reference and/or stored data signals to generate the quantity and/or quality of parameters of interest. In an example, the three (or more) working electrodes are used to detect the concentration of the same analyte (e.g., glucose).

The presented device has a unique advantage of having multiple sensing electrodes (e.g., multiple working electrodes) on a single device. The data from these multiple electrodes can help improve the quality of the sensor data. Different approaches can be used to do so and generally referred to as data fusion techniques. For example, in one method, the signal from all 3 working electrodes can be averaged to minimize the effect of noise or skewness from the data. In another case, the median of all readings can be used to do so. In a different method, the readings from all 3 working electrodes can be compared to eliminate any outliers (e.g., if one electrode reading is significantly different than the other two). This method is called voting. In case of outliers, interpolation can be used to fill in the gap of the missing outlier data. Or that sensor's data can be discarded in decision making for a particular duration.

In general, the sensor reading at any given time is a function of the reading from all the working electrodes (referred to as "sensors" below for brevity). For example, for the case of 3 glucose sensors, the sensor output can be written as a function of the 3 sensors' readings as $$g = f(g^1, g^2, g^3)$$

The function can be of many types. In a simple way, an arithmetic function (e.g., weighted average) can be defined based upon the sensor values $$g = \sum_{k=1}^{n} a^k g^k$$

In a simple case, the equation can become $$g = a^1 g^1 + a^2 g^2 + a^3 g^3$$

The above equation describes a weighted averaging technique to convert the data from 3 sensors into a single data stream. The coefficients ($a^1$, $a^2$, $a^3$) can be calculated during testing of the sensors in known glucose concentrations in the lab and in test subjects, i.e., in calibration (done at the factory, in the field, or in a combination). The sensor values ($g^1$, $g^2$, $g^3$) are readings of the 3 sensors, respectively.

A control logic (e.g., a processor, a processing unit, a controller, or a microcontroller etc.) may be employed to implement the function f. The control logic may be part of the monolithic integrated sensor circuit 1. For example, the control logic may be part of the sensor signal acquisition unit 130. Alternatively, the control logic may be incorporated within the transmitter 2, and for example be part of the processor 211 (FIG. 35). Further alternatively, the control logic may be external to the transmitter 2 and the monolithic integrated sensor circuit 1. In an example, the control logic may be part of the smartphone 4 (FIG. 1) or part of a computer which processes the data of the secure database.

In real-time use, several different approaches can be used to take advantage from the multiple sensors. For example, a mathematical function (e.g., arithmetic averaging) can be applied to all sensors and any sensor with large deviation from the result (e.g., mean value) is considered to have erroneous reading. Also, an average of a subset of sensors (e.g., 2 sensors out of 3) can be taken and compared against the reading from the sensors. If any sensor has large deviation from this average, the sensor is considered to have erroneous reading. This process is repeated for all sensor combinations. At the end, any sensor with an unacceptably large error (its combinations have largest error) is considered to have erroneous reading at that point, which means its reading is eliminated (its weighting coefficient becomes 0). FIG. 40 shows a scheme for using the multiple on-chip sensors (working electrodes) data as well as previous readings and a personalized (for each patient) patient-sensor model to generate the best outcome (glucose value) at a given time. The scheme uses the current data from all sensors (e.g., 3 electrochemical and 1 temperature) and uses that to calculate errors among the sensor values. It also compares the readings with the previous reading to decide if the new values are physiologically accurate. By comparing the sensor readings among themselves and the errors, the system decided if a sensor has unacceptable level of error. In that case, it discards that sensors and uses rest of the sensors data to generate a weighted average as the current value of the sensor.

TABLE 1

| T(m) | Ref | S1 | S2 | S3 | Wavg | M | Avg 1-2 | Avg 1-3 | Avg 2-3 | E1 | E 2 | E3 | M E | SME | DS | BS | AE | EWD |
|---|---|---|---|---|---|---|---|---|---|---|---|---|---|---|---|---|---|---|
| 0 | 10.05 | 10 | 10.1 | 8 | 9.37 | 10 | 10.05 | 9 | 9.05 | 0 | 0.1 | 2 | 2 | 3 | 3 | 10.05 | 0 | 0.68 |
| 5 | 10.3 | 10.2 | 10.5 | 8.2 | 9.63 | 10.2 | 10.35 | 9.2 | 9.35 | 0 | 0.3 | 2 | 2 | 3 | 3 | 10.35 | 0.05 | 0.67 |
| 10 | 10.3 | 10.1 | 10.3 | 9.1 | 9.83 | 10.1 | 10.2 | 9.6 | 9.7 | 0 | 0.2 | 1 | 1 | 3 | 3 | 10.2 | 0.1 | 0.47 |
| 15 | 9.6 | 9.5 | 9.75 | 10 | 9.75 | 9.75 | 9.625 | 9.75 | 9.875 | 0.25 | 0 | 0.25 | 0.25 | 3 | 3 | 9.625 | 0.025 | 0.15 |
| 20 | 10.2 | 10.1 | 10.4 | 15 | 11.83 | 10.4 | 10.25 | 12.55 | 12.7 | 0.3 | 0 | 4.6 | 4.6 | 3 | 3 | 10.25 | 0.05 | 1.63 |
| 25 | 13.38 | 13.5 | 13.3 | 19 | 15.27 | 13.5 | 13.4 | 16.25 | 16.15 | 0 | 0.2 | 5.5 | 5.5 | 3 | 3 | 13.4 | 0.02 | 1.89 |
| 30 | 15.45 | 15.2 | 15.4 | 32 | 20.87 | 15.4 | 15.3 | 23.6 | 23.7 | 0.2 | 0 | 16.6 | 16.6 | 3 | 3 | 15.3 | 0.15 | 5.42 |
| 35 | 18 | 17.8 | 17.4 | 21 | 18.73 | 17.8 | 17.6 | 19.4 | 19.2 | 0 | 0.4 | 3.2 | 3.2 | 3 | 3 | 17.6 | 0.4 | 0.73 |
| 40 | 19.3 | 19.9 | 19.5 | 25 | 21.47 | 19.9 | 19.7 | 22.45 | 22.25 | 0 | 0.4 | 5.1 | 5.1 | 3 | 3 | 19.7 | 0.4 | 2.17 |
| 45 | 21.5 | 21.75 | 21.9 | 18 | 20.55 | 21.75 | 21.825 | 19.875 | 19.95 | 0 | 0.15 | 3.75 | 3.75 | 3 | 3 | 21.825 | 0.325 | 0.95 |
| 50 | 23.05 | 23.1 | 23.9 | 22.9 | 23.30 | 23.1 | 23.5 | 23 | 23.4 | 0 | 0.8 | 0.2 | 0.8 | 2 | 2 | 23 | 0.05 | 0.25 |
| 55 | 22.5 | 22.3 | 22.9 | 22.5 | 22.57 | 22.5 | 22.6 | 22.4 | 22.7 | 0.2 | 0.4 | 0 | 0.4 | 2 | 2 | 22.4 | 0.1 | 0.07 |
| 60 | 20.25 | 20.3 | 20.1 | 21 | 20.47 | 20.3 | 20.2 | 20.65 | 20.55 | 0 | 0.2 | 0.7 | 0.7 | 3 | 3 | 20.2 | 0.05 | 0.22 |
| 65 | 19.55 | 19.1 | 19.6 | 19.5 | 19.40 | 19.5 | 19.35 | 19.3 | 19.55 | 0.4 | 0.1 | 0 | 0.4 | 1 | 1 | 19.55 | 0 | 0.15 |
| 70 | 18.4 | 18.5 | 18.9 | 18.4 | 18.60 | 18.5 | 18.7 | 18.45 | 18.65 | 0 | 0.4 | 0.1 | 0.4 | 2 | 2 | 18.45 | 0.05 | 0.20 |
| | | | | | | | | | | | | | | | | | 1.77 | 15.64 |

Table 1 above provides an example of fusing sensor data from three sensors presented by the present disclosure. Table 1 is based upon EXAMPLE 6 below. Each of the three sensors is used to detect the concentration of glucose within a patient. The column "T(m)" indicates the relative time at which the sensor readings were taken. It can be seen that the sensor readings were taken once every 5 minutes. The column "Ref" indicates a glucose reading of the same patient using a DEXCOM® sensor. The columns "1", "2" and "3" indicate the glucose readings of the three sensors presented by the present disclosure, respectively. The column "Wavg" indicates the weighted average value of the glucose readings of the three sensors, with the weights being 1 for each sensor in this example. In other words, weighted average "Wavg" is equal to (S1+S2+S3)/3. The column "M" indicates the median value of the glucose readings of the three sensors. The median value is the middle value of the glucose readings of the three sensors, which is higher than the lowest glucose reading and lower than the highest glucose reading. For example, at time '0', the median value is the glucose reading of sensor 1, and at time '55', the median value is the glucose reading of sensor 3. The column "Avg 1-2" indicates the average value of the glucose readings of Sensor 1 and Sensor 2. Similarly, the columns "Avg 1-3" and "Avg 2-3" indicate the average value of the glucose readings of Sensor 1 and Sensor 3, and the average value of the glucose readings of Sensor 2 and Sensor 3, respectively. The column "E1" indicates the abstract value of the difference between the glucose reading of Sensor 1 and the Median value. Similarly, the columns "E2" and "E3" indicates the abstract value of the difference between the glucose reading of Sensor 2 and the Median value, and the abstract value of the difference between the glucose reading of Sensor 3 and the Median value, respectively. The column "ME" indicates the maximum error, i.e., the highest value amongst E1, E2 and E3, and the column "SME" indicates which sensor has the maximum error value. For example, at time '0', it is Sensor 3 which has the maximum error value with respect to the median value. The column "DS" indicates the identity of the sensor of which the glucose reading is to be discarded. In this example, the identity of the sensor of which the glucose reading is to be discarded is the same as the sensor which has the maximum error value. For example, at time '0', the glucose reading of Sensor 3 is to be discarded. The column "BS" ('best signal') indicates the output glucose reading (i.e., the fused sensor data), which is generated as an average of the glucose readings of the remaining two sensors. For example, at time '0', the value BS is equal to Avg 1-2, because the glucose reading of Sensor 3 is discarded.

The columns "AE" ('actual error') is used to assess the quality of the fused sensor data. In this example, the actual error indicates the abstract value of the difference between the best signal "BS" (i.e., the fused sensor data) and the reference "Ref". In generating the best signal "BS", a sensor signal which is significantly different than the other two sensor signals (e.g., an outlier) has been eliminated. The elimination of the outlier has significantly improved the accuracy of the fused sensor data. This is evident by comparing the column "AE" and the column "EWD" ('error without discarding worst sensor'). The column "EWD" indicates the abstract value of the difference between the weighted average "Wavg" of the three sensor readings and the reference "Ref". It can be seen that when the worst sensor reading (i.e., outlier) is not discarded, the fused sensor data produces an accumulated error which is 8.8 times the accumulated error generated when the worst sensor reading is discarded.

Since the sensor can provide a reading much faster (e.g., 10 milliseconds) than the reporting rate (e.g., 1 minute), different filtering schemes (e.g., averaging) can be used in time domain also to remove some of the noise. Different types of filters (e.g., Kalman filters) can be used to filter the data to remove noise. The filter coefficients can initially be assigned based upon sensor design and testing data from. The coefficients can be updated after CGM data is available (e.g., from a training model or from the same patient via reference sources) to improve its functionality.

Since not only the recent data but the rate of change of glucose (owing to several last readings) is available, an estimate of the next reading can also be calculated based upon these readings using different estimation techniques like least square estimation (LSE). This estimate can be compared against the reading from the sensors and the difference is used to see if the sensor is reading an expected or an erroneous reading. Based upon the difference, a confidence level can be assigned to the reading of each sensor. Furthermore, based upon the rate of change, a prediction level can be assigned to hypo/hyper glycemia occurrence, and the user can be alerted.

The data from the on-chip sensors can be used to test system state, integrity, and operation. For example, the typical readings from the electrochemical sensors can be used to check if the sensor was properly inserted in the body. Since the current range of the sensor in different conditions, i.e., in the air, in saline, in the skin, etc. are known, the value of the sensor current after possible insertion can be used to check whether the sensor is being properly wetted from the tissue fluid.

In a data analysis method, the next reading may be predicted based upon a number of previous readings and a patient-sensor model. The patient sensor model may indicate, for instance, the daily variation of the glucose concentration of a particular patient. The confidence level of the best reading may be determined based upon a comparison between the predicted next reading and the fused reading (i.e., best signal described above).

Note that a control logic may carry out processing steps as shown in FIG. 40 and/or other data analysis processes above.

Temperature Effects

The glucose sensor readings can be further improved by calibrating those with the local temperature measured by the on-chip temperature sensor (shown in FIGS. 4 and 5). In general, the instantaneous glucose readings can be represented by the following relationship between the sensor current (i(t)), the calibration coefficients (a,b), reference body temperature (e.g., 37° C.), and the instantaneous local temperature (T(t)), $$g(t)=f(i(t),a,b,T(t))$$

For example, one example of the relationship can be (for temperature in degree Celsius)

$$g(t)=(a*i(t)+b)*(T_B/T(t))$$

The exact relationship is determined by testing a subset of devices from a manufacturing batch and by fitting the relationship between the sensor current and glucose reading. The calibration coefficients are adjusted to represent the decrease in sensor current in the body as compared to the in vitro testing.

The following table shows that by calibrating the glucose sensor reading with the local temperature data, the error of the final, calibrated, glucose reading can be reduced significantly.

Within the monolithic integrated sensor circuit 1, the temperature sensor can be located within 10 microns of the sensing element 160, such that the output of the temperature sensor and the output of the sensing element 160 are measured from roughly the same portion of human tissue. Alternatively, the temperature sensor can be within 5 or 2 millimeters of the entirety of all working electrodes. Alternatively, the temperature sensor is connected within 0.5 millimeter or 400 microns to the entirety of the working electrodes.

These arrangements improve the accuracy of the calibrated glucose reading, as compared to an arrangement where the temperature sensor and the sensing element 160 are sufficiently away from one another.

| Current (nA) | Glucose (mg/dl) | Reduction in error in mg/dl by temperature sensor |
|---|---|---|
| 30 | 130 | 20 |
| 50 | 285 | 85 |

The temperature sensor data can also be used for system, operation, and signal integrity purposes. For example, since the body temperature has a defined range (e.g., 37° C.+−2° C.), the temperature sensor reading after insertion can be used to determine if the insertion was successful as shown in FIG. 58B. Together with electrochemical sensor signal change in the body, this can provide a multi-modal and hence more reliable than a single-sensor scheme to confirm successful sensor insertion in the tissue. Since there would be a temperature sensor available in the transmitter, the gradient of temperature reading between the two can also be a good indicator of the successful insertion as well as of sensor depth. In extreme environments, this gradient can be used to calibrate the sensor if it moves too far from the normal body temperature.

In some cases when other sources of temperature variations are minimal, hypoglycemia can also be detected by a drop in the peripheral temperature. Hence, a drop in the on-chip temperature sensor without a significant drop in the environment temperature (e.g., measured by an external temperature sensor like one in the transmitter) can be an indicative of hypoglycemia. Such effects are documented in our human studies as seen in the EXAMPLES and further show the value of the on-chip temperature sensor.

An increase in environment temperature can also cause an increase in subcutaneous tissue temperature which can increase the enzymatic activity which in turn can increase sensor current. This can make detecting hypoglycemia harder in a hot environment. This can be mitigated by using the temperature sensor which can calibrate the sensor response according to the surrounding temperature and hence can mitigate this risk substantially as compared to other sensors without such temperature sensor. An opposite effect (considering higher glucose as hypoglycemia) can occur in colder environments. The integrated temperature sensor can avoid this problem as well.

A control logic (e.g., a processor, a processing unit, a controller, or a microcontroller etc.) may be used to process (or calibrate) the information from the sensing element 160 by taking into account the temperature measurement obtain from the temperature sensor. The control logic may be part of the monolithic integrated sensor circuit 1. For example, the control logic may be the control logic of the power management unit 120, or may be part of the sensor signal acquisition unit 130. Alternatively, the control logic may be incorporated within the transmitter 2, and be part of the processor 211 (FIG. 35). Further alternatively, the control logic may be external to the transmitter 2 and the monolithic integrated sensor circuit 1. In an example, the control logic may be part of the smartphone 4 (FIG. 1) or part of a computer which processes the data of the secure database 5 (FIG. 1).

Sensor Calibration

After sensor fabrication, the calibration schemes are tested and stored either on the sensor memory or the transmitter memory or on both. The manufacturing batch (e.g., a wafer or a batch of wafers) is tested in known environments (e.g., known temperature range, known glucose range) by following a sampling scheme (e.g., 10% sensors). The results from the testing scheme are mathematically analyzed to determine a relationship between sensor response and the sensor outputs. This relationship is called the calibration algorithm and is stored so that the system can convert the response from the other (remaining 90%) sensors into calibrated values of temperature and glucose. The variations among the sensors in the test sample lead to some variations in the calibrated output. The results can be further improved by doing a personalized calibration by a user. After the system is used for each user, any potential calibration results are stored in the user profile and can be used to personalize the calibration algorithm for that person in future. Moreover, this data along with any demographic data shared by the user can be used to further optimize the calibration algorithm for that uses as well as for that particular demographic population.

For temperature sensor calibration, the sensors are tested in a saline test solution for body temperature range (e.g., 35-41° C.). For glucose sensor calibration, the sensors are calibrated in physiological concentration (e.g., 40-400 mg/dl). The data is fed to the mathematical model formed during the clinical trials that formalizes the relationship between the in-vitro performance and the in-vivo performance of the sensor. The model generates calibration coefficients which are then stored in system memory (e.g., typically in the transmitter but can be done on the monolithic integrated sensor 1 or on both).

Sensor Application

One or more sensors 1 can be placed in desired tissue locations using an applicator. In a simple embodiment, the applicator consists of a plastic body to hold the transmitter and a needle to hold the sensor as well as to pierce the skin. The transmitter and sensor assembly can be placed inside the injector from the top side by using a removable top cover of the injector body. Once the sensor is in place, the top cover can be put back. The whole assembly can then be placed on the skin (away from major organs, preferably on the arm, thighs, or the belly) and pressed down. This inserts the needle under the skin and allows analyte transfer to the sensor.

FIG. 41 shows how the monolithic integrated circuit, wire, and transmitter are placed inside an injector system consisting of an external plastic body 81, adhesive patch 82, and needle 83. FIG. 34 also shows the placement of the sensor and injector assembly under the skin when the system is pushed down. This allows body analyte to reach the sensor surface and the system to start monitoring the concentration of one or more analyte in the body.

However, such a simple applicator suffers from several disadvantages. Specifically, needle 83 is left in place which can irritate surrounding tissue. Accordingly, in a more preferred embodiment an applicator is used which leaves the integrated sensor 1 in place while itself being completely removed from the user.

Such an applicator 8 is designed to place the integrated sensor 1 connected with the connector 3 at desired depth and position under the skin (e.g., 1-10 mm under the skin, straight or at an angle) wherein the connector 3 is attached to the transmitter 2. An exemplary embodiment can be seen in FIG. 42.

The applicator 8 uses a cylindrical design consisting of 11 components. The external body 81, internal compression spring 812-813, chassis 82, a triggering arm 83, needle holder 84, needle compression spring 85, hypodermic needle 86, transmitter (also known as antenna) holder 87, and transmitter assembly 21. The push-retract mechanism of this applicator is initiated through the external body 81 in which two cylinders, height 24.6 mm and radius 3.38 mm diameter, that mate through the chassis 82 and onto the antenna holder 87. The internal compression springs 812-813 are 25.4 mm long, have a maximum load of 1.05 lbs, and are grade 302 stainless steel. Once the push mechanism is complete, the retraction mechanism will begin by releasing the triggering arm 83 and allowing needle compression spring 85 to decompress and retract the needle into the compartment at the base of the external body 81. This will allow the user to avoid any injuries by safely capturing the needle and allowing for it to be a onetime inject device.

The applicator 8 comprises an external cover 81 (plastic body to enable tactile holding of the applicator on the skin). The external cover can be shaped as a cylinder with the bottom posterior side forming an open circular aperture and a top anterior side being closed, wherein the side curved surface may include a major groove 89 to allow fingers of a user to more easily grab the applicator 8.

Inside the applicator lies a triggering guide 82. It is a cylindrical shape with a slot 823 in it to receive the two bars of the triggering arm 83 (explained below). The external cover 81 contains multiple protrusions 88 extending towards the triggering guide 82 and longitudinally from the interior of the anterior top towards the bottom posterior open circular aperture. The protrusions 88 assist alignment of the triggering guide 82 during assembly and prevent the assembly guide 82 from contacting the interior top anterior surface of the external cover 81 during operation. The external cover also includes two rods 810 extending from the interior of the anterior top towards the bottom posterior open circular aperture. The rods 810 function as guide poles for springs 812 wherein the rods are configured to have an exterior diameter smaller than the mean diameter of the respective spring. The rods can extend from bases which can be similarly shaped to protrusions 88 and can operate as bases for the tip of the coil of springs 812 to sit thereon.

A triggering arm 83 passes through triggering guide 82. The triggering arm 83 can comprise a disc with an open central aperture extending from the top and bottom surface of the disc as well as two bars extending from opposite sides of the disc. The triggering arm 83 can guide needle holder 84 into the appropriate position based upon the status of the trigger mechanism as the two bars extending from opposite sides of the triggering arm 83. The triggering arm 83 is further in contact with a spring 85 which is used to store a spring force for activation of the trigger mechanism. The needle 86 is held inside the needle holder 84 via the spring 85 and is attached to an assembly holder 87. The far end of the assembly holder is also used to hold the external transmitter 81 inside the applicator. The transmitter 2 is kept inside the transmitter assembly holder 87. The applicator components are shown in FIG. 42.

The system is designed to fit and move smoothly via groves and matching patterns on different parts. Briefly, the external cover 81 has three groves 814 to fit the assembly holder 87 via three features 874. It also has two springs 812 and 813 to provide smooth movement of the assembly. The triggering guide 82 has corresponding holes 821 and 822 to match with the springs 812 and 813 of the cover 81. Additionally, it has three cut-outs 824 to allow sliding movement of the assembly holder 87 via three holders 872 on the assembly holder 87. It also has 4 slots 825 to enable alignment of assembly holder 87 with it (triggering guide 82). The needle holder 84 has a holding structure 841 that enables it to slide with the assembly holder 87 within the groves 824 of the triggering guide 82.

During the initial stage, the applicator is in the armed state (as shown in FIG. 44) by the assembly process. Briefly, the assembly process starts with placing the assembly holder 87 into the triggering guide 82. Next, the spring 85 is put on the needle side of the needle holder 84 and the triggering arm 83 is placed on top of needle holder 84. Next, the triggering arm is pushed down and rotated clockwise to lock the triggering arm in the armed state. The entire assembly is then fitted inside the external cover. Now the spring is loaded and the needle 86 is below the transmitter assembly holder 87. The sensor 1 lies inside the needle 86.

The assembly of the applicator involved mating 4 mm internal alignment markers 871 and 825, and then mating 3 mm external alignment markers 872 and 824. Once the antenna holder 87 and chassis 82 are completely mated, the needle holder 84 and the triggering arm 83 must be loaded into the antenna holder from the rear end using grade 416 Stainless steel bowel pins attached to the link. After loading the needle, the sensor-transmitter (also known as antenna) assembly 21 must slide through the top end of the previous assembly and then into the external body 81.

The hypodermic needle 86 is cylindrical needle that is laser fabricated to create a rectangular slot through the needle and is re-siliconized using 3M MED 4159 to ensure the sensor is not tampered during the push-retract mechanism. The applicator was prototyped by tough 1500 photopolymer resin produced by Formlabs. This applicator can be manufactured at a low cost by high volume manufacturing like injection molding process. An example embodiment of plastic for this process will be polypropylene as it is resistant to steam sterilization and has good mechanical strength that enables it to withstand some force required for insertion process.

The user places the armed applicator on the skin (e.g. upper arm) and gently presses it against the skin. This pushes the needle and the needle assembly towards the skin. Once the assembly reaches to the trigger height defined by the groves 823 in the triggering guide 82, the triggering arm is pushed up by the spring to take the system to the unarmed stage, i.e., the needle is fully retracted inside the system as shown in FIG. 46. The trigger stage is shown in FIG. 45 and the release (unarmed) stage is shown in FIG. 46. The trigger stage is important as it enables the release stage after which the applicator operation is completed. A close-up of the action of the triggering arm to enable this trigger operation is shown in FIG. 48.

Once the applicator assembly is released, the transmitter 2 is left attached to the external surface of the skin with help of adhesives (biocompatible adhesives like 3M 4077) while the sensor 1 is left under the skin and the connector 3 is connecting these two. All the steps of sensor insertion using the applicator are shown in FIG. 43. An example of the transmitter above the skin and the sensor under the skin, after the applicator use, is shown in FIG. 47.

At the end of insertion, the needle is retracted back inside the applicator to prevent injury or misuse.

The applicator requires small amount of force for operation as the needle used is small and sharp. The force range depends upon the needle size and shape and the force and speed with which the user applies the device on the skin.

The applicator is unique as it inserts a sensor 1 under the skin that is already electrically connected to its transmitter 2 via connector 3; the transmitter 2 and the connector 3 being connected with the connector 220 (or mated connection of connectors 32 and 34). This is different than other wired CGMs (e.g., Medtronic Guardian 3, Dexcom G6, Abbott Libre 2) in which the sensor and the transmitter are initially not attached but rather are attached during the sensor insertion or afterwards. In the IMS case, this is enabled by assembling applicator 8 with the sensor-transmitter assembly 21 in advance. The close-up of this sensor assembly with the applicator is shown in FIG. 49. It shows that the needle is not a complete cylinder but has a slot or cut out. In FIG. 49, the slot extends along the entire length of the needle. As such, the needle resembles an open channel, with its internal space (surrounded by a sidewall of the needle) exposed to exterior by the slot. In other words, the slot extends through the side wall of the needle. The purpose of the slot is to enable the needle to retract, leaving the sensor under the skin. This slot basically allows the needle to move around the sensor (up and down) to enable the needle to pierce the skin going down and also enabling it to go around the sensor during retraction without touching the sensor such that the sensor remain under the skin while the needle retracts. The design can use a hypodermic needle with such a slot. The slot can be either cut into a standard hypodermic needle (e.g., using laser cutting) or the needles can be made using the slot (e.g., by using a tube with a slot). Alternatively, the needles can be made using a sheet metal process e.g., by using lithographic processing (e.g., wet etching) to create sharp tips followed by forming and stamping. It would be appreciated that the slot may extend along majority of the length of the needle (not necessarily the entire length of the needle).

The applicator has been used for successful insertion of multiple sensors under the skin of multiple animals and human subjects. An example of the complete applicator loaded with a sensor-transmitter assembly and a picture of the successful insertion on an arm is shown in FIG. 50A and FIG. 50B.

Sensor Removal

At the end of sensor life, or when desired, the sensor(s) can be extracted by pulling on the external transmitter which is connected to the sensor using the two-wire flexible connector. The change in sensor reading (e.g., temperature sensor, electrochemical sensors) is used to confirm safe removal of the device.

Example 1

The CMOS sensor circuits were designed in CAD tools using process design kits (e.g., TSMC 180 nm PDK) and were sent to a CMOS foundry (TSMC) for fabrication. After the fabricated sensors were received, those were inspected to match the dimensions and similar physical features with the submitted design. Afterwards, postprocessing was started to replace the top metal with more suitable metals. Briefly, AZ5214E resist was spun at 4000 rpm, baked at 95 degrees C. for 5 minutes, and exposed using i-Line (e.g., 365 nm UV radiation) exposure in a mask aligner (e.g., MA6) for 5 seconds. Next, a post-exposure bake at 120 degrees C. for 5 minutes was performed followed by a flood exposure for 3 seconds. Next, the resist was developed in AZ300 developer. This was followed by sputtering of Ti (e.g., 20 nm) followed by Pt (100 nm). After sputtering, a conformal coating is achieved. The next step of post-processing was lift-off to remove metal layers from the unwanted regions by soaking the coated devices in Acetone followed by agitation in an ultrasonic bath. Next, the dies were cut using mechanical saw dicing to cingulate the multiple sensors from one design. Next, several sensors (9 in one example) were die attached to a flexible PCB substrate using 31CL epoxy, followed by baking at 100 C for 1 hour to cure the epoxy. Next, the sensor pads were wire-bonded to corresponding pads on the flexible PCB using 1 mil gold wire in a K&S wire bonder. The wire bonds were then encapsulated in an insulating material (e.g., 31CL) which was then cured at 100 C for 1 hour. Afterwards, a connector was soldered to the other end of the flexible PCB to form an interface to the transmitter. Afterwards, the enzyme was immobilized on the sensor in a hydrogel (e.g., a cross-linked protein matrix) at a thickness of 3 µm. This was done through immobilization of the enzyme GOx (Glucose Oxidase) in a hydrogel created by Human Serum Albumin (HSA) with glutaraldehyde as the crosslinking agent. The dispensed solutions were made by mixing GOx and HSA (1200 mg, and 1000 mg respectively) in 15 ml DPBS and a crosslinking agent solution of 1 w/w glutaraldehyde in DPBS. A 1 microliter solution was dispensed on the sensor, followed by spinning at 1000 rpm to control the thickness of the hydrogel layer more precisely. Next, a polymer layer (e.g., 2.5% PU in THF with HMDI, Jeffamine, ED-600, DMS-A15 Mn 3000, DEG, Dibutyltin bis(2-ethylhexanoate) as described in patent 4) on the enzyme layer. It serves to control glucose and oxygen diffusion to optimize the sensor response. The chemistry stack was allowed to dry in a convention oven at 35° C. for 12 hours. Then the sensors are allowed to stabilize in PBS (Sigma Aldrich, St. Louis MO) for 24 hours and characterized (sample testing) for glucose response. Next, the flexible PCB panel was laser cut to separate individual sensors for next steps.

After cutting, the sensors from the panel were tested in-vitro. First, a sample sensor was powered up by connecting it to the transmitter and initial current was allowed to stabilize. Once a stable baseline was achieved, the test solution was spiked with small volumes of a stock glucose solution to create an increasing glucose concentration in the solution. The concentration was measured using a benchtop glucose monitor from Yellowstone Instruments (YSI 2700) for validation. Three readings were taken from YSI for statistical validation. As the solution was spiked with more and more glucose, the glucose concentration in the test solution was increased sequentially. The testing results showed that the sensor current increased when glucose concentration was increased in a statistically significant manner. Similar results were obtained from several sensors to establish the validity of the sensor.

FIG. 51 shows testing results of the sensor assembly testing. The solid-state sensors were tested in different concentrations of hydrogen peroxide as it is the most common analyte generated by the oxidase-based enzymes in the presence of their substrate e.g., Glucose Oxidase in the presence of glucose, Lactate Oxidase in the presence of Lactate. It shows that the sensor is quite sensitive to hydrogen peroxide and generates a significantly high current (in 10's of nanoamperes) proportional to peroxide concentration. It shows that the 2× gain circuit design shows 2× the current of the 1× gain design, as desired. It also shows the repeatability of the same sensor tested in the solution of the same concentration several times in FIG. 51B. FIG. 51C shows that for the integrated sensor having 3 district sensors on-chip, all 3 are sensitive to peroxide with small variation among them due to process variations (e.g., surface cleaning after packaging). These variations can be substantially decreased by increasing process control, by using trimming, and by adding algorithmic features (e.g., calibrating the individual sensors to different slope factors to minimize the differences in current readings). This scheme allows for redundant sensing of and calibration for the same analyte (e.g., glucose), sensing of different analytes (e.g., glucose, BHB, creatinine, urea, etc.) on the same chip.

FIG. 55 shows the response of a single sensor to increasing glucose concentrations after surface coating with glucose oxidase and PU membrane. The nonlinearity in response can be improved by adding the thickness of the PU membrane. FIG. 55 shows the response of another single sensor to increasing glucose concentrations after surface functionalization with glucose oxidase and PU membrane. Both these are 1× gain sensors and show very similar responses to the same glucose concentrations. FIG. 55 shows the response of a sensor with 2× gain to glucose. It shows almost 2× the current as compared to the 1× gain sensors, thus proving this design feature. FIG. 55 shows the result of testing a glucose sensing platform with 3 on-chip glucose sensors. The platform was tested in PBS in different glucose concentrations as shown on the graph, and the current for all 3 sensors was read using the transmitter 2 and the reader 4. It shows that there are variations among sensors for the same glucose concentration, likely due to the process variations. These variations can be decreased by improving process control (e.g., surface cleanliness). In any case, the results indicate that if the median of the 3 readings is used, it minimizes the effect of sensor-to-sensor variations and provides a more accurate glucose reading as compared to the reading from any single sensor.

FIG. 52A, FIG. 52B, and FIG. 52C show a similar test for a 3-sensor platform, showing time variations in sensor current as it is subjected to varying glucose concentrations. It shows the 3 on-chip sensors respond in a synchronized manner to glucose, with small variations in actual current due to process variations. The temporary spikes are due to spiking the test solution with glucose. These don't appear in the body as there is no spiking of the body fluids with concentrated glucose.

FIG. 53A, FIG. 53B, and FIG. 53C show a similar test for a 3-sensor platform, showing time variations in sensor current as it is subjected to varying glucose concentrations. It shows the 3 on-chip sensors respond in a synchronized manner to glucose, with small variations in actual current due to process variations. This shows that multiple copies of the platform perform similarly within the bounds of process variations.

FIG. 54A and FIG. 54B show the advantage of average and median of the 3 on-chip sensors' readings on the same device to decrease the variation between 3 on-chip sensors.

Example 2

The sensors here were made using the methods described in example 1. In addition, some of the sensors were coated with an additional layer of PVA using methods described in example 3.

FIG. 56 shows the results of testing different chemistry layers on test sensors. It shows that the sensor coated with the stack of Glucose Oxidase hydrogel, Polyurethane, and Polyvinyl Alcohol (GOx+PU+PVA) has smaller current than the sensor coated with just GOx+PVA. The GOx coating was done with spin coating GOx+HSA+Glutarladehyde mixture, the PU coating was done by spin coating PU mixture in THF, and PVA coating was done by spin coating PVA mixture in DI water, as detailed in example 4. The mixtures were all prepared as described below (example 3). The lesser sensor current with PU layer as compared to without PU layer is understandable as the PU layer regulates the diffusion of glucose and hence decrease the glucose generated current. These results do indicate the suitability of both chemistry stacks for further testing. The devices with GOx+PU+PVA were selected for human testing as better linearity can be achieved from this chemistry stack over a larger glucose range as required in later testing in diabetic patients.

Example 3

The solid-state sensors for this example were prepared same as in Example 2. After postprocessing, the devices were coated with GOx in a hydrogel (e.g., a cross-linked protein matrix) at a thickness of ~3 µm. This was done through immobilization of the enzyme GOx (Glucose Oxidase) in a hydrogel created by Human Serum Albumin (HSA) with glutaraldehyde as the crosslinking agent. The dispensed solutions were made by mixing GOx and HSA (1200 mg, and 1000 mg respectively) in 15 ml DPBS and a crosslinking agent solution of 1% w/w glutaraldehyde in DPBS. A 1 microliter solution was dispensed on the sensor, followed by spinning at 1000 rpm to control the thickness of the hydrogel layer more precisely. Next, a polymer layer (e.g., 2.5% PU in THF with HMDI, Jeffamine, ED-600, DMS-A15 Mn 3000, DEG, Dibutyltin bis(2-ethylhexanoiate) as described in patent 4) on the enzyme layer. It serves to control glucose and oxygen diffusion to optimize the sensor response. Finally, a layer of 4% PVA solution was also spun-coated on the PU layer. Namely, PVA gel solution was formed by adding 0.02% (0.005%-0.1% acceptable) Glutaraldehyde to 4% PVA solution (v/v), vortexing to mix. Surface of the PU coated sensors were activated with plasma treatment (80-250 W, 5-90 seconds, Oxygen plasma is preferred). 2 ul of gel solution was then deposited on PU coated sensors and spun at 500 rpm.

The chemistry stack was then baked for 12 hours (2-48 hours acceptable) at 40 degrees Celsius (30-42 C acceptable), in an incubator.

Then the sensors were allowed to stabilize in PBS (Sigma Aldrich, St. Louis MO) for 24 hours and characterized (sample testing) for glucose response. Next, the flexible PCB panel was laser cut to separate individual sensors for next steps.

After cutting, the sensor was soaked in PBS for 2 hours (overnight is preferable) before testing. Next, the sensors were tested in different glucose concentrations and at different temperatures (close to body temperature) to determine their suitability for sensing in the body.

The validated sensing devices were then connected to the transmitter and the assembly was loaded inside the applicator and the entire assembly was sterilized (e.g., by Synergy Health (San Diego, CA)) using electron-beam sterilization using 25 kGray of e-beam irradiation. These sensors can be placed in the upper arm using the applicator (aka the injector). After the sensors are placed in the skin, their data is read via the IMS transmitter and the IMS reader application on a PC.

FIG. 57A shows the modeling and laboratory results of the IMS temperature sensor testing. FIG. 57B shows the sensor current should decrease with increase in temperature as per the simulation.

FIG. 58A shows the sensor can track environmental temperature changes for more than 1 week when kept inside a PBS solution without any temperature control.

FIG. 58B shows the temperature sensor can detect if the sensor is at the room temperature (before insertion) or at the body temperature (after insertion in a person). Hence, it can be used as an additional validation check of successful sensor insertion. This is in addition to the change in sensor current in air (before insertion) and in the tissue (after insertion). Such multi-modal validation of insertion can be more reliable than a single sensor validation.

Example 4

The solid-state sensors for this example were prepared same as in example 3. After postprocessing, the devices were coated with GOx in a hydrogel (e.g., a cross-linked protein matrix) at a thickness of ~3 µm. This was done through immobilization of the enzyme GOx (Glucose Oxidase) in a hydrogel created by Human Serum Albumin (HSA) with glutaraldehyde as the crosslinking agent. The dispensed solutions were made by mixing GOx and HSA (1200 mg, and 1000 mg respectively) in 15 ml DPBS and a crosslinking agent solution of 1% w/w glutaraldehyde in DPBS. A 1 microliter solution was dispensed on the sensor, followed by spinning at 1000 rpm to control the thickness of the hydrogel layer more precisely. Next, a polymer layer (e.g., 2.5% PU in THF with HMDI, Jeffamine, ED-600, DMS-A15 Mn 3000, DEG, Dibutyltin bis(2-ethylhexanoiate) as described in patent 4) on the enzyme layer. It serves to control glucose and oxygen diffusion to optimize the sensor response. Finally, a layer of 4% PVA solution was also spun-coated on the PU layer. Namely, PVA gel solution was formed by adding 0.02% (0.005%-0.1% acceptable) Glutaraldehyde to 4% PVA solution (v/v), vortexing to mix. Surface of the PU coated sensors were activated with plasma treatment (80-250 W, 5-90 seconds, Oxygen plasma is preferred). 2 microliter of gel solution was then deposited on PU coated sensors and spun at 500 rpm.

The chemistry stack was then baked for 12 hours (2-48 hours acceptable) at 40 degrees Celsius (30-42 C acceptable), in an incubator.

Then the sensors were allowed to stabilize in PBS (Sigma Aldrich, St. Louis MO) for 24 hours and characterized (sample testing) for glucose response. Next, the flexible PCB panel was laser cut to separate individual sensors for next steps.

After cutting, the sensor was soaked in PBS for 2 hours (overnight is preferable) before testing. Next, the sensors were tested in different glucose concentrations and at different temperatures (close to body temperature) to determine their suitability for sensing in the body.

The validated sensing devices were then connected to the transmitter and the assembly was loaded inside the applicator and the entire assembly was sterilized (e.g., by Synergy Health (San Diego, CA)) using electron-beam sterilization using 25 kGray of e-beam irradiation. These sensors can be placed in the upper arm using the applicator (aka the injector). After the sensors are placed in the skin, their data is read via the IMS transmitter and the IMS reader application on a PC.

FIG. 60A, FIG. 60B, and FIG. 60C show the response of two IMS sensors prepared using the method above and inserted in a human subject, in comparison with a contour blood glucose meter, a Dexcom G6 comparator (inserted a day before the IMS sensor for FIG. 60A; was not available for use for experiment shown in FIG. 60B), and an abbot libre sensor (inserted the same day as the IMS sensor). These results show that the IMS sensor can track glucose changes created by mealtime excursion. The human subject was prediabetic and was told to fast overnight. This resulted in their starting glucose level to be close to 100 mg/dl. Then they were given a controlled meal which increases their blood glucose level (excursion), causing all the sensors to pick-up the increase. The study could only capture 1 hour of this excursion as it was limited in duration as per IRB approval and the user had to leave early to attend an event. The user returned after 3 days to get the sensors removed. No adverse safety event was observed. After the first sensor was removed, a second study was conducted with the user via a different sensor. The purpose this time was to study the effect of low glucose on sensor performance. The user did start around 100 mg/dl and went to around 82 mg/dl during the duration of the study. The IMS sensor (as shown in FIG. 60B) could detect the decrease in glucose in a smooth manner whereas the Libre 2 struggled in reading the low glucose value accurately.

FIGS. 61A and 61B show the IMS sensor response before and after the human testing. FIG. 61A shows the sensor had sufficient linearity and sensitivity before inserting it in a person. FIG. 61B shows the sensor was still functioning after it was removed from the human subject. This shows that the sensor can function for longer duration (the current test was subject to IRB approval duration of the study). These results indicate the suitability of the IMS CGM platform, including its construction and chemistry, for glucose monitoring in humans.

The study also showed the value of temperature sensor in detecting sensor insertion in the body. FIG. 58B shows the sensor can detect a change from room temperature (around 25° C. in this example) to body temperature (around 37.5° C. in this example). This sudden and large temperature change and stabilization near the body temperature indicates the sensor insertion in the body. It also shows the change in tissue temperature, as detected by the sensor, due to variations in the surrounding temperature are typically smaller and can also be detected by the temperature sensor.

The temperature sensor can also detect changes in the peripheral body temperature due to an impending hypoglycemia, thus leading to the platform's ability for a multimodal (e.g., electrochemical and thermal schemes or modes in this example) hypoglycemia detection which would be better than just relying on one measurement of glucose to make this decision. FIG. 59A and FIG. 59B show the effect of decreasing glucose concentration (going towards hypoglycemia) on the peripheral (e.g., subcutaneous tissue) temperature. The decrease in temperature was measured by both sensors on the same person (temperature sensor reads higher for lower temperature and reads lower for higher temperature). This is consistent with some studies which find out a change in peripheral temperature in hypoglycemia. Such multi-modal hypoglycemia detection can provide early warning as well as increase the reliability and accuracy of hypoglycemia detection, a key limitation of current CGM platforms.

An increase in environment temperature can also cause an increase in subcutaneous tissue temperature which can increase the enzymatic activity which in turn can increase sensor current. This can make detecting hypoglycemia harder in a hot environment. This can be mitigated by using the IMS temperature sensor which can calibrate the sensor response according to the surrounding temperature and hence can mitigate this risk substantially as compared to other sensors without such temperature sensor. An opposite effect (considering higher glucose as hypoglycemia) can occur in colder environments. The integrated temperature sensor can avoid this problem as well.

Example 5

The IMS sensors for this example were prepared using the same methods as described in Example 4.

This example shows that the IMS sensor can track a reference CGM (Dexcom G6 in this case, inserted 1 day before IMS sensor insertion to enable it to get past day 1 issues) over a period of 3 days (limited by test duration, not sensor lifetime). The Day 1, Day 2, and Day 3 graphs of FIG. 62A, FIGS. 62B, and 63C show that the IMS CGM platform has similar trends as Dexcom G6 (considered to be the most accurate CGM in the market), whereas the Libre 2 CGM reads lower than the two sensors. The Day 1 graph of FIG. 62A shows that the IMS sensor (Day 1 of IM sensor) is well matched to the Dexcom G6 data (Day 2 for Dexcom G5 since it was inserted a day before the IMS sensor to avoid day 1 noise issues present in current CGMs). Libre 2 has similar trends but shows lower glucose concentrations for some reason. Also, there are some locations (e.g., 18:43) where the Dexcom and the IMS sensor show different trend than the Libre 2. Similar trend can be seen on Day 2 in FIG. 62B. There are sometimes (e.g., 6:36, around noon) where the IMS sensor matches better with the Libre 2 trend than the Dexcom G6 trend. On Day 3 in FIG. 62C, the test subject's glucose goes through a nice and clear excursion cycle which is traced by the IMS sensor very well except towards the end when the sensor support (skin tape) starts peeling off due to the end of the wear period for the tape. Overall, IMS values tracked the Dexcom G6 data quite well while Libre 2 data was significantly off from the Dexcom G6 reading. There was no contour reference data available beyond first few hours on day 1 as the test subject didn't want to prick routinely outside the clinic. This IMS sensor data only uses signal averaging to match the IMS data points with the reference method and doesn't rely on any detailed signal processing methods described earlier. This shows that the IMS sensor is fundamentally accurate by design and doesn't require complex signal processing to improve its output. Signal processing can be used though to improve certain features like prediction of future values and detection of hypoglycemia before it causes health issues or fainting.

The three-day wear period was limited by the transmitter tape peel off. The sensor was still operational after the test (as shown in FIG. 61B) which shows the device can perform for longer duration. We have since then found a better tape that causes less skin irritation and works better with the skin for a longer duration.

Example 6

The IMS sensors for this example were prepares using the same methods as described in Example 4. This example shows the value of having multiple on-chip sensors for glucose sensing. FIG. 63 shows that in case some sensors (e.g., sensor 3) run into a noise issue momentarily, other sensors can be used to detect this issue (e.g., by detecting the erroneous sensor's reading to be >10% different than other sensors). After this, this erroneous sensor's weight can be changed (e.g., 0 to discard its reading fully for some time) to increase the accuracy of the overall reading (e.g., weighted average of the 3 sensors). The algorithm to perform these calculations is provided in the "multi-sensor signal processing schemes" section. FIG. 63 is plotted based upon Table 1. The results show that the error in the weighted average (after the 'outlier' sensor readings are discarded, as shown by black dotted line in FIG. 63) is <2% whereas the error in the direct (simple) arithmetic average (assuming equal weights for all sensors at all times; as shown by the green line in FIG. 63) is >15%.

This example shows the value of multi-sensor scheme. In case of a single sensor system, a sensor error is difficult to be detected and even if it can be detected (e.g., based upon sudden changes being larger than physiologically possible), it is difficult to detect the actual value. In case of the IMS design having multiple sensors, this is not a problem as a single sensor reading erroneous readings can be detected by comparing its reading with others and hence its weight from the weighted average can be reduced or its reading can be eliminated from the calculations to minimize its effect. This makes the IMS platform more accurate and reliable as compared to others. Also, once several readings from a sensor have been obtained, the next reading can be predicted based upon rate of change and physiological models. Hence, the sensor readings can be compared against this expected reading to determine erroneous readings and those can be eliminated from the calculations (this is not shown in this example for simplicity reasons but can be done).

Example 7

The IMS sensor for this example was prepares using the same methods as described in Example 4.

The example shows the rate of change of the Libre 2, IMS, and Dexcom G5 sensors in response to a step change in glucose concentration as the result of a spike (addition of high-concentration stock solution to the test buffer under stirring). The reference concentration was measured using a YSI 2700 at regular intervals. Please see FIG. 64. The example shows that Libre 2 couldn't detect the lower concentration (90 mg/dl) and kept reading 'glucose concentration too low' till the higher concentration (180 mg/dl) was achieved in the test solution. It still took around 20 minutes after the spike to register the change and was off from the YSI reference reading by a large margin (>120 mg/dl) for the rest of the experiment. Dexcom G5 performed better and was reading reasonably accurate before the spike (around 100 mg/dl). After the spike, it did detect the change initially within 5 minutes but took >20 minutes in total to get close to the actual value as measured by the YSI. The IMS sensor was reading accurately before the solution was spiked. After the spike, it took <5 minutes (approximately 4 minutes) to reach to the steady-state value close to the actual value. Therefore, according to FIG. 64, the IMS sensor is capable of detecting a rate of change of glucose concentration at approximately 22.5 mg/dl/min. This is due to the thin diffusion barriers (e.g., thin enzyme layer, thin polymer membrane, thin biocompatibility layer as described above) as compared to the commercially available devices (which use thicker diffusion barriers to minimize the effect of larger manufacturing variations), enabled by the planar nature of the IMS device (e.g., enable spin coating).

To allow the IMS sensor to detect a rate of change of >10 mg/dl/minute, the thickness of the enzyme layer is preferably less than 3500 nm, and more preferably, less than 1000 nm. In an example, the enzyme layer may be between 200 nm and 800 nm in thickness, and more specifically, between 600 nm and 800 nm in thickness.

To allow the IMS sensor to detect a rate of change of >10 mg/dl/minute, the polymer membrane preferably has a thickness of between 200 nm and 10500 nm, and more preferably, has a thickness of between 200 nm and 1500 nm. The thickness of the biocompatibility layer may be between 1000 nm and 20000 nm. A biocompatibility layer with a thickness of less than 1000 nm may be used alternatively.

The faster response is also enabled by the fact that the IMS sensor is very accurate and hence doesn't need to perform heavy signal processing (e.g., long moving averages) to reduce the effect of sensor noise. Hence, the IMS sensor has the least lag among the 3 CGMs tested in this experiment. This effect is expected to translate to in-vivo sensing as well since the transport mechanisms through the surface chemistry layers are same in both cases. This also shows that the IMS sensor can achieve highest rates of change (e.g., >20 mg/dl/minute) as compared to Dexcom G5 (<4 mg/dl/minute) and Abbott Libre 2 (<2 mg/dl/minute).

While specific embodiments of the invention have been described above, it will be appreciated that the invention may be practiced otherwise than as described and that that the described embodiments are for all purposes exemplary, not limiting. Various modifications can be made to the described embodiments without departing from the scope of the present invention which is defined by the appended claims.

Further implementations are summarised in the following examples:

Example 1: A transdermal analyte concentration measurement system comprising:
1) an implantable monolithic integrated circuit containing:

an integrated sensing element which senses one or more analytes and generates a signal representative of an analyte concentration;

an integrated sensor signal acquisition unit which receives and processes the signal from the integrated sensing element;

an integrated communication unit connected to the integrated sensor signal acquisition unit which transmits data representative of said analyte concentration; and an integrated power management unit connected to and providing power to the sensing element, the sensor signal acquisition unit, and the communications unit; and 2) a transmitter, configured for operation outside of the body of a user, connected by a wire to the integrated communication unit and integrated power management unit of the implantable monolithic integrated circuit, said transmitter providing power to the integrated power management unit of the implantable monolithic integrated circuit via the wire and receiving data from the integrated communication unit of the implantable monolithic integrated circuit via the wire, and said wire configured to cross from the skin surface into the user to span the dermis of a user.

Example 2: The transdermal analyte concentration measurement system of example 1, wherein the integrated sensing element of the implantable monolithic integrated circuit includes one or more integrated electrodes.

Example 3: The transdermal analyte concentration measurement system of example 2, wherein at least one of the one or more integrated electrode comprises a conductive surface of one or more conductive materials.

Example 4: The transdermal analyte concentration measurement system of example 2 or 3, wherein the integrated electrodes are made using lithography.

Example 5: The transdermal analyte concentration measurement system of any one of examples 2 to 4, wherein the integrated electrodes are coated with a hydrogel including a cross linking agent, an enzyme, and a proteinaceous material.

Example 6: The transdermal analyte concentration measurement system of example 5, wherein the hydrogel further comprises a co-protein.

Example 7: The transdermal analyte concentration measurement system of example 5 or 6, wherein: the cross-linking agent comprises glutaraldehyde; the enzyme comprises glucose oxidase; and the proteinaceous material comprises human serum albumin.

Example 8: The transdermal analyte concentration measurement system of any one of example 5 to 7, wherein the hydrogel further comprises a co-protein of catalase or horseradish peroxidase.

Example 9: The transdermal analyte concentration measurement system of any one of examples 1 to 8, wherein the wire is comprised within a flexible printed circuit board.

Example 10: A glucose sensor system comprising:
a transmitter containing a battery for placement on top of patient skin;
a transcutaneous connector comprising at least one conductive path; and
a potentiostat and an electrochemical sensing element for placement beneath the patient skin;
wherein the potentiostat is electrically coupled to the transmitter via the transcutaneous connector, and the electrochemical sensing element is configured to sense glucose concentration and generate an electrical signal representative of the glucose concentration, and wherein the potentiostat is electrically connected to the electrochemical sensing element.

Example 11: The glucose sensor system of example 10, wherein the potentiostat is continuously powered by the battery.

Example 12: The glucose sensor system of example 10 or 11, wherein the glucose sensor system is a continuous glucose sensor system.

Example 13: The glucose sensor system of any one of examples 10 to 12, wherein the transcutaneous connector is a flexible connector.

Example 14: The glucose sensor system of any one of examples 10 to 13, wherein the potentiostat is placed at a depth of 1 to 10 mm beneath the patient skin.

Example 15: The glucose sensor system of any one of examples 10 to 14, wherein the electrochemical sensing element comprises at least one working electrode coated with a chemistry which converts glucose concentration into current.

Example 16: The glucose sensor system of example 15, wherein the potentiostat is connected within half a millimeter to the entirety of at least one working electrode.

Example 17: The glucose sensor system of example 15 or 16, wherein the electrodes are patterned to increase surface area.

Example 18: The glucose sensor system of any one of examples 15 to 17, wherein the electrodes are patterned by forming pillars.

Example 19: The glucose sensor system of example 18, wherein the pillar spacing is 0.25 μm-25 μm and height 0.1 μm-10 μm.

Example 20: The glucose sensor system of any one of examples 15 to 19, wherein the electrodes are integrated with the potentiostat into the same CMOS die.

Example 21: The glucose sensor system of example 20, wherein the CMOS die is from 30 microns to 600 microns in thickness, 500 microns to 10,000 microns in length and in a range from 100 microns to 4,000 microns in width.

Example 22: The glucose sensor system of example 20, wherein the CMOS dies is from 50 microns to 150 microns in thickness, 1,500 microns to 3,000 microns in length and in a range from 100 microns to 4,000 microns in width.

Example 23: The glucose sensor system of any one of examples 10 to 22, wherein the potentiostat is at a depth of 1 to 5 mm beneath the patient skin.

Example 24: The glucose sensor system of any one of examples 10 to 23, wherein the electrochemical sensing element comprises at least three working electrodes with each connected to a respective potentiostat.

Example 25: The glucose sensor system of any one of examples 10-24, further comprising an analog to digital converter connected to the potentiostat.

Example 26: The glucose sensor system of example 25 as dependent from example 24, further comprising a control logic programmed to process digital information from the analog to digital converter and consider the information from one or more of the at least three working electrodes.

Example 27: The glucose sensor system of example 26, wherein the control logic is configured to denoise the information from one or more of the at least three working electrodes.

Example 28: The glucose sensor system of any one of examples 10 to 27, wherein the transcutaneous connector comprises a printed circuit board.

Example 29: The glucose sensor system of examples 10 to 28, further comprising a temperature sensor monolithically integrated with the potentiostat.

Example 30: The glucose sensor system of example 29, wherein the temperature sensor comprising a bandgap circuitry to generate current proportional to absolute temperature (PTAT) and current complementary to absolute temperature (CTAT).

Example 31: The glucose sensor system of example 29 or 30 as dependent from example 15, further comprising a control logic programmed to process information from the at least one working electrode by taking into account information from the temperature sensor.

Example 32: The glucose sensor system of any one of examples 10 to 31, wherein the transcutaneous connector comprises at least two conductive paths.

Example 33: The glucose sensor system of example 32, wherein one of the conductive paths is a ground connected to the potentiostat and another one of the conductive paths functions as data over power.

Example 34: The glucose sensor system of examples 10 to 33, wherein the potentiostat is formed in a CMOS die.

Example 35: The glucose sensor system of example 34, wherein the CMOS die is bonded to the flexible connector and the at least one conductive path by wire bonding.

Example 36: The glucose sensor system of example 35, wherein the CMOS die is bonded to the flexible connector and the at least one conductive path by flip chip packaging.

Example 37: The glucose sensor system of examples 16-36 as dependent from example 15, wherein the at least one working electrode is coated with a glucose oxidase hydrogel.

The invention claimed is:

1. A glucose sensor system comprising:
    a transmitter for containing a battery, the transmitter being for placement on top of patient skin;
    a transcutaneous connector comprising at least one conductive path; and
    an implantable monolithic integrated circuit for placement beneath the patient skin, wherein the implantable monolithic integrated circuit comprises a potentiostat and an electrochemical element, said electrochemical sensing element comprising at least one working electrode patterned to increase surface area and coated with a chemistry which converts glucose concentration into current;
    wherein the potentiostat is electrically coupled to the transmitter via the transcutaneous connector, and the electrochemical sensing element is configured to sense glucose concentration and generate an electric signal representative of the glucose concentration, and wherein the potentiostat is electrically connected to the electrochemical sensing element.

2. The continuous analyte monitoring system of claim 1, wherein the potentiostat is connected within half a millimeter to the entirety of at least one working electrode.

3. The continuous analyte monitoring system of claim 1, wherein the at least one working electrode is patterned by forming holes.

* * * * *